US009457183B2

(12) United States Patent
Sallberg et al.

(10) Patent No.: US 9,457,183 B2
(45) Date of Patent: Oct. 4, 2016

(54) INJECTION NEEDLE AND DEVICE

(75) Inventors: Matti Sallberg, Stockholm (SE); Lars Frelin, Tullinge (SE)

(73) Assignee: TRIPEP AB, Huddinge (SE)

( * ) Notice: Subject to any disclaimer, the term of this patent is extended or adjusted under 35 U.S.C. 154(b) by 0 days.

(21) Appl. No.: 14/125,905

(22) PCT Filed: Jun. 13, 2012

(86) PCT No.: PCT/IB2012/001321

§ 371 (c)(1),
(2), (4) Date: Dec. 12, 2013

(87) PCT Pub. No.: WO2012/172424

PCT Pub. Date: Dec. 20, 2012

(65) Prior Publication Data

US 2014/0121587 A1 May 1, 2014

Related U.S. Application Data

(60) Provisional application No. 61/642,356, filed on May 3, 2012, provisional application No. 61/597,112, filed on Feb. 9, 2012, provisional application No. 61/587,066, filed on Jan. 16, 2012, provisional application No. 61/500,066, filed on Jun. 22, 2011, provisional application No. 61/497,442, filed on Jun. 15, 2011.

(51) Int. Cl.
*A61N 1/30* (2006.01)
*A61N 1/05* (2006.01)
(Continued)

(52) U.S. Cl.
CPC ............ *A61N 1/306* (2013.01); *A61N 1/0502* (2013.01); *A61N 1/327* (2013.01); *C12M 35/02* (2013.01); *A61M 5/3291* (2013.01); *A61M 5/3298* (2013.01)

(58) Field of Classification Search
CPC ... A61B 5/0492; C12M 35/02; A61N 1/306; A61N 1/627; A61N 1/0502
USPC ............ 604/20–21, 27, 173, 187, 191, 501; 435/173.6
See application file for complete search history.

(56) References Cited

U.S. PATENT DOCUMENTS 5,439,440 A 8/1995 Hoffman
5,468,223 A 11/1995 Mir
(Continued)

FOREIGN PATENT DOCUMENTS

CN 101001665 A 7/2007
EP 0874663 B1 9/1999
(Continued)

OTHER PUBLICATIONS

International Search Reporting and Written Opinion dated Jan. 30, 2013, issued in PCT/IB2012/001321.
(Continued)

*Primary Examiner* — Theodore Stigell
*Assistant Examiner* — Amber Stiles
(74) *Attorney, Agent, or Firm* — Knobbe Martens Olson & Bear LLP

(57) ABSTRACT

Several needle assemblies and intracellular delivery devices that are used for the delivery of prophylactic and/or therapeutic material (i.e., delivered agents) into a tissue of a subject are disclosed. Preferably, the needle assemblies and/or the intracellular delivery devices comprise needles and/or needle electrodes, which are disposed in an array (e.g., a Y-type array having three outer needles and a center needle), wherein each needle in the array has a closed end and a plurality of apertures along each needle barrel, and the apertures on the needle barrels of the outer needles of the array are positioned to deliver the delivered agent toward the apertures of the center needle and/or an adjacent needle, but not outside of the active zone defined by the area within the needle array and the apertures on the needle barrel of the center needle are positioned to deliver the delivered agent toward the outer needles.

17 Claims, 77 Drawing Sheets

(51) Int. Cl.

| | |
|---|---|
| ***A61N 1/32*** | (2006.01) |
| ***C12M 1/42*** | (2006.01) |
| *A61M 5/32* | (2006.01) |

(56) References Cited

U.S. PATENT DOCUMENTS 5,697,901 A 12/1997 Eriksson
5,702,359 A 12/1997 Hoffman et al.
5,810,762 A 9/1998 Hoffman
5,873,849 A 2/1999 Bernard
5,993,434 A 11/1999 Dev et al.
6,009,347 A 12/1999 Hoffman
6,055,453 A 4/2000 Hofmann et al.
6,068,650 A 5/2000 Hoffman et al.
6,120,493 A 9/2000 Hofmann
6,135,990 A 10/2000 Heller et al.
6,181,964 B1 1/2001 Hoffman et al.
6,208,893 B1 3/2001 Hoffman et al.
6,216,034 B1 4/2001 Hoffman et al.
6,233,482 B1 5/2001 Hofmann et al.
6,241,701 B1 6/2001 Hofmann
6,278,895 B1 8/2001 Bernard
6,314,317 B1 11/2001 Willis
6,334,856 B1 1/2002 Allen et al.
6,418,341 B1 7/2002 Hoffman et al.
6,451,002 B1 9/2002 Dev et al.
6,503,231 B1 1/2003 Prausnitz et al.
6,516,223 B2 2/2003 Hofmann
6,520,950 B1 2/2003 Hofmann et al.
6,537,242 B1 3/2003 Palmer
6,564,093 B1 5/2003 Ostrow et al.
6,567,694 B2 5/2003 Hayakawa
6,569,149 B2 5/2003 Dev et al.
6,603,998 B1 8/2003 King et al.
6,654,636 B1 11/2003 Dev et al.
6,656,636 B2 12/2003 Ogasawara et al.
6,678,556 B1 1/2004 Nolan et al.
6,678,558 B1 1/2004 Dimmer et al.
6,697,669 B2 2/2004 Dev et al.
6,697,670 B2 2/2004 Chornenky et al.
6,713,291 B2 3/2004 King et al.
6,733,485 B1 5/2004 Whitehurst et al.
6,763,264 B2 7/2004 Hoffman
6,778,853 B1 8/2004 Heller et al.
6,795,728 B2 9/2004 Chornenkey et al.
6,892,099 B2 5/2005 Jaafar et al.
6,969,373 B2 * 11/2005 Schwartz et al. ........ 604/170.03
6,972,013 B1 12/2005 Zhang et al.
7,113,821 B1 9/2006 Sun et al.
7,171,264 B1 1/2007 Hofmann et al.
7,245,963 B2 7/2007 Draghia-Akli et al.
7,315,758 B2 1/2008 Kwiatkowski et al.
7,328,064 B2 2/2008 Mathiesen et al.
7,344,499 B1 3/2008 Prausnitz et al.
7,412,284 B2 8/2008 Hofmann
7,570,992 B2 8/2009 Nolan et al.
7,664,545 B2 2/2010 Westersten et al.
7,776,373 B2 8/2010 Pelletier
7,781,195 B1 8/2010 Heller et al.
RE42,277 E 4/2011 Jaafar et al.
7,922,709 B2 4/2011 Zhang et al.
7,938,824 B2 5/2011 Chornenky et al.
8,014,854 B2 9/2011 Schroeppel et al.
8,024,048 B2 9/2011 Schroeppel et al.
RE42,835 E 10/2011 Chornenky et al.
8,066,984 B2 11/2011 Szalay et al.
RE43,099 E 1/2012 Laroia et al.
2002/0040203 A1 4/2002 Sen et al.
2002/0138049 A1 9/2002 Allen et al.
2004/0059285 A1 3/2004 Mathiesen et al.
2004/0092860 A1 5/2004 Dev et al.
2004/0147964 A1 * 7/2004 Nolan .................... A61N 1/325 607/3
2004/0193097 A1 9/2004 Hofmann et al.
2004/0203124 A1 10/2004 King et al.
2004/0204669 A1 10/2004 Hofmann
2005/0004060 A1 1/2005 Draghia-Akli et al.
2005/0054594 A1 3/2005 Zhang et al.
2005/0070841 A1 3/2005 Mathiesen et al.
2005/0080028 A1 4/2005 Catchpole
2005/0154434 A1 * 7/2005 Simon .................... A61N 1/325 607/116
2005/0165359 A1 7/2005 Dalton
2005/0192542 A1 9/2005 Dev et al.
2005/0215941 A1 * 9/2005 Bernard et al. ................. 604/20
2005/0245857 A1 11/2005 Pizzi et al.
2006/0036210 A1 2/2006 Zhang et al.
2006/0134067 A1 6/2006 Liu et al.
2006/0224192 A1 10/2006 Dimmer et al.
2006/0259006 A1 11/2006 Mckay et al.
2007/0060989 A1 3/2007 Deem et al.
2007/0156082 A1 * 7/2007 Scherman ....................... 604/20
2007/0232984 A1 10/2007 Lovell et al.
2007/0239099 A1 10/2007 Goldfarb et al.
2007/0287950 A1 12/2007 Kjeken et al.
2008/0015571 A1 1/2008 Rubinsky et al.
2008/0045880 A1 2/2008 Kjeken et al.
2008/0058706 A1 3/2008 Zhang et al.
2008/0091135 A1 4/2008 Draghia-Akli et al.
2008/0234655 A1 9/2008 Mathiesen et al.
2008/0269666 A1 10/2008 Wang et al.
2008/0287857 A1 11/2008 Kjeken et al.
2009/0030364 A1 1/2009 Harmon et al.
2009/0104153 A1 * 4/2009 Barber ................... A61K 39/21 424/93.2
2009/0131905 A1 5/2009 Allen et al.
2010/0204640 A1 8/2010 Mingozzi et al.
2010/0305516 A1 12/2010 Xu et al.
2010/0311671 A1 12/2010 Johnson et al.
2010/0323001 A1 12/2010 Pachuk
2011/0009807 A1 1/2011 Kjeken et al.
2011/0009860 A1 1/2011 Chornenky et al.
2011/0125075 A1 5/2011 Takei et al.
2011/0160514 A1 6/2011 Long et al.
2011/0166501 A1 7/2011 Walters et al.
2011/0229502 A1 9/2011 Har-Noy
2011/0236979 A1 9/2011 Beebe et al.
2011/0245728 A1 10/2011 Eppstein et al.
2011/0263922 A1 10/2011 Dornberger et al.
2011/0282265 A1 11/2011 Walters et al.
2012/0046658 A1 2/2012 Kreindel
2012/0076808 A1 3/2012 Wang et al.

FOREIGN PATENT DOCUMENTS

EP 1163024 B1 12/2003
EP 1240917 B1 6/2004
EP 1100576 B1 8/2007
EP 0999867 B1 8/2010
EP 1711187 B1 12/2010
JP 2005-087519 4/2005
JP 2005-531383 10/2005
JP 2007-501071 1/2007
WO WO 96/39226 A1 12/1996
WO WO 99/37358 A1 7/1999
WO WO 00/02621 A9 3/2000
WO WO 00/23143 A1 4/2000
WO WO 00/00250 A1 6/2000
WO WO 01/41657 A1 6/2001
WO WO 2004/004825 A2 1/2004
WO WO 2005/016441 A1 2/2005
WO WO 2006/010837 A2 2/2006
WO WO 2010/110910 A1 9/2010
WO WO 2011/073796 A2 6/2011

OTHER PUBLICATIONS

PCT, International Preliminary Report on Patentability, for International Application No. PCT/IB2010/003399, dated Jul. 10, 2012.
PCT, International Search Report and Written Opinion, for International Application No. PCT/IB2010/003399, dated Jun. 23, 2011.

* cited by examiner

Regular needle
(0,9mg/0,3mL;115L)

HIP/small
(0,9mg/0,3mL;117R)

HIP/large
(0,9mg/0,3mL;115R)

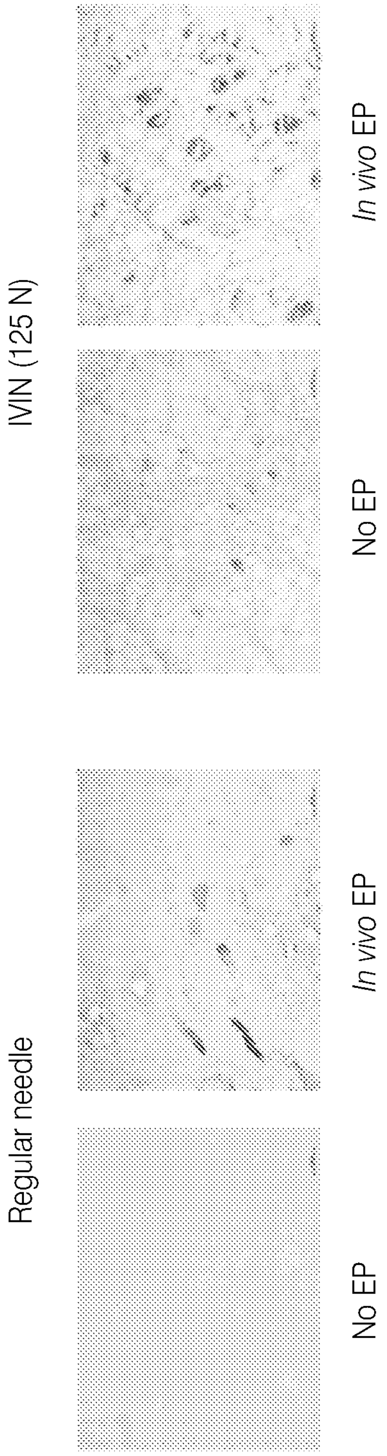
FIG. 56A1 FIG. 56A2 FIG. 56B1 FIG. 56B2

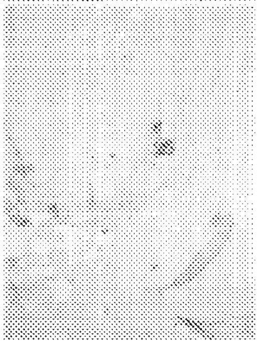
FIG. 57A1
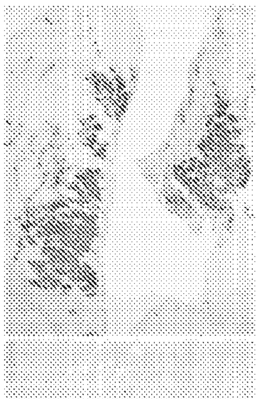
FIG. 57B1
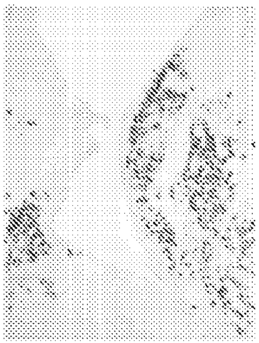
FIG. 57C1
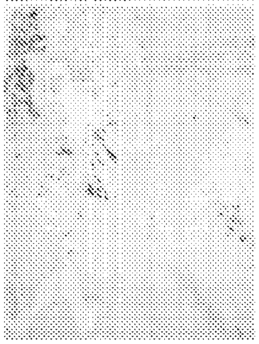
Regular needle/EP
FIG. 57A2
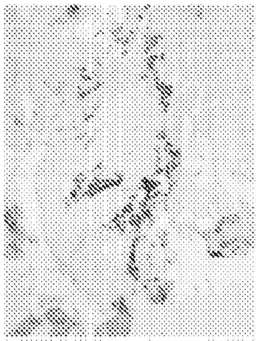
IVIN 75N/EP
FIG. 57B2
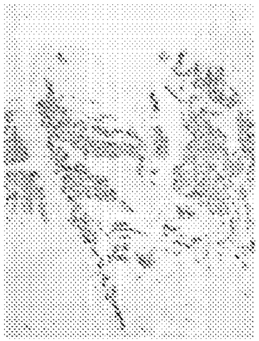
IVIN 125N/EP
FIG. 57C2

SEQUENCE LISTING

```
<160> NUMBER OF SEQ ID NOS: 33

<210> SEQ ID NO 1
<211> LENGTH: 183
<212> TYPE: PRT
<213> ORGANISM: Artificial Sequence
<220> FEATURE:
<223> OTHER INFORMATION: HBCAg (amino acid seq)

<400> SEQUENCE: 1

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180


<210> SEQ ID NO 2
<211> LENGTH: 552
<212> TYPE: DNA
<213> ORGANISM: Hepatitis B

<400> SEQUENCE: 2

atggacatcg acccttataa agaatttgga gctactgtgg agttactctc gtttttgccc      60

tccgacttct ttccttcagt acgagatctt ctagataccg cctcagctct gtatcgggaa     120
```

-continued

```
gccttagagt ctcctgagca ttgttcacct caccatactg cactcaggca agcaattctt    180

tgctgggggg aactaatgac tctagctacc tgggtgggtg ttaatttgga agatccagcg    240

tctagagacc tagtagtcag ttatgtcaac actaatatgg gcctaaagtt caggcaactc    300

ttgtggtttc acatttcttg tctcactttt ggaagagaaa cagttataga gtatttggtg    360

tctttcggag tgtggattcg cactcctcca gcttatagac caccaaatgc ccctatccta    420

tcaacacttc cggagactac tgttgttaga cgacgaggca ggtcccctag aagaagaact    480

ccctcgcctc gcagacgaag gtctcaatcg ccgcgtcgca gaagatctca atctcgggaa    540

tctcaatgtt ag                                                        552
```

<210> SEQ ID NO 3
<211> LENGTH: 552
<212> TYPE: DNA
<213> ORGANISM: Artificial Sequence
<220> FEATURE:
<223> OTHER INFORMATION: HBCAg (codon optimized nt seq)

<400> SEQUENCE: 3

```
atggacatcg acccctacaa ggagttcggc gccaccgtgg agctgctgag cttcctgccc     60

agcgacttct tccccagcgt gcgcgacctg ctggacaccg ccagcgccct gtaccgcgag    120

gccctggaga gccccgagca ctgcagcccc caccacaccg ccctgcgcca ggccatcctg    180

tgctggggcg agctgatgac cctggccacc tgggtgggcg tgaacctgga ggaccccgcc    240

agccgcgacc tggtggtgag ctacgtgaac accaacatgg gcctgaagtt ccgccagctg    300

ctgtggttcc acatcagctg cctgaccttc ggccgcgaga ccgtgatcga gtacctggtg    360

agcttcggcg tgtggatccg caccccccc gcctaccgcc cccccaacgc ccccatcctg    420

agcaccctgc ccgagaccac cgtggtgcgc cgccgcggcc gcagccccccg ccgccgcacc    480

cccagccccc gccgccgccg cagccagagc ccccgccgcc gccgcagcca gagccgcgag    540

agccagtgct ag                                                        552
```

<210> SEQ ID NO 4
<211> LENGTH: 18
<212> TYPE: PRT
<213> ORGANISM: Artificial Sequence
<220> FEATURE:
<223> OTHER INFORMATION: NS3/4A junction (amino acid sequence)

<400> SEQUENCE: 4

```
Ser Ala Asp Leu Glu Val Val Thr Ser Thr Trp Val Leu Val Gly Gly
 1               5                  10                  15

Val Leu
```

<210> SEQ ID NO 5
<211> LENGTH: 54
<212> TYPE: DNA
<213> ORGANISM: Artificial Sequence
<220> FEATURE:
<223> OTHER INFORMATION: NS3/4A junction (codon optimized nt seq)

<400> SEQUENCE: 5

```
agcgccgacc tggaggtggt gaccagcacc tgggtgctgg tgggcggcgt gctg           54
```

<210> SEQ ID NO 6
<211> LENGTH: 16
<212> TYPE: PRT
<213> ORGANISM: Artificial Sequence -continued
<220> FEATURE:
<223> OTHER INFORMATION: NS4A/B junction (amino acid sequence)

<400> SEQUENCE: 6

Asp Glu Met Glu Glu Cys Ser Gln His Leu Pro Tyr Ile Glu Gln Gly
 1               5                  10                  15

<210> SEQ ID NO 7
<211> LENGTH: 48
<212> TYPE: DNA
<213> ORGANISM: Artificial Sequence
<220> FEATURE:
<223> OTHER INFORMATION: NS4A/B junction (nucleotide sequence)

<400> SEQUENCE: 7
gacgagatgg aggagtgcag ccagcacctg ccctacatcg agcagggc                  48

<210> SEQ ID NO 8
<211> LENGTH: 869
<212> TYPE: PRT
<213> ORGANISM: Artificial Sequence
<220> FEATURE:
<223> OTHER INFORMATION: CONSTR-1 NS3/4A-HBcAg (NS3-NS4A-HBcAg fusion
      with active protease) (amino acid sequence)

<400> SEQUENCE: 8

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

-continued

```
Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
```

```
        675                 680                 685

Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865


<210> SEQ ID NO 9
<211> LENGTH: 2610
<212> TYPE: DNA
<213> ORGANISM: Artificial Sequence
<220> FEATURE:
<223> OTHER INFORMATION: NS3/4A-HBcAg (NS3-NS4A-HBcAg fusion with active
      protease) (nucleotide sequence sequence)

<400> SEQUENCE: 9

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900
```

-continued

```
atcctgggca tcggcaccgt gctggaccag gccgagaccg ccggcgcccg cctgaccgtg     960

ctggccaccg ccaccccccc cggcagcgtg accgtgcccc accccaacat cgaggaggtg    1020

gccctgagca ccaccggcga gatccccttc tacggcaagg ccatccccct ggaggccatc    1080

aagggcggcc gccacctgat cttctgccac agcaagaaga agtgcgacga gctggccgcc    1140

aagctggtgg ccctgggcgt gaacgccgtg gcctactacc gcggcctgga cgtgagcgtg    1200

atccccacca gcggcgacgt ggtggtggtg gccaccgacg ccctgatgac cggcttcacc    1260

ggcgacttcg acagcgtgat cgactgcaac acctgcgtga cccagaccgt ggacttcagc    1320

ctggacccca ccttcaccat cgagaccatc accctgcccc aggacgccgt gagccgcacc    1380

cagcgccgcg gccgcaccgg ccgcggcaag cccggcatct accgcttcgt ggcccccggc    1440

gagcgcccca gcggcatgtt cgacagcagc gtgctgtgcg agtgctacga cgccggctgc    1500

gcctggtacg agctgacccc cgccgagacc accgtgcgcc tgcgcgccta catgaacacc    1560

cccggcctgc ccgtgtgcca ggaccacctg gagttctggg agggcgtgtt caccggcctg    1620

acccacatcg acgcccactt cctgagccag accaagcaga gcggcgagaa cctgccctac    1680

ctggtggcct accaggccac cgtgtgcgcc cgcgcccagg cccccccccc cagctgggac    1740

cagatgtgga agtgcctgat ccgcctgaag cccaccctgc acggccccac cccccctgctg    1800

taccgcctgg gcgccgtgca gaacgaggtg accctgaccc accccgtgac caagtacatc    1860

atgacctgca tgagcgccga cctggaggtg gtgaccccca cctgggtgct ggtgggcggc    1920

gtgctggccg ccctggccgc ctactgcctg agcaccggct gcgtggtgat cgtgggccgc    1980

atcgtgctga gcggcaagcc cgccatcatc cccgaccgcg aggtgctgta ccgcgagttc    2040

gacgagatgg aggagtgcat ggacatcgac ccctacaagg agttcggcgc caccgtggag    2100

ctgctgagct tcctgcccag cgacttcttc cccagcgtgc gcgacctgct ggacaccgcc    2160

agcgccctgt accgcgaggc cctggagagc cccgagcact gcagccccca ccacaccgcc    2220

ctgcgccagg ccatcctgtg ctggggcgag ctgatgaccc tggccacctg ggtgggcgtg    2280

aacctggagg accccgccag ccgcgacctg gtggtgagct acgtgaacac caacatgggc    2340

ctgaagttcc gccagctgct gtggttccac atcagctgcc tgaccttcgg ccgcgagacc    2400

gtgatcgagt acctggtgag cttcggcgtg tggatccgca ccccccccgc ctaccgcccc    2460

cccaacgccc ccatcctgag caccctgccc gagaccaccg tggtgcgccg ccgcggccgc    2520

agcccccgcc gccgcacccc cagcccccgc cgccgccgca gccagagccc ccgccgccgc    2580

cgcagccaga gccgcgagag ccagtgctag                                     2610
```

```
<210> SEQ ID NO 10
<211> LENGTH: 869
<212> TYPE: PRT
<213> ORGANISM: Artificial Sequence
<220> FEATURE:
<223> OTHER INFORMATION: CONSTR-2 Mutant(catalytic triade)NS3/4A-HBcAg
      (NS3-NS4A-HBcAg fusion with inactive protease)
      (amino acid sequence)

<400> SEQUENCE: 10

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45
```

-continued

```
Ile Asn Gly Val Cys Trp Thr Val Tyr Ala Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Ala Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
```

-continued

```
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865
```

<210> SEQ ID NO 11

```
<211> LENGTH: 2610
<212> TYPE: DNA
<213> ORGANISM: Artificial Sequence
<220> FEATURE:
<223> OTHER INFORMATION: Mutant(catalytic triade)NS3/4A-HBcAg
      (NS3-NS4A-HBcAg fusion with inactive protease)
      (nucleotide sequence)

<400> SEQUENCE: 11

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta cgccggcgcc    180

ggcacccgca ccatcgccag ccccaagggc cccgtgatcc agatgtacac caacgtggac    240

caggccctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccaccccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcat ggacatcgac ccctacaagg agttcggcgc caccgtggag   2100
```

```
ctgctgagct tcctgcccag cgacttcttc cccagcgtgc gcgacctgct ggacaccgcc   2160

agcgccctgt accgcgaggc cctggagagc cccgagcact gcagccccca ccacaccgcc   2220

ctgcgccagg ccatcctgtg ctggggcgag ctgatgaccc tggccacctg ggtgggcgtg   2280

aacctggagg accccgccag ccgcgacctg gtggtgagct acgtgaacac caacatgggc   2340

ctgaagttcc gccagctgct gtggttccac atcagctgcc tgaccttcgg ccgcgagacc   2400

gtgatcgagt acctggtgag cttcggcgtg tggatccgca ccccccccgc ctaccgcccc   2460

cccaacgccc ccatcctgag caccctgccc gagaccaccg tggtgcgccg ccgcggccgc   2520

agcccccgcc gccgcacccc cagcccccgc cgccgccgca gccagagccc ccgccgccgc   2580

cgcagccaga gccgcgagag ccagtgctag                                    2610
```

<210> SEQ ID NO 12
<211> LENGTH: 869
<212> TYPE: PRT
<213> ORGANISM: Artificial Sequence
<220> FEATURE:
<223> OTHER INFORMATION: CONSTR-3 NS3/4A-HBcAg (NS3 and NS4A-HBcAg fusion) (amino acid sequence)

<400> SEQUENCE: 12

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
```

-continued

```
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685
```

```
Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865


<210> SEQ ID NO 13
<211> LENGTH: 2610
<212> TYPE: DNA
<213> ORGANISM: Artificial Sequence
<220> FEATURE:
<223> OTHER INFORMATION: NS3/4A-HBcAg (NS3 and NS4A-HBcAg fusion)
      (nucleotide sequence)

<400> SEQUENCE: 13

atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgccccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480

acccgcggcg tggccaaggc cgtggacttc atccccgtgg agagcctgga gaccaccatg     540

cgcagccccg tgttcagcga caacagcagc ccccccgccg tgccccagag ctaccaggtg     600

gcccacctgc acgcccccac cggcagcggc aagagcacca aggtgcccgc cgcctacgcc     660

gcccagggct acaaggtgct ggtgctgaac cccagcgtgg ccgccaccat gggcttcggc     720

gcctacatga gcaaggccca cggcatcgac cccaacatcc gcaccggcgt gcgcaccatc     780

accaccggca gccccatcac ctacagcacc tacggcaagt tcctggccga cggcggctgc     840

agcggcggcg cctacgacat catcatctgc gacgagtgcc acagcaccga cgccaccagc     900

atcctgggca tcggcaccgt gctggaccag gccgagaccg ccggcgcccg cctgaccgtg     960
```

```
ctggccaccg ccaccccccc cggcagcgtg accgtgcccc accccaacat cgaggaggtg   1020

gccctgagca ccaccggcga gatccccttc tacggcaagg ccatcccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcat ggacatcgac ccctacaagg agttcggcgc caccgtggag   2100

ctgctgagct tcctgcccag cgacttcttc cccagcgtgc gcgacctgct ggacaccgcc   2160

agcgccctgt accgcgaggc cctggagagc cccgagcact gcagccccca ccacaccgcc   2220

ctgcgccagg ccatcctgtg ctggggcgag ctgatgaccc tggccacctg ggtgggcgtg   2280

aacctggagg accccgccag ccgcgacctg gtggtgagct acgtgaacac caacatgggc   2340

ctgaagttcc gccagctgct gtggttccac atcagctgcc tgaccttcgg ccgcgagacc   2400

gtgatcgagt acctggtgag cttcggcgtg tggatccgca cccccccccgc ctaccgcccc   2460

cccaacgccc ccatcctgag caccctgccc gagaccaccg tggtgcgccg ccgcggccgc   2520

agcccccgcc gccgcacccc cagcccccgc cgccgccgca gccagagccc ccgccgccgc   2580

cgcagccaga gccgcgagag ccagtgctag                                    2610
```

<210> SEQ ID NO 14
<211> LENGTH: 879
<212> TYPE: PRT
<213> ORGANISM: Artificial Sequence
<220> FEATURE:
<223> OTHER INFORMATION: CONSTR-4 NS3/4A-4Bjunct-HBcAg (NS3 AND NS4A AND HBcAg) (amino acid sequence)

<400> SEQUENCE: 14

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60
```

-continued

```
Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480
```

-continued

```
Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Ile Asp Pro Tyr Lys Glu
    690                 695                 700

Phe Gly Ala Thr Val Glu Leu Leu Ser Phe Leu Pro Ser Asp Phe Phe
705                 710                 715                 720

Pro Ser Val Arg Asp Leu Leu Asp Thr Ala Ser Ala Leu Tyr Arg Glu
                725                 730                 735

Ala Leu Glu Ser Pro Glu His Cys Ser Pro His His Thr Ala Leu Arg
            740                 745                 750

Gln Ala Ile Leu Cys Trp Gly Glu Leu Met Thr Leu Ala Thr Trp Val
        755                 760                 765

Gly Val Asn Leu Glu Asp Pro Ala Ser Arg Asp Leu Val Val Ser Tyr
    770                 775                 780

Val Asn Thr Asn Met Gly Leu Lys Phe Arg Gln Leu Leu Trp Phe His
785                 790                 795                 800

Ile Ser Cys Leu Thr Phe Gly Arg Glu Thr Val Ile Glu Tyr Leu Val
                805                 810                 815

Ser Phe Gly Val Trp Ile Arg Thr Pro Pro Ala Tyr Arg Pro Pro Asn
            820                 825                 830

Ala Pro Ile Leu Ser Thr Leu Pro Glu Thr Thr Val Val Arg Arg Arg
        835                 840                 845

Gly Arg Ser Pro Arg Arg Arg Thr Pro Ser Pro Arg Arg Arg Arg Ser
    850                 855                 860

Gln Ser Pro Arg Arg Arg Arg Ser Gln Ser Arg Glu Ser Gln Cys
865                 870                 875
```

<210> SEQ ID NO 15
<211> LENGTH: 2640
<212> TYPE: DNA

<213> ORGANISM: Artificial Sequence
<220> FEATURE:
<223> OTHER INFORMATION: NS3/4A-4Bjunct-HBcAg (NS3 AND NS4A AND HBcAg)
(nucleotide sequence)

<400> SEQUENCE: 15

```
atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960

ctggccaccg ccacccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcag ccagcacctg ccctacatcg agcagggcat ggacatcgac   2100

ccctacaagg agttcggcgc caccgtggag ctgctgagct tcctgcccag cgacttcttc   2160
```

-continued

```
cccagcgtgc gcgacctgct ggacaccgcc agcgccctgt accgcgaggc cctggagagc   2220

cccgagcact gcagccccca ccacaccgcc ctgcgccagg ccatcctgtg ctggggcgag   2280

ctgatgaccc tggccacctg ggtgggcgtg aacctggagg accccgccag ccgcgacctg   2340

gtggtgagct acgtgaacac caacatgggc ctgaagttcc gccagctgct gtggttccac   2400

atcagctgcc tgaccttcgg ccgcgagacc gtgatcgagt acctggtgag cttcggcgtg   2460

tggatccgca ccccccccgc ctaccgcccc cccaacgccc ccatcctgag caccctgccc   2520

gagaccaccg tggtgcgccg ccgcggccgc agcccccgcc gccgcacccc cagcccccgc   2580

cgccgccgca gccagagccc ccgccgccgc cgcagccaga gccgcgagag ccagtgctag   2640
```

```
<210> SEQ ID NO 16
<211> LENGTH: 933
<212> TYPE: PRT
<213> ORGANISM: Artificial Sequence
<220> FEATURE:
<223> OTHER INFORMATION: CONSTR-5
      NS3/4A-4Bjunct-HBcAg1-44-NS3/4Ajunct-HBc45-87-NS3/4Ajunct-HBc88-
      141-NS3/4Ajunct-HBc142-183 (amino acid sequence)

<400> SEQUENCE: 16

Met Ala Pro Ile Thr Ala Tyr Ala Gln Gln Thr Arg Gly Leu Leu Gly
 1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270
```

```
Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Ile Asp Pro Tyr Lys Glu
```

```
    690                 695                 700

Phe Gly Ala Thr Val Glu Leu Leu Ser Phe Leu Pro Ser Asp Phe Phe
705                 710                 715                 720

Pro Ser Val Arg Asp Leu Leu Asp Thr Ala Ser Ala Leu Tyr Arg Glu
                725                 730                 735

Ala Leu Glu Ser Ser Ala Asp Leu Glu Val Val Thr Ser Thr Trp Val
            740                 745                 750

Leu Val Gly Gly Val Leu Pro Glu His Cys Ser Pro His His Thr Ala
        755                 760                 765

Leu Arg Gln Ala Ile Leu Cys Trp Gly Glu Leu Met Thr Leu Ala Thr
    770                 775                 780

Trp Val Gly Val Asn Leu Glu Asp Pro Ala Ser Arg Asp Leu Val Val
785                 790                 795                 800

Ser Ser Ala Asp Leu Glu Val Val Thr Ser Thr Trp Val Leu Val Gly
                805                 810                 815

Gly Val Leu Tyr Val Asn Thr Asn Met Gly Leu Lys Phe Arg Gln Leu
            820                 825                 830

Leu Trp Phe His Ile Ser Cys Leu Thr Phe Gly Arg Glu Thr Val Ile
        835                 840                 845

Glu Tyr Leu Val Ser Phe Gly Val Trp Ile Arg Thr Pro Pro Ala Tyr
    850                 855                 860

Arg Pro Pro Asn Ala Pro Ile Leu Ser Ser Ala Asp Leu Glu Val Val
865                 870                 875                 880

Thr Ser Thr Trp Val Leu Val Gly Gly Val Leu Thr Leu Pro Glu Thr
                885                 890                 895

Thr Val Val Arg Arg Arg Gly Arg Ser Pro Arg Arg Arg Thr Pro Ser
            900                 905                 910

Pro Arg Arg Arg Arg Ser Gln Ser Pro Arg Arg Arg Arg Ser Gln Ser
        915                 920                 925

Arg Glu Ser Gln Cys
    930
```

<210> SEQ ID NO 17
<211> LENGTH: 2802
<212> TYPE: DNA
<213> ORGANISM: Artificial Sequence
<220> FEATURE:
<223> OTHER INFORMATION: NS3/4A-4Bjunct-HBcAg1-44-NS3/4Ajunct-HBc45-87-
NS3/4Ajunct-HBc88-141-NS3/4Ajunct-HBc142-183 (nucleotide sequence)

<400> SEQUENCE: 17

```
atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660
```

```
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac cccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcag ccagcacctg ccctacatcg agcagggcat ggacatcgac   2100
ccctacaagg agttcggcgc caccgtggag ctgctgagct tcctgcccag cgacttcttc   2160
cccagcgtgc gcgacctgct ggacaccgcc agcgccctgt accgcgaggc cctggagagc   2220
agcgccgacc tggaggtggt gaccagcacc tgggtgctgg tgggcggcgt gctgcccgag   2280
cactgcagcc cccaccacac cgccctgcgc caggccatcc tgtgctgggg cgagctgatg   2340
accctggcca cctgggtggg cgtgaacctg gaggaccccg ccagccgcga cctggtggtg   2400
agcagcgccg acctggaggt ggtgaccagc acctgggtgc tggtgggcgg cgtgctgtac   2460
gtgaacacca acatgggcct gaagttccgc cagctgctgt ggttccacat cagctgcctg   2520
accttcggcc gcgagaccgt gatcgagtac ctggtgagct tcggcgtgtg gatccgcacc   2580
ccccccgcct accgcccccc caacgccccc atcctgagca gcgccgacct ggaggtggtg   2640
accagcacct gggtgctggt gggcggcgtg ctgaccctgc ccgagaccac cgtggtgcgc   2700
cgccgcggcc gcagcccccg ccgccgcacc cccagccccc gccgccgccg cagccagagc   2760
ccccgccgcc gccgcagcca gagccgcgag agccagtgct ag                      2802
```

<210> SEQ ID NO 18
<211> LENGTH: 933
<212> TYPE: PRT
<213> ORGANISM: Artificial Sequence
<220> FEATURE:

<223> OTHER INFORMATION: CONSTR-6
NS3/4A-4Bjunct-HBcAg142-183-NS3/4Ajunct-HBc45-87-NS3/4Ajunct-
HBc88-141-NS3/4Ajunct-HBc1-44 (amino acid sequence)

<400> SEQUENCE: 18

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
```

-continued

```
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Pro Glu His Cys Ser Pro His His Thr Ala Leu Arg
        755                 760                 765

Gln Ala Ile Leu Cys Trp Gly Glu Leu Met Thr Leu Ala Thr Trp Val
    770                 775                 780

Gly Val Asn Leu Glu Asp Pro Ala Ser Arg Asp Leu Val Val Ser Ser
785                 790                 795                 800

Ala Asp Leu Glu Val Val Thr Ser Thr Trp Val Leu Val Gly Gly Val
                805                 810                 815
```

```
Leu Tyr Val Asn Thr Asn Met Gly Leu Lys Phe Arg Gln Leu Leu Trp
            820                 825                 830

Phe His Ile Ser Cys Leu Thr Phe Gly Arg Glu Thr Val Ile Glu Tyr
        835                 840                 845

Leu Val Ser Phe Gly Val Trp Ile Arg Thr Pro Pro Ala Tyr Arg Pro
    850                 855                 860

Pro Asn Ala Pro Ile Leu Ser Ser Ala Asp Leu Glu Val Val Thr Ser
865                 870                 875                 880

Thr Trp Val Leu Val Gly Gly Val Leu Met Asp Ile Asp Pro Tyr Lys
                885                 890                 895

Glu Phe Gly Ala Thr Val Glu Leu Leu Ser Phe Leu Pro Ser Asp Phe
            900                 905                 910

Phe Pro Ser Val Arg Asp Leu Leu Asp Thr Ala Ser Ala Leu Tyr Arg
        915                 920                 925

Glu Ala Leu Glu Ser
    930


<210> SEQ ID NO 19
<211> LENGTH: 2802
<212> TYPE: DNA
<213> ORGANISM: Artificial Sequence
<220> FEATURE:
<223> OTHER INFORMATION: NS3/4A-4Bjunct-HBcAg142-183-NS3/4Ajunct-HBc45-
      87-NS3/4Ajunct-HBc88-141-NS3/4Ajunct-HBc1-44 (nucleotide sequence)

<400> SEQUENCE: 19

atggccccca tcaccgccta cgcccagcag acccgcggcc tgctgggctg catcatcacc      60

agcctgaccg gccgcgacaa gaaccaggtg gagggcgagg tgcagatcgt gagcaccgcc     120

gcccagacct tcctggccac ctgcatcaac ggcgtgtgct ggaccgtgta ccacggcgcc     180

ggcacccgca ccatcgccag ccccaagggc cccgtgatcc agatgtacac caacgtggac     240

caggacctgg tgggctggcc cgcccccag ggcgcccgca gcctgacccc ctgcacctgc     300

ggcagcagcg acctgtacct ggtgacccgc cacgccgacg tgatccccgt gcgccgccgc     360

ggcgacggcc gcggcagcct gctgagcccc cgccccatca gctacctgaa gggcagcagc     420

ggcggccccc tgctgtgccc cgccggccac gccgtgggca tcttccgcgc cgccgtgtgc     480

acccgcggcg tggccaaggc cgtggacttc atccccgtgg agagcctgga gaccaccatg     540

cgcagccccg tgttcagcga caacagcagc ccccccgccg tgccccagag ctaccaggtg     600

gcccacctgc acgcccccac cggcagcggc aagagcacca aggtgcccgc cgcctacgcc     660

gcccagggct acaaggtgct ggtgctgaac cccagcgtgg ccgccaccat gggcttcggc     720

gcctacatga gcaaggccca cggcatcgac cccaacatcc gcaccggcgt gcgcaccatc     780

accaccggca gccccatcac ctacagcacc tacggcaagt tcctggccga cggcggctgc     840

agcggcggcg cctacgacat catcatctgc gacgagtgcc acagcaccga cgccaccagc     900

atcctgggca tcggcaccgt gctggaccag gccgagaccg ccggcgcccg cctgaccgtg     960

ctggccaccg ccaccccccc cggcagcgtg accgtgcccc accccaacat cgaggaggtg    1020

gccctgagca ccaccggcga gatccccttc tacggcaagg ccatccccct ggaggccatc    1080

aagggcggcc gccacctgat cttctgccac agcaagaaga agtgcgacga gctggccgcc    1140

aagctggtgg ccctgggcgt gaacgccgtg gcctactacc gcggcctgga cgtgagcgtg    1200

atccccacca gcggcgacgt ggtggtggtg gccaccgacg ccctgatgac cggcttcacc    1260

ggcgacttcg acagcgtgat cgactgcaac acctgcgtga cccagaccgt ggacttcagc    1320
```

```
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac cccccctgctg   1800 taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcag ccagcacctg ccctacatcg agcagggcac cctgcccgag   2100
accaccgtgg tgcgccgccg cggccgcagc ccccgccgcc gcacccccag cccccgccgc   2160
cgccgcagcc agagccccccg ccgccgccgc agccagagcc gcgagagcca gtgcagcgcc   2220
gacctggagg tggtgaccag cacctgggtg ctggtgggcg gcgtgctgcc cgagcactgc   2280
agcccccacc acaccgccct gcgccaggcc atcctgtgct ggggcgagct gatgaccctg   2340
gccacctggg tgggcgtgaa cctggaggac cccgccagcc gcgacctggt ggtgagcagc   2400
gccgacctgg aggtggtgac cagcacctgg gtgctggtgg gcggcgtgct gtacgtgaac   2460
accaacatgg gcctgaagtt ccgccagctg ctgtggttcc acatcagctg cctgaccttc   2520
ggccgcgaga ccgtgatcga gtacctggtg agcttcggcg tgtggatccg cacccccccc   2580
gcctaccgcc cccccaacgc ccccatcctg agcagcgccg acctggaggt ggtgaccagc   2640
acctgggtgc tggtgggcgg cgtgctgatg gacatcgacc cctacaagga gttcggcgcc   2700
accgtggagc tgctgagctt cctgcccagc gacttcttcc ccagcgtgcg cgacctgctg   2760
gacaccgcca gcgccctgta ccgcgaggcc ctggagagct ag                      2802
```

```
<210> SEQ ID NO 20
<211> LENGTH: 933
<212> TYPE: PRT
<213> ORGANISM: Artificial Sequence
<220> FEATURE:
<223> OTHER INFORMATION: CONSTR-7
      NS3/4A-4Bjunct-HBcAg142-183-NS3/4Ajunct-HBc88-141-NS3/4Ajunct-
      HBc45-87-NS3/4Ajunct-HBc1-44 (amino acid sequence)

<400> SEQUENCE: 20

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
```

-continued

```
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510
```

```
Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Tyr Val Asn Thr Asn Met Gly Leu Lys Phe Arg Gln
        755                 760                 765

Leu Leu Trp Phe His Ile Ser Cys Leu Thr Phe Gly Arg Glu Thr Val
    770                 775                 780

Ile Glu Tyr Leu Val Ser Phe Gly Val Trp Ile Arg Thr Pro Pro Ala
785                 790                 795                 800

Tyr Arg Pro Pro Asn Ala Pro Ile Leu Ser Ser Ala Asp Leu Glu Val
                805                 810                 815

Val Thr Ser Thr Trp Val Leu Val Gly Gly Val Leu Pro Glu His Cys
            820                 825                 830

Ser Pro His His Thr Ala Leu Arg Gln Ala Ile Leu Cys Trp Gly Glu
        835                 840                 845

Leu Met Thr Leu Ala Thr Trp Val Gly Val Asn Leu Glu Asp Pro Ala
    850                 855                 860

Ser Arg Asp Leu Val Val Ser Ser Ala Asp Leu Glu Val Val Thr Ser
865                 870                 875                 880

Thr Trp Val Leu Val Gly Gly Val Leu Met Asp Ile Asp Pro Tyr Lys
                885                 890                 895

Glu Phe Gly Ala Thr Val Glu Leu Leu Ser Phe Leu Pro Ser Asp Phe
            900                 905                 910

Phe Pro Ser Val Arg Asp Leu Leu Asp Thr Ala Ser Ala Leu Tyr Arg
        915                 920                 925
```

Glu Ala Leu Glu Ser
930

<210> SEQ ID NO 21
<211> LENGTH: 2802
<212> TYPE: DNA
<213> ORGANISM: Artificial Sequence
<220> FEATURE:
<223> OTHER INFORMATION: NS3/4A-4Bjunct-HBcAg142-183-NS3/4Ajunct-HBc88-141-NS3/4Ajunct-HBc45-87-NS3/4Ajunct-HBc1-44 (nucleotide sequence)

<400> SEQUENCE: 21
atggccccca tcaccgccta cgcccagcag acccgcggcc tgctgggctg catcatcacc 60
agcctgaccg gccgcgacaa gaaccaggtg gagggcgagg tgcagatcgt gagcaccgcc 120
gcccagacct tcctggccac ctgcatcaac ggcgtgtgct ggaccgtgta ccacggcgcc 180
ggcacccgca ccatcgccag ccccaagggc cccgtgatcc agatgtacac caacgtggac 240
caggacctgg tgggctggcc cgcccccag ggcgcccgca gcctgacccc ctgcacctgc 300
ggcagcagcg acctgtacct ggtgacccgc cacgccgacg tgatccccgt gcgccgccgc 360
ggcgacggcc gcggcagcct gctgagcccc cgccccatca gctacctgaa gggcagcagc 420
ggcggccccc tgctgtgccc cgccggccac gccgtgggca tcttccgcgc cgccgtgtgc 480
acccgcggcg tggccaaggc cgtggacttc atccccgtgg agagcctgga gaccaccatg 540
cgcagccccg tgttcagcga caacagcagc ccccccgccg tgccccagag ctaccaggtg 600
gcccacctgc acgcccccac cggcagcggc aagagcacca aggtgcccgc cgcctacgcc 660
gcccagggct acaaggtgct ggtgctgaac cccagcgtgg ccgccaccat gggcttcggc 720
gcctacatga gcaaggccca cggcatcgac cccaacatcc gcaccggcgt gcgcaccatc 780
accaccggca gccccatcac ctacagcacc tacggcaagt tcctggccga cggcggctgc 840
agcggcggcg cctacgacat catcatctgc gacgagtgcc acagcaccga cgccaccagc 900
atcctgggca tcggcaccgt gctggaccag gccgagaccg ccggcgcccg cctgaccgtg 960
ctggccaccg ccaccccccc cggcagcgtg accgtgcccc accccaacat cgaggaggtg 1020
gccctgagca ccaccggcga gatccccttc tacggcaagg ccatccccct ggaggccatc 1080
aagggcggcc gccacctgat cttctgccac agcaagaaga agtgcgacga gctggccgcc 1140
aagctggtgg ccctgggcgt gaacgccgtg gcctactacc gcggcctgga cgtgagcgtg 1200
atccccacca gcggcgacgt ggtggtggtg gccaccgacg ccctgatgac cggcttcacc 1260
ggcgacttcg acagcgtgat cgactgcaac acctgcgtga cccagaccgt ggacttcagc 1320
ctggacccca ccttcaccat cgagaccatc accctgcccc aggacgccgt gagccgcacc 1380
cagcgccgcg gccgcaccgg ccgcggcaag cccggcatct accgcttcgt ggcccccggc 1440
gagcgcccca gcggcatgtt cgacagcagc gtgctgtgcg agtgctacga cgccggctgc 1500
gcctggtacg agctgacccc cgccgagacc accgtgcgcc tgcgcgccta catgaacacc 1560
cccggcctgc ccgtgtgcca ggaccacctg gagttctggg agggcgtgtt caccggcctg 1620
acccacatcg acgcccactt cctgagccag accaagcaga gcggcgagaa cctgccctac 1680
ctggtggcct accaggccac cgtgtgcgcc cgcgcccagg cccccccccc cagctgggac 1740
cagatgtgga agtgcctgat ccgcctgaag cccaccctgc acggccccac ccccctgctg 1800
taccgcctgg gcgccgtgca gaacgaggtg accctgaccc accccgtgac caagtacatc 1860
atgacctgca tgagcgccga cctggaggtg gtgaccagca cctgggtgct ggtgggcggc 1920
gtgctggccg ccctggccgc ctactgcctg agcaccggct gcgtggtgat cgtgggccgc 1980

```
atcgtgctga gcggcaagcc cgccatcatc cccgaccgcg aggtgctgta ccgcgagttc   2040

gacgagatgg aggagtgcag ccagcacctg ccctacatcg agcagggcac cctgcccgag   2100

accaccgtgg tgcgccgccg cggccgcagc ccccgccgcc gcacccccag cccccgccgc   2160

cgccgcagcc agagcccccg ccgccgccgc agccagagcc gcgagagcca gtgcagcgcc   2220

gacctggagg tggtgaccag cacctgggtg ctggtgggcg gcgtgctgta cgtgaacacc   2280

aacatgggcc tgaagttccg ccagctgctg tggttccaca tcagctgcct gaccttcggc   2340

cgcgagaccg tgatcgagta cctggtgagc ttcggcgtgt ggatccgcac cccccccgcc   2400

taccgccccc ccaacgcccc catcctgagc agcgccgacc tggaggtggt gaccagcacc   2460

tgggtgctgg tgggcggcgt gctgcccgag cactgcagcc cccaccacac cgccctgcgc   2520

caggccatcc tgtgctgggg cgagctgatg accctggcca cctgggtggg cgtgaacctg   2580

gaggaccccg ccagccgcga cctggtggtg agcagcgccg acctggaggt ggtgaccagc   2640

acctgggtgc tggtgggcgg cgtgctgatg gacatcgacc cctacaagga gttcggcgcc   2700

accgtggagc tgctgagctt cctgcccagc gacttcttcc ccagcgtgcg cgacctgctg   2760

gacaccgcca gcgccctgta ccgcgaggcc ctggagagct ag                      2802
```

<210> SEQ ID NO 22
<211> LENGTH: 933
<212> TYPE: PRT
<213> ORGANISM: Artificial Sequence
<220> FEATURE:
<223> OTHER INFORMATION: CONSTR-8
NS3/4A-4Bjunct-HBcAg142-183-NS3/4Ajunct-HBc88-141-NS3/4Ajunct-
HBc1-44-NS3/4Ajunct-HBc45-87 (amino acid sequence)

<400> SEQUENCE: 22

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205
```

```
Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620
```

-continued

```
Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Tyr Val Asn Thr Asn Met Gly Leu Lys Phe Arg Gln
        755                 760                 765

Leu Leu Trp Phe His Ile Ser Cys Leu Thr Phe Gly Arg Glu Thr Val
    770                 775                 780

Ile Glu Tyr Leu Val Ser Phe Gly Val Trp Ile Arg Thr Pro Pro Ala
785                 790                 795                 800

Tyr Arg Pro Pro Asn Ala Pro Ile Leu Ser Ser Ala Asp Leu Glu Val
                805                 810                 815

Val Thr Ser Thr Trp Val Leu Val Gly Gly Val Leu Met Asp Ile Asp
            820                 825                 830

Pro Tyr Lys Glu Phe Gly Ala Thr Val Glu Leu Leu Ser Phe Leu Pro
        835                 840                 845

Ser Asp Phe Phe Pro Ser Val Arg Asp Leu Leu Asp Thr Ala Ser Ala
    850                 855                 860

Leu Tyr Arg Glu Ala Leu Glu Ser Ser Ala Asp Leu Glu Val Val Thr
865                 870                 875                 880

Ser Thr Trp Val Leu Val Gly Gly Val Leu Pro Glu His Cys Ser Pro
                885                 890                 895

His His Thr Ala Leu Arg Gln Ala Ile Leu Cys Trp Gly Glu Leu Met
            900                 905                 910

Thr Leu Ala Thr Trp Val Gly Val Asn Leu Glu Asp Pro Ala Ser Arg
        915                 920                 925

Asp Leu Val Val Ser
    930
```

```
<210> SEQ ID NO 23
<211> LENGTH: 2802
<212> TYPE: DNA
<213> ORGANISM: Artificial Sequence
<220> FEATURE:
<223> OTHER INFORMATION: NS3/4A-4Bjunct-HBcAg142-183-NS3/4Ajunct-HBc88-
      141-NS3/4Ajunct-HBc1-44-NS3/4Ajunct-HBc45-87 (nucleotide sequence)

<400> SEQUENCE: 23

atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240
```

-continued

```
caggacctgg tgggctggcc cgccccccag ggcgcccgca gcctgacccc ctgcacctgc    300
ggcagcagcg acctgtacct ggtgacccgc cacgccgacg tgatccccgt gcgccgccgc    360
ggcgacggcc gcggcagcct gctgagcccc cgccccatca gctacctgaa gggcagcagc    420
ggcggccccc tgctgtgccc cgccggccac gccgtgggca tcttccgcgc cgccgtgtgc    480
acccgcggcg tggccaaggc cgtggacttc atccccgtgg agagcctgga gaccaccatg    540
cgcagccccg tgttcagcga caacagcagc ccccccgccg tgccccagag ctaccaggtg    600
gcccacctgc acgcccccac cggcagcggc aagagcacca aggtgcccgc cgcctacgcc    660
gcccagggct acaaggtgct ggtgctgaac cccagcgtgg ccgccaccat gggcttcggc    720
gcctacatga gcaaggccca cggcatcgac cccaacatcc gcaccggcgt gcgcaccatc    780
accaccggca gccccatcac ctacagcacc tacggcaagt tcctggccga cggcggctgc    840
agcggcggcg cctacgacat catcatctgc gacgagtgcc acagcaccga cgccaccagc    900
atcctgggca tcggcaccgt gctggaccag gccgagaccg ccggcgcccg cctgaccgtg    960
ctggccaccg ccaccccccc cggcagcgtg accgtgcccc accccaacat cgaggaggtg   1020
gccctgagca ccaccggcga gatccccttc tacggcaagg ccatccccct ggaggccatc   1080
aagggcggcc gccacctgat cttctgccac agcaagaaga agtgcgacga gctggccgcc   1140
aagctggtgg ccctgggcgt gaacgccgtg gcctactacc gcggcctgga cgtgagcgtg   1200
atccccacca gcggcgacgt ggtggtggtg gccaccgacg ccctgatgac cggcttcacc   1260
ggcgacttcg acagcgtgat cgactgcaac acctgcgtga cccagaccgt ggacttcagc   1320
ctggacccca ccttcaccat cgagaccatc accctgcccc aggacgccgt gagccgcacc   1380
cagcgccgcg gccgcaccgg ccgcggcaag cccggcatct accgcttcgt ggcccccggc   1440
gagcgcccca gcggcatgtt cgacagcagc gtgctgtgcg agtgctacga cgccggctgc   1500
gcctggtacg agctgacccc cgccgagacc accgtgcgcc tgcgcgccta catgaacacc   1560
cccggcctgc ccgtgtgcca ggaccacctg gagttctggg agggcgtgtt caccggcctg   1620
acccacatcg acgcccactt cctgagccag accaagcaga gcggcgagaa cctgccctac   1680
ctggtggcct accaggccac cgtgtgcgcc cgcgcccagg cccccccccc cagctgggac   1740
cagatgtgga agtgcctgat ccgcctgaag cccaccctgc acggccccac cccccctgctg   1800
taccgcctgg gcgccgtgca gaacgaggtg accctgaccc accccgtgac caagtacatc   1860
atgacctgca tgagcgccga cctggaggtg gtgaccagca cctgggtgct ggtgggcggc   1920
gtgctggccg ccctggccgc ctactgcctg agcaccggct gcgtggtgat cgtgggccgc   1980
atcgtgctga gcggcaagcc cgccatcatc cccgaccgcg aggtgctgta ccgcgagttc   2040
gacgagatgg aggagtgcag ccagcacctg ccctacatcg agcagggcac cctgcccgag   2100
accaccgtgg tgcgccgccg cggccgcagc ccccgccgcc gcacccccag cccccgccgc   2160
cgccgcagcc agagcccccg ccgccgccgc agccagagcc gcgagagcca gtgcagcgcc   2220
gacctggagg tggtgaccag cacctgggtg ctggtgggcg gcgtgctgta cgtgaacacc   2280
aacatgggcc tgaagttccg ccagctgctg tggttccaca tcagctgcct gaccttcggc   2340
cgcgagaccg tgatcgagta cctggtgagc ttcggcgtgt ggatccgcac cccccccgcc   2400
taccgccccc ccaacgcccc catcctgagc agcgccgacc tggaggtggt gaccagcacc   2460
tgggtgctgg tgggcggcgt gctgatggac atcgacccct acaaggagtt cggcgccacc   2520
gtggagctgc tgagcttcct gcccagcgac ttcttcccca gcgtgcgcga cctgctggac   2580
accgccagcg ccctgtaccg cgaggccctg gagagcagcg ccgacctgga ggtggtgacc   2640
```

```
agcacctggg tgctggtggg cggcgtgctg cccgagcact gcagccccca ccacaccgcc   2700

ctgcgccagg ccatcctgtg ctggggcgag ctgatgaccc tggccacctg ggtgggcgtg   2760

aacctggagg accccgccag ccgcgacctg gtggtgagct ag                       2802
```

<210> SEQ ID NO 24
<211> LENGTH: 933
<212> TYPE: PRT
<213> ORGANISM: Artificial Sequence
<220> FEATURE:
<223> OTHER INFORMATION: NS3/4A-4Bjunct-HBcAg142-183-NS3/4Ajunct-HBc88-
      141-NS3/4Ajunct-HBc1-44-NS3/4Ajunct-HBc45-87 (nucleotide sequence)

<400> SEQUENCE: 24

```
Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
                 20                  25                  30

Glu Val Gln Ile Val Ser Thr Ala Ala Gln Thr Phe Leu Ala Thr Cys
             35                  40                  45

Ile Asn Gly Val Cys Trp Thr Val Tyr His Gly Ala Gly Thr Arg Thr
         50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
```

```
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Tyr Val Asn Thr Asn Met Gly Leu
    690                 695                 700

Lys Phe Arg Gln Leu Leu Trp Phe His Ile Ser Cys Leu Thr Phe Gly
705                 710                 715                 720

Arg Glu Thr Val Ile Glu Tyr Leu Val Ser Phe Gly Val Trp Ile Arg
                725                 730                 735

Thr Pro Pro Ala Tyr Arg Pro Pro Asn Ala Pro Ile Leu Ser Ser Ala
            740                 745                 750
```

```
Asp Leu Glu Val Val Thr Ser Thr Trp Val Leu Val Gly Gly Val Leu
        755                 760                 765

Thr Leu Pro Glu Thr Thr Val Val Arg Arg Arg Gly Arg Ser Pro Arg
    770                 775                 780

Arg Arg Thr Pro Ser Pro Arg Arg Arg Arg Ser Gln Ser Pro Arg Arg
785                 790                 795                 800

Arg Arg Ser Gln Ser Arg Glu Ser Gln Cys Ser Ala Asp Leu Glu Val
            805                 810                 815

Val Thr Ser Thr Trp Val Leu Val Gly Gly Val Leu Met Asp Ile Asp
            820                 825                 830

Pro Tyr Lys Glu Phe Gly Ala Thr Val Glu Leu Leu Ser Phe Leu Pro
        835                 840                 845

Ser Asp Phe Phe Pro Ser Val Arg Asp Leu Leu Asp Thr Ala Ser Ala
    850                 855                 860

Leu Tyr Arg Glu Ala Leu Glu Ser Ser Ala Asp Leu Glu Val Val Thr
865                 870                 875                 880

Ser Thr Trp Val Leu Val Gly Gly Val Leu Pro Glu His Cys Ser Pro
            885                 890                 895

His His Thr Ala Leu Arg Gln Ala Ile Leu Cys Trp Gly Glu Leu Met
            900                 905                 910

Thr Leu Ala Thr Trp Val Gly Val Asn Leu Glu Asp Pro Ala Ser Arg
        915                 920                 925

Asp Leu Val Val Ser
    930
```

<210> SEQ ID NO 25
<211> LENGTH: 2802
<212> TYPE: DNA
<213> ORGANISM: Artificial Sequence
<220> FEATURE:
<223> OTHER INFORMATION: NS3/4A-4Bjunct-HBcAg88-141-NS3/4Ajunct-HBc142-183-NS3/4Ajunct-HBc1-44-NS3/4Ajunct-HBc45-87 (nucleotide sequence)

<400> SEQUENCE: 25

```
atggccccca tcaccgccta cgcccagcag acccgcggcc tgctgggctg catcatcacc     60

agcctgaccg gccgcgacaa gaaccaggtg gagggcgagg tgcagatcgt gagcaccgcc    120

gcccagacct tcctggccac ctgcatcaac ggcgtgtgct ggaccgtgta ccacggcgcc    180

ggcacccgca ccatcgccag ccccaagggc cccgtgatcc agatgtacac caacgtggac    240

caggacctgg tgggctggcc cgccccccag ggcgcccgca gcctgacccc ctgcacctgc    300

ggcagcagcg acctgtacct ggtgacccgc cacgccgacg tgatccccgt gcgccgccgc    360

ggcgacggcc gcggcagcct gctgagcccc cgccccatca gctacctgaa gggcagcagc    420

ggcggccccc tgctgtgccc cgccggccac gccgtgggca tcttccgcgc cgccgtgtgc    480

acccgcggcg tggccaaggc cgtggacttc atccccgtgg agagcctgga gaccaccatg    540

cgcagccccg tgttcagcga caacagcagc ccccccgccg tgccccagag ctaccaggtg    600

gcccacctgc acgcccccac cggcagcggc aagagcacca aggtgcccgc cgcctacgcc    660

gcccagggct acaaggtgct ggtgctgaac cccagcgtgg ccgccaccat gggcttcggc    720

gcctacatga gcaaggccca cggcatcgac cccaacatcc gcaccggcgt gcgcaccatc    780

accaccggca gccccatcac ctacagcacc tacggcaagt tcctggccga cggcggctgc    840

agcggcggcg cctacgacat catcatctgc gacgagtgcc acagcaccga cgccaccagc    900

atcctgggca tcggcaccgt gctggaccag gccgagaccg ccggcgcccg cctgaccgtg    960
```

```
ctggccaccg ccaccccccc cggcagcgtg accgtgcccc accccaacat cgaggaggtg   1020

gccctgagca ccaccggcga gatccccttc tacggcaagg ccatccccct ggaggccatc   1080

aagggcggcc gccacctgat cttctgccac agcaagaaga agtgcgacga gctggccgcc   1140

aagctggtgg ccctgggcgt gaacgccgtg gcctactacc gcggcctgga cgtgagcgtg   1200

atccccacca gcggcgacgt ggtggtggtg gccaccgacg ccctgatgac cggcttcacc   1260

ggcgacttcg acagcgtgat cgactgcaac acctgcgtga cccagaccgt ggacttcagc   1320

ctggacccca ccttcaccat cgagaccatc accctgcccc aggacgccgt gagccgcacc   1380

cagcgccgcg gccgcaccgg ccgcggcaag cccggcatct accgcttcgt ggcccccggc   1440

gagcgcccca gcggcatgtt cgacagcagc gtgctgtgcg agtgctacga cgccggctgc   1500

gcctggtacg agctgacccc cgccgagacc accgtgcgcc tgcgcgccta catgaacacc   1560

cccggcctgc ccgtgtgcca ggaccacctg gagttctggg agggcgtgtt caccggcctg   1620

acccacatcg acgcccactt cctgagccag accaagcaga gcggcgagaa cctgccctac   1680

ctggtggcct accaggccac cgtgtgcgcc cgcgcccagg cccccccccc cagctgggac   1740

cagatgtgga agtgcctgat ccgcctgaag cccaccctgc acggccccac cccccctgctg   1800

taccgcctgg gcgccgtgca gaacgaggtg accctgaccc accccgtgac caagtacatc   1860

atgacctgca tgagcgccga cctggaggtg gtgaccagca cctgggtgct ggtgggcggc   1920

gtgctggccg ccctggccgc ctactgcctg agcaccggct gcgtggtgat cgtgggccgc   1980

atcgtgctga gcggcaagcc cgccatcatc cccgaccgcg aggtgctgta ccgcgagttc   2040

gacgagatgg aggagtgcag ccagcacctg ccctacatcg agcagggcta cgtgaacacc   2100

aacatgggcc tgaagttccg ccagctgctg tggttccaca tcagctgcct gaccttcggc   2160

cgcgagaccg tgatcgagta cctggtgagc ttcggcgtgt ggatccgcac cccccccgcc   2220

taccgccccc ccaacgcccc catcctgagc agcgccgacc tggaggtggt gaccagcacc   2280

tgggtgctgg tgggcggcgt gctgaccctg cccgagacca ccgtggtgcg ccgccgcggc   2340

cgcagccccc gccgccgcac ccccagcccc cgccgccgcc gcagccagag cccccgccgc   2400

cgccgcagcc agagccgcga gagccagtgc agcgccgacc tggaggtggt gaccagcacc   2460

tgggtgctgg tgggcggcgt gctgatggac atcgacccct acaaggagtt cggcgccacc   2520

gtggagctgc tgagcttcct gcccagcgac ttcttcccca gcgtgcgcga cctgctggac   2580

accgccagcg ccctgtaccg cgaggccctg gagagcagcg ccgacctgga ggtggtgacc   2640

agcacctggg tgctggtggg cggcgtgctg cccgagcact gcagccccca ccacaccgcc   2700

ctgcgccagg ccatcctgtg ctggggcgag ctgatgaccc tggccacctg ggtgggcgtg   2760

aacctggagg accccgccag ccgcgacctg gtggtgagct ag                      2802
```

<210> SEQ ID NO 26
<211> LENGTH: 869
<212> TYPE: PRT
<213> ORGANISM: Artificial Sequence
<220> FEATURE:
<223> OTHER INFORMATION: NS3/4A HBcAg Fusion Protein

<400> SEQUENCE: 26

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30
```

```
Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
```

```
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Pro Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Ser Gln Ser
    850                 855                 860

Arg Glu Ser Gln Cys
865
```

<210> SEQ ID NO 27
<211> LENGTH: 869
<212> TYPE: PRT
<213> ORGANISM: Artificial Sequence
<220> FEATURE:
<223> OTHER INFORMATION: NS3/4A-HBcAg Fusion Protein

<400> SEQUENCE: 27

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr Ala Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Ala Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365
```

-continued

```
Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Ile Asp Pro Tyr Lys Glu Phe Gly Ala Thr Val Glu Leu Leu Ser Phe
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780
```

-continued

```
Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865


<210> SEQ ID NO 28
<211> LENGTH: 869
<212> TYPE: PRT
<213> ORGANISM: Artificial Sequence
<220> FEATURE:
<223> OTHER INFORMATION: NS3/4A-HBcAg Fusion Protein

<400> SEQUENCE: 28

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270
```

-continued

```
Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Met Asp
        675                 680                 685

Ile Asp Pro Tyr Lys Glu Phe Gly Ala Thr Val Glu Leu Leu Ser Phe
```

```
    690                 695                 700

Leu Pro Ser Asp Phe Phe Pro Ser Val Arg Asp Leu Leu Asp Thr Ala
705                 710                 715                 720

Ser Ala Leu Tyr Arg Glu Ala Leu Glu Ser Pro Glu His Cys Ser Pro
                725                 730                 735

His His Thr Ala Leu Arg Gln Ala Ile Leu Cys Trp Gly Glu Leu Met
            740                 745                 750

Thr Leu Ala Thr Trp Val Gly Val Asn Leu Glu Asp Pro Ala Ser Arg
        755                 760                 765

Asp Leu Val Val Ser Tyr Val Asn Thr Asn Met Gly Leu Lys Phe Arg
    770                 775                 780

Gln Leu Leu Trp Phe His Ile Ser Cys Leu Thr Phe Gly Arg Glu Thr
785                 790                 795                 800

Val Ile Glu Tyr Leu Val Ser Phe Gly Val Trp Ile Arg Thr Pro Pro
                805                 810                 815

Ala Tyr Arg Pro Pro Asn Ala Pro Ile Leu Ser Thr Leu Pro Glu Thr
            820                 825                 830

Thr Val Val Arg Arg Arg Gly Arg Ser Pro Arg Arg Arg Thr Pro Ser
        835                 840                 845

Pro Arg Arg Arg Arg Ser Gln Ser Pro Arg Arg Arg Arg Ser Gln Ser
    850                 855                 860

Arg Glu Ser Gln Cys
865
```

<210> SEQ ID NO 29
<211> LENGTH: 879
<212> TYPE: PRT
<213> ORGANISM: Artificial Sequence
<220> FEATURE:
<223> OTHER INFORMATION: NS3/4A-HBcAg Fusion Protein

<400> SEQUENCE: 29

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
```

```
        180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605
```

```
Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Ile Asp Pro Tyr Lys Glu
    690                 695                 700

Phe Gly Ala Thr Val Glu Leu Leu Ser Phe Leu Pro Ser Asp Phe Phe
705                 710                 715                 720

Pro Ser Val Arg Asp Leu Leu Asp Thr Ala Ser Ala Leu Tyr Arg Glu
                725                 730                 735

Ala Leu Glu Ser Pro Glu His Cys Ser Pro His His Thr Ala Leu Arg
            740                 745                 750

Gln Ala Ile Leu Cys Trp Gly Glu Leu Met Thr Leu Ala Thr Trp Val
        755                 760                 765

Gly Val Asn Leu Glu Asp Pro Ala Ser Arg Asp Leu Val Val Ser Tyr
    770                 775                 780

Val Asn Thr Asn Met Gly Leu Lys Phe Arg Gln Leu Leu Trp Phe His
785                 790                 795                 800

Ile Ser Cys Leu Thr Phe Gly Arg Glu Thr Val Ile Glu Tyr Leu Val
                805                 810                 815

Ser Phe Gly Val Trp Ile Arg Thr Pro Pro Ala Tyr Arg Pro Pro Asn
            820                 825                 830

Ala Pro Ile Leu Ser Thr Leu Pro Glu Thr Thr Val Val Arg Arg Arg
        835                 840                 845

Gly Arg Ser Pro Arg Arg Arg Thr Pro Ser Pro Arg Arg Arg Arg Ser
    850                 855                 860

Gln Ser Pro Arg Arg Arg Arg Ser Gln Ser Arg Glu Ser Gln Cys
865                 870                 875


<210> SEQ ID NO 30
<211> LENGTH: 933
<212> TYPE: PRT
<213> ORGANISM: Artificial Sequence
<220> FEATURE:
<223> OTHER INFORMATION: NS3/4A-HBcAg Fusion Protein

<400> SEQUENCE: 30

Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ala Arg Ser Leu Thr
                85                  90                  95
```

-continued

```
Pro Cys Thr Cys Gly Ser Ser Asp Leu Tyr Leu Val Thr Arg His Ala
            100                 105                 110

Asp Val Ile Pro Val Arg Arg Arg Gly Asp Gly Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser Pro Val Phe Ser Asp Asn Ser Ser Pro Pro
            180                 185                 190

Ala Val Pro Gln Ser Tyr Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Met Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300

Gly Thr Val Leu Asp Gln Ala Glu Thr Ala Gly Ala Arg Leu Thr Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
            340                 345                 350

Lys Ala Ile Pro Leu Glu Ala Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510
```

-continued

```
Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Met Asp Ile Asp Pro Tyr Lys Glu
    690                 695                 700

Phe Gly Ala Thr Val Glu Leu Leu Ser Phe Leu Pro Ser Asp Phe Phe
705                 710                 715                 720

Pro Ser Val Arg Asp Leu Leu Asp Thr Ala Ser Ala Leu Tyr Arg Glu
                725                 730                 735

Ala Leu Glu Ser Ser Ala Asp Leu Glu Val Val Thr Ser Thr Trp Val
            740                 745                 750

Leu Val Gly Gly Val Leu Pro Glu His Cys Ser Pro His His Thr Ala
        755                 760                 765

Leu Arg Gln Ala Ile Leu Cys Trp Gly Glu Leu Met Thr Leu Ala Thr
    770                 775                 780

Trp Val Gly Val Asn Leu Glu Asp Pro Ala Ser Arg Asp Leu Val Val
785                 790                 795                 800

Ser Ser Ala Asp Leu Glu Val Val Thr Ser Thr Trp Val Leu Val Gly
                805                 810                 815

Gly Val Leu Tyr Val Asn Thr Asn Met Gly Leu Lys Phe Arg Gln Leu
            820                 825                 830

Leu Trp Phe His Ile Ser Cys Leu Thr Phe Gly Arg Glu Thr Val Ile
        835                 840                 845

Glu Tyr Leu Val Ser Phe Gly Val Trp Ile Arg Thr Pro Pro Ala Tyr
    850                 855                 860

Arg Pro Pro Asn Ala Pro Ile Leu Ser Ser Ala Asp Leu Glu Val Val
865                 870                 875                 880

Thr Ser Thr Trp Val Leu Val Gly Gly Val Leu Thr Leu Pro Glu Thr
                885                 890                 895

Thr Val Val Arg Arg Arg Gly Arg Ser Pro Arg Arg Arg Thr Pro Ser
            900                 905                 910

Pro Arg Arg Arg Arg Ser Gln Ser Pro Arg Arg Arg Arg Ser Gln Ser
        915                 920                 925

Arg Glu Ser Gln Cys
```

930

<210> SEQ ID NO 31
<211> LENGTH: 933
<212> TYPE: PRT
<213> ORGANISM: Artificial Sequence
<220> FEATURE:
<223> OTHER INFORMATION: NS3/4A-HBcAg Fusion Protein

<400> SEQUENCE: 31

Met Ala Pro Ile Thr Ala Tyr Ala Gln Gln Thr Arg Gly Leu Leu Gly
1 5 10 15

Cys Ile Ile Thr Ser Leu Thr Gly Arg Asp Lys Asn Gln Val Glu Gly
20 25 30

Glu Val Gln Ile Val Ser Thr Ala Ala Gln Thr Phe Leu Ala Thr Cys
35 40 45

Ile Asn Gly Val Cys Trp Thr Val Tyr His Gly Ala Gly Thr Arg Thr
50 55 60

Ile Ala Ser Pro Lys Gly Pro Val Ile Gln Met Tyr Thr Asn Val Asp
65 70 75 80

Gln Asp Leu Val Gly Trp Pro Ala Pro Gln Gly Ala Arg Ser Leu Thr
85 90 95

Pro Cys Thr Cys Gly Ser Ser Asp Leu Tyr Leu Val Thr Arg His Ala
100 105 110

Asp Val Ile Pro Val Arg Arg Arg Gly Asp Gly Arg Gly Ser Leu Leu
115 120 125

Ser Pro Arg Pro Ile Ser Tyr Leu Lys Gly Ser Ser Gly Gly Pro Leu
130 135 140

Leu Cys Pro Ala Gly His Ala Val Gly Ile Phe Arg Ala Ala Val Cys
145 150 155 160

Thr Arg Gly Val Ala Lys Ala Val Asp Phe Ile Pro Val Glu Ser Leu
165 170 175

Glu Thr Thr Met Arg Ser Pro Val Phe Ser Asp Asn Ser Ser Pro Pro
180 185 190

Ala Val Pro Gln Ser Tyr Gln Val Ala His Leu His Ala Pro Thr Gly
195 200 205

Ser Gly Lys Ser Thr Lys Val Pro Ala Ala Tyr Ala Ala Gln Gly Tyr
210 215 220

Lys Val Leu Val Leu Asn Pro Ser Val Ala Ala Thr Met Gly Phe Gly
225 230 235 240

Ala Tyr Met Ser Lys Ala His Gly Ile Asp Pro Asn Ile Arg Thr Gly
245 250 255

Val Arg Thr Ile Thr Thr Gly Ser Pro Ile Thr Tyr Ser Thr Tyr Gly
260 265 270

Lys Phe Leu Ala Asp Gly Gly Cys Ser Gly Gly Ala Tyr Asp Ile Ile
275 280 285

Ile Cys Asp Glu Cys His Ser Thr Asp Ala Thr Ser Ile Leu Gly Ile
290 295 300

Gly Thr Val Leu Asp Gln Ala Glu Thr Ala Gly Ala Arg Leu Thr Val
305 310 315 320

Leu Ala Thr Ala Thr Pro Pro Gly Ser Val Thr Val Pro His Pro Asn
325 330 335

Ile Glu Glu Val Ala Leu Ser Thr Thr Gly Glu Ile Pro Phe Tyr Gly
340 345 350

Lys Ala Ile Pro Leu Glu Ala Ile Lys Gly Gly Arg His Leu Ile Phe

```
        355                 360                 365

Cys His Ser Lys Lys Lys Cys Asp Glu Leu Ala Ala Lys Leu Val Ala
    370                 375                 380

Leu Gly Val Asn Ala Val Ala Tyr Tyr Arg Gly Leu Asp Val Ser Val
385                 390                 395                 400

Ile Pro Thr Ser Gly Asp Val Val Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Thr Val
            500                 505                 510

Arg Leu Arg Ala Tyr Met Asn Thr Pro Gly Leu Pro Val Cys Gln Asp
        515                 520                 525

His Leu Glu Phe Trp Glu Gly Val Phe Thr Gly Leu Thr His Ile Asp
    530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Ile Val Leu Ser Gly Lys Pro Ala Ile Ile Pro Asp
            660                 665                 670

Arg Glu Val Leu Tyr Arg Glu Phe Asp Glu Met Glu Glu Cys Ser Gln
        675                 680                 685

His Leu Pro Tyr Ile Glu Gln Gly Thr Leu Pro Glu Thr Thr Val Val
    690                 695                 700

Arg Arg Arg Gly Arg Ser Pro Arg Arg Arg Thr Pro Ser Pro Arg Arg
705                 710                 715                 720

Arg Arg Ser Gln Ser Pro Arg Arg Arg Arg Ser Gln Ser Arg Glu Ser
                725                 730                 735

Gln Cys Ser Ala Asp Leu Glu Val Val Thr Ser Thr Trp Val Leu Val
            740                 745                 750

Gly Gly Val Leu Pro Glu His Cys Ser Pro His His Thr Ala Leu Arg
        755                 760                 765

Gln Ala Ile Leu Cys Trp Gly Glu Leu Met Thr Leu Ala Thr Trp Val
    770                 775                 780
```

-continued

```
Gly Val Asn Leu Glu Asp Pro Ala Ser Arg Asp Leu Val Val Ser Ser
785                 790                 795                 800

Ala Asp Leu Glu Val Val Thr Ser Thr Trp Val Leu Val Gly Gly Val
                805                 810                 815

Leu Tyr Val Asn Thr Asn Met Gly Leu Lys Phe Arg Gln Leu Leu Trp
            820                 825                 830

Phe His Ile Ser Cys Leu Thr Phe Gly Arg Glu Thr Val Ile Glu Tyr
        835                 840                 845

Leu Val Ser Phe Gly Val Trp Ile Arg Thr Pro Pro Ala Tyr Arg Pro
    850                 855                 860

Pro Asn Ala Pro Ile Leu Ser Ser Ala Asp Leu Glu Val Val Thr Ser
865                 870                 875                 880

Thr Trp Val Leu Val Gly Gly Val Leu Met Asp Ile Asp Pro Tyr Lys
                885                 890                 895

Glu Phe Gly Ala Thr Val Glu Leu Leu Ser Phe Leu Pro Ser Asp Phe
            900                 905                 910

Phe Pro Ser Val Arg Asp Leu Leu Asp Thr Ala Ser Ala Leu Tyr Arg
        915                 920                 925

Glu Ala Leu Glu Ser
```

<210> SEQ ID NO 32
<211> LENGTH: 569
<212> TYPE: DNA
<213> ORGANISM: Artificial Sequence
<220> FEATURE:
<223> OTHER INFORMATION: Codon Optimized HBcAg

<400> SEQUENCE: 32

```
gaattcgcac catggacatc gacccctaca aggagttcgg cgccaccgtg gagctgctga     60

gcttcctgcc cagcgacttc ttccccagcg tgagagacct gctggacacc gccagcgccc    120

tgtacagaga ggccctggag agccccgagc actgcagccc ccaccacacc gccctgagac    180

aggccatcct gtgctggggc gagctgatga ccctggccac ctgggtgggc gtgaacctgg    240

aggaccccgc cagcagagac ctggtggtga gctacgtgaa caccaacatg ggcctgaagt    300

tcagacagct gctgtggttc cacatcagct gcctgacctt cggcagagag accgtgatcg    360

agtacctggt gagcttcggc gtgtggatca gaaccccccc cgcctacaga ccccccaacg    420

cccccatcct gagcaccctg cccgagacca ccgtggtgag aagaagaggc agaagcccca    480

gaagaagaac ccccagcccc agaagaagaa gaagccagag ccccagaaga agaagaagcc    540

agagcagaga gagccagtgc tagtctaga                                      569
```

<210> SEQ ID NO 33
<211> LENGTH: 20
<212> TYPE: DNA
<213> ORGANISM: Artificial Sequence
<220> FEATURE:
<223> OTHER INFORMATION: A CpG containing Oligonucleotide

<400> SEQUENCE: 33

```
tccatgacgt tcctgacgtt                                                 20
```

INJECTION NEEDLE AND DEVICE

CROSS REFERENCE TO RELATED APPLICATIONS

Any and all applications for which a foreign or domestic priority claim is identified in the Application Data Sheet as filed with the present application are hereby incorporated by reference under 37 CFR 1.57. This application is a U.S. National Phase Application of PCT International Application Number PCT/IB2012/001321, filed on Jun. 13, 2012, designating the United States of America and published in the English language, which is an International Application of and claims the benefit of priority U.S. Provisional Applications 61/642,356, filed May 3, 2012; 61/597,112, filed Feb. 9, 2012; 61/587,066, filed Jan. 16, 2012; 61/500,066, filed Jun. 22, 2011; and 61/497,442, filed Jun. 15, 2011. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SequenceListingTRIPEP125.TXT, created Jun. 6, 2012, which is 146 KB in size. The information in the electronic format of the Sequence Listing is incorporated herein by reference in its entirety.

FIELD OF THE INVENTION

Aspects of the embodiments disclosed herein relate generally to devices and methods for the delivery and uptake of therapeutic material (e.g., chemicals, compounds, proteins and nucleic acids) by tissue of a subject (e.g. a human). Preferred embodiments concern devices and methods for the delivery of genetic material or nucleic acids including, but not limited to, DNA, RNA, and modified nucleic acids into a plurality of cells, preferably animal cells, such as human cells.

BACKGROUND OF THE INVENTION

The delivery of therapeutic material, such as genetic material, into tissue has a wide range of useful applications including vaccination, replacement of a defective gene, DNA immunization, introduction of an immunogen, antisense therapy, and miRNA, RNAi, aptamer, or siRNA therapy. For instance, nucleic acids, such as DNA, for example, can be injected into tissue, wherein the nucleic acids are taken up by the surrounding cells albeit inefficiently. DNA introduced in this manner will produce the protein that the DNA encodes. The successful delivery of nucleic acids into tissue and the uptake of the nucleic acids by the cells is difficult, especially when significant amounts of protein expression are desired (e.g., as is desired for DNA-based vaccination). Conventional injection of genetic material into tissue generally results in poor uptake by the cells and low levels of protein expression, if any at all.

Gene therapy is an important tool in the future for treatment of human and animal disease. Some clinical progress has been made in recent years with one example of a patient with partial restoration of vision following gene therapy (Bainbridge New Engl J Med. 2008 358(21):2231). A major area for clinical application of gene therapy is genetic vaccination for infectious diseases. However, a major limitation to make gene therapy a reality is the difficulty to reproducibly deliver the genetic material. Genes can be delivered either by viral vectors or in the form of plasmid DNA. Viral vectors have limitations in that they generate anti-vector responses that limit their repeated use, and they are expensive to produce and to store. DNA has the advantage that it does not induce anti-vector responses and is relatively cheap to produce and to store. However, the major problem with DNA is the poor uptake into human cells in vivo. Thus, new robust and tolerable ways for DNA delivery to human cells in vivo can accelerate the whole field of gene therapy.

Intravascular administration approaches have also been developed to deliver therapeutic agents to animals (see e.g., U.S. Pat. Nos. 6,379,966; 6,897,068; 7,015,040; 7,214,369; 7,473,419; and 7,589,059, all of which are hereby expressly incorporated by reference in their entireties). Intravascular administration can be very difficult to implement in practice; however, requiring skilled clinicians and, if performed incorrectly, the procedure can lead to punctured blood vessels, hematomas, and the development of internal blood clots, which could lead to an embolism. Furthermore, the intravascular administration approach can produce a wide dispersion of the introduced therapeutic agent (e.g., nucleic acid and protein), which is undesirable when trying to encourage the body to mount an immune response to the delivered agent. Accordingly, there remains a need for devices and methods that facilitate the delivery and uptake of therapeutic molecules such as nucleic acids and proteins.

SUMMARY OF THE INVENTION

Disclosed herein are devices and methods that deliver a prophylactic and/or therapeutic agent (e.g. a chemical, a compound, a chemotherapeutic agent, a protein, a specificity exchanger, a nucleic acid, such as DNA, RNA, other natural nucleic acid, a modified nucleic acid, or a DNA or nucleic acid aptamer) into tissue of an animal (e.g., a human), whereby said agent (a "delivered agent") can be taken up by cells in the tissue surrounding the injection site and, the agent is expressed so as to provide a therapeutic or cosmetic benefit. As used herein, the term "delivered agent" may refer a prophylactic and/or therapeutic agent including any of those listed above, both prior to injection or delivery to a tissue or subject or after delivery to a tissue or subject.

In some embodiments, one or more of the needles and/or devices described herein are used to administer cell populations (e.g., regenerative cells, stem cells, progenitor cells, or a mixture thereof) to effectuate therapeutic and/or cosmetic benefit. In these embodiments, the cells are introduced into tissue (e.g., fatty tissue of the breast, heart, kidney, bone, skin, fat tissue, intervertebral discs) of a subject in need thereof to promote therapeutic or cosmetic benefit (e.g., to facilitate or effectuate breast reconstruction, ameliorate an ischemic region, repair degenerative discs, promote bone repair, promote wound healing, or to ameliorate wrinkles or pock marks on the skin).

Several embodiments disclosed herein include intracellular delivery devices that can be used with living animals, including humans. Some of the intracellular delivery devices operate by overloading a tissue of the animal locally (e.g., within an area defined by a needle array of the device) with the delivered agent and providing an electrical field to this area or injection region so as to promote greater delivery and/or uptake of the delivered agent. Some embodiments, for example, comprise: an intracellular delivery apparatus that comprises a delivery unit, which controls an injection parameter, a hub connected to the delivery unit comprising at least one electrical connector; a plurality of needles connected to the hub, wherein each needle of the plurality of needles comprises: a closed end; a needle barrel; a plurality of apertures that are disposed on the needle barrel, wherein the apertures on each needle barrel oppose the apertures on at least one other needle barrel so as to generate an opposing direction of delivery of a delivered agent or a cross-spray pattern of delivery of a delivered agent; an electrode; and an electrical power supply configured to generate an electric field at the electrode, wherein the electrical power supply is connected to the electrode through the at least one electrical connector.

In some embodiments, at least one needle of the plurality of needles of the intracellular delivery apparatus is a needle-electrode, which is electrically connected to the electrical power supply and is configured to generate an electric field.

In some embodiments, the intracellular delivery apparatus comprises a plurality of needle-electrodes, which are electrically connected to the electrical power supply, and configured to generate an electric field.

In some embodiments the intracellular delivery apparatus comprises four needles arranged in a Y-type pattern with a center needle and three outer needles disposed around the center needle, wherein the center needle is a needle-electrode configured to apply a first polarity voltage, and the three outer needles are needle-electrodes, configured to apply a second polarity voltage.

In some embodiments of the intracellular delivery apparatus, the center needle comprises apertures along the needle barrel, which are positioned to direct delivery of a delivered agent toward apertures that are present on each of the three outer needles and each of the three outer needles comprises apertures along the needle barrel, which are positioned to direct delivery of a delivered agent toward apertures that are present on the center needle, and wherein the outer needles do not have apertures positioned to deliver a delivered agent away from the center needle.

In some embodiments, the intracellular delivery apparatus comprises an array of needles comprising a center needle and a plurality of outer needles disposed around the center needle, wherein the center needle is a needle-electrode configured to apply a first polarity voltage, and the outer needles are needle-electrodes, configured to apply a second polarity voltage, wherein the center needle comprises apertures along the needle barrel, which are positioned to direct delivery of a delivered agent toward the outer needles and the outer needles comprise apertures along the needle barrel, which are positioned to direct delivery of a delivered agent toward the center needle and/or an adjacent needle, and wherein the outer needles do not have apertures that allow delivery of a delivered agent away from an active zone defined by an area within the array of needles.

In some embodiments, the intracellular delivery apparatus further comprises seven needles that are arranged in a hexagonal pattern, wherein one needle, which is a needle-electrode, located at the center of the hexagonal pattern.

Some embodiments disclosed herein describe an intracellular delivery apparatus as described above comprising a syringe in fluid communication with the hub; a channel configured to receive the syringe; a collar operable to fasten the syringe within the channel; a handle, which operates to enclose the syringe and hub within the channel such that the closed ends of the needle barrels protrude from the channel and are available to engage a subject; a charging element configured to be charged by the operation of the handle, the charging element coupled to a trigger and the syringe such that operation of the trigger releases the charging element and the charging element acts on the syringe, thereby displacing prophylactic and/or therapeutic material out of the syringe; and an electrical port configured to mate with the electrical connector on the hub of the hypodermic needle device thereby establishing electrical contact between the electrical power supply and the electrodes and/or needle-electrodes.

In some embodiments, the hub is a pocket hub, comprising an individual reservoir of a delivered agent for each needle or needle-electrode.

In some embodiments, the hub comprises a single reservoir of a delivered agent for each needle or needle-electrode.

In some embodiments, at least one needle of the plurality of needles is at least partially laminated with an electrically non-conductive material.

In some embodiments, the intracellular delivery apparatus further comprises an electrical power supply controller configured to control generation of the electric field.

In some embodiments, controlling generation of the electric field comprises controlling one or more of the pulse voltage, polarity of the needle-electrodes, the number of pulses, the pulse pattern, or the pulse duration.

In some embodiments, the charging element is a spring configured to be compressed by the operation of the handle and configured to decompress upon operation of the trigger.

In some embodiments, the electric field applied at the electrode and/or needle electrodes is commutating.

Additional embodiments disclosed herein include methods of introducing a delivered agent into a tissue of a subject comprising: providing the intracellular delivery apparatus as described herein; providing a voltage source; inserting a plurality of needles and a plurality of electrodes or a plurality of needle-electrodes of said electroporation apparatus into a tissue of a subject; displacing the delivered agent through the lumen of the plurality of needles or the plurality of needle electrodes and into the tissue of the subject; and applying an electric field to the tissue of the subject.

In some embodiments, the displacing of the delivered agent is performed prior to applying the electric field to the tissue.

In some embodiments, the displacing of the delivered agent is performed subsequent to applying the electric field to the tissue.

In some embodiments, the displacing of the delivered agent is performed in a two stage process, wherein the first stage comprises displacing the delivered agent into the tissue into an active area and the second stage comprises energizing one or more electrodes or needle electrodes to electroporate the cells within the active area.

In some embodiments, the injection parameter is injection speed or injection pressure.

In some embodiments the electroporation apparatus described herein is for use in DNA vaccination.

In some embodiments the DNA vaccination comprises introduction of a polynucleotide encoding a hepatitis antigen.

In some embodiments the hepatitis antigen is a hepatitis C virus (HCV) antigen.

In some embodiments the HCV antigen comprises NS3.

BRIEF DESCRIPTION OF THE DRAWINGS

FIGS. 56A1-B2 are example results of injection using a regular needle and injection using an intracellular delivery apparatus described herein coupled with electroporation.

FIGS. 57A1-C2 are example results of injection using an intracellular delivery apparatus described herein at two injection force values coupled with electroporation compared to a conventional needle with electroporation.

DETAILED DESCRIPTION

Figure 1A:
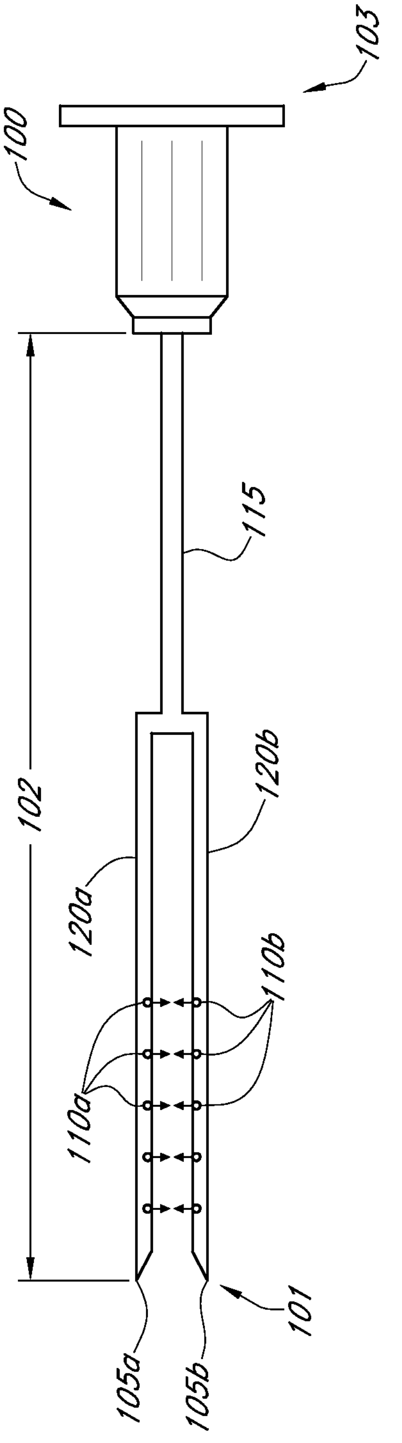
FIG. 1A illustrates a side view of an embodiment of an intracellular delivery apparatus having two barrels, each barrel having five apertures for delivering a prophylactic and/or therapeutic agent to an area in between the barrels.

Aspects of this invention described herein concern devices and methods for the delivery of agents (e.g., nucleic acids) into a tissue. Some embodiments concern an intracellular delivery apparatus configured to introduce agents, such as nucleic acids, especially DNA, into a target tissue, wherein the molecules are taken up by the cells in a region localized to a site near or proximal to the site of injection (e.g., within a region defined by the area within a needle array of an intracellular delivery apparatus described herein).

The needle(s) of an intracellular delivery apparatus may comprise a fitting connector or a needle hub, which may comprise a sleeve with an internal thread. The fitting connector or needle hub is configured to attach the needle to the syringe or vessel containing the agent to be introduced. In some embodiments, the sleeve forms the attachment means and can be screwed onto an outer thread on an attachment part of a syringe. The fitting connectors or needle hubs can also comprise a press-on assembly, a snap-on assembly, or a Luer Taper connection, such as a Luer Lok or Luer Slip connection or a butterfly connector.

The needle(s) of an intracellular delivery apparatus described herein may be attached to one or more syringe barrels (e.g., permanently affixed or removably attached) and said syringe barrels or the device may contain the prophylactic and/or therapeutic agent that is to be delivered. For example, in some embodiments, the needle(s) and attached syringe may be pre-loaded with a prophylactic and/or therapeutic agent, such as a nucleic acid, protein, modified nucleic acid, aptamer, or cell population for a single-use application. In some embodiments, the agent may be drawn into the syringe through apertures disposed on the needles(s). The syringe barrels can be of a variety of sizes (e.g., 0.3 cc-100 cc or more). That is, the syringe barrels can be greater than or equal to or any number in between 0.1, 0.3, 0.4, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cc size. The syringe barrels can be constructed from a variety of materials (e.g., metal, plastic, nylon, polyethylene, glass).

The needle(s) of an intracellular delivery apparatus described herein may be attached to one or more devices that facilitate delivery of prophylactic and/or therapeutic molecules or agents to tissue, including but not limited to gene guns, electroporation systems, and microneedle devices. The injection needle(s) described herein can be modified for use with existing technologies, including gene gun delivery systems (see e.g., U.S. Pat. Nos. 5,036,006; 5,240,855; and 5,702,384, the disclosures of which are hereby expressly incorporated by reference in their entireties), delivery systems using electroporation (see e.g., U.S. Pat. Nos. 6,610,044 and 5,273,525, 6,132,419, and 6,527,216, the disclosures of which are hereby expressly incorporated by reference in their entireties) and microneedle delivery systems (see e.g., U.S. Pat. Nos. 6,960,193; 6,623,457; 6,334,856; 5,457,041; 5,527,288; 5,697,901; 6,440,096; 6,743,211; and 7,226,439, the disclosures of which are hereby expressly incorporated by reference in their entireties).

As described herein, the intracellular delivery devices comprising the needle(s) may also contain a variety of prophylactic and/or therapeutic agents (e.g. a cell population, such as a cell population comprising stem cells, a chemical, a compound, a chemotherapeutic agent, a protein, a specificity exchanger, a nucleic acid such as DNA, RNA, other natural nucleic acid, a modified nucleic acid, or a DNA or nucleic acid aptamer). In some embodiments, the intracellular delivery devices comprising one or more of the needle(s) described herein comprise a DNA that encodes an immunogen (preferably a viral antigen, such as hepatitis C virus (HCV), hepatitis B virus (HBV), human immunodeficiency virus (HIV), influenza, Japanese encephalitis virus (JEV), human papilloma virus (HPV), or a parasite antigen, such as a malaria antigen, or a plant antigen, such as birch antigen, or a bacterial antigen, such as a staphylococcal or anthrax antigen, or a tumor antigen). In some embodiments, the intracellular delivery devices comprising one or more of the needles described herein comprise one or more of the aforementioned DNAs pre-loaded (e.g., a pre-loaded, single use syringe with coupled needle(s) containing a measured dose of delivered agent).

In some embodiments, the prophylactic and/or therapeutic agent that is delivered or contained in a syringe, needle, or injection device, as described herein, comprises a natural nucleic acid and in other embodiments, the prophylactic and/or therapeutic agent that is delivered or contained in a syringe, needle, or an intracellular delivery device, as described herein, comprises an unnatural nucleic acid (e.g., containing an artificial nucleotide, universal base, or spacer). Natural nucleic acids that can be used as the therapeutic agent that is delivered or contained in a syringe or injection device, as described herein, comprise a deoxyribose- or ribose-phosphate backbone. An artificial or synthetic polynucleotide that can be used as the prophylactic and/or therapeutic agent that is delivered or contained in a syringe, needle, or intracellular delivery device, as described herein, can comprise any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases that may be included in one or more embodiments described herein include purines and pyrimidines, which further include the natural compounds adenine, thymine, guanine, cytosine, uracil, inosine, and natural analogs. Synthetic derivatives of purines and pyrimidines that may be included in one or more embodiments described herein include, but are not limited to, modifications which place new reactive groups such as, but not limited to, amines, alcohols, thiols, carboxylates, and alkylhalides.

The term "base," as used herein, encompasses any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The term polynucleotide includes deoxyribonucleic acid (DNA) and ribonucleic acid (RNA) and combinations on DNA, RNA and other natural and synthetic nucleotides.

The prophylactic and/or therapeutic agent that is delivered or contained in a syringe, needle, or an intracellular delivery device, as described herein, can comprise DNA, which may be in the form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), miRNA (micro RNA), ribozymes, or derivatives of these groups. The prophylactic and/or therapeutic agent that is delivered or contained in a syringe, needle, or an intracellular delivery device, as described herein, can also comprise an anti-sense polynucleotide that is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15 to 50 base pairs and preferably 21 to 25 base pairs and having a nucleotide sequence identical or nearly identical to an expressed target gene or RNA within the cell. Interference may result in suppression of expression. The polynucleotide can be a sequence whose presence or expression in a cell alters the expression or function of cellular genes or RNA. In addition, DNA and RNA may be single, double, triple, or quadruple stranded. Double, triple, and quadruple stranded polynucleotide may contain both RNA and DNA or other combinations of natural and/or synthetic nucleic acids. These polynucleotides can be delivered to a cell to express an exogenous nucleotide sequence, to inhibit, eliminate, augment, or alter expression of an endogenous nucleotide sequence, or to express a specific physiological characteristic not naturally associated with the cell. Polynucleotides may be coded to express a whole or partial protein, or may be anti-sense. The delivered polynucleotide can stay within the cytoplasm or nucleus apart from the endogenous genetic material. Alternatively, the polymer could recombine with or become a part of the endogenous genetic material. For example, the therapeutic agent that is delivered or contained in a syringe or an intracellular delivery device, as described herein, can comprise a DNA that can insert itself into chromosomal DNA by either homologous or non-homologous recombination.

The prophylactic and/or therapeutic agent that is delivered or contained in a syringe, needle, or an intracellular delivery device, as described herein, can also comprise an RNA inhibitor, which is any nucleic acid or nucleic acid analog containing a sequence whose presence or expression in a cell causes the degradation of or inhibits the function or translation of a specific cellular RNA, usually a mRNA, in a sequence-specific manner. An RNA inhibitor may also inhibit the transcription of a gene into RNA. Inhibition of RNA can effectively inhibit expression of a gene from which the RNA is transcribed. RNA inhibitors include, but are not limited to, siRNA, microRNAs (miRNAs), interfering RNA or RNAi, dsRNA, RNA Polymerase III transcribed DNAs, ribozymes, and antisense nucleic acid, which may be RNA, DNA, or an artificial nucleic acid. MicroRNAs (miRNAs) also typically have a length of between about 15-50 nucleotides, preferably between about 20-25 nucleotides in length, and miRNAs can be used as post-transcriptional regulators that bind to complementary sequences on target messenger RNA transcripts (mRNAs), usually resulting in translational repression and gene silencing. Antisense polynucleotides can include, but are not limited to: morpholinos, 2'-O-methyl polynucleotides, DNA, RNA and the like. RNA polymerase III transcribed DNAs can contain promoters, such as the U6 promoter. These DNAs can be transcribed to produce small hairpin RNAs in the cell that can function as siRNA or linear RNAs that can function as antisense RNA. The RNA inhibitor may be polymerized in vitro, recombinant RNA, contain chimeric sequences, or derivatives of these groups. The RNA inhibitor may contain ribonucleotides, deoxyribonucleotides, synthetic nucleotides, or any suitable combination such that the target RNA and/or gene are inhibited. In addition, these forms of nucleic acid may be single, double, triple, or quadruple stranded.

The prophylactic and/or therapeutic agent that is delivered or contained in a syringe, needle, or an intracellular delivery device, as described herein, can also include a nucleic acid that is incorporated into a vector (e.g., an expression vector). Vectors are polynucleic molecules originating from a virus, a plasmid, or the cell of a higher organism into which another nucleic fragment of appropriate size can be integrated; vectors typically introduce foreign DNA into host cells, where it can be reproduced. Examples are plasmids, cosmids, and yeast artificial chromosomes; vectors are often recombinant molecules containing DNA sequences from several sources.

As used herein, term "vector" refers any DNA molecule that could include associate molecules to transfer DNA sequences into a cell for expression. Examples include naked DNA, non-viral DNA complexes (e.g. DNA plus polymers [cationic or anionic], DNA plus transfection enhancing compounds, and DNA plus amphipathic compounds) and viral particles. As used herein, vector may also include a viral vector: for example, adenovirus; DNA; adenoassociated viral vectors (AAV) which are derived from adenoassociated viruses and are smaller than adenoviruses; and retrovirus (any virus in the family Retroviridae that has RNA as its nucleic acid and uses the enzyme reverse transcriptase to copy its genome into the DNA of the host cell's chromosome; examples include VSV G and retroviruses that contain components of lentivirus including HIV type viruses).

The prophylactic and/or therapeutic agent that is delivered or contained in a syringe, needle, or an intracellular delivery device, as described herein, can also comprise one or more compounds that enhance the uptake of the therapeutic agent (e.g., a nucleic acid, as described herein). The therapeutic agent that is delivered or contained in a syringe, needle, or an intracellular delivery device, as described herein, can comprise a polymer, for example, which is a molecule built up by repetitive bonding together of smaller units called monomers. The term "polymer" can include both oligomers, which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

The prophylactic and/or therapeutic agent that is delivered or contained in a syringe, needle, or an intracellular delivery devices, as described herein, may also comprise a nucleic acid-polycation complex. Cationic proteins like histones and protamines or synthetic polymers like polylysine, polyarginine, polyornithine, DEAE dextran, polybrene, and polyethylenimine are effective intracellular delivery agents. A polycation is a polymer containing a net positive charge, for example poly-L-lysine hydrobromide. The polycation can contain monomer units that are charge positive, charge neutral, or charge negative, however, the net charge of the polymer is desirably positive. The term "polycation" also can refer to a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. The term "polyanion" can also refer to a non-polymeric molecule that contains two or more negative charges. The term "polyion" includes polycation, polyanion, zwitterionic polymers, and neutral polymers that contain equal amounts of anions and cations. The term "zwitterionic" refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations.

The prophylactic and/or therapeutic agent that is delivered or contained in a syringe, needle, or an intracellular delivery device, as described herein, may also comprise a specificity exchanger. Several types of specificity exchangers are known and any one or more of these molecules can be delivered or contained in a syringe, needle, or injection device, as described herein. For example, U.S. Pat. Nos. 7,318,926; 7,019,111; 6,933,366; 6,660,842; 6,469,143; 6,245,895; 6,040,137; 5,869,232; 7,943,149; 6,417,324 describe specificity exchangers, the disclosure of which are expressly incorporated by reference in their entireties. Preferably, specificity exchangers that comprise a ligand for a receptor on a pathogen joined to an oligosaccharide (e.g., the gal epitope or Galα1-3Gal-β1-4GlcNAc-R (preferably synthetically assembled specificity exchangers or glycoconjugates are used, for example, specificity exchangers or glycoconjugates prepared by solid phase peptide synthesis).

Some embodiments relate to an intracellular delivery device that comprises a plurality of needles, which are arranged or configured to deliver a therapeutic agent to a targeted tissue. In some embodiments, the agent is delivered through the proximal end of the injection device by a syringe and the agent is delivered to the targeted tissue through a plurality of apertures disposed on or near the distal ends of the plurality of needle barrels. In other embodiments, the end of the apertures can be disposed on the proximal ends of the needles barrels. In some embodiments, a plurality of needles of any one or more of the design features described herein are provided on an injection device. Embodiments described herein also include a cannula that comprises a plurality of needles configured as described above. That is, in some embodiments the intracellular delivery device and/or cannula can comprise, consist, or consist essentially of 1, 2, 3, 4, 5, 6, 7, 8, 9, or 10 or more needles. The needles can be of the same size and length or can be of different sizes and lengths. Each needle in embodiments that have more than one needle can have a plurality of apertures, which can be in a first or second zone, as described above, or both (e.g., along the length of the band). Preferably, the needles of the intracellular delivery devices have a closed end, as described above. Intracellular delivery devices and/or cannulas that comprise, consist, or consist essentially of 2, 3, 4, 5, 6, 7, 8, 9, or 10 needles can be configured such that at least two needles have a different amount of apertures and/or different sizes of apertures and/or different shapes of apertures and/or different positions of apertures and said needles preferably have a closed end. Preferably, the needles and apertures are oriented such that the apertures on each needle oppose the apertures on another needle so as to generate an opposing field of delivery of a delivered agent or a cross-spray pattern of delivery of a delivered agent (e.g., in a four needle array having a central needle and three outer needles, the outer needles can have apertures that direct delivered agent toward apertures present on the central needle and the central needle has apertures in three zones, wherein each zone opposes apertures present on the outer needles and delivered agent exiting the central needle is directed to apertures present on each of the outer needles). In some embodiments of an intracellular delivery device, such needle arrays are connected to or disposed on a hub that comprises at least one electrical connector. Again, preferably, the apertures on each needle in the array oppose the apertures on another needle so as to generate a cross-spray pattern or a region of opposing delivery of a delivered agent. In this way, a region within the needle array is overloaded locally with the delivered agent, thereby providing a high concentration of the delivered agent within the region, which is particularly useful when an electric field is applied thereby inducing uptake of the delivered agent. The injection devices, hypodermic needle assemblies, or intracellular delivery devices also preferably include an electrode (in some embodiments, one or more of the needles themselves are electrodes) and an electrical power supply configured to generate an electric field at the electrode, wherein the electrical power supply is connected to the electrode through the at least one electrical connector. In some embodiments, one needle or a plurality of needles has apertures in a first zone proximal to a closed end of the barrel and one needle or a plurality of needles that has apertures in a second zone that is distal to a closed end of the needle barrel. Additionally, some embodiments may have a first needle (e.g., a single needle on a single needle device, as described below, or the first needle in a device having a plurality of needles) or a first plurality of needles with apertures that are a size equal to, greater than or less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.0, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, or 4.0 mm in its widest portion). In some embodiments, one needle or a plurality of needles has apertures that less than 1 μm at its widest portion. In some embodiments, one needle or a plurality of needles has apertures that less than about 900 nm at its widest portion. In some embodiments, one needle or a plurality of needles has apertures that less than about 500 nm at its widest portion. In some embodiments, the first needle in an intracellular delivery device having a plurality of needles has apertures that are smaller or substantially smaller than a second needle or a second plurality of needles in the device.

In some embodiments, the intracellular delivery device includes only one needle. The needle can include any of the design features disclosed herein. For example the needle can have a closed or open end. The needle may include a plurality of apertures, for example, at least, greater than or equal to or any number in between about 5, 10, 20, 30, 50, 70, 100, 120, 140, 160, 180, 200, 500 apertures (e.g., at least about 5-100, 10-100, 20-100, 30-100, 40-100, 50-100 or 5-200, 10-200, 20-200, 30-200, 40-200, 50-200, 100-200, 100-500, 140-500, 150-500, 200-500 apertures). The apertures can be evenly spaced, or randomly distributed. The apertures may, in some embodiments, form a regular pattern on the needle. For example, the apertures may form a pattern having a rotational symmetry along the axis of the needle. The rotational symmetry may include 2-fold, 3-fold, 4-fold, 5-fold, six-fold, or a higher degree of rotational symmetry. As another example, the apertures may form a pattern having a screw axis symmetry. The screw axis symmetry can be include 2-fold, 3-fold, 4-fold, 5-fold, six-fold, or a higher degree of rotational symmetry. The translation vector for the screw axis can, for example, be about, at least, at least about, not more than, not more than about 0.01 mm, 0.05 mm, 0.1 mm, 0.15 mm, 0.2 mm, 0.25 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 1 cm, 2 cm or 3 cm. In some embodiments, the apertures are configured to produce a radial pattern when a prophylactic and/or therapeutic material is injected.

In some embodiments, the intracellular delivery device comprises one or more needles that are fluidly coupled to a syringe or a reservoir containing the prophylactic and/or therapeutic material so that the relative orientation of the one or more needles with the syringe or reservoir is fixed. The end(s) of the one or more needles may, in some embodiments, be both fluidly coupled and disposed near the syringe or a reservoir containing the prophylactic and/or therapeutic material. For example, an end of the one or more needles may be about, not more than, not more than about 1 mm, 5 mm, 1 cm, 2 cm, 3 cm, 4 cm, 5 cm, 6 cm, 7 cm, 8 cm, 9 cm, or 10 cm apart from the syringe or a reservoir containing the prophylactic and/or therapeutic material. In some embodiments, the end(s) of the one or more needles are no more than about 10 cm apart from the syringe or a reservoir that is fluidly coupled with the needle(s) and contains the prophylactic and/or therapeutic material.

Some embodiments relate to injection devices, intracellular delivery devices, cannulas, and needles comprising a fluid containing an agent, as described herein (e.g., a medicinal compound, chemical, nucleic acid, peptide, specificity exchanger, and, in particular, a DNA). In some embodiments, the intracellular delivery devices, cannulas, and needles, described herein, are for single use. That is, some embodiments comprise one or more of the needle designs, described herein, joined to a receptacle (preferably a sterile container, such as a sterilized syringe) that comprises a single application or dose of delivered agent (e.g., medicinal compound, chemical, nucleic acid, peptide, specificity exchanger, and, in particular a DNA). Accordingly, a single application or device can be conveniently packaged and provided to medical practitioners or end-consumers, which can administer said agent at an appropriate site and, following administration, the used injection device, needle, or cannula comprising a plurality of needles can be appropriately discarded. Some embodiments also include methods of making and using the aforementioned devices and methods of inducing an immune response to a desired antigen.

In some embodiments, the intracellular delivery device is not configured to apply an electric field shortly after or simultaneous with the introduction of the prophylactic and/or therapeutic material (e.g., DNA) at the tissue around and/or through the site of the injection. For example, the intracellular delivery device may not include a voltage source coupled to the device and configured to apply an electric field to the tissue at or near the site of injection. In other embodiments, the intracellular delivery device is configured to apply an electric field shortly after or simultaneous with the introduction of the prophylactic and/or therapeutic material (e.g., DNA) at the tissue around and/or through the site of the injection. For example, the intracellular delivery device may include a voltage source coupled to the device and configured to apply an electric field to the tissue at or near the site of injection.

Some embodiments disclosed herein include a method of delivering a prophylactic and/or therapeutic material to a subject in need thereof, where the prophylactic and/or therapeutic material is administered using any of the intracellular delivery devices disclosed herein. The prophylactic and/or therapeutic material may be any of those materials disclosed herein. In some embodiments, the method may also include maintaining the one or more needles inserted within the tissue for at least a predetermined time after injecting the prophylactic and/or therapeutic material but before withdrawing the one or more needles. The one or more needles may be maintained in the tissue, for example, at least, greater than or equal to 1 s, 2 s, 3 s, 4 s, 5 s, or more after injecting the therapeutic material but before withdrawing the one or more needles. In some embodiments, the entire dosage is delivered in a period of time less than about 60 seconds, 40 seconds, 30 seconds, 20 seconds, 15 seconds, 10 seconds, 5 seconds, 4 seconds, 3 seconds, 2 seconds, 1.5 seconds, 1.0 second, 0.8 seconds, 0.5 seconds, 0.4 seconds, 0.3 seconds, or 0.2 seconds.

The period of time between inserting the one or more needles into the tissue and removing the one or more needles into the tissue can also vary. The period of time may, for example, be about, at least, at least about, not more than, not more than 0.5 seconds, 1 second, 2 seconds, 3 seconds, 4 seconds, 5 seconds, 6 seconds, 7 seconds, 8 seconds, 9 seconds, 10 seconds, 15 seconds, 30 seconds, 45 seconds, or 60 seconds.

In some embodiments, the needle(s) and any of the devices described herein can be affixed to the body of a subject for greater periods of time so as to allow for a long term delivery of a prophylactic and/or therapeutic agent (e.g., delivery for at least, greater than or equal to 1, 2, 3, 4, 5, 6, 7, 8, 9, 10, 11, 12, 13, or 14 days) and such needles and devices can be affixed to miniature pumps so as to administer small amounts of prophylactic and/or therapeutic material (e.g. a cell population, such as a cell population comprising stem cells, chemical, a compound, a chemotherapeutic agent, a protein, a nucleic acid, such as DNA, RNA, other natural nucleic acid, a modified nucleic acid, or a DNA or nucleic acid aptamer), to said subjects over an extended period of time.

The prophylactic and/or therapeutic material may be delivered to the body, in some embodiments, at high pressures through any of the intracellular delivery devices disclosed herein, using a pressure generation element. The pressure generation element may be a plunger on a syringe, and may comprise a spring or other element which depresses the plunger to generate a high force or pressure on the prophylactic and/or therapeutic material. The high force or pressure generated by the pressure generation element is applied to the prophylactic and/or therapeutic material to displace it through the needle (e.g., by applying force to a plunger on a syringe coupled to the needle(s)). The maximum force can, for example, be about, at least, at least about, not more than, not more than about 25 N, 40 N, 50 N, 75 N, 100 N, 150 N, 200 N, or 500N. The maximum pressure applied to the therapeutic material can, for example, be about, at least, at least about, not more than, not more than 50 kPa, 100 kPa, 200 kpa, 300, kPa, 400 kPa, 500 kPa, 600 kPa, 700 kPa, 800 kPa, 900 kPa, 1000 kPa, 1100 kPa, 1200 kPa, 1300 kPa, 1400 kPa, 1500 kPa, 1600 kPa, 1700 kPa, 1800 kPa, 1900 kPa, 2000 kPa, 2100 kPa, 2200 kPa, 2300 kPa, 2400 kPa, 2500 kPa, 2600 kPa, 2700 kPa, 2800 kPa, 2900 kPa, 3000 kPa, 3100 kPa, 3200 kPa, 3300 kPa, 3400 kPa, 3500 kPa, 3600 kPa, 3700 kPa, 3800 kPa, 3900 kPa, 4000 kPa, 4100 kPa, 4200 kPa, 4300 kPa, 4400 kPa, 4500 kPa, 4600 kPa, 4700 kPa, 4800 kPa, 4900 kPa, 5000 kPa, 6000 kPa, 7000 kPa, 8000 kPa, 9000 kPa, 10 MPa, 15 MPa, 20 MPa, 25 MPa, or 30 MPa.

In some embodiments, the prophylactic and/or therapeutic material can be delivered at high hole velocities (i.e., the average velocity of the fluid exiting the apertures). The hole velocity can be, for example, be about, at least, at least about, not more than, not more than about 1 mm/s, 1.5 mm/s, 2 mm/s, 2.5 mm/s, 3 mm/s, 3.5 mm/s, 4 mm/s, 5 mm/s, 6 mm/s, 7 mm/s, 8 mm/s, 9 mm/s or 10 mm/s. In a preferred embodiment, the hole velocity can be at least about 3 mm/s. The hole velocity may be determined, for example, by the volume rate of injecting the prophylactic and/or therapeutic material relative the average size of the apertures. The intracellular delivery devices disclosed herein may optionally be configured to delivery at any of the hole velocities disclosed above. For example, the intracellular delivery device can be coupled with a spring piston configured to inject prophylactic and/or therapeutic material at a volume rate sufficient to produce the desired hole velocity.

Some aspects of the invention concern a intracellular delivery device comprising a needle that comprises a lumen adapted for the passage of a prophylactic and/or therapeutic material and a needle barrel that comprises a plurality of apertures on the length of the barrel, wherein said needle barrel has a closed-end; and a connector configured to join said needle to a pressure generation element. In some embodiments, the intracellular delivery device above comprises a plurality of needles as described herein and in some embodiments, the intracellular delivery device comprises a circular, diamond, triangular, square, rectangle, trapezoidal, ovoid, or otherwise shaped array of needles. Preferably, the intracellular delivery device is designed such that the plurality of said needles is configured such that the apertures on the needle barrels face each other but in some embodiments, the hypodermic needle assembly has a plurality of said needles that is configured such that the apertures on the needle barrels face away from each other. In some embodiments, the intracellular delivery device further comprises a pressure generation element joined to said intracellular delivery devices and this pressure generation element can be a syringe. The intracellular delivery devices above of can have apertures that have a diameter of about 10 nm-4 mm, 0.01 mm-4 mm, 0.1 mm-4 mm, 1.0 mm-4 mm, 1.5 mm-4 mm, 2.0 mm-4 mm, or 3.0 mm-4 mm.

In some embodiments, the intracellular delivery device above comprises a single syringe joined to at least three of said needles. In some embodiments, the at least three of said needles are between about 2 and about 10 mm apart. In other embodiments, the intracellular delivery device above can comprise a single syringe joined to at least four hypodermic needles. In some embodiments, the intracellular delivery device has at least four hypodermic needles that are between about 3 and about 6 mm apart. A single use intracellular delivery device is also an embodiment and such devices preferably comprise a plurality of needles attached to at least one syringe, wherein the needles comprise a plurality of apertures distributed along the barrel of said needles and a closed end; and said at least one syringe comprises a single dose of a prophylactic and/or therapeutic agent. In some embodiments, the prophylactic and/or therapeutic agent in the intracellular delivery device is a nucleic acid. The prophylactic and/or therapeutic agent can be a DNA that encodes a protein. In some embodiments, the intracellular delivery device above comprises a single syringe joined to at least three hypodermic needles and in some embodiments, the at least three hypodermic needles are between about 2 and about 10 mm apart. In other embodiments, the intracellular delivery device above comprises a single syringe joined to at least four needles and in some embodiments, the at least four hypodermic needles are between about 3 and about 6 mm apart.

Aspects of the invention also include methods of making and using the aforementioned devices. By one approach, some of the devices described herein are used to deliver a prophylactic and/or therapeutic agent to a subject and said methods are practiced by providing one of the delivery devices described herein, inserting the needles of said device into a tissue of a subject; and displacing the therapeutic agent from the syringe through the needles and into the tissue. In some embodiments, the prophylactic and/or therapeutic agent is a nucleic acid, the nucleic acid can encode an antigen, such as a viral antigen, preferably, a hepatitis antigen such as an HCV or HBV antigen such that some of the delivery devices described herein can be used for the purposes of inducing an immune response in a subject to an antigen that is delivered by said device.

Additional embodiments include an intracellular delivery device for the delivery of prophylactic and/or therapeutic material into tissue, the device comprising a connection to a pressure generation element; a lumen adapted for the passage of a prophylactic and/or therapeutic material; and a needle barrel, wherein the needle barrel comprises a plurality of apertures that extend along the length of the barrel. In some embodiments, the therapeutic material comprises a nucleic acid, a polypeptide, a carbohydrate, a specificity exchanger, a steroid, a cell population, a chemical or an immunogen. In some embodiments, the prophylactic and/or therapeutic agent induces the immune system.

The needle barrel can be adapted to transmit an electric current and the device can further comprise an electrode adapted to transmit an electromagnetic field. In some embodiments, the prophylactic and/or therapeutic agent enters a cell and in others it remains extracellular. In some embodiments, the pressure is transmitted using a fluid medium or a gas medium. In some embodiments, the nucleic acid comprises a sequence from a hepatitis virus such as a hepatitis B antigen (HBV), such as HBcAg, or a hepatitis C virus (HCV) antigen, such as NS3/4A, or a combination thereof, such as HBcAg from an HBV virus that infects stork or heron joined to NS3/4A. In other embodiments, the nucleic acid comprises a sequence from a human simian virus antigen. Preferably, the nucleic acid comprises a sequence encoding an antigen capable of generating a proliferative T-cell response and in some embodiments, the nucleic acid comprises a sequence from a human immunodeficiency virus.

Additional embodiments include, a intracellular delivery device for the delivery of prophylactic and/or therapeutic material into tissue comprising a prophylactic and/or therapeutic material pressure generation element; an array of needle barrels coupled to the pressure generation element; wherein at least one of the needle barrels in the array comprises a plurality of apertures adapted to deliver a pressure transmitted from the pressure generation element into a tissue to cause an increase in the permeability of a cell membrane, and at least one of the needle barrels in the array is adapted for the passage of the prophylactic and/or therapeutic material as described elsewhere herein.

More embodiments, include an intracellular delivery device having a longitudinal axis, the device comprising a connector configured to engage a source of pressurized fluid; and a needle assembly, the needle assembly comprising a stem extending from the connector in a direction substantially parallel to the longitudinal axis of the device, the stem comprising a first lumen that is fluidly coupled with the connector, a first needle barrel extending from the stem in a direction substantially parallel to the longitudinal axis of the device, the first needle barrel comprising a second lumen that is fluidly coupled with the stem and at least one aperture that is fluidly coupled with the second lumen, and a second needle barrel extending from the stem in a direction substantially parallel to the longitudinal axis of the device, the second needle barrel comprising a third lumen that is fluidly coupled with the stem and at least one aperture that is fluidly coupled with the third lumen.

In some embodiments, the first needle barrel and the second needle barrel form an injection cavity space therebetween. In some embodiments, the injection cavity space is configured to receive at least a portion of a subject, such as a tissue. In some embodiments, the first needle barrel and second needle barrel each comprise the same number of apertures. In some embodiments, each aperture on the first needle barrel faces an aperture on the second needle barrel. In some embodiments, the first needle barrel and the second needle barrel comprise a pointed distal tip disposed opposite the stem. In some embodiments, the apertures are generally curvilinear. In some embodiments, the apertures are generally polygonal. In some embodiments, the apertures are evenly disposed along a line segment that is substantially parallel to the longitudinal axis of the device. In some embodiments, a third needle barrel extending from the stem in a direction substantially parallel to the longitudinal axis of the device, the third needle barrel comprising a fourth lumen that is fluidly coupled with the stem and at least one aperture that is fluidly coupled with the fourth lumen. In some embodiments, at least one aperture is configured to apply negative pressure to the injection cavity space.

Still more embodiments concern an intracellular delivery device for delivering a prophylactic and/or therapeutic agent to subject, the device having a longitudinal axis and comprising a plurality of syringes disposed generally parallel to the longitudinal axis of the device, each syringe comprising a needle with a plurality of apertures disposed along a length of the needle, wherein the apertures face the longitudinal axis of the device. In these embodiments, the at least one syringe comprises a prophylactic and/or therapeutic agent comprising a gene. In some embodiments, each needle comprises a tip and the tips of the plurality of needles are disposed on a plane that lies substantially normal to the longitudinal axis of the device. Additional embodiments include a hypodermic needle comprising a plurality of apertures distributed along the barrel of said needle, wherein the end of said needle is closed. In some embodiments, said closed end is blunt.

In some embodiments, the assembly further comprises a syringe attached to the needle. In some embodiments, said syringe comprises a prophylactic and/or therapeutic agent, which can be a nucleic acid such as a DNA that encodes a protein. Still more aspects of the invention concern an intracellular delivery device comprising a plurality of hypodermic needles that comprise a plurality of apertures distributed along the barrel of said needles joined to one or more syringes. Preferably, the end of said needles are closed. In some embodiments, the end of said needles are blunt. In some embodiments, said syringe comprises a prophylactic and/or therapeutic agent such as a DNA that encodes a protein. In some embodiments, the injection device above comprises a single syringe joined to at least three hypodermic needles. Some embodiments concern a single use intracellular delivery device comprising a plurality of needles attached to at least one syringe, wherein the needles comprise a plurality of apertures distributed along the barrel of said needles and said at least one syringe comprises a single dose of a prophylactic and/or therapeutic agent. In some embodiments, the end of said needles are closed. In some embodiments, the end of said needles are blunt. In some embodiments, the prophylactic and/or therapeutic agent is a nucleic acid. In some embodiments, the nucleic acid is a DNA that encodes a protein.

In some embodiments, the intracellular delivery device comprises a needle hub having a plurality of needles partially disposed therein; the plurality of needles each comprising a lumen adapted for the passage of a therapeutic material and a needle barrel, the needle barrel comprising a plurality of apertures along the length of the barrel, wherein said barrel has a closed-end and wherein the apertures are evenly spaced apart on each of the needle barrels and have an average diameter in the range of about 0.01 mm to about 6 mm; a syringe comprising a plunger; a connector configured to fluidly couple the syringe and needle hub, the connector configured to form a gap between the connector and needle hub. In some embodiments, the hypodermic needle comprises zones on the needle barrel, wherein each zone is configured to pass therapeutic material in a different direction. In some embodiments, the hypodermic needle comprises a slit having a first dimension corresponding to the axis of the needle barrel and a second dimension perpendicular to the axis of the needle barrel wherein the first dimension is longer than the second dimension.

Methods of using anyone or more of the aforementioned devices are also embodiments, including a method of delivering a nucleic acid into a cell comprising using the injection devices as described herein In some embodiments, the method of delivering to a subject a prophylactic and/or therapeutic agent comprises using electroporation by providing a voltage source, inserting one or more needles of an intracellular delivery device into a tissue of a subject, wherein the one or more needles each comprises a barrel having a lumen and a plurality of apertures, the barrel made from an electrically conductive material, and an electrical connection to the voltage source; displacing the prophylactic and/or therapeutic agent through the lumen of the needle and into the tissue through the plurality of apertures, wherein the one or more needles are joined to a syringe containing said prophylactic and/or therapeutic agent such that the syringe and one or more needles form a rigid or non-flexible structure; and applying an electric field to the tissue of the subject using the one or more needles as electrodes. In some embodiments, displacing the prophylactic and/or therapeutic agent is performed prior to applying the electric field to the tissue. In some embodiments, displacing the prophylactic and/or therapeutic agent is performed subsequent to applying the electric field to the tissue. In some embodiments, displacing the prophylactic and/or therapeutic agent is performed prior to applying the electric field to the tissue. In some embodiments, displacing the prophylactic and/or therapeutic agent is performed at about the same time as applying the electric field to the tissue (e.g., a prophylactic and/or therapeutic agent, such as a nucleic acid encoding an antigen, can be administered by passing the prophylactic and/or therapeutic agent through the apertures on the needle barrel before, during, or after applying an electric field to the recipient tissue at or near the site of injection of the prophylactic and/or therapeutic agent. In some embodiments, the nucleic acid is a DNA that encodes a protein, such as an antigen.

Some embodiments relate to an intracellular delivery device comprising a plurality of pairs of needles, each needle of the plurality of pairs of needles comprising a closed end, a barrel, and a plurality of apertures along the barrel, wherein the apertures on at least one of the needles of the plurality of pairs of needles is aligned in relation to at least one other needle to generate a cross-spray pattern; wherein at least one of the plurality of pairs of needles comprises a pair of electrodes having opposite polarity, the electrodes configured to apply an electric field to a subject.

In some embodiments, said DNA encodes a viral antigen. In some embodiments, said viral antigen is an HCV or HBV antigen. Furthermore, in some embodiments a use of a HBcAg or a fragment thereof or a nucleic acid encoding HBcAg or a fragment thereof as an adjuvant. By some approaches, said HBcAg or a fragment thereof or a nucleic acid encoding HBcAg or a fragment thereof is a sequence selected from the group consisting of SEQ. ID NOs. 1-32. Methods of enhancing an immune response to an antigen are also embodiments and said methods can comprise providing said antigen or a nucleic acid encoding said antigen to a subject in mixture with or shortly after providing said subject with HBcAg or a fragment thereof or a nucleic acid encoding HBcAg or a fragment thereof. In some methods, said HBcAg or a fragment thereof or a nucleic acid encoding HBcAg or a fragment thereof is a sequence selected from the group consisting of SEQ. ID NOs. 1-32. In some methods, the DNA encodes NS3/4A and/or HBcAg (e.g., an HBcAg derived from a virus that infects stork and heron).

In some embodiments, the intracellular delivery devices described herein are used to deliver an immunogenic composition to a subject in need thereof. Preferably, the immunogenic composition is a nucleic acid encoding an antigen (e.g., an HCV antigen, such as NS3/4A or NS5, and/or an HBV antigen, such as HBcAg, preferably from an HBV that infects stork or heron). In some of these approaches, the immune response to the immunogenic composition (e.g., the antigen encoded by the nucleic acid, such as NS3/4A, NS5, or HBcAg), is evaluated, measured, analyzed, or observed. A preferred device for delivery of such immunogenic compositions is one that comprises a syringe capable of connecting to one or more of the needles described herein such that the syringe and needle assembly is non-flexible or rigid (i.e., not a catheter). In some embodiments, at least about 0.3 mL of prophylactic and/or therapeutic material (e.g., an immunogenic composition suspended in 0.2, 0.3, 0.4, or 0.5 ml) is delivered to said subject in less than 60, 45, 30, 15, 10, 5, or 1 second and the pressure of delivery is at least about 200 kpa. In some embodiments, the amount of prophylactic and/or therapeutic material may be at least about 1 mL.

Accordingly, aspects of the invention concern an intracellular delivery device that is configured for delivery of a prophylactic and/or therapeutic agent (e.g. a cell population, such as a cell population comprising stem cells, chemical, a compound, a chemotherapeutic agent, a protein, a specificity exchanger, a nucleic acid, such as DNA, RNA, other natural nucleic acid, a modified nucleic acid, or a DNA or nucleic acid aptamer), wherein said intracellular delivery device comprises a plurality of needles that comprise a closed or open end and a plurality of apertures that extend along the length of each needle. In some embodiments the intracellular delivery device comprises one needle as described herein. In some embodiments, the intracellular delivery device comprises a plurality of needles as described herein. The needle(s) can be blunt-ended (e.g., having a closed end) or can have a beveled, pointed, or a sharp end, each of which may also have a closed end. The needle can be made to a variety of gauges (e.g., at least, equal to or greater than 7, 8, 9, 10, 11, 12, 13, 14, 15, 16, 17, 18, 19, 20, 21, 22, 23, 24, 25, 26, 27, 28, 29, 30, 31, 32, 33, or 34 gauge). Preferably, the needle(s) is of a gauge that is greater than or equal to 20 (e.g., greater than or equal to 20, 21, 22, 23, 24, 25, 26, 27, 28, 29, 30, 31, 32, 33, or 34 gauge) and more preferably, the needle(s) is of a gauge that is greater than or equal to 23 (e.g., 23, 24, 25, 26, 27, 28, 29, 30, 31, 32, 33, or 34 gauge) and most preferably, the needle(s) is of a gauge that is greater than or equal to 25 (e.g., 25, 26, 27, 28, 29, 30, 31, 32, 33, or 34 gauge). In some embodiments, the apertures are not located at or near the tip of the one or more needles. For example, the apertures can be located at least 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 2 cm, 3 cm, 4 cm, or more from the tip of the needle.

The length of the needle(s) can vary according to the type of delivery desired. In order to target specific cells in the skin or particular tissues, for example, the preferred target depth depends on the particular cell or tissue being targeted and the thickness of the skin of the particular subject (e.g., to target the Langerhan's cells in the dermal space of human skin, it is desired that the delivery encompass, at least, in part, the epidermal tissue depth typically ranging from about 0.025 mm to about 0.2 mm in humans). Accordingly, in embodiments, wherein delivery to Langerhan's cells is desired, needle lengths can be between about 0.025 mm to about 0.2 mm. In some embodiments, it is desired that the therapeutic agents are delivered at a targeted depth just under the stratum corneum and encompassing the epidermis and upper dermis (e.g., in these embodiments preferred needle lengths include between about 0.025 mm to about 2.5 mm). In other embodiments, the therapeutic agents are delivered into the muscle tissue or adipose tissue (e.g., in these embodiments, it is desired that the preferred needle lengths include between about 0.5 cm to about 15 cm). Accordingly, aspects of the invention concern intracellular delivery devices that comprise one or more needles and uses thereof, wherein the length of the needle(s) is greater than, equal to, less than or any number in between about 0.025 mm, 0.05 mm, 0.075 mm, 0.1 mm, 0.2 mm, 0.3 mm, 0.4 mm, 0.5 mm, 0.6 mm, 0.7 mm, 0.8 mm, 0.9 mm, 1 mm, 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 125 mm, 150 mm, 175 mm, 200 mm, 225 mm, 250 mm, 275 mm, 300 mm, 325 mm, 350 mm, 375 mm, 400 mm, 425 mm, 450 mm, 475 mm, 500 mm, 525 mm, 550 mm, 575 mm, 600 mm, 625 mm, 650 mm, 675 mm, 700 mm, 725 mm, 750 mm, 775 mm, 800 mm, 825 mm, 850 mm, 875 mm, 900 mm, 925 mm, 950 mm, 975 mm, 1 cm, 1.25 cm, 1.5 cm, 2.0 cm, 2.25 cm, 2.5 cm, 2.75 cm, 3.0 cm, 3.25 cm, 3.5 cm, 3.75 cm, 4.0 cm, 4.25 cm, 4.5 cm, 4.75 cm, 5.0 cm, 5.25 cm, 5.5 cm, 5.75 cm, 6.0 cm, 6.25 cm, 6.5 cm, 6.75 cm, 7.0 cm, 7.25 cm, 7.5 cm, 7.75 cm, 8.0 cm, 8.25 cm, 8.5 cm, 8.75 cm, 9.0 cm, 9.25 cm, 9.5 cm, 9.75 cm, 10.0 cm, 10.25 cm, 10.5 cm, 10.75 cm, 11.0 cm, 11.25 cm, 11.5 cm, 11.75 cm, 12.0 cm, 12.25 cm, 12.5 cm, 12.75 cm, 13.0 cm, 13.25 cm, 13.5 cm, 13.75 cm, 14.0 cm, 15.25 cm, 14.5 cm, 14.75 cm, or 15 cm. In some embodiments, the length of the needle(s) is greater than 10 mm. In some embodiments, the length of the needle(s) is greater than about 15 mm. In some embodiments, the length of the needle(s) is greater than about 20 mm. In some embodiments, the length of the needle(s) is greater than about 30 mm.

Any of the needle(s) described herein (e.g., any one or more of the needles of the shapes and dimensions described above) can include a plurality of apertures of a variety of sizes and shapes (e.g., oval, circular, slit, or ovoid shape), which can be produced by machine cutting or laser. The one or more needles can each comprise, for example, greater than, equal to, less than, or any number between 2, 3, 4, 5, 6, 7, 8, 9, 10, 11, 12, 13, 14, 15, 16, 17, 18, 19, 20, 21, 22, 25, 26, 27, 28, 29, 30, 31, 32, 33, 34, 35, 36, 37, 38, 39, 40, 50, 60, 70, 80, 90, 100, 110, 120, 130, 140, 150, 160, 170, 180, 190, 200, 300, 400, or 500 apertures. In preferred embodiments, the total number of apertures in all of the one or more needles in the device can be 72, 96, or 144. In some embodiments, the apertures can be evenly spaced along the length of the needle. In some embodiments, the apertures can be grouped in one area (e.g., spaced in a first or a second zone of the needle, (such as, wherein the two zones are demarcated by the two sides opposing the middle point of the length of the needle) or said apertures can be along the length of the needle), or unevenly spaced along the length of the needle. The needle(s) can have a closed or open end but a closed end is preferred, as such a design is configured to increase the pressure of delivery when small diameter apertures (e.g., a size equal to or less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0 mm in its widest portion) are employed. The needle(s)

can be composed of surgical steel, stainless steel, or a metal alloy (e.g., consisting essentially of at least about 52% Ni and at least about 48% Ti). In some embodiments, the needle may comprise an electrically conductive material. In some embodiments, when the needle is attached or coupled to a pressurized fluid reservoir, such as a syringe, for example by a luer lock mechanism, the syringe and needle form a rigid, non-flexible body such that the syringe and needle assembly is not a catheter. Similarly, many of the embodiments described herein comprise a syringe joined to one or more of the needles described herein such that the syringe and needle assembly lack an exterior outer sheath covering the needle, as is required for catheters. While many of the devices described herein have features similar to that found in a catheter, many of the embodiments of the present invention are not catheters and many of the devices described herein are rigid and non-flexible when the syringe is connected to the needle (e.g., when a syringe is directly coupled to a hub comprising one or more of the needles described herein.

Embodiments disclosed herein are not limited to any particular manufacturing process to create the barrels or apertures disclosed. The needle barrels can be manufactured using any of the standard needle manufacturing techniques including, by way of example only, die-casting, injection molding, blow molding, machine tooling, laser fabrication and others. Similarly, the material for the needle can be chosen from any number of well-known needle materials such as stainless steel, carbon steel, and various metal alloys. The apertures on the barrels can be created as a part of the barrel manufacturing process, or can be added later by drilling or laser etching. These various manufacturing methods are all well-known in the art.

Aspects of the present invention also relate generally to methods of transmembrane delivery of drugs, nucleic acids, or other bioactive molecules and compounds using the intracellular delivery devices described above. The active ingredients (e.g. DNA, RNA, nucleic acids, protein, or compounds) can be formulated in a number of solutions for delivery through the needles described herein. In some embodiments, the active ingredients (e.g. DNA, RNA, nucleic acids, protein, or compounds) may be mixed in with a carrier solution such water, a buffer, saline, an oil emulsion, oil, or glycerin. The liquid can then be passed through a needle as described herein. In some embodiments the active ingredients (e.g. DNA, RNA, nucleic acids, protein, or compounds) can be attached to a support (e.g. a nanoparticle, protein, sugar, or pellet) and mixed with one or more of the aforementioned carrier solutions (e.g. water, a buffer, saline, an oil emulsion, oil, or glycerin) and the support bound agent is passed through the needles described herein. It will be understood that there exists a variety of carrier mediums and supports, and using carrier mediums or supports not specifically mentioned herein will not depart from the spirit of the invention. For instance, the carrier medium may be a cationic oil.

The nucleic acid contemplated for use with the intracellular delivery devices described herein can be nucleic acids from human, non-human primates, mice, bacteria, viruses, mold, protozoa, bird, reptiles, birds such as stork, and heron, mice, hamsters, rats, rabbits, guinea pigs, woodchucks, pigs, micro-pigs, goats, dogs, cats, humans and non-human primates, e.g., baboons, monkeys, and chimpanzees, as mentioned above. In certain embodiments, the intracellular delivery devices described herein can be used for the delivery of nucleic acids encoding proteins found in the hepatitis C virus (HCV). The HCV gene products can be viruses known to infect animals of any species, including, but not limited to, amphibians, reptiles, birds such as stork, and heron, mice, hamsters, rats, rabbits, guinea pigs, woodchucks, pigs, micro-pigs, goats, dogs, cats, humans and non-human primates, e.g., baboons, monkeys, and chimpanzees. In certain embodiments, the intracellular delivery devices described herein can be used for the delivery of nucleic acids encoding proteins found in the hepatitis B virus (HBV). The HBV gene products can be viruses known to infect animals of any species, including, but not limited to, amphibians, reptiles, birds such as stork, and heron, mice, hamsters, rats, rabbits, guinea pigs, woodchucks, pigs, micro-pigs, goats, dogs, cats, humans and non-human primates, e.g., baboons, monkeys, and chimpanzees.

In certain embodiments an adjuvant is used in addition to the active ingredient. For instance, a pharmacologic agent can be added to a drug being delivered by a device described herein as needed to increase or aid its effect. In another example, an immunological agent that increases the antigenic response can be utilized with a device described herein. For instance, U.S. Pat. No. 6,680,059, which is hereby incorporated in its entirety by reference, describes the use of vaccines containing ribavirin as an adjuvant to the vaccine. However, an adjuvant may refer to any material that has the ability to enhance or facilitate an immune response or to increase or aid the effect of a prophylactic and/or therapeutic agent. In some embodiments, an adjuvant administered in conjunction with one or more of the antigens or nucleic acids encoding an antigen (e.g., NS3/4A) disclosed herein is IL-12 or a nucleic acid encoding IL-12, which may or may not be present on the same construct as the nucleic acid encoding the antigen of interest (e.g., NS3/4A).

In certain embodiments, any nucleic acid can be used with the device and methods presented, for example, plasmid DNA, linear DNA, antisense DNA and RNA. For instance, the nucleic acid can be a DNA expression vector of the type well known in the art. In some embodiments, the invention is used for the purpose of DNA or RNA vaccination. That is, the invention includes a method of enhancing the transmembrane flux rate of an injected DNA or RNA nucleic acid into the intracellular space.

In certain embodiments, the intracellular delivery device can be used for high pressure injection into various tissues of organisms, wherein it is desirable to deliver a prophylactic and/or therapeutic material. For instance, the tissue could be skeletal muscle, adipose tissue, an internal organ, bone, connective tissue, nervous tissue, dermal tissue, and others. For instance, DNA vaccines may delivered by intramuscular injection into skeletal muscle or by intradermal injection into the dermis of an animal. In other embodiments, a therapeutic material may be delivered via parenteral delivery into subcutaneous or intraperitoneal tissues. Depending on the target tissue and prophylactic and/or therapeutic agent or agents being delivered, parameters of the needles may be appropriately modified to accommodate the desired physical properties necessary to achieve generation of the pressure sufficient to enhance agent delivery.

In some embodiments, the intracellular delivery device may be configured to deliver a prophylactic and/or therapeutic material at a predetermined delivery rate. For example, the syringe may controlled by a spring-actuated device that produces a desired stroke speed for pressing the syringe plunger to produce a desired delivery rate. U.S. Pat. No. 6,019,747 discloses one example of such a device and is hereby incorporated by reference in its entirety. In some embodiments, the syringe may be controlled by a gas spring, an electromechanical device, compressed air, or other similar actuation mechanism. The delivery rate may, for example, be at least 0.1 mL/s, 0.3 mL/s, 0.5 mL/s, 0.8 mL/s, 0.9 mL/s, 1.0 mL/s, 1.1 mL/s, 1.2 mL/s, 1.3, mL/s, 1.4 mL/s, 1.5 mL/s, 2.0 mL/s, or 3.0 mL/s. The delivery rate may, for example, be no more than 20.0 mL/s, 10.0 mL/s, 7 mL/s, 6 mL/s, 5 mL/s, 4 mL/s, 3 mL/s, or 2 mL/s. As discussed further below, the present application includes methods of using the injection device. Accordingly, the method may include delivering a therapeutic material at a predetermined rate, such as any of the rates disclosed above.

In some embodiments, an intracellular delivery device contains a prophylactic and/or therapeutic agent. The device can comprise, for example, a nucleic acid that is formulated for intra muscular delivery. Desirably, DNA encoding an immunogen or a DNA-containing immunogenic composition (e.g., a DNA vaccine) is provided in a device comprising one or more of the needles described herein. However, a wide variety of nucleic acids can be delivered by an embodiment described herein. That is, one or more of the embodiments described herein can comprise one or more of a nucleic acid selected from the group consisting of: mRNA, tRNA, rRNA, cDNA, miRNA (microRNA), siRNA, (small interfering RNA), RNAi (interfering RNA), piRNA (Piwi-interacting RNA), aRNA (Antinsense RNA), snRNA (Small nuclear RNA), snoRNA (Small nucleolar RNA), gRNA (Guide RNA), shRNA (Small hairpin RNA), stRNA (Small Temporal RNA), ta-siRNA (Trans-acting small interfeing RNA), cpDNA, (Chloroplast DNA), gDNA (Genomic DNA), msDNA (Multicopy single-stranded DNA), mtDNA (Mitochondrial DNA), GNA (Glycol nucleic acid), LNA (Locked nucleic acid), PNA (Peptide nucleic acid), TNA (Threose nucleic acid), Morpholino containing nucleic acids, sulfur-containing nucleic acids, 2-O-methyl nucleic acids, and nucleic acids containing one or more modified bases or spacers.

The concentration of the nucleic acid contained in or delivered by a device described herein can vary from about 0.1 ng/ml to about 50 mg/ml. In some aspects, the nucleic acid concentration that is contained in or delivered by a device described herein (e.g., a suitable dose of nucleic acid for delivery by a device described herein) is between about 10 ng/ml to 25 mg/ml. In still other aspects, the nucleic acid concentration is between 100 ng/ml to 10 mg/ml. In some aspects, the nucleic acid concentration contained in or delivered by a device described herein (e.g., a suitable dose of nucleic acid for delivery by a device described herein) is greater than or equal to or less than about 100 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml, 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 16 μg/ml, 17 μg/ml, 18 μg/ml, 19 μg/ml, 20 μg/ml, 21 μg/ml, 22 μg/ml, 23 μg/ml, 24 μg/ml, 25 μg/ml, 26 μg/ml, 27 μg/ml, 28 μg/ml, 29 μg/ml, 30 μg/ml, 31 μg/ml, 32 μg/ml, 33 μg/ml, 34 μg/ml, 35 μg/ml, 36 μg/ml, 37 μg/ml, 38 μg/ml, 39 μg/ml, 40 μg/ml, 41 μg/ml, 42 μg/ml, 43 μg/ml, 44 μg/ml, 45 μg/ml, 46 μg/ml, 47 μg/ml, 48 μg/ml, 49 μg/ml, 50 μg/ml, 55 μg/ml, 60 μg/ml, 65 μg/ml, 70 μg/ml, 75 μg/ml, 80 μg/ml, 85 μg/ml, 90 μg/ml, 95 μg/ml, 100 μg/ml, 150 μg/ml, 200 μg/ml, 250 μg/ml, 300 μg/ml, 350 μg/ml, 400 μg/ml, 450 μg/ml, 500 μg/ml, 550 μg/ml, 600 μg/ml, 650 μg/ml, 700 μg/ml, 750 μg/ml 800 μg/ml, 850 μg/ml, 900 μg/ml, 950 μg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, 5.1 mg/ml, 5.2 mg/ml, 5.3 mg/ml, 5.4 mg/ml, 5.5 mg/ml, 5.6 mg/ml, 5.7 mg/ml, 5.8 mg/ml, 5.9 mg/ml, 6.0 mg/ml, 6.1 mg/ml, 6.2 mg/ml, 6.3 mg/ml, 6.4 mg/ml, 6.5 mg/ml, 6.6 mg/ml, 6.7 mg/ml, 6.8 mg/ml, 6.9 mg/ml, 7.0 mg/ml, 7.1 mg/ml, 7.2 mg/ml, 7.3 mg/ml, 7.4 mg/ml, 7.5 mg/ml, 7.6 mg/ml, 7.7 mg/ml, 7.8 mg/ml, 7.9 mg/ml, 8.0 mg/ml, 8.1 mg/ml, 8.2 mg/ml, 8.3 mg/ml, 8.4 mg/ml, 8.5 mg/ml, 8.6 mg/ml, 8.7 mg/ml, 8.8 mg/ml, 8.9 mg/ml, 9.0 mg/ml, 9.1 mg/ml, 9.2 mg/ml, 9.3 mg/ml, 9.4 mg/ml, 9.5 mg/ml, 9.6 mg/ml, 9.7 mg/ml, 9.8 mg/ml, 9.9 mg/ml, 10.0 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, or within a range defined by, and including, any two of these values.

The amount of nucleic acid provided by an intracellular delivery device described herein can vary from about 1 ng to 10 g. In some aspects, the amount of nucleic acid contained in the intracellular delivery device or provided by the intracellular delivery device is less than greater than or equal to about 1 ng, 5 ng, 10 ng, 20 ng, 30 ng, 40 ng, 50 ng, 60 ng, 70 ng, 80 ng, 90 ng, 100 ng, 150 ng, 200 ng, 250 ng, 300 ng, 350 ng, 400 ng, 500 ng, 600 ng, 700 ng, 800 ng, 900 ng, 1 μg, 2 μg, 3 μg, 4 μg, 5 μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 36 μg, 37 μg, 38 μg, 39 μg, 40 μg, 41 μg, 42 μg, 43 μg, 44 μg, 45 μg, 46 μg, 47 μg, 48 μg, 49 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg 150 μg, 155 μg, 160 μg, 165 μg, 170 μg, 175 μg, 180 μg, 185 μg, 190 μg, 195 μg 200 μg, 205 μg, 210 μg, 215 μg, 220 μg, 225 μg, 230 μg, 235 μg, 240 μg, 245 μg 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg 350 μg, 355 μg, 360 μg, 365 μg, 370 μg, 375 μg, 380 μg, 385 μg, 390 μg, 395 μg 400 μg, 405 μg, 410 μg, 415 μg, 420 μg, 425 μg, 430 μg, 435 μg, 440 μg, 445 μg 450 μg, 455 μg, 460 μg, 465 μg, 470 μg, 475 μg, 480 μg, 485 μg, 490 μg, 495 μg 500 μg, 505 μg, 510 μg, 515 μg, 520 μg, 525 μg, 530 μg, 535 μg, 540 μg, 545 μg 550 μg, 555 μg, 560 μg, 565 μg, 570 μg, 575 μg, 580 μg, 585 μg, 590 μg, 595 μg 600 μg, 605 μg, 610 μg, 615 μg, 620 μg, 625 μg, 630 μg, 635 μg, 640 μg, 645 μg 650 μg, 655 μg, 660 μg, 665 μg, 670 μg, 675 μg, 680 μg, 685 μg, 690 μg, 695 μg, 700 μg, 705 μg, 710 μg, 715 μg, 720 μg, 725 μg, 730 μg, 735 μg, 740 μg, 745 μg 750 μg, 755 μg, 760 μg, 765 μg, 770 μg, 775 μg, 780 μg, 785 μg, 790 μg, 795 μg, 800 μg, 805 μg, 810 μg, 815 μg, 820 μg, 825 μg, 830 μg, 835 μg, 840 μg, 845 μg 850 μg, 855 μg, 860 μg, 865 μg, 870 μg, 875 μg, 880 μg, 885 μg, 890 μg, 895 μg 900 μg, 905 μg, 910 μg, 915 μg, 920 μg, 925 μg, 930 μg, 935 μg, 940 μg, 945 μg 950 μg, 955 μg, 960 μg, 965 μg, 970 μg, 975 μg, 980 μg, 985 μg, 990 μg, 995 μg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 2 g, 3 g, 4 g, 5 g, 6 g, 7 g, 8 g, 9 g, 10 g or within a range defined by, and including, any two of these values.

The volume of prophylactic and/or therapeutic material provided by an intracellular delivery device described herein can vary, for example, from about 100 μL to 100 mL. In some aspects, the volume of prophylactic and/or therapeutic material contained in the hypodermic injection pressure device or provided by the hypodermic injection pressure device is less than greater than or equal to about 100 μL, 150 μL, 200 μL, 250 μL, 300 μL, 350 μL, 400 μL, 500 μL, 600 μL, 700 μL, 800 μL, 900 μL, 1 mL, 2 mL, 3 mL, 4 mL, 5 mL, 6 mL, 7 mL, 8 mL, 9 mL, 10 mL, 20 mL, 30 mL, 40 mL, 50 mL, 60 mL, 70 mL, 80 mL, 90 mL, or 100 mL or within a range defined by, and including, any two of these values.

Aspects of the invention also concern methods of making one or more of the aforementioned devices. By one approach, one or a plurality of the needles described herein are provided and said needle(s) are attached to a syringe that contains a therapeutic agent (e.g., a nucleic acid such as DNA, RNA, protein, or a compound). The attachment of the needle(s) and the syringe can be made such that the needle cannot be removed from the syringe (e.g., the needle and syringe are molded together) or the attachment can be made such that the needle and the syringe are detachable. Preferably, the attachment of the needle(s) and the syringe is done prior to loading the syringe with the therapeutic agent. The needle and syringe can be sterilized prior to or after adding the therapeutic agent. Preferably, the needle and syringe assembly is sterilized prior to addition of the therapeutic agent and shortly after sterilization, sterilized therapeutic agent is added in a sterile fashion. Desirable manufacturing processes are used to produce a single use device comprising one or more of the sterilized needles described herein, which are attached to one or more sterilized syringes that contain a single dose of one or more sterilized therapeutic agents. These single use devices can be separately sterile packaged such that a user merely needs to tear open a package and inject the therapeutic agent into a suitable tissue (e.g., single use DNA vaccination by injection into muscle).

Aspects of the invention also concern methods of using one or more of the devices described herein. By one approach, methods of intracellular delivery of a compound are provided, wherein a compound contained in a device described herein is administered to a subject. In some embodiments, a compound (e.g., a nucleic acid, such as DNA or protein) is provided in a device described herein (e.g., a syringe comprising one or more of the needles described herein). The compound is then delivered to the subject by inserting the needles into tissue of the subject, deploying the plunger to provide pressure on the solution in the syringe thereby pressing the compound out the apertures of the needles at a desired pressure. The increased pressure in the tissue promotes the uptake of the compound by the cells thereby allowing for the intracellular delivery of the compound. Indeed, any prophylactic and/or therapeutic material in which it is desirable for the material to be injected into under a high-injection pressure can be used in conjunction with the invention, including, but not limited to, polypeptides, carbohydrates, microparticles, steroids, or low-molecular weight molecules. For instance, nucleic acid and proteins can be simultaneously or serially introduced into an tissue undergoing high injection pressure.

Some embodiments concern methods of expressing a protein from DNA, wherein a device as described herein is provided (e.g., a syringe comprising one or more of the needles described herein and a DNA), the needles are inserted into a tissue of a subject (e.g., muscle), the DNA is introduced into the tissue by exiting the apertures under pressure (e.g., pressure exerted by deploying the plunger and pressing it toward the DNA solution in the syringe), and the DNA is taken up by the muscle cells. Optionally, the device containing the DNA is introduced or deployed in a manner that promotes an inflammatory response (e.g., mobilization of or activation of cells associated with an inflammatory response). Optionally, the needle design (e.g., plurality of apertures) or configuration of the device produces an inflammatory response (e.g., mobilization of or activation of cells associated with an inflammatory response). Optionally, the amount of protein expression and/or mobilization of cells associated with an inflammatory response is measured. Such measurements can be made using immunology and/or histochemistry.

Accordingly, some aspects of the invention concern methods of inducing an immune response to a desired antigen, whereby, a device as described herein is provided (e.g., a syringe comprising one or more of the needles described herein and a DNA), the needles are inserted into a tissue of a subject (e.g., muscle), the DNA is introduced into the tissue by exiting the apertures under pressure (e.g., pressure exerted by deploying the plunger and pressing it toward the DNA solution in the syringe), and the DNA is taken up by the muscle cells. Subsequently, protein encoded by the DNA is made in the cells, and the immune system responds to the protein. Optionally, an immune response to the antigen produced from the introduced DNA is measured (e.g., presence of antibody, specific T cells, reduction or clearance of infection, or a reduction or disappearance of disease symptoms). Using certain embodiments of the invention, gene constructs may be administered directly into a skeletal muscle tissue for the uptake of the gene by a cell for the subsequent synthesis of the encoded product. In some methods of the invention, a high-pressure injection needle may be used to propel a liquid that contains DNA or RNA molecules into a subject's tissue. The liquid is propelled at a sufficient velocity such that upon impact with the tissue the liquid exerts a high pressure onto the tissue, increasing cell permeability, and causing the DNA or RNA molecule to permeate the cells in the area. In some embodiments, an intracellular delivery device as described herein may be used to deliver genetic material to tissue of other organs in order to introduce a nucleic acid molecule to cells of that organ. Indeed, it will be readily recognized that other gene delivery mechanisms well known in the art can be adapted to be used with embodiments of the present invention, including liposome-derived systems, artificial viral envelopes, and other systems known in the art (Rossi, J. J. (1995) Br. Med. Bull. 51:217-225; Boado, R. J. et al. (1998) J. Pharm. Sci.

87:1308-1315; Morris, M. C. et al. (1997) Nucleic Acids Res. 25:2730-2736, all of which are hereby included in their entirety by reference). Additionally, one may use a variety of adjuvants (e.g., ribavirin or IL-12 or a nucleic acid encoding IL-12), to either enhance immunogenicity and/or cell permeability.

For instance, by way of example only and not by way of any limitation, certain embodiments of the invention can be used in conjunction with the constructs described in U.S. Publication Number 2005-0277192 and U.S. Publication Number 2005-0124573, the entireties of which are hereby expressly incorporated by reference. These references describe the use of a nucleic acid encoding hepatitis C virus (HCV) nonstructural protein 3/4A (NS3/4A) to promote an immune response in humans. For example, it was observed that when HCV NS3/4A gene was transfected into mammalian cells, vis a vis a eukaryotic expression vector, appreciable levels of expression of NS3 were observed. Further, mice immunized with the NS3/4A gene were found to have primed high levels of 1\153-specific antibodies and antigen specific T cells. Recently, similar constructs have been found to produce a potent immune response in clinical trials with patients that are infected with HCV.

Accordingly, some embodiments concern methods of treating and preventing HCV infection, wherein one or more of the devices described herein, which contain one or more of the HCV DNA constructs that have been shown to produce a potent immune response in humans, is provided to a patient that is infected with or who is at risk of infection by HCV. Optionally, an individual in need of a medicament that prevents and/or treats HCV infection is identified and said individual is then provided a medicament comprising one or more of the HCV constructs that have been found to produce a potent immune response in humans (e.g., an expression construct encoding NS3/4A) using a high-pressure injection needle device, as described herein. Optionally, an immune response to NS3/4A, a reduction in viral titer, or production anti-HCV antibodies is measured in the inoculated individual after treatment or during the course of treatment. However, the current invention is not limited to antigens of HCV for DNA immunization. Indeed, the invention can be used any time in which expression of any antigenic peptide within cell is desirable. For instance, some non-limiting examples of known antigenic peptides in relation to specific disease states include the following:

HBV: PreS1, PreS2 and Surface env proteins, core and pol

HIV: gp120, gp40, gp160, p24, gag, pol, env, vif, vpr, vpu, tat, rev, nef

Papilloma: E1, E2, E3, E4, E5, E6, E7, E8, L1, L2

HSV: gL, gH, gM, gB, gC, gK, gE, gD, ICP47, ICP36, ICP4, as taught in U.S. Pat. No. 7,074,770 to Charo, et al., entitled "Method of DNA vaccination," and which is hereby incorporated by reference in its entirety. Some of the embodiments described herein also include and/or administer one or more of the nucleic acids selected from the group consisting of: mRNA, tRNA, rRNA, cDNA, miRNA (microRNA), siRNA, (small interfering RNA), piRNA (Piwi-interacting RNA), aRNA (Antinsense RNA), snRNA (Small nuclear RNA), snoRNA (Small nucleolar RNA), gRNA (Guide RNA), shRNA (Small hairpin RNA), stRNA (Small Temporal RNA), ta-siRNA (Trans-acting small interfeing RNA), cpDNA, (Chloroplast DNA), gDNA (Genomic DNA), msDNA (Multicopy single-stranded DNA), mtDNA (Mitochondrial DNA), GNA (Glycol nucleic acid), LNA (Locked nucleic acid), PNA (Peptide nucleic acid), TNA (Threose nucleic acid), Morpholino containing nucleic acids, sulfur-containing nucleic acids, 2-O-methyl nucleic acids, and nucleic acids containing one or more modified bases or spacers.

Referring to the Figures, FIG. 1A depicts a side view of an embodiment of a hypodermic needle device also referred to as an intracellular delivery device having two barrels, each barrel having five apertures for delivering a prophylactic and/or therapeutic agent to an area in between the barrels. Referring to FIG. 1A, the embodiment of a hypodermic needle device includes a proximal end 103, a distal end 101 opposite the proximal end, and a longitudinal axis running from the distal end 101 to the proximal end 103. In some embodiments, an intracellular delivery device can contain one or a plurality of needles. In some embodiments, the an intracellular delivery device comprises 2, 3, 4, 5, 6, 7, 8, 9, 10, 11, 12, 13, 14, 15, 16, 17, 18, 19, 20, 21, 22, 23, 24, 25, 26, 27, 28, 29, or 30 needles. The an intracellular delivery device comprises a standard connector 100 and a needle body 102 extending from the connector 100. The standard connector 100 and needle body 102 are disposed on an axis that is substantially parallel to the longitudinal axis. In some embodiments, the standard connector 100 is a luer lock or similar mechanism configured to connect the device to a pressure delivery device (not shown), for example, a syringe or pump.

The distal tip of the needle can be blunt, beveled, tapered, sharpened, or pointed to permit an operator to pierce the skin of a subject (e.g., a human, domestic animal, such as a cat or dog, or farm animal, such as a horse, cow, pig, or chicken) in order to reach the underlying desired target tissue. For example, the tips 105*a*, 105*b* can comprise a regular medical point (e.g., a "lancet point"). In some embodiments, the tips 105*a*, 105*b* can be blunted. In some embodiments, the distal tip of the needle is closed such that the tip does not establish fluid communication between the lumens of the needle barrel and the distal end of the needle body. In other embodiments, the distal tip is open such that the tip establishes fluid communication between the needle barrel and the distal end of the needle.

In some embodiments, the hypodermic needle device or an intracellular delivery device can be configured to be a one-time disposable device, wherein the prophylactic and/or therapeutic agent is contained within the device and no additional connection is required. The needle body 102 may comprise one or more needle delivery barrels 120*a* and 120*b* that extend from a stem or cannula 115. The stem 115 can include a central lumen or channel. Each needle barrel 120*a*, 120*b* also includes at least one lumen that is fluidly connected to the stem 115 and standard connector 100. In the illustrated embodiment, the needle body 102 includes two needle delivery barrels 120*a*, 120*b* with each needle barrel 120 including a distal tip 105*a*, 105*b*. The lengths of the needle barrels 120*a*, 120*b* can vary. In some embodiments, the needle barrels 120*a*, 120*b* are each about the same length and in some embodiments, the needle barrels are different lengths. The needle barrels 120*a*, 120*b* can range from about 2 mm to about 100 mm. The gauges of the needles barrels 120*a* and 120*b* can vary from device to device or from barrel 120*a* to barrel 120*b* on a single device.

In some embodiments, the opening created by the space between the needle barrels 120*a*, 120*b* at the distal end of the device is sufficiently large in size to enable the needle barrels 120*a*, 120*b* to surround one or more cells.

The needle barrels 120*a*, 120*b* can each comprise apertures 110*a*, 110*b* disposed along a length of the barrels. In some embodiments, each needle barrel 120*a*, 120*b* comprises at least one aperture 110*a*, 110*b*. In other embodiments, at least one needle barrel 120*a*, 120*b* does not comprise an aperture 110*a*, 110*b*. In some embodiments, the size and shape of each aperture 110*a*, 110*b* can vary from barrel to barrel. In some embodiments, the length of the needle can vary from barrel to barrel.

Each needle barrel 120*a*, 120*b* may comprise 0 to 100 apertures. In some embodiments, the needle has 1 or 2 apertures along the length of the needle (e.g., a closed ended needle having at least two apertures along the length of the needle). In other embodiments, the needle has a number of apertures that is exactly, less than, or greater than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. The apertures can be located near the distal end of a barrel or anywhere along the length of the barrel. The apertures on each barrel may each be disposed in a plane that is substantially parallel to the longitudinal axis. The apertures can also be disposed along a line segment that is substantially parallel to, and facing, the longitudinal axis of the device. In other embodiments, the apertures may be disposed on one or more planes that are not substantially parallel to the longitudinal axis of the device. Each aperture can face a common point, for example, a point on an axis that is substantially parallel to the longitudinal axis or each aperture can face a different point or direction.

The apertures can vary in size and shape. For example, apertures can be circular, round, generally curvilinear, square, rectangular, triangular, generally polygonal, generally symmetrical, generally asymmetrical, or irregularly shaped. Additionally, the apertures can vary in size and shape within each barrel. For example, in some embodiments, a first aperture on a barrel can be generally curvilinear and have a diameter of about 1 mm and a second aperture on the barrel can have the same shape as the first aperture and have a diameter of about 1.50 mm. In some embodiments, each aperture can have generally the same shape and same size. The apertures can vary in size and shape. For example, apertures can be circular, round, generally curvilinear, square, rectangular, triangular, generally polygonal, generally symmetrical, generally asymmetrical, or irregularly shaped. Additionally, the apertures can vary in size and shape within each barrel. For example, in one embodiment, a first aperture on barrel can be generally curvilinear and have a diameter of about 1 mm and a second aperture on barrel can have the same shape as the first aperture and have a diameter of about 1.50 mm. In other embodiments, each aperture can have generally the same shape and same size.

Figure 1B:
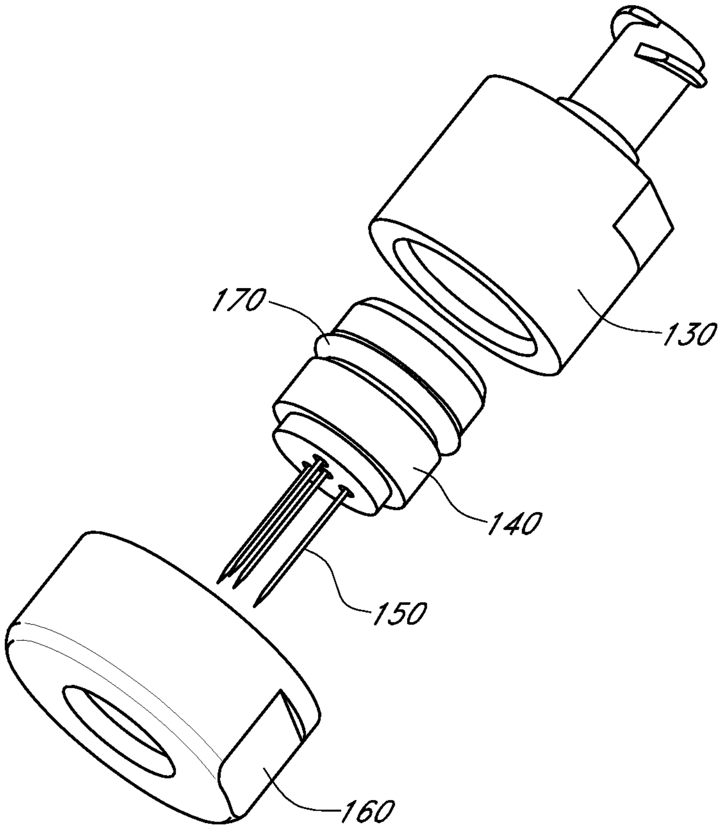
FIG. 1B illustrates an exploded perspective view of one embodiment of a hypodermic needle hub with four barrels for delivering a prophylactic and/or therapeutic agent to an area in between the barrels.

FIG. 1B illustrates an exploded perspective view of one embodiment of a needle hub with four barrels for delivering a prophylactic and/or therapeutic agent to an area in between the barrels. Threaded luer adaptor 130 is configured to engage a syringe (not shown) containing a prophylactic and/or therapeutic material. Hub insert 140 comprises a plurality of needles 150 at the distal side of hub insert 140. Needles 150 may be of varying configuration, including any configuration described herein. Collar 160 is configured to engage threaded luer adaptor 130 and secure hub insert 140. Gasket 170 may optionally be disposed on hub insert 140 to maintain a sealed channel from a syringe to plurality of needles 150. The needles may optionally include a plurality of apertures (e.g., as depicted in FIG. 1A), as discussed above.

Figure 2A:
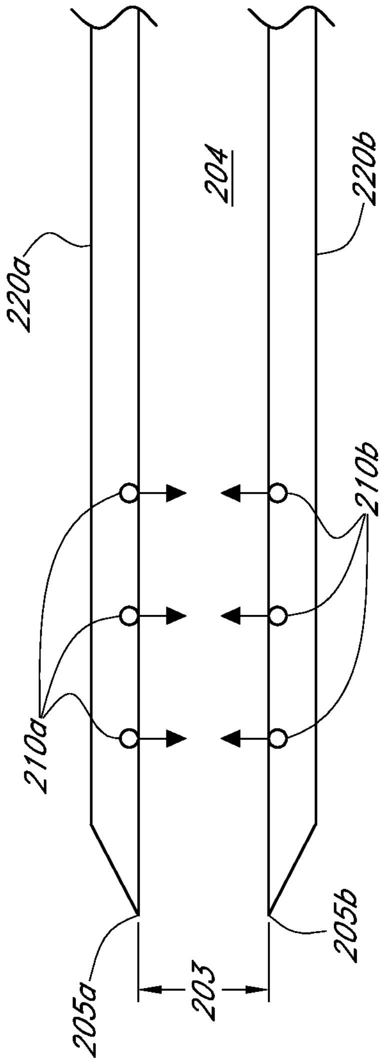
FIG. 2A illustrates a side view of an embodiment of an intracellular delivery apparatus with two barrels, each barrel having three apertures for delivering a prophylactic and/or therapeutic agent to an area in between the barrels.

The size, shape, and quantity of apertures can be selected in order to maximize the efficient delivery of injected fluid or genetic material, to create the optimal pressure within the injection cavity space to enhance cell membrane permeability, or both. Referring to FIG. 2A, an intracellular delivery device includes two needle barrels 220*a*, 220*b* each including three apertures 210*a*, 210*b* and a pointed distal tip 205*a*, 205*b*. The distal tips 205*a*, 205*b* are separated from one another by a distance 203. Moving in the proximal direction from the distal tips 205*a*, 205*b* the opening 203 forms an injection cavity space 204 formed between the needle barrels 220*a*, 220*b*. In some embodiments, the opening 203 created by the space between needle barrels 220*a*, 220*b* between the tips 205*a*, 205*b* is sufficiently large in size to enable the needle barrels 220*a*, 220*b* to surround one more or cells in the injection cavity space 204.

In some embodiments, in order to create an intracellular delivery device for the delivery of a fluid containing a desired agent to targeted tissue, a needle 220*a* and/or 220*b* may comprise a plurality of generally curvilinear apertures 210*a*, 210*b* with widths or diameters ranging from about 0.01 to about 4.0 mm. In some embodiments, the width of the apertures 210*a*, 210*b* at their widest portion is greater than, less than or equal to about 0.01 μm, 0.04 μm, 0.04 μm, 0.04 μm, 0.04 μm, 0.04 μm, 0.07 μm, 0.04 μm, 0.09 μm, 0.1 μm, 0.14 μm, 0.2 μm, 0.24 μm, 0.3 μm, 0.34 μm, 0.4 μm, 0.44 μm, 0.5 μm, 0.54 μm, 0.6 μm, 0.64 μm, 0.7 μm, 0.74 μm, 0.8 μm, 0.84 μm, 0.9 μm, 0.94 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 0.01 mm, 0.02 mm, 0.03 mm, 0.04 mm, 0.05 mm, 0.06 mm, 0.07 mm, 0.08 mm, 0.09 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1.0 mm, 1.05 mm, 1.10 mm, 1.15 mm, 1.20 mm, 1.25 mm, 1.30 mm, 1.35 mm, 1.40 mm, 1.45 mm, 1.50 mm, 1.55 mm, 1.60 mm, 1.65 mm, 1.70 mm, 1.75 mm, 1.80 mm, 1.85 mm, 1.90 mm, 1.95 mm, 2.0 mm, 2.05 mm, 2.10 mm, 2.15 mm, 2.20 mm, 2.25 mm, 2.30 mm, 2.35 mm, 2.40 mm, 2.45 mm, 2.50 mm, 2.55 mm, 2.60 mm, 2.65 mm, 2.70 mm, 2.75 mm, 2.80 mm, 2.85 mm, 2.90 mm, 2.95 mm, 3.0 mm, 3.05 mm, 3.10 mm, 3.15 mm, 3.20 mm, 3.25 mm, 3.30 mm, 3.35 mm, 3.40 mm, 3.45 mm, 3.50 mm, 3.55 mm, 3.60 mm, 3.65 mm, 3.70 mm, 3.75 mm, 3.80 mm, 3.85 mm, 3.90 mm, 3.95 mm, or within a range defined by, and including, any two of these values. In other embodiments, one can select a plurality (e.g., ten) generally curvilinear apertures 210*a*, 210*b* with diameters ranging from about 10 nm to about 2.0 mm.

By adjusting the size, shape, and quantity of apertures 210*a*, 210*b* and taking into account the physical properties of the pressure transmitting medium into which needle 220*a* and 220*b* are inserted, the intracellular delivery device can deliver a local pressure in the range of about 1 to about 5000 kilopascals. The needles described herein may be configured to deliver a fluid at a pressure in the range of greater than, less than, equal to, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 300, 400, 500, 1000, 2000, 3000, 4000, or 5000 kilopascals or any number in between these numbers. An increased local pressure in the tissue contained within the injection cavity space 204 alters the cell membrane permeability characteristics of cells within the tissue and promotes entry of an agent (e.g., DNA) into the cells.

The length of the needles 220*a* and 220*b* can vary from about 0.5 cm to about 15 cm. In certain embodiments, the needle is, is about, is at least, is at least about, is not more than, is not more than about 0.5, 0.75, 1.0, 1.25, 1.5, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 15.25, 14.5, 14.75, or 15 cm, or any number between these values. In some embodiments, the needle(s) have a length more than 1 cm. In some embodiments, the needle(s) have a length more than 15 mm. In some embodiments, the needle(s) have a length more than 20 mm.

Although the tips 205*a*, 205*b* are shown with the beveling angling towards the longitudinal axis of the device, the bevels may be angled in the opposite direction, or different directions (see FIG. 4), in order to spread tissue and deliver at least some targeted tissue through an area disposed between the needle barrels 220*a*, 220*b* and into an injection cavity space 204 disposed therebetween. In some embodiments, each tip can include multiple beveled edges, such two, three, four, five, six, or more beveled edges. This can result in a tip having generally a rotational symmetry about its axis and may provide for uniform insertion of each needle. In some embodiments, tips 205*a* and 205*b* may comprise a trocar tip, or a "quadcar" tip which has four beveled edges which may used on one or more needles in the injection devices disclose herein. In some embodiments, needles 220*a* and 220*b* may similar or different tips 205*a* and 205*b*. In some embodiments, at least one beveled edge on the needle tip faces generally the same direction as one or more apertures on the same needle. In some embodiments, none of the beveled edges on the needle tip face in generally the same direction as any of the apertures on the same needle.

The delivery pressure of an agent may affect the efficacy and safety of a treatment. For example, applying too much pressure may result in undesirable damage to the cell, while applying too little pressure may not yield a sufficient permeability shift so as to allow for uptake of the agent. The laws of fluid dynamics and associated equations can be used to generate a profile of acceptable pressures in the injection cavity space 204. For example, the needle barrel 220*a*, 220*b* geometry and the fluid characteristics of the agent, for example, viscosity and density, will affect the local pressure in the injection cavity space 204. In some embodiments, the size and shape of the apertures 210*a*, 210*b*, the fluid and delivered agent, as well as the driving pressure may be selected to produce a desired local pressure in the injection cavity space 204. The Darcy-Weisbach equation, for example, may be used to define the pressure drop with regards to the velocity of flow, the viscosity of the fluid, and the ratio of the diameter of the barrel lumen to the pipe length. The equation is useful, among other things, in determining the appropriate aperture 210*a*, 210*b* size when using different carrier medium fluids (e.g. phosphate buffered saline, glycerin, ethanol, deionized water, filtered water, various oils, emulsions, etc.), as each type of fluid has its own viscosity properties. Standard computational fluid dynamics software can be utilized in determining the optimal physical parameters of the needle barrels and apertures to achieve a desired pressure drop. However, the invention is not limited to the use of fluid for the creation of the pressure drop, and can utilize other types of pressure transmitting mediums. For instance, in some embodiments, air or other gas, such as $CO_2$ or $N_2$, may be used to transmit pressure onto tissue.

Figure 2B:
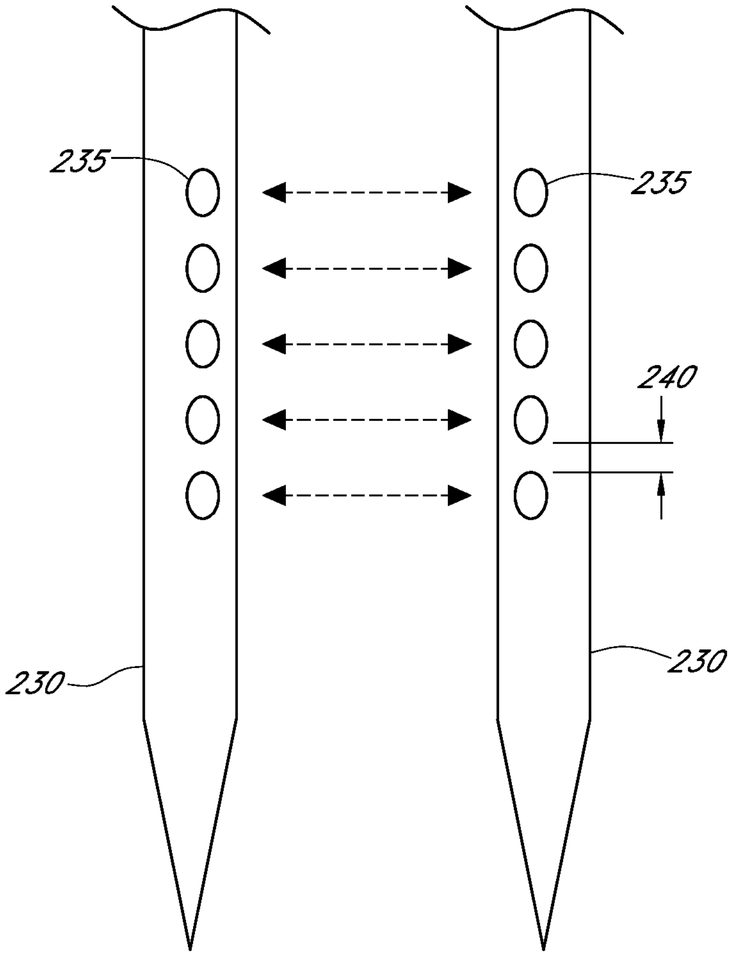
FIG. 2B illustrates an embodiment of an intracellular delivery apparatus with five apertures on each needle that are equally spaced apart.

FIG. 2B illustrates an embodiment of a hypodermic needle device or an intracellular delivery device having five apertures on each needle, the apertures spaced equally apart. Needles 230 each comprise five apertures 235 having a distance 240 between each aperture, measured from the center of each aperture, or from a corresponding edge of each aperture. The spacing between the apertures may, in some embodiments, be the same for all the apertures in the needles, or in some embodiments, distance 240 may vary. The spacing may, be about, at least, at least about, not more than, not more than about 0.01 mm, 0.05 mm, 0.1 mm, 0.15 mm, 0.2 mm, 0.25 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 1 cm, 2 cm or 3 cm. Apertures 235 are configured such that each aperture on a first needle faces a corresponding second aperture on a second needle. This arrangement results in opposing fluid flow or a cross-spray of the therapeutic material between apertures that face each other. In some embodiments, all of the apertures are configured to face (or oppose) another aperture on a different needle. In some embodiments, at least 2, 4, 6, 8, 10, 16, 20, 30, 40, 50, or 60 of the apertures are configured to face (or oppose) another aperture on a different needle.

Figure 2C:
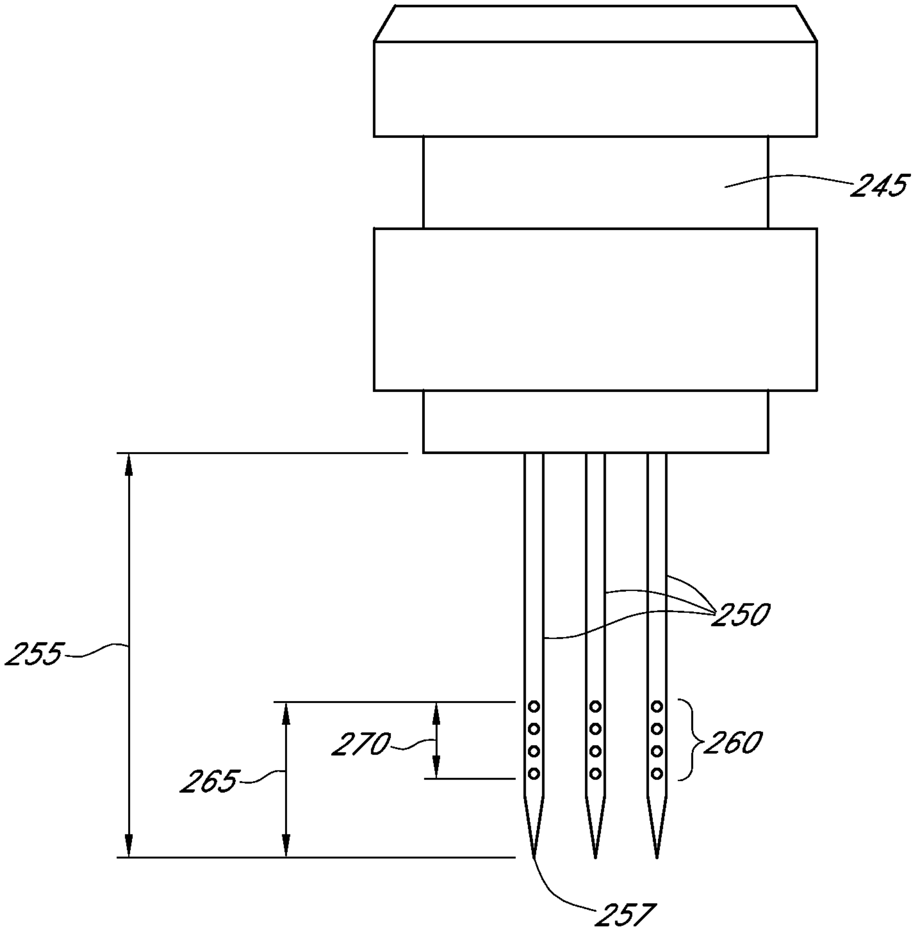
FIG. 2C illustrates an embodiment of a needle hub with three needles and depicts dimensions of the hypodermic needle hub.

FIG. 2C illustrates an embodiment of a needle hub with three needles and depicts dimensions of the hypodermic needle hub. Hub 245 includes three needles 250 fluidly coupled to a distal end of hub 245. Needles 250 each have a needle length 255 from the distal end of hub 245 to needle tip 257. Needle length 255 may vary depending upon the target tissue for delivering a prophylactic and/or therapeutic material. Distance 265 between needle point 257 and the aperture 235 on the needle furthest from needle point 257 can vary. For example, distance 265 may be between 0.1 mm and 5 cm, such as about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm 3 cm, 3.5 cm, 4 cm or more, or a range between any two of these values. In some embodiments, distance 265 may be greater than 10 mm. In some embodiments, distance 265 may be greater than 11 mm. In some embodiments, distance 265 may be greater than 15 mm. In some embodiments, distance 265 may be greater than 20 mm. Similarly, distance 270 between the aperture 235 closest to needle point 257 and the aperture furthest from needle point 257 may also vary. In some embodiments, distance 257 may be between 0.5 mm and 10 cm, such as 1 mm, 2 mm, 3 mm, 4 mm, 5 mm, 6, mm, 7 mm, 8 mm, 9 mm, 1 cm, 2 cm, 3 cm, 4 cm, 5 cm, 6 cm, 7 cm, 8 cm, 9 cm, or more.

Figure 2D:
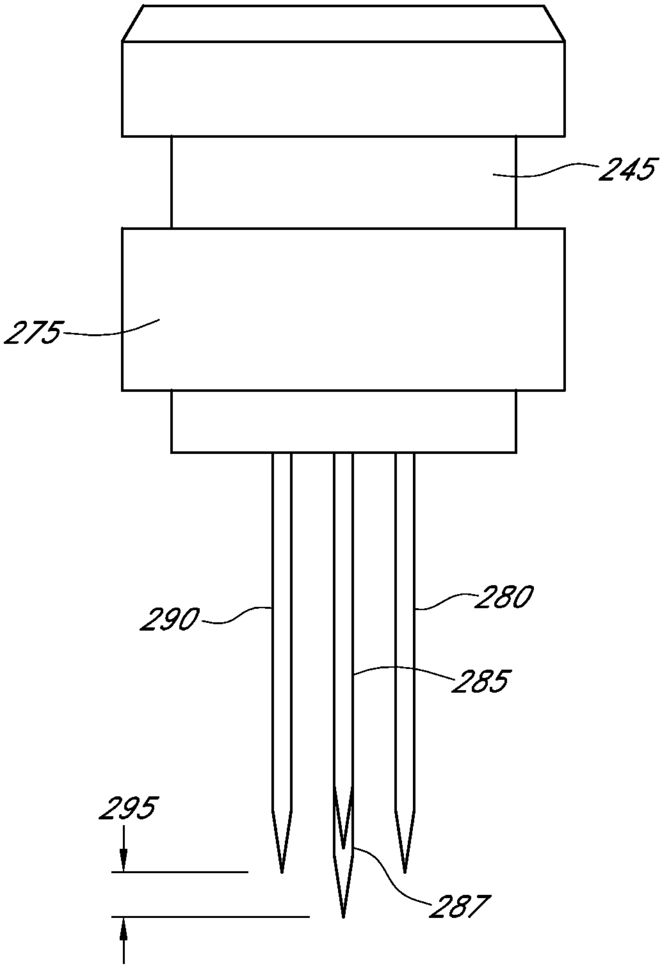
FIG. 2D illustrates an embodiment of a needle hub with four needles in a staggered configuration.

FIG. 2D illustrates an embodiment of a needle hub with four needles in a staggered configuration. Hub 275 includes four needles 280, 285, 287, and 290 fluidly coupled to the distal end of hub 245. Needle 287 is longer than needle 290 by distance 295. Needle 280 is longer than needles 285, 290 but shorter than needle 287. Numerous other variations of the staggered arrangement may also be used. In some embodiments, the injection device includes a plurality of needles, where at least one or more needles have a first length and one or more needles have second length that is longer than the first length. In some embodiments, the each needle may have a different length. In some embodiments, distance 295 may be, for example, at least 0.1 mm, 0.15 mm, 0.2 mm, 0.25 mm, 0.3 mm, 0.4 mm, 0.5 mm, 0.6 mm, 0.7 mm, 0.8 mm, 0.9 mm, 1 mm, 2 mm, 3 mm, 4 mm, or 5 mm. The difference in length between the needles may, for example, be no more than 5 cm, 2 cm, 1 cm, 5 mm, 4 mm, 3 mm, 2 mm, or 1 mm.

Figure 3:
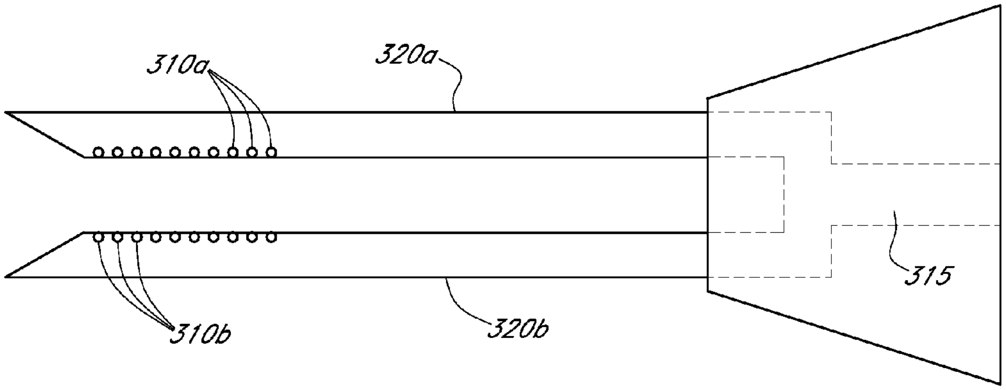
FIG. 3 illustrates a side view of an embodiment of an intracellular delivery apparatus with two barrels, each barrel having ten apertures for delivering a therapeutic agent to an area in between the barrels.

FIG. 3 illustrates a side view an embodiment of a hypodermic needle device or an intracellular delivery device having two barrels, each barrel having ten apertures for delivering a therapeutic agent to an area in between the barrels. The needle barrels 320*a*, 320*b* include lumens that are in fluid communication with a central lumen 315. A pressurized prophylactic and/or therapeutic agent can be directed through the central lumen 315 to the needle barrels 320*a*, 320*b* and can exit the needle barrels 320*a*, 320*b* via apertures 310*a*, 310*b*. Needle barrels 320*a*, 320*b* each comprise ten curvilinear apertures evenly distributed along a distal length of the barrels. The apertures 310*a*, 310*b* are configured to direct the pressurized agent towards the longitudinal axis of the device and thus, the apertures 310*a* on needle barrel 320*a* face the apertures 310*b* on needle barrel 320*b*. In one embodiment, the apertures can be disposed proximally from the tips of the barrels 320*a*, 320*b* between about 1 and about 3 mm towards the proximal ends of the barrels.

Figure 4:
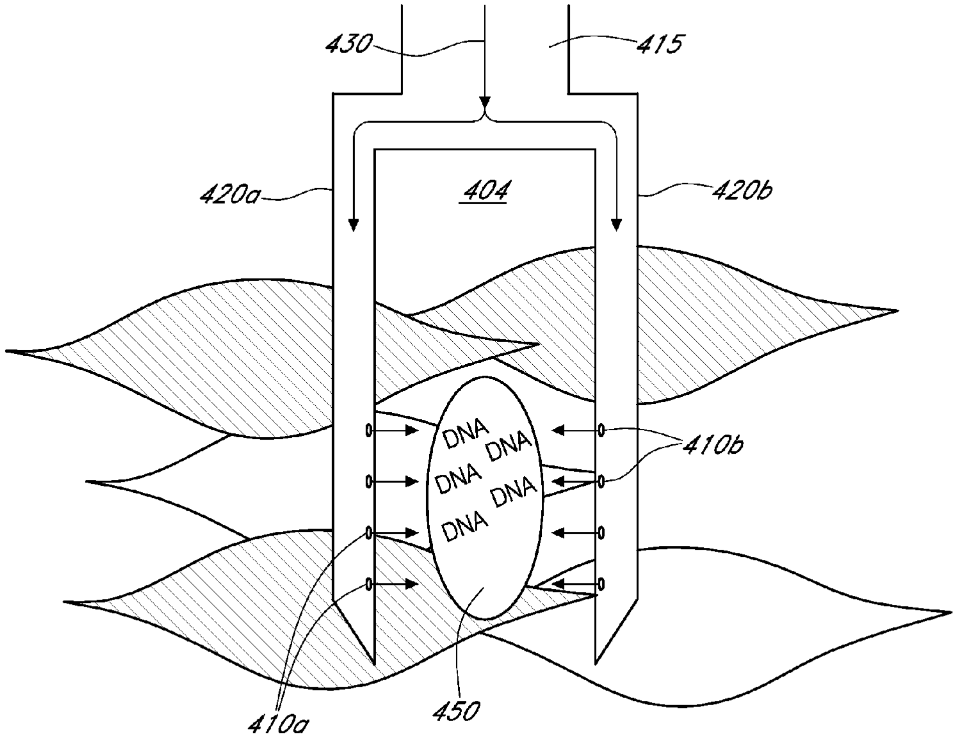
FIG. 4 illustrates a side view of an embodiment of an intracellular delivery apparatus useful for delivering a prophylactic and/or therapeutic agent including DNA into a muscle cells.

FIG. 4 illustrates a side view of an embodiment of a hypodermic needle device or an intracellular delivery device delivering a prophylactic and/or therapeutic agent including DNA into a muscle cell. The prophylactic and/or therapeutic agent 430 may comprise a gene, a nucleic acid, protein, or other large molecule for delivery into part of a cell 450, or into multiple cells, as described herein. As depicted in FIG. 4, the an intracellular delivery device has been introduced into the muscle tissue such that the injection cavity space 404 surrounds at least part of one muscle cell 450. A high pressure source of fluid (not shown) is directed into the central lumen 415 of the device and through the lumens of each of the needles barrels 420*a*, 420*b* before it is expelled through the apertures 410*a*, 410*b* into the injection cavity space 404. The high pressure that exists at each aperture 410*a*, 410*b* results from pressure applied to the fluid as it is expelled into the tissue located in the injection cavity space 404. The resulting increase in local pressure alters the permeability properties of the membrane in order to enhance uptake of the injected element. The resulting permeability change allows pharmaceutical drugs, nucleic acids and other compounds to gain access to the interior of the cell.

As described herein, the number of needle barrels may vary depending on the intended application for the injection device, the manufacturing process used to create the injection device, the amount of local pressure desired, and/or other factors. In some embodiments, the number of barrels can be equal or greater than 1, 2, 3, 4, 5, 6, 7, 8, 8, 10, or more.

Figure 5A:
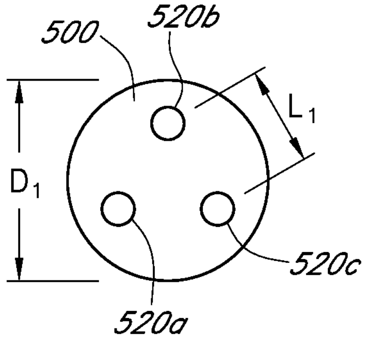
FIG. 5A is a top view of an intracellular delivery apparatus having three needles.
Figure 5B:
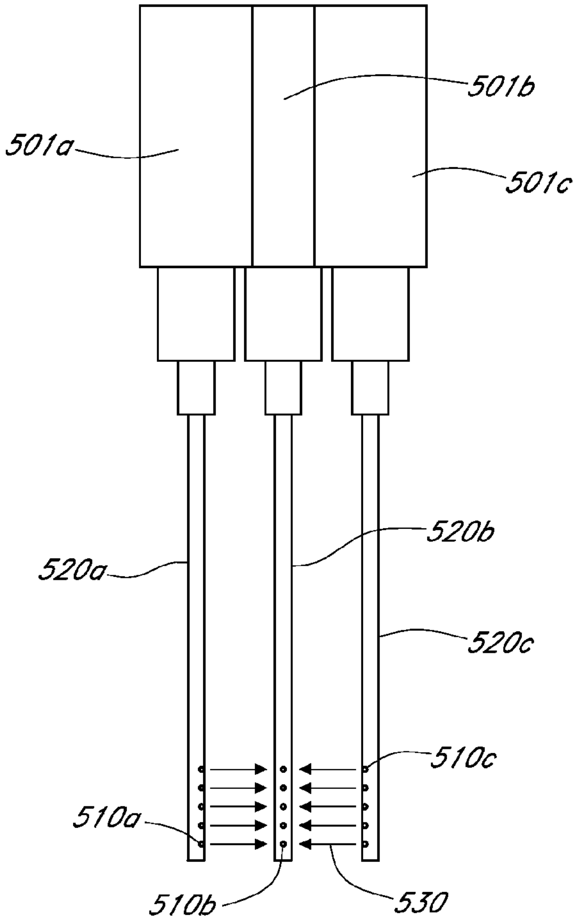
FIG. 5B illustrates a side view of an embodiment of an intracellular delivery apparatus with three barrels.

FIG. 5A illustrates a top view of an intracellular delivery device. Needle barrels 520*a*, 520*b*, 520*c* are disposed around the center of the connector or central lumen housing 500. The needle barrels 520*a*, 520*b*, 520*c* can form an equilateral, isosceles, scalene, or right triangle. The diameter $D_1$ of connector 500 can vary as can the length $L_1$ between the needle barrels 520. In some embodiment, the diameter $D_1$ of the connector 500 ranges from about 3 to about 25 mm and the length $L_1$ between the needle barrels ranges from about 1 to about 8 mm, or more. $L_1$ may be measured from the center of a barrel to the center of an adjacent barrel, or from the edge of one barrel to the corresponding edge of an adjacent barrel FIG. 5B illustrates a side view of an embodiment of a hypodermic needle device or an intracellular delivery device having three barrels. Barrels 520*a-c* are connected to three separate syringes 501*a*, 501*b*, 501*c*, respectively. The syringes can be configured to contain similar or different volumes of a therapeutic agent for delivery to a patient. In one embodiment, each syringe is configured to contain 1 mL of a prophylactic and/or therapeutic agent. Each syringe 501*a*, 501*b*, 501*c* includes a needle barrel 520*a*, 520*b*, 520*c* extending longitudinally therefrom. Each needle barrel 520 includes a plurality of apertures 510*a*, 510*b*, 510*c* facing the longitudinal axis of the device. The number of apertures 510*a*, 510*b*, 510*c* on each needle barrel 520*a*, 520*b*, 520*c* can range from one to twenty. In one embodiment, the apertures 510 on a barrel 520 are evenly distributed with one aperture disposed about over 0.2 mm. The volume range per length of needle barrel 520 can vary depending on the distance between apertures 510. In one embodiment, each millimeter of length of needle barrel 520 corresponds to 75 μl of prophylactic and/or therapeutic agent. The three syringes 501 can be arranged in an equilateral triangle shape centered around the longitudinal axis of the device with each needle barrel 520 being about equal distance from each of the other two needle barrels.

The distance between the needle barrels 520 can vary depending on the number of apertures 510. In one embodiment, each needle barrel 520 comprises ten apertures 510 and the needles are disposed about 3.0 mm apart from one another. In another embodiment, each needle barrel 520 comprises 8 apertures 510 and the needles are disposed about 2.2 mm apart from one another. In another exemplary embodiment, each needle barrel 520 comprises six apertures and the needles are disposed about 1.5 mm apart from one another. In yet another embodiment, each needle barrel 520 comprises apertures 510*a-c* and the needles are disposed about 1.0 mm apart from one another. Apertures 510*a-c* may be oriented in a variety of orientations. In some embodiments, apertures 510*a-c* may face an adjacent needle. In some embodiments, apertures 510*a-c* may face an opposite needle, and produce a cross-spray pattern as illustrated in FIG. 5C.

Figure 5C:
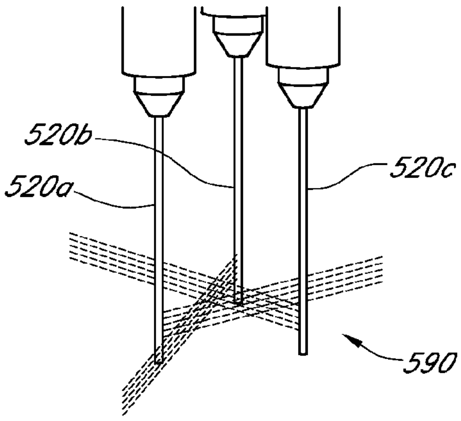
FIG. 5C illustrates a perspective view of the intracellular delivery apparatus of FIG. 5B delivering a therapeutic agent to the tissue of a subject by providing a cross-spray pattern.

FIG. 5C illustrates a perspective view of the hypodermic needle device or the intracellular delivery device of FIG. 5B delivering a therapeutic agent to the tissue of a subject 590.

Figure 6A:
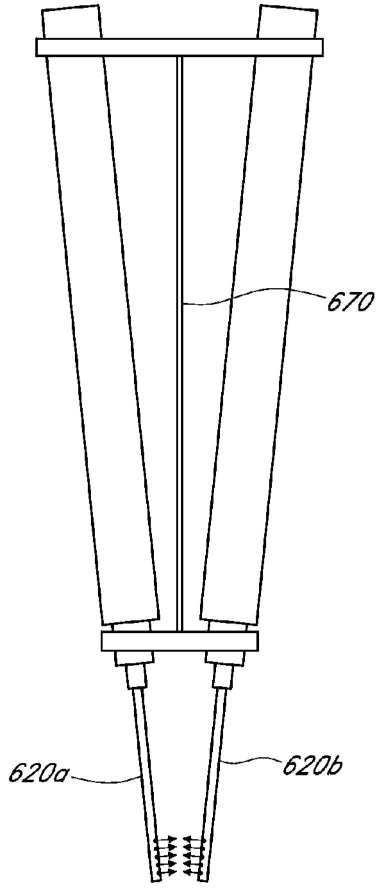
FIG. 6A illustrates a side view of an embodiment of an intracellular delivery apparatus having two barrels, wherein each barrel is disposed at an angle relative to the longitudinal axis of the device.

Referring now to FIG. 6A, a side view of an embodiment of a hypodermic needle device or an intracellular delivery device having two barrels, each barrel being disposed at an angle relative to the longitudinal axis of the device is illustrated. The injection device in FIG. 6A comprises two syringes 620*a*, 620*b* each disposed at an angle relative to the longitudinal axis of the device. A support 670 holds the syringes 620 in position relative to one another and is generally aligned with the longitudinal axis of the device.

Figure 6B:
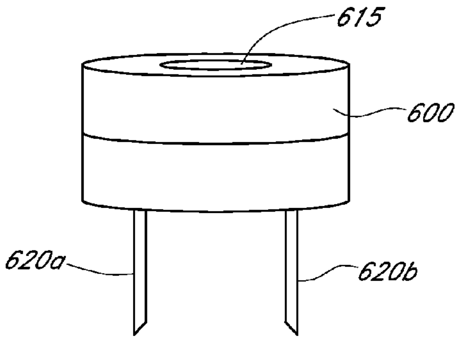
FIG. 6B illustrates a perspective view of an embodiment of an intracellular delivery apparatus with two barrels and a connector fitting.

FIG. 6B illustrates a perspective view of an embodiment of a hypodermic needle device or an intracellular delivery device having two barrels and a connector fitting. Needle barrels 620*a*, 620*b* are fluidly connected to a common lumen 615 that is housed within a housing or connector 600. Needle barrels 620*a*, 620*b* are generally parallel to one another and distribute a prophylactic and/or therapeutic agent to a subject that is directed to the barrels by the common lumen 615.

Figure 6C:
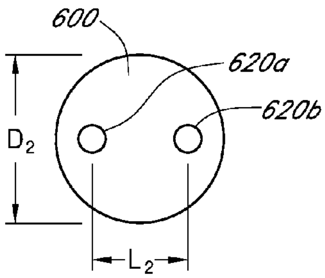
FIG. 6C illustrates a top view of an intracellular delivery apparatus with a connector fitting.

FIG. 6C illustrates a top view of the hypodermic needle device or the intracellular delivery device with a connector fitting. Needles barrels 620*a*, 620*b* can be separated one another by a length $L_2$ and the connector 600 can have a diameter or width $D_2$. The diameter $D_2$ of the connector 600 can vary as can the length $L_2$ between the needle barrels 620. In one embodiment, the diameter $D_2$ of the connector 600 ranges from about 3 to about 25 mm and the length $L_2$ between the needle barrels ranges from about 1 to about 6 mm.

Figure 7A:
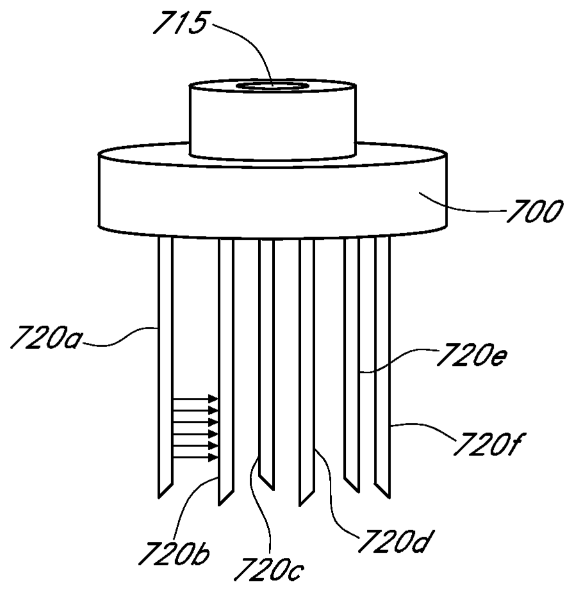
FIG. 7A illustrates a perspective view of an embodiment of an intracellular delivery apparatus with six barrels, each barrel having a plurality of apertures for delivering a prophylactic and/or therapeutic agent to the tissue of a subject.

FIG. 7A illustrates a perspective view of an embodiment of a hypodermic needle device or an intracellular delivery device having six barrels, each barrel having a plurality of apertures for delivering a prophylactic and/or therapeutic agent to the tissue of a subject. Six needle barrels 720*a-f* extend generally parallel to one another from a connector 700. The connector 700 houses a common lumen 715 that distributes a pressurized prophylactic and/or therapeutic agent to the needle barrels 720.

Figure 7B:
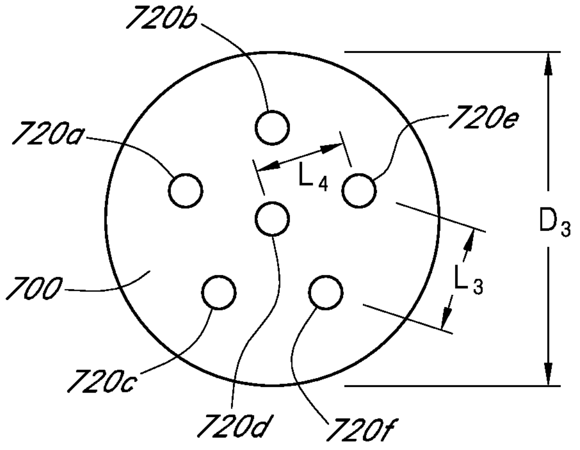
FIG. 7B is a top view of the intracellular delivery apparatus of FIG. 7A.

FIG. 7B illustrates a top view of the injection device of FIG. 7A. As shown in FIG. 7B, five of the needles barrels 720 form a pentagram or five-sided polygon centered around the center of the connector 700. Each of these five needle barrels 720 can be separated from a left and right needle barrel 720 by a length $L_3$. The sixth needle barrel 720 is disposed in the center of the five-sided polygon and separated from the other five needle barrels by a length $L_4$. The connector 700 can also have a diameter of maximum width $D_3$. In some embodiments, the diameter $D_3$ can be between about 3 and about 25 mm. The lengths $L_4$ and $L_3$ can be equal to one another or different. In some embodiments, length $L_4$ ranges from about 1 to about 6 mm and length $L_3$ ranges from about 1 to about 6 mm.

Figure 8A:
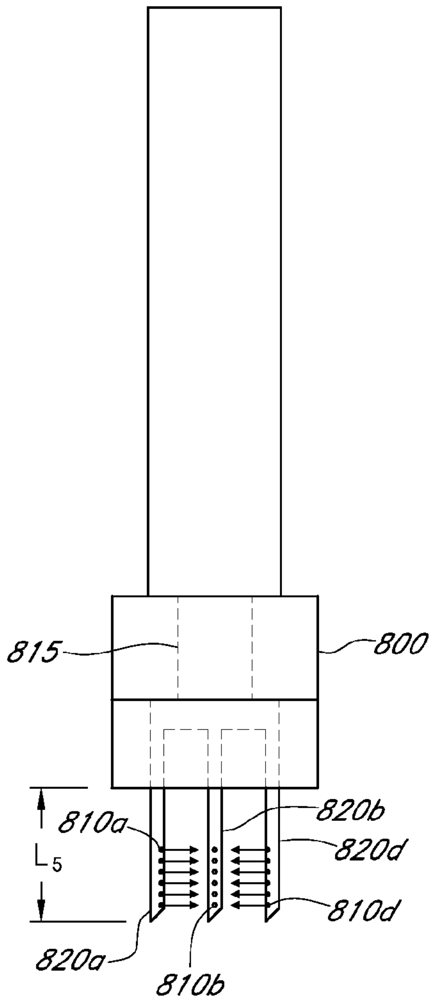
FIG. 8A illustrates a side view of an embodiment of an intracellular delivery apparatus with four barrels.

FIG. 8A illustrates a side view of an embodiment of a hypodermic needle device or an intracellular delivery device having four barrels. Needle barrels 820 are fluidly connected with a common lumen 815 housed within a connector 800. Each needle barrel 820 can include any number of inner facing apertures 810*a-d*, for example, six or ten. In some embodiments, a needle barrel 820*a-d* is disposed along the longitudinal axis of the device and includes no apertures 810*a-d*, or includes apertures 810*a-d* that face away from the center or longitudinal axis of the device. For example, needle barrel 820*b* may comprise three zones of apertures, where each zone includes apertures that face one needle selected from needle 820*a*, needle 820*c* or needle 820*d*. The zones may include apertures which each face a separate needle 820*a-d* as compared with the other zones. The needle barrels 820*a-d* can extend from the connector 800 for a length $L_5$ between about 3 and about 100 mm.

Figure 8B:
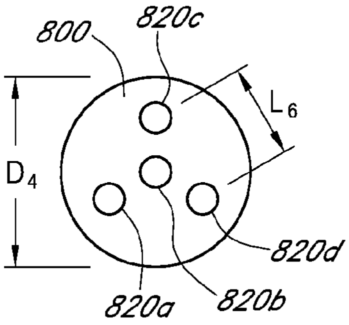
FIG. 8B illustrates a top view of an embodiment of the intracellular delivery apparatus of FIG. 8A having a "Y"-type pattern.

FIG. 8B illustrates a top view of the injection device of FIG. 8A including the connector 800 and the needle barrels 820*a-d*. Three of the needle barrels 820*a*, 820*c*, and 820*d* can be disposed in a triangle, centered around the longitudinal axis of the device and sharing a common center with the connector 800. Needle barrel 820*b* is located equidistant from the surrounding needle barrels 820*a*, 820*c*, and 820*d*. This needle arrangement may be termed a "Y-type configuration." Needle barrels 820*a-d* can be separated from one another by a length $L_6$. This length $L_6$ can vary between about 2 and about 12 mm. For example, $L_6$ can be about 3 mm or about 6 mm. The connector 800 can have a diameter or maximum width $D_4$ dimension ranging from about 3 to about 20 mm.

The an intracellular delivery device may comprise four needles as depicted in FIG. 8B. In some embodiments, $L_6$ is 6 mm. In some embodiments, $L_6$ may be from about 0.1 mm to about 6 mm. The total number of apertures in the four needles is 72. The center needle includes 36 apertures distributed in three rows along the axis of the needle, each row facing an outer needle. The three outer needles each include a single row of 12 apertures facing the center needle to produce a cross-flow between needles. The apertures may have a diameter of 0.1 mm and a spacing of about 0.2 mm. In a Y-type configuration, the central needle may have apertures positioned to provide flow in 3 directions, out from the barrel toward each of the outer needles. Similarly, the outer needles may have apertures disposed along the length of the barrel such that therapeutic agent flows from each needle barrel toward the center needle.

In some embodiments, the an intracellular delivery device includes four needles as depicted in FIG. 8B, where $L_6$ is 3 mm. The total number of apertures is the four needles is 72. The center needle includes 36 apertures distributed in three rows along the axis of the needle, each row facing an outer needle. The three outer needles each include a single row of 12 apertures facing the center needle to produce a cross-flow between needles. The apertures may have a diameter of 0.05 mm and a spacing of about 0.2 mm.

Figure 8C:
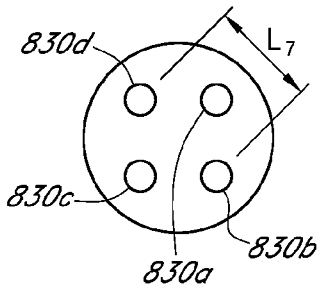
FIG. 8C illustrates another top view of an embodiment of the intracellular delivery apparatus of FIG. 8A having an "O"-type pattern.

FIG. 8C illustrates a top view of an embodiment of an intracellular delivery device of FIG. 8A. Needles 830*a-d* are arranged as the points of a square, or any other quadrilateral, such as a trapezoid, isosceles trapezoid, parallelogram, kite, rhombus, or rectangle, having a length $L_7$ between needle 830*d* and needle 830*b*. This length $L_7$ can vary between about 2 and about 12 mm, such as 3 mm or 6 mm. In some embodiments, $L_7$ may be from about 0.1 mm to about 6 mm or any distance therebetween.

In some embodiments, each needle may be configured with a first zone of apertures that face a first adjacent needle. For example, needle 830*b* may include a first zone of apertures that face needle 830*a*. In some embodiments, each needle may be configured with a second zone of apertures that oppose a second adjacent needle. For example, needle 830*b* may include a first zone of apertures that face needle 830*a* and a second zone of apertures that face needle 830*c*. In some embodiments, each needle may be configured with a third zone of apertures that oppose a third adjacent needle. For example, needle 830*b* may include: a first zone of apertures that face needle 830*a*, a second zone of apertures that face needle 830*c*, and a third zone of apertures that face needle 830*d*. In some embodiments, each needle is configured with the same number of zones. In some embodiments, each zone includes the same number of apertures. In some embodiments, each needle may comprise any one of, or a combination of the three zones. Needles 830 may optionally be configured to form a diamond-shape, such as a parallelogram or rhombus. This needle arrangement may be called an "O-type or X-type pattern," depending on the specific composition of aperture zones. In an O-type pattern, the zones on a needle 830*a-d* are configured to face only adjacent needles, resulting in a spray pattern that resembles an "O". In an X-type pattern, the zones on a needle 830*a-d* are configured to face adjacent and opposite needles, resulting in a spray pattern that, in part, resembles an "X."

In some embodiments, the injection device includes needles as depicted in FIG. 8C, where $L_7$ is 3 mm and each needle includes 18 apertures (4 times 18 is 72 total apertures) distributed in three rows along the axis of the needle. Each row faces one of the three other needles to produce a cross-flow between the needles and converging flows at about the center equidistant from the four needles. The apertures may have a diameter of 0.05 mm and a spacing of about 0.2 mm.

In some embodiments, the intracellular delivery device includes needles as depicted in FIG. 8C, where $L_7$ is 3 mm and each needle includes 24 apertures (4 times 24 is 96 total apertures) distributed in two rows along the axis of the needle. Each row faces an adjacent needle to produce a cross-flow between needles. The apertures may have a diameter of 0.1 mm and a spacing of about 0.2 mm.

In some embodiments, the intracellular delivery device comprises needles as depicted in FIG. 8C, where $L_7$ is 6 mm and each needle includes 36 apertures (4 times 36 is 144 total apertures) distributed in three rows along the axis of the needle. Each row faces one of the three other needles to produce a cross-flow between the needles and converging flows at about the center equidistant from the four needles. The apertures may have a diameter of 0.1 mm and a spacing of about 0.2 mm.

In some embodiments, the intracellular delivery device comprises needles as depicted in FIG. 8C, where $L_7$ is 6 mm and each needle includes 18 apertures (4 times 18 is 72 total apertures) distributed in two rows along the axis of the needle. Each row faces an adjacent needle to produce a cross-flow between needles. The apertures may have a diameter of 0.05 mm and a spacing of about 0.2 mm.

FIGS. 9-15 illustrate top views of various other embodiments of injection devices. Each of these injection devices includes a plurality of needle barrels and can include apertures disposed on the needle barrels. The apertures can be configured to deliver a pressurized prophylactic and/or therapeutic agent to a subject and/or apply a negative pressure to a subject.

Figure 9:
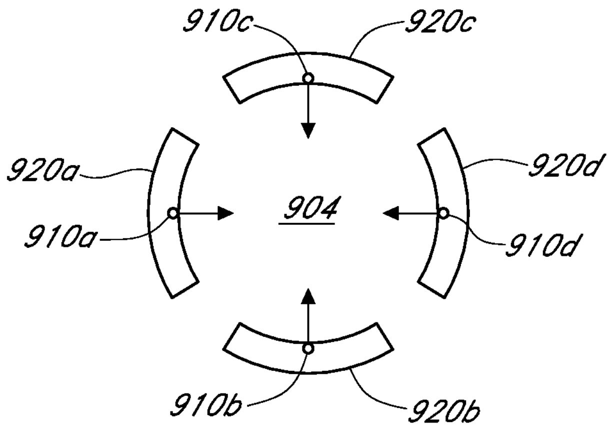
FIG. 9 illustrates a top view of an embodiment of an intracellular delivery apparatus comprising four barrels.

FIG. 9 illustrates a top view of an embodiment of a hypodermic needle device or an intracellular delivery device comprising four needle barrels. Each needle barrel 920*a-d* comprises at least one inward or center facing aperture 910 configured to deliver a pressurized prophylactic and/or therapeutic material into an injection space 904.

Figure 10A:
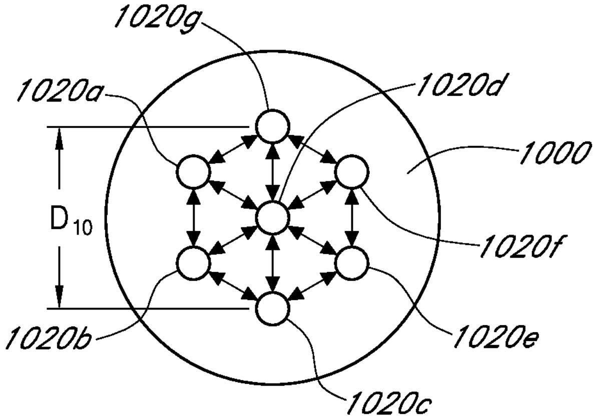
FIG. 10A illustrates a top view of an embodiment of an intracellular delivery apparatus comprising seven barrels having a star-type pattern.

FIG. 10A illustrates a top view of an embodiment of a hypodermic needle device or an intracellular delivery device comprising seven barrels. Six of the needle barrels 1020 form a hexagon with the seventh needle barrel disposed near the center of the hexagon.

Figure 10B:
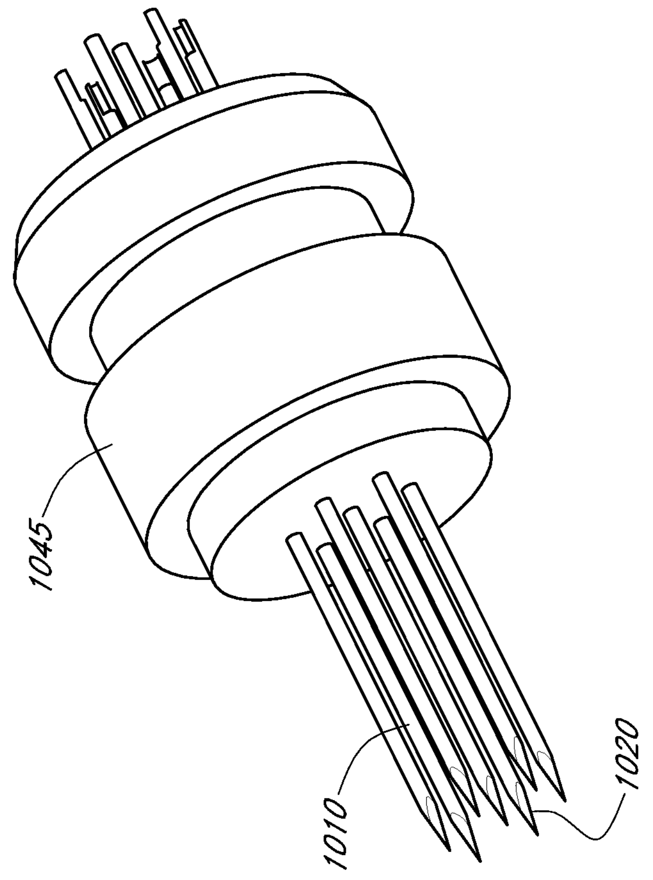
FIG. 10B illustrates a perspective view of a needle hub comprising seven barrels.

FIG. 10B illustrates a perspective view of a hypodermic needle hub comprising seven barrels. Needle barrels 1020*a-g* are disposed at least partially within a hub 1045. Referring to FIGS. 10A and 10B, six needle barrels 1020*a-c* and 1020*e-g* are arranged around a seventh center needle barrel 1020*d*. The apertures 1010 may be arranged in zones such that the apertures are directed to adjacent needle barrels and the center needle barrel. For example, on one needle barrel 1020*a* in a first zone face a first adjacent needle barrel 1020*g*, the apertures in a second zone face the second adjacent needle barrel 1020*b*, and the apertures in a third zone face the center needle barrel 1020*d*, as depicted by the arrows on FIG. 10A. Length $D_{10}$ may, in some embodiments, be any distance from about 0.5 mm to about 12 mm or any distance therebetween. In some embodiments, $D_{10}$ may be about 3 mm. In some embodiments $D_{10}$ may be about 6 mm.

Figure 11:
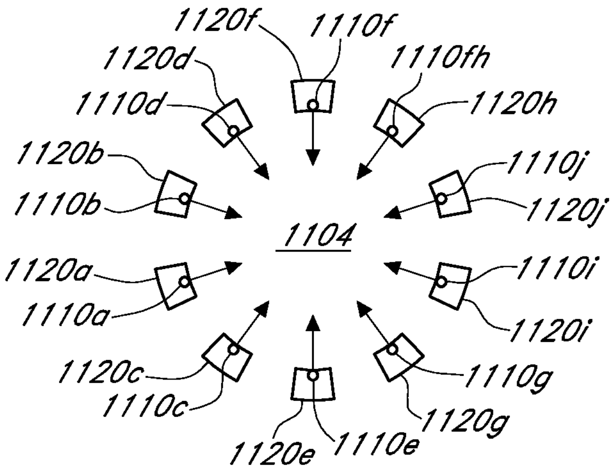
FIG. 11 illustrates a top view of an embodiment of an intracellular delivery apparatus including ten barrels.

FIG. 11 illustrates an embodiment of an intracellular delivery device having ten needle barrels 1120*a-j* with each needle barrel comprising at least one inward or center facing aperture 1110*a-j* configured to deliver a pressurized prophylactic and/or therapeutic material into an injection space 1104.

Figure 12:
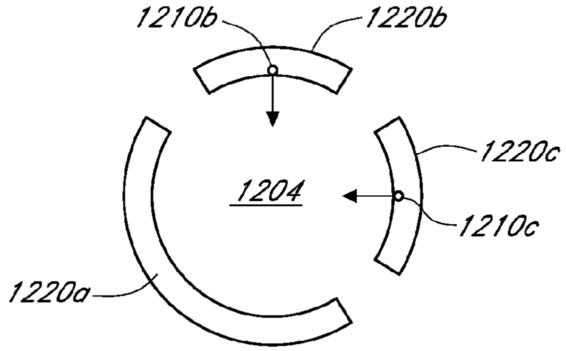
FIG. 12 illustrates a top view of an embodiment of an intracellular delivery apparatus including three barrels.
Figure 13:
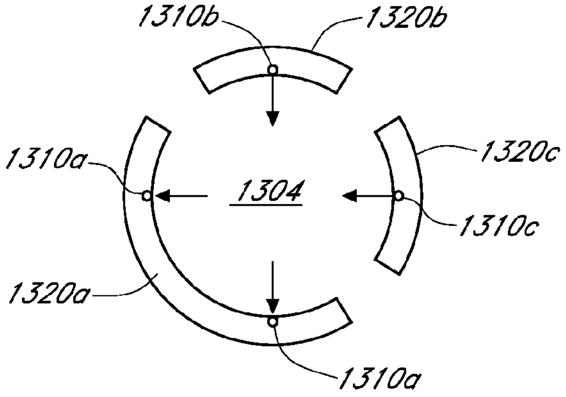
FIG. 13 illustrates a top view of an embodiment of an intracellular delivery apparatus including three barrels.
Figure 14:
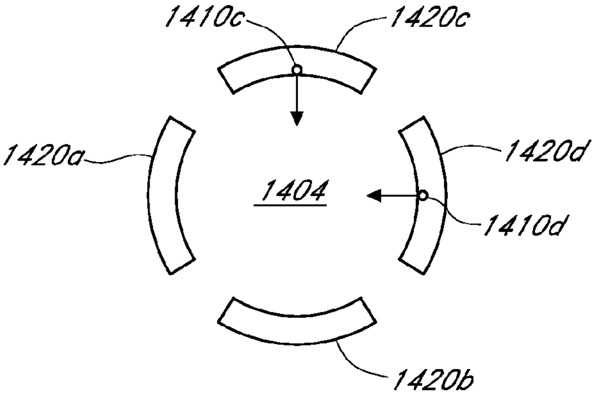
FIG. 14 illustrates a top view of an embodiment of an intracellular delivery apparatus including four barrels.

FIGS. 12-14 illustrate embodiments of intracellular delivery devices wherein a pressurized therapeutic agent is delivered asymmetrically about an injection cavity space. This may be desirable in some circumstances, for instance, to deliver more focused positive pressure on only a portion or region of the tissue, rather than on all sides.

FIG. 12 illustrates an embodiment of an intracellular delivery device having three needle barrels 1220*a-c* with two of the three needle barrels comprising at least one inward or center facing aperture 1210*b-c* configured to deliver a pressurized prophylactic and/or therapeutic material into an injection space 1204. The third needle barrel 1220*a* does not comprise any apertures configured to deliver pressurized fluid to the injection space 1204.

In some embodiments, a hypodermic needle device or an intracellular delivery device is configured to apply negative pressure via one or more apertures to an injection cavity space. Negative or counter-pressure can be used to deliver an optimal amount of pressure onto a cell membrane. In these embodiments, negative pressure is represented by arrows directed toward one or more of the needle barrels. Negative pressure can be applied by connecting certain apertures to a different lumen than other apertures.

FIG. 13 illustrates an embodiment of an intracellular delivery device having three needle barrels 1320*a-c* with two of the three needle barrels 1320*b-c* comprising at least one inward or center facing aperture 1310*b*, 1310*c* configured to deliver a pressurized prophylactic and/or therapeutic material into an injection space 1304. The third needle barrel 1320*a* comprises at least two inward or center facing apertures 1310*a* configured to apply a negative pressure to the injection space 1304.

FIG. 14 illustrates an embodiment of an intracellular delivery device having four needle barrels 1420*a-d* with two of the four needle barrels 1420*c-d* comprising at least one inward or center facing aperture 1410*c-d* configured to deliver a pressurized prophylactic and/or therapeutic material to an injection space 1404. The third and fourth needle barrels 1420*a-b* do not comprise any apertures configured to deliver pressurized fluid into the injection space 1404.

Figure 15:
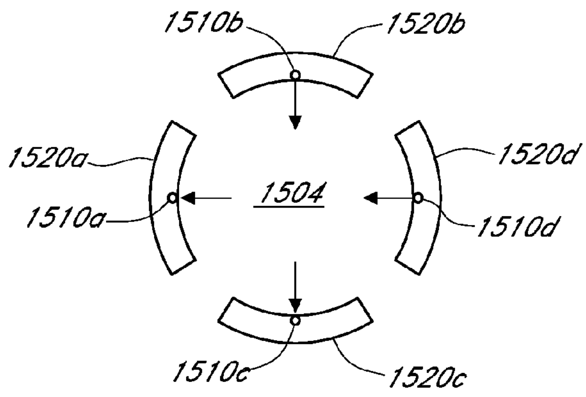
FIG. 15 illustrates a top view of an embodiment of an intracellular delivery apparatus including four barrels.

FIG. 15 illustrates an embodiment of an intracellular delivery device having four needle barrels 1520*a-d* with two of the four needle barrels 1520*b*, 1520*d* comprising at least one inward or center facing aperture 1510*b*, 1510*d* configured to deliver a pressurized prophylactic and/or therapeutic material into an injection space 1504. The third and fourth needle barrels 1520*a*, 1520*c* comprise apertures 1510*a*, 1510*c* configured to apply a negative pressure to the injection space 1504.

Figure 16:
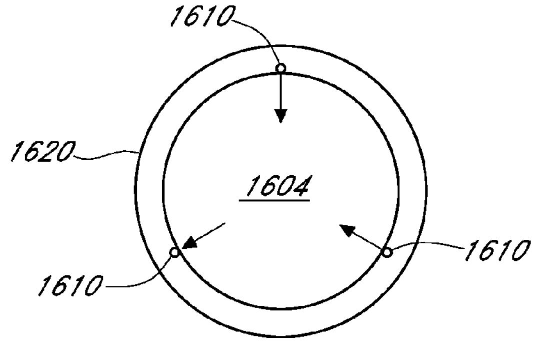
FIG. 16 illustrates a top view of an embodiment of an intracellular delivery apparatus including a ring-shaped barrel.
Figure 17:
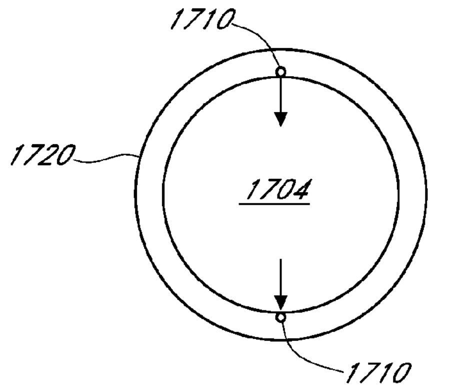
FIG. 17 illustrates a top view of an embodiment of an intracellular delivery apparatus including a ring-shaped barrel.
Figure 18:
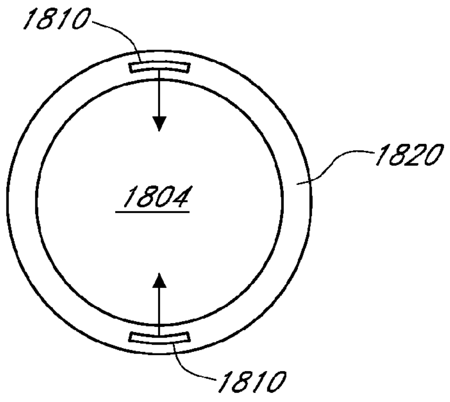
FIG. 18 illustrates a top view of an embodiment of an intracellular delivery apparatus including a ring-shaped barrel.

As described herein, the shape of each needle barrel can vary. FIGS. 16-18 illustrate embodiments of ring shaped needle barrels that include inward or center facing apertures. FIG. 16 illustrates a needle barrel 1620 that is ring shaped and includes three inward or center facing apertures 1610. Two of the three apertures 1610 are configured to deliver a pressurized prophylactic and/or therapeutic material into an injection space 1604 and the third aperture 1610 is configured to apply a negative pressure to the injection space. The apertures 1610 can form a triangle, for example, an equilateral triangle. FIG. 17 illustrates a needle barrel 1720 that is ring shaped and includes two inward or center facing apertures 1710 that face one another. One of the two apertures 1710 is configured to deliver a pressurized prophylactic and/or therapeutic material into an injection space 1704 and the other aperture 1710 is configured to apply a negative pressure to the injection space. FIG. 18 illustrates a needle barrel 1820 that is ring shaped and includes two inward or center facing apertures 1810 that face one another. Both of the apertures 1820 are configured to deliver a pressurized prophylactic and/or therapeutic material into an injection space 1804. The apertures 1810 can comprise any suitable shape, for example, a generally polygonal shape.

Figure 19:
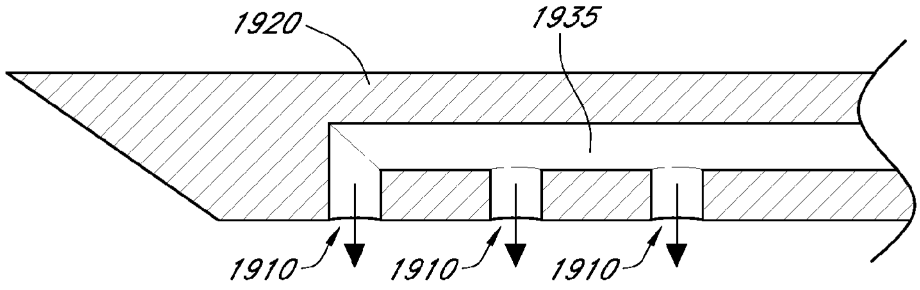
FIG. 19 illustrates a cut-away view of an embodiment of a barrel including a single lumen.

In some embodiments, a needle barrel can comprise one lumen that is fluidly connected to a plurality of apertures or more than one lumen. FIG. 19 illustrates a cut-away view of an embodiment of a barrel including a single lumen. Needle barrel 1920 comprises a single lumen 1935 and three apertures 1910 that are each fluidly connected with the single lumen 1935. The lumen 1935 is used for both the transmission of pressure and the delivery of the prophylactic and/or therapeutic agent.

Figure 20:
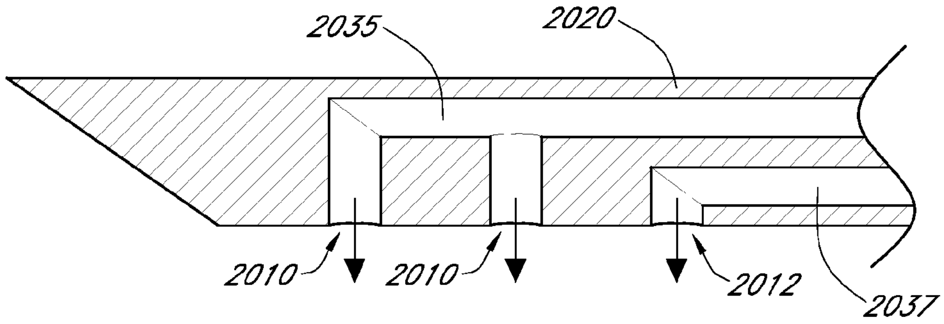
FIG. 20 illustrates a cut-away view of an embodiment of a barrel including two lumens.

FIG. 20 illustrates a cut-away view of an embodiment of a barrel including two lumens. Needle barrel 2020 comprises a first lumen 2035 that is fluidly connected with two apertures 2010. The needle barrel 2035 also includes a second lumen 2037 that is fluidly connected with a third aperture 2012. This embodiment may be employed, for example, if it becomes desirable to use a first lumen for the delivery of a pressurized prophylactic and/or therapeutic agent and a second lumen for the delivery of another fluid, prophylactic and/or therapeutic agent, and/or the application of negative pressure, or vice versa.

In some embodiments, an adjustable delivery unit for use with an adjustable intracellular delivery device comprises a channel configured to receive the hypodermic needle, a handle which operates to enclose the syringe and needle hub within the channel such that the closed ends of the needle barrels protrude from the channel and are available to engage a biological specimen, a charging element configured to be charged by the operation of the handle, the charging element coupled to a trigger and the syringe such that operation of the trigger releases the charging element, wherein the charging element acts on the syringe, thereby displacing prophylactic and/or therapeutic material out of the syringe. In some embodiments, the adjustable delivery unit comprises a spring configured to be compressed by the operation of the handle and configured to decompress upon operation of the trigger.

Figure 21A:
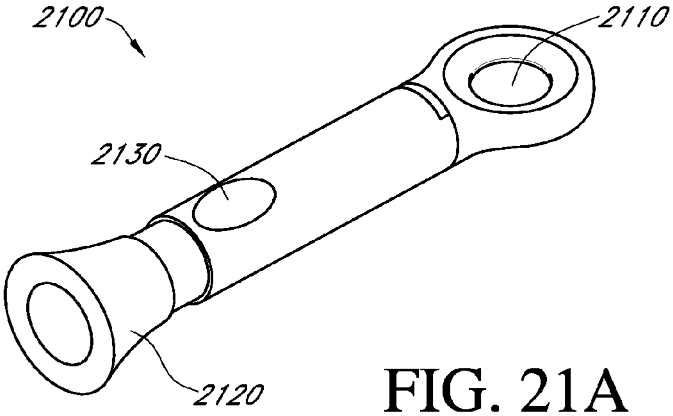
FIG. 21A-D are perspective and side views of one embodiment of a spring-actuated feature for use with the intracellular delivery devices described herein.

FIG. 21A is one example of spring-actuated device that can be used with the needles devices described herein. Spring-actuated device 2100 includes loading ring grip 2110 on one side and depth adjusting member 2120 on an opposite side. Depth adjustment member 2120 may rotatably engage spring-actuated device 2100 and be configured to adjust the depth that needles penetrate tissue when administering to a subject. Trigger button 2130 can be pressed to trigger the device to compress the needle plunger and inject prophylactic and/or therapeutic material.

Figure 21B:
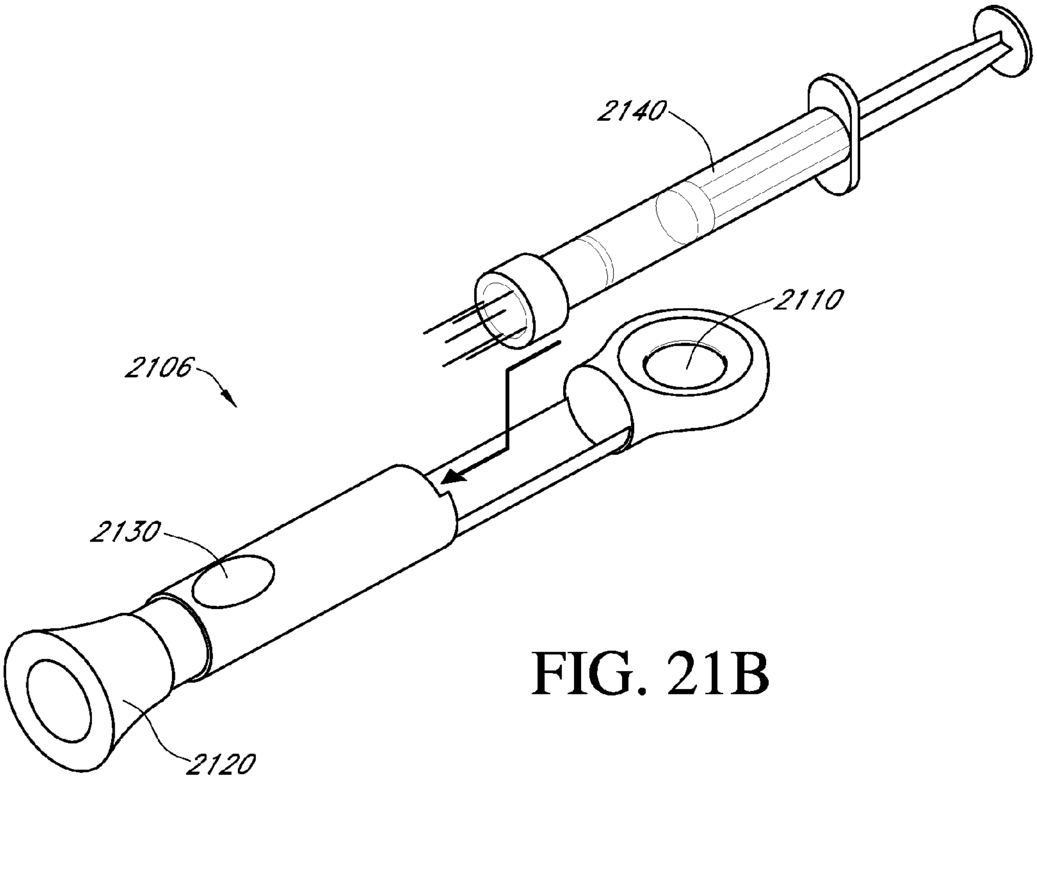
Figure 21C:
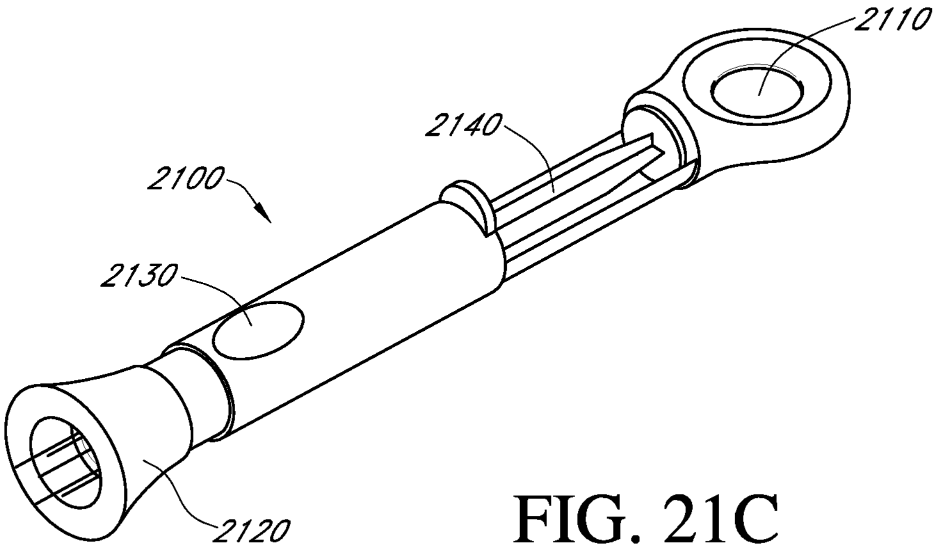
Figure 21D:
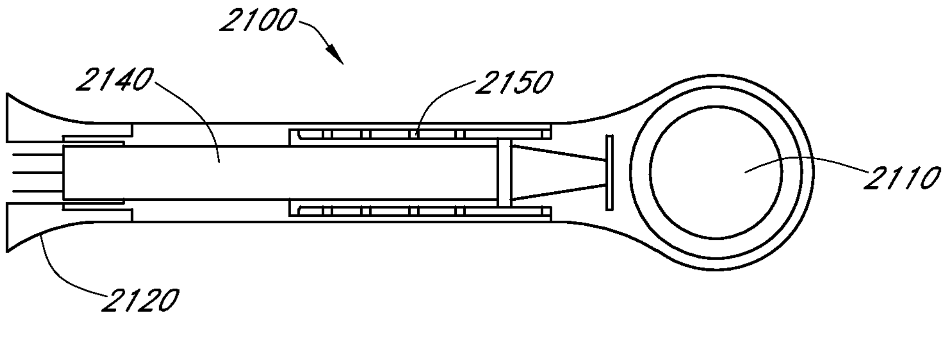

FIG. 21B shows intracellular delivery device 2140 being inserted into spring actuated device 2100. Loading ring grip 2110 is withdrawn so that the needles can be inserted into a cavity of spring actuated device 2100. FIG. 21C shows an intracellular delivery device 2140 loaded within spring actuated device 2100. FIG. 21D shows a side view of spring-actuated device 2100 where springs 2150 are disposed along the lumen of spring-actuated device 2120 extending along a length of intracellular delivery device 2140. Springs 2150 are configured to extend when loading ring grip 2110 is withdrawn and compress the plunger of syringe 2140 upon pressing trigger button 2130.

Figure 22A:
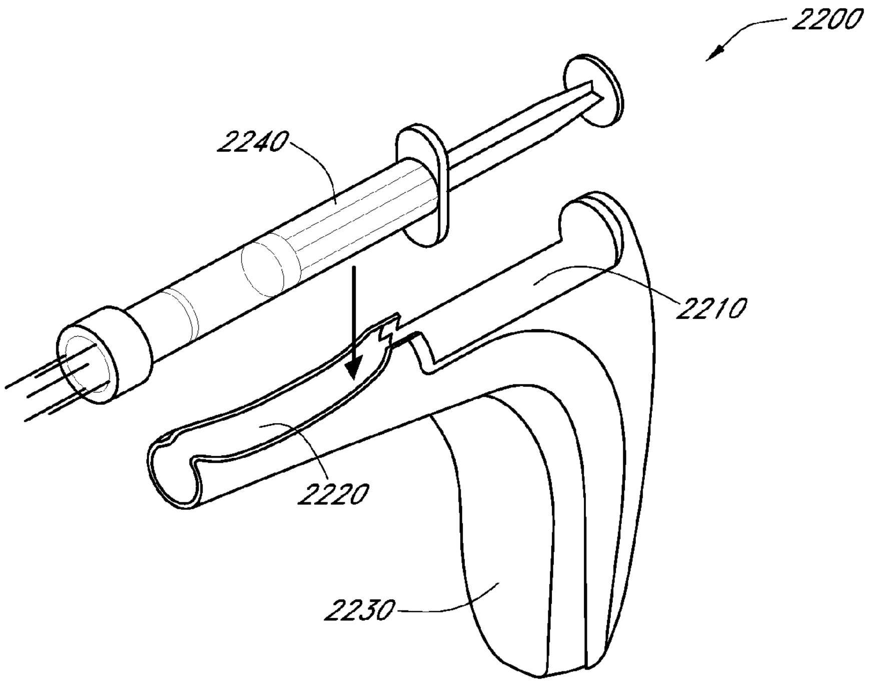
FIG. 22A-B are perspective and side view of one embodiment of a trigger feature for use with the intracellular delivery devices described herein.
Figure 22B:
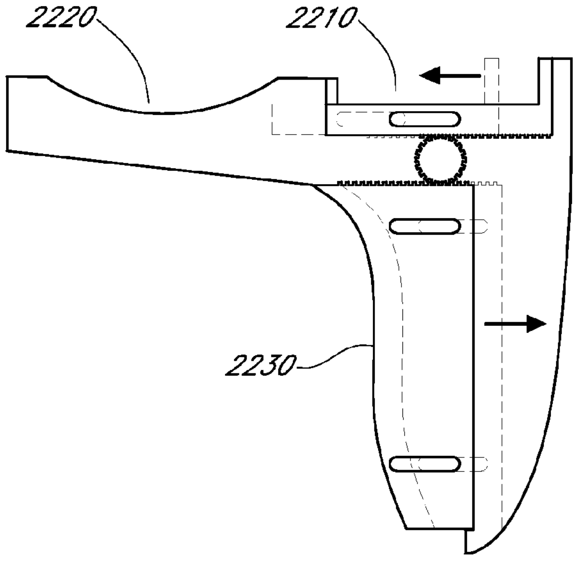

FIG. 22A is a perspective view of one embodiment of a spring-actuated delivery device for using with the injection needle devices of the present application. Spring actuated trigger device 2200 includes plunger aperture 2210 configured to receive the plunger portion of the syringe, and barrel aperture 2220 configured to receive the barrel portion of the syringe. Trigger 2230 is configured so that squeezing trigger 2230 depresses the plunger of a syringe. FIG. 22A depicts needle device 2240 being inserted into trigger device 2200. Needle device 2240 may be any needle device or needle hub as described herein.

FIG. 22D is a side view of trigger device 2200 where trigger 2230 is coupled to plunger aperture 2210 (e.g., coupled by a lever or gear) so that squeezing trigger 2230 compressed the plunger of the needle device and injects the prophylactic and/or therapeutic material.

Figure 23B:
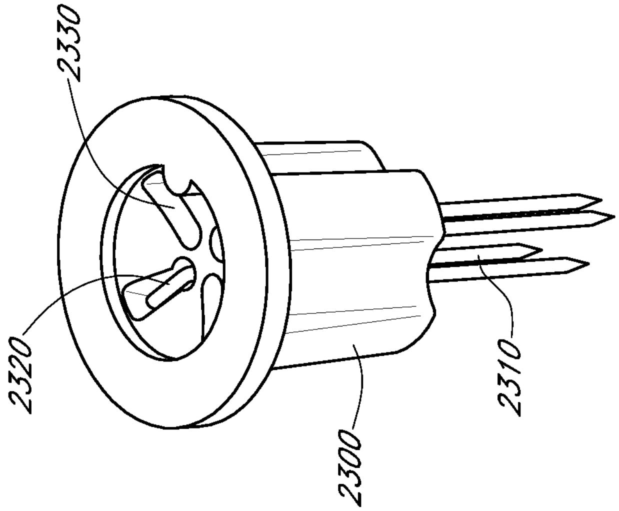
FIG. 23A-C illustrate an embodiment of a needle hub having a top hub portion and a bottom hub portion.
Figure 23A:
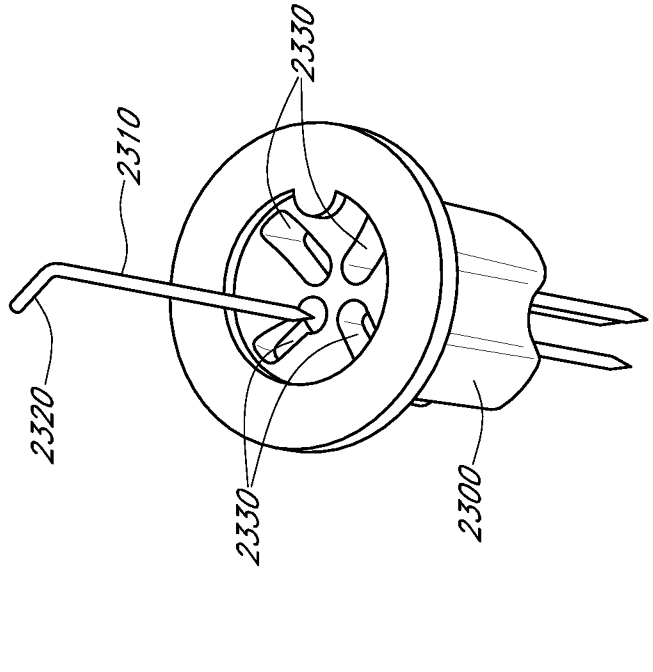
Figure 23C:
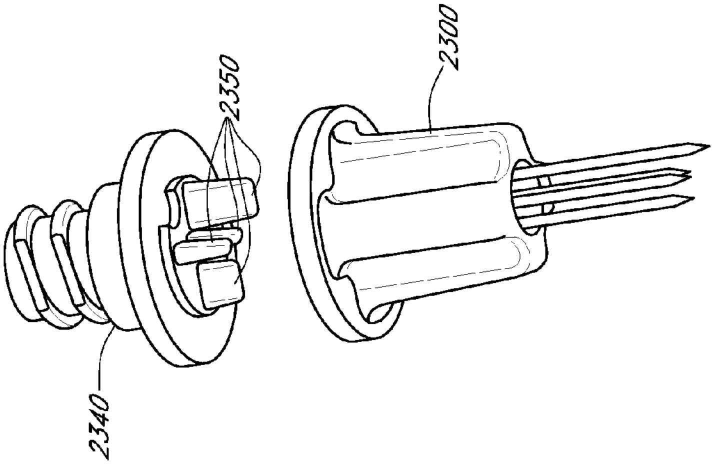

FIG. 23A illustrate an embodiment of a needle hub. Bottom-hub component 2300 is configured to receive a plurality of needles, each needle having needle barrel 2310 and hub-engaging member 2320 disposed at one end of the needle. Bottom-hub component 2300 includes apertures 2330 that receive the needle barrel 2310 and engage hub-engaging member 2320 to maintain the needle within the hub. FIG. 23B illustrates the needles after being inserted into apertures 2330. The depth of apertures 2330 may vary so that the needles are staggered relative to each other (e.g., as depicted in FIG. 2D). FIG. 23C shows top-hub component 2340 having aperture-engaging members 2350 that are configured to engage apertures 2330 when top-hub component 2340 is disposed on bottom-hub component 2300. Aperture-engaging members 2350 can secure the hub-engaging member 2320 within the hub. Bottom-hub component 2300 and top-hub component 2340 may be secured together by, for example, welding the two components together.

Figure 24:
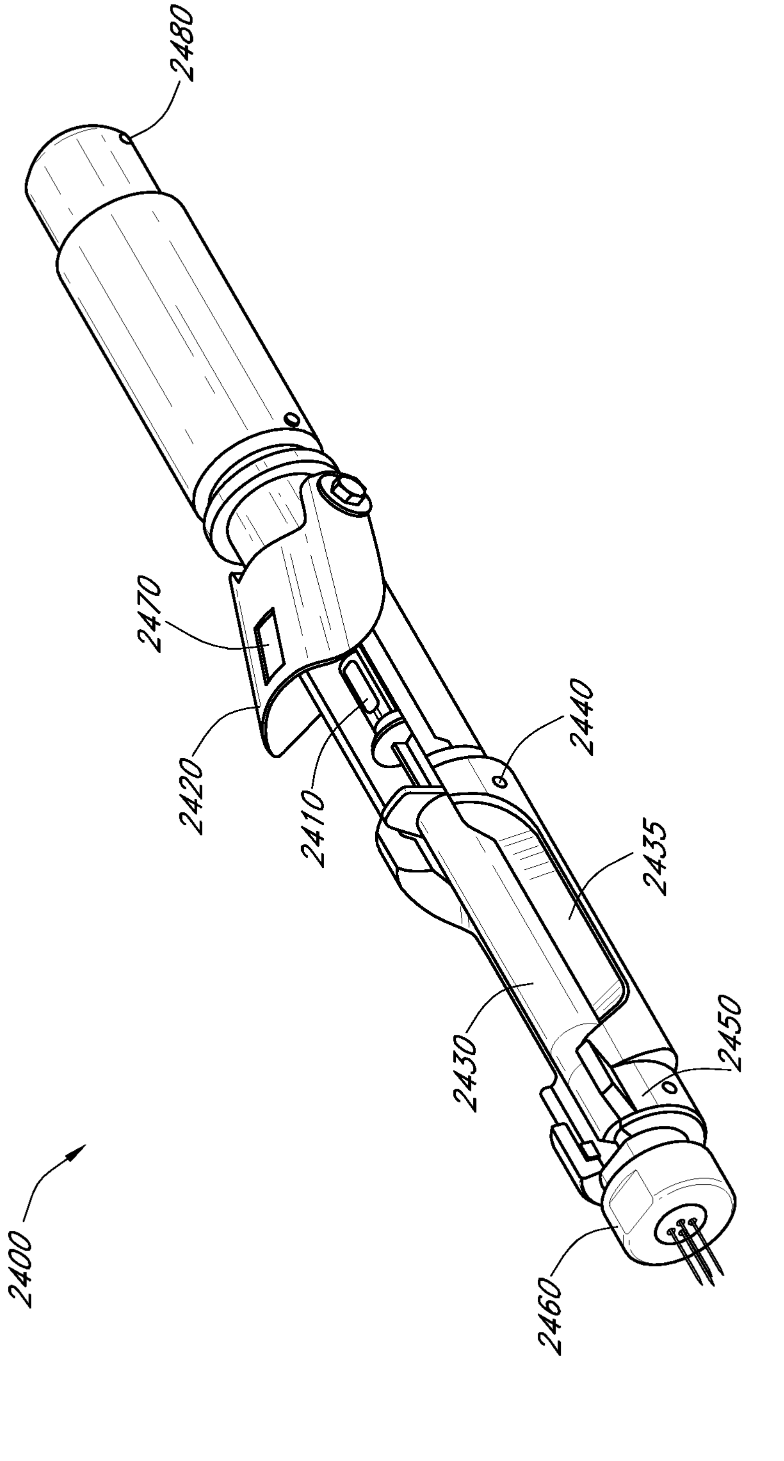
FIG. 24 illustrates a perspective view of one embodiment of an adjustable delivery feature for use with the intracellular delivery devices described herein.

FIG. 24 is perspective view of one embodiment of an adjustable delivery device or adjustable delivery unit for use with an intracellular delivery device. Adjustable delivery unit (ADU) 2400 includes spring piston 2410 coupled to spring trigger 2420. Spring piston 2410 is configured to depress the plunger in syringe 2430 when spring trigger 2420 is actuated (e.g., by depressing). Syringe 2430 is secured within lumen 2435 of ADU 2400 by ball-bearing 2440 and collar 2450. Syringe 2430 is coupled to hub 2460 including one or more needles for injecting a prophylactic and/or therapeutic material. Hub 2460 can have any of the designs disclosed herein. ADU 2400 may optionally include slot 2470 through the body of ADU 2400 and spring trigger 2420. Slot 2400 can be configured to receive a priming member that compresses spring piston 2410 before delivering the prophylactic and/or therapeutic material. ADU 2400 may also optionally include threaded adjuster 2480 that is rotatably coupled to spring piston 2410 and configured to adjust the force (or pressure) applied to the syringe when spring trigger 2420 is actuated.

Figure 25:
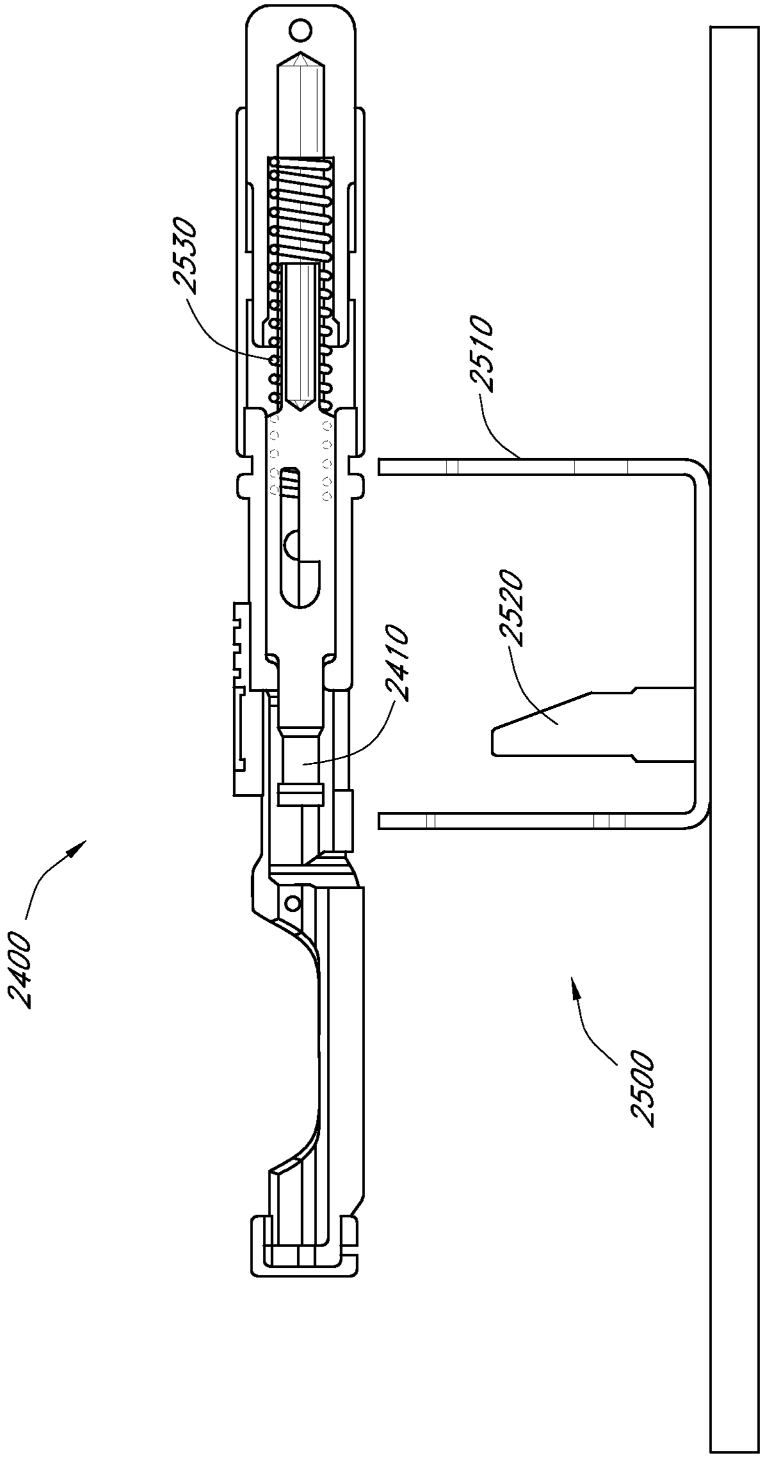
FIG. 25 illustrates a cross-sectional view of one embodiment of an adjustable delivery unit for use with an intracellular delivery device.

FIG. 25 illustrates a cross-sectional view of one embodiment an adjustable delivery unit with a priming jig. ADU 2400 may be configured to be operated with priming member which couples to an alignment aid 2510 and a priming jig 2520. The ADU 2400 may be seated in alignment aid 2510 and engaged with priming jig 2520, thereby raising spring trigger 2420, and allowing access to lumen 2435. Syringe 2430 is inserted into lumen 2435, and syringe 2430 is fastened to secure the syringe within the lumen of ADU 2400. The primed ADU 2400 can now be removed from alignment aid 2510 for use in a subject. To dispense the prophylactic and/or therapeutic material, spring trigger 2420 is depressed, spring 2530 is released, thereby operating spring piston 2410 which, in turn, operates the plunger of syringe 2435.

In some embodiments, the trigger device and spring can be configured to perform any of the methods of delivering the prophylactic and/or therapeutic material using the needles devices disclosed herein. For example, the trigger device can configured to deliver the prophylactic and/or therapeutic material within a time period (e.g., about 1 second or less), apply a maximum force or pressure to the prophylactic and/or therapeutic material (e.g., about 50-150 N or about 50 to 5000 kPa), or deliver the therapeutic material at a maximum rate (e.g., at least about 2.5 mL/s).

Figure 26:
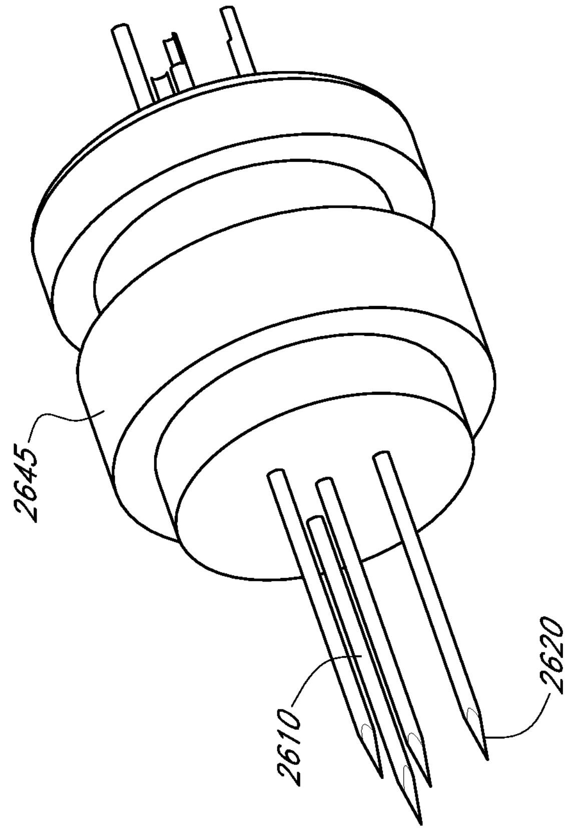
FIG. 26 illustrates an embodiment of an intracellular delivery apparatus having slit-type apertures and closed ends.

FIG. 26 illustrates an embodiment of an intracellular delivery device having slit-type apertures and closed ends.

Four needle barrels 2620 arranged in a Y-type pattern. The four needle barrels 9120 are disposed partially within hub 2645 with a center needle and three outer needles positioned equidistant from the center needle and from each other. The aperture 2610 may comprise at least one elongate slit having a first dimension along the axis of the needle barrel and a second dimension perpendicular to the axis of the needle barrel.

The first dimension of aperture 2610 may, for example, be greater than, equal to, or less than about 0.01 μm, 0.04 μm, 0.04 μm, 0.04 μm, 0.04 μm, 0.04 μm, 0.07 μm, 0.04 μm, 0.09 μm, 0.1 μm, 0.14 μm, 0.2 μm, 0.24 μm, 0.3 μm, 0.34 μm, 0.4 μm, 0.44 μm, 0.5 μm, 0.54 μm, 0.6 μm, 0.64 μm, 0.7 μm, 0.74 μm, 0.8 μm, 0.84 μm, 0.9 μm, 0.94 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 0.1 mm, 0.2 mm, 0.3 mm, 0.4 mm, 0.5 mm, 0.6 mm, 0.7 mm, 0.8 mm, 0.9 mm, 1 mm, 1.05 mm, 1.10 mm, 1.15 mm, 1.20 mm, 1.25 mm, 1.30 mm, 1.35 mm, 1.40 mm, 1.45 mm, 1.50 mm, 1.55 m, 1.60 mm, 1.65 mm, 1.70 mm, 1.75 mm, 1.80 mm, 1.85 mm, 1.90 mm, 1.95 mm, or 2.0 mm or within a range defined by, and including, any two of these values.

The second dimension of aperture 2610 may, for example, be greater than, equal to, or less than about 0.01 μm, 0.04 μm, 0.04 μm, 0.04 μm, 0.04 μm, 0.04 μm, 0.07 μm, 0.04 μm, 0.09 μm, 0.1 μm, 0.14 μm, 0.2 μm, 0.24 μm, 0.3 μm, 0.34 μm, 0.4 μm, 0.44 μm, 0.5 μm, 0.54 μm, 0.6 μm, 0.64 μm, 0.7 μm, 0.74 μm, 0.8 μm, 0.84 μm, 0.9 μm, 0.94 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 0.1 mm, 0.2 mm, 0.3 mm, 0.4 mm, 0.5 mm, 0.6 mm, 0.7 mm, 0.8 mm, 0.9 mm, 1 mm, 1.05 mm, 1.10 mm, 1.15 mm, 1.20 mm, 1.25 mm, 1.30 mm, 1.35 mm, 1.40 mm, 1.45 mm, 1.50 mm, 1.55 m, 1.60 mm, 1.65 mm, 1.70 mm, 1.75 mm, 1.80 mm, 1.85 mm, 1.90 mm, 1.95 mm, 2.0 mm, 2.05 mm, 2.10 mm, 2.15 mm, 2.20 mm, 2.25 mm, 2.30 mm, 2.35 mm, 2.40 mm, 2.45 mm, 2.50 mm, 2.55 mm, 2.60 mm, 2.65 mm, 2.70 mm, 2.75 mm, 2.80 mm, 2.85 mm, 2.90 mm, 2.95 mm, 3.0 mm, 3.1 mm, 3.2 mm, 3.3 mm, 3.4 mm, 3.5 mm, 3.6 mm, 3.7 mm, 3.8 mm, 3.9 mm, or 4.0 mm or within a range defined by, and including, any two of these values.

In some embodiments, the at least one slit may have a first dimension of about 2.15 mm and a second dimension of about 0.05 mm. The elongate slits may have any aperture dimensions as described herein, provided that the first dimension is greater than the second dimension. The apertures 2610 on the outer needles 2620 may be configured such that they face the center needle, and the apertures on the center needle may be configured to face each outer needle respectively.

Figure 27A:
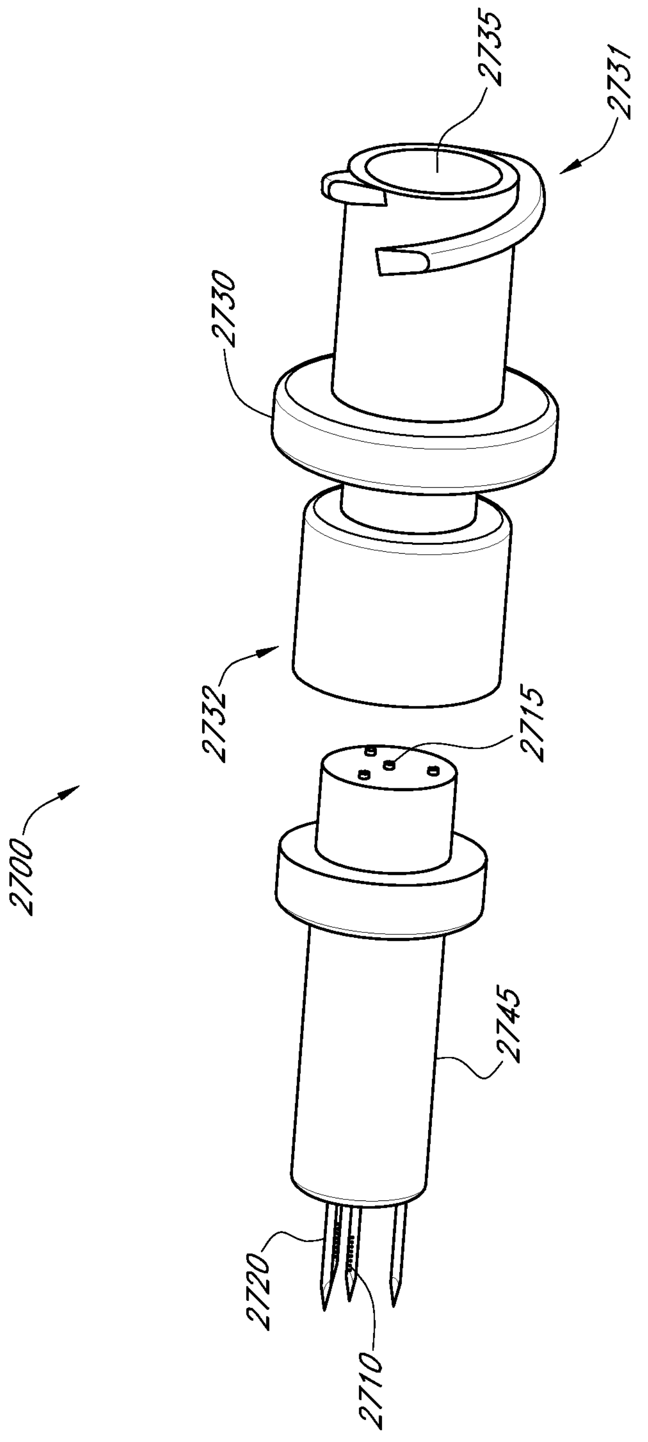
FIGS. 27A-C illustrate embodiments of an intracellular delivery apparatus having a micro-hub and closed ended needles.
Figure 27B:
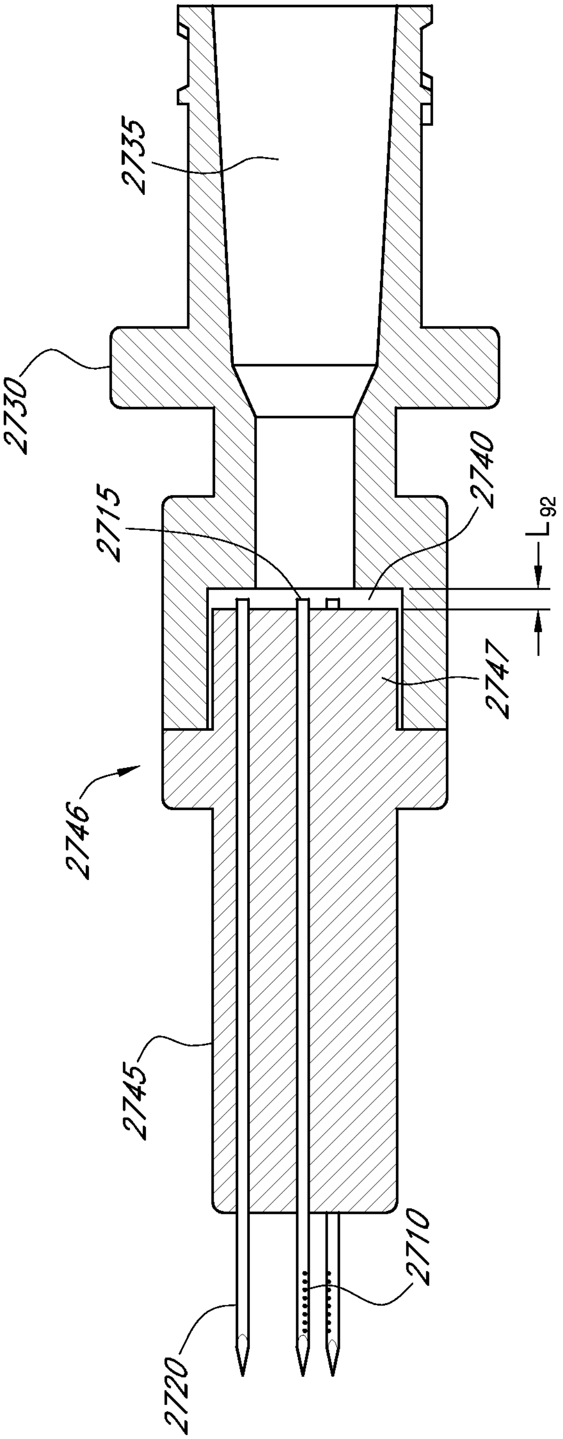
Figure 27C:
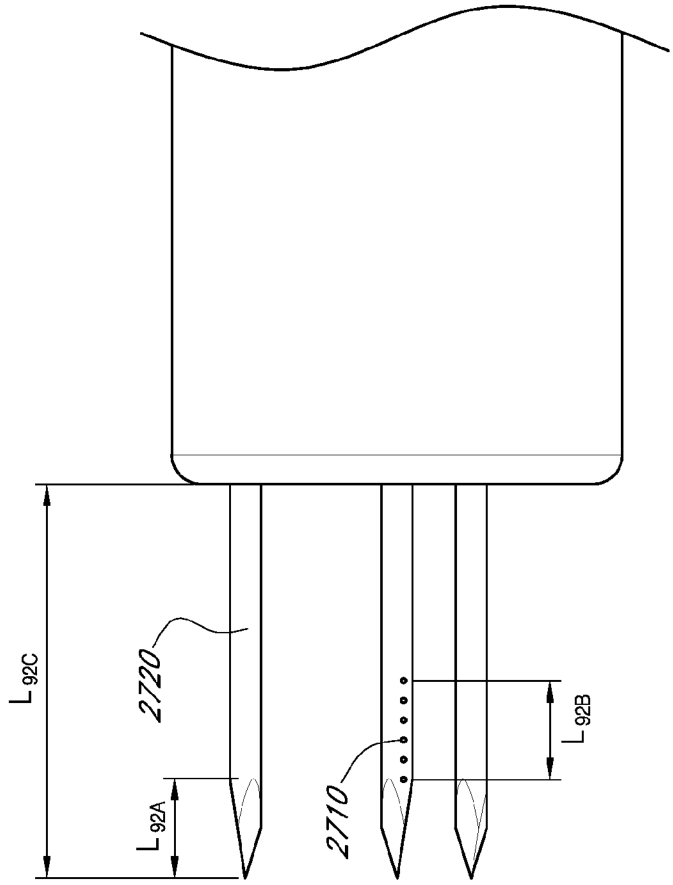

FIGS. 27A-C illustrate an embodiment of an intracellular delivery device having a plurality of needles partially disposed within a micro-hub. The hub of this device is a micro-hub because of its smaller size relative to the injection devices described elsewhere herein.

Referring to FIG. 27A, an exploded perspective view of a micro-hub injection device 2700 is depicted. Referring to FIG. 27B, side cutaway view of a micro-hub injection device is depicted. Micro-hub injection device 2700 comprises a plurality of needle barrels 2720 disposed within micro-hub 2745 such that the portion of the needle barrel comprising apertures is not disposed within the micro-hub. Needle barrels 2720 comprise a plurality of apertures 2710 as described elsewhere herein. The apertures are disposed along the length of the needle barrels and are disposed on the portion of needle barrel 2720 not disposed within micro-hub 2745. Micro-hub 2745 may be generally of cylindrical shape.

The micro-hub intracellular delivery device also comprises a luer connector 2730. Luer connector 2730 is configured to mate with a luer fitting on a syringe on a first end 2731 and micro-hub 2745 on a second end 2732. Luer connector forms a conduit 2735 passing through the center of luer connector 2730. The conduit 2735 provides a flow path for fluid through luer connector 2735. The first end 2731 of luer connector 2730 may mate with a luer fitting on a syringe using a threaded connection, a friction fit, or other suitable attaching method. The second end 2732 of luer connector 2730 which mates with micro-hub 2745 has an internal hollow diameter sized to receive a first cylindrical diameter of hub 2745.

Micro-hub 2745 has a first cylindrical diameter 2746, which is sized to provide a surface which is in direct contact with a surface of luer connector 2730. Micro-hub 2745 has a second cylindrical diameter 2747, which is sized to fit within second end 2732 of a portion of luer connector 2730. The second cylindrical diameter 2747 of micro-hub 2745 which corresponds to the portion of micro-hub 2745 which is disposed within second end 2732 of luer connector 2730 is sized such that a gap $L_{92}$ is created when needle holder 2745 is fully engaged within luer connector 2730. In some embodiments, $L_{92}$ may be approximately 0.5 mm. The gap is sized to create a chamber 2740 between an end of micro-hub 2745 and the second end 2732 of luer connector 2730 which allows for fluid which flows through luer connector 2730 to access the open end 2715 of each needle barrel 2720. Chamber 2740 provides fluid communication between the open end 2715 of each needle barrel 2720 and chamber 2735 such that fluid from an attached syringe may ultimately flow through all apertures 2710 on all needle barrels 2720.

FIG. 27C illustrates a view of a micro-hub intracellular delivery device having trocar-tip needles. Trocar-tip needles have three beveled surfaces defined by planes intersecting at an angle relative the long axis of the needle barrel and culminating in a point. Referring to FIG. 27C, $L_{92A}$ may, in some embodiments, be from about 0.01 mm to about 3 mm. In some embodiments, $L_{92A}$ is about 1 mm. In some embodiments, $L_{92B}$ may be from about 0.01 mm to about 4 mm. In some embodiments, $L_{92B}$ is about 1 mm. In some embodiments, $L_{92c}$ may be from about 1 to about 6 mm. In some embodiments, $L_{92c}$ is about 4 mm. Needle barrels 2720 may, for example, have 6 apertures 2710 per needle barrel, each aperture having a diameter of about 0.5 mm and spaced about 0.2 mm apart. In some embodiments, the apertures may have a diameter of 0.05 mm.

Figure 28A:
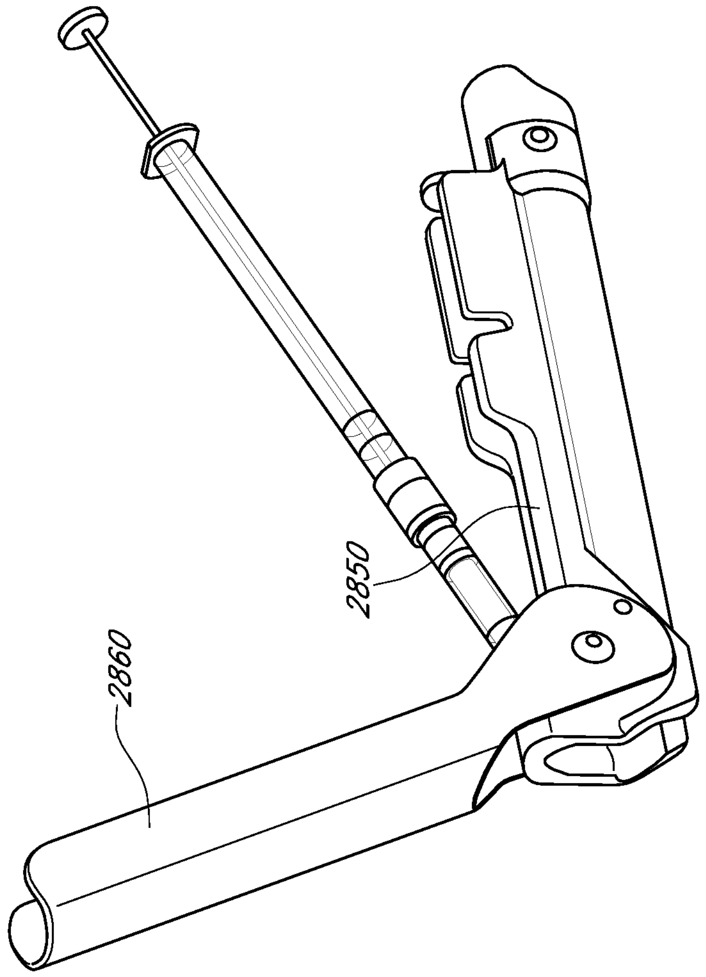
FIGS. 28A-B illustrate perspective views of an adjustable delivery device being operated with an intracellular delivery apparatus having a micro-hub attached to a syringe.
Figure 28B:
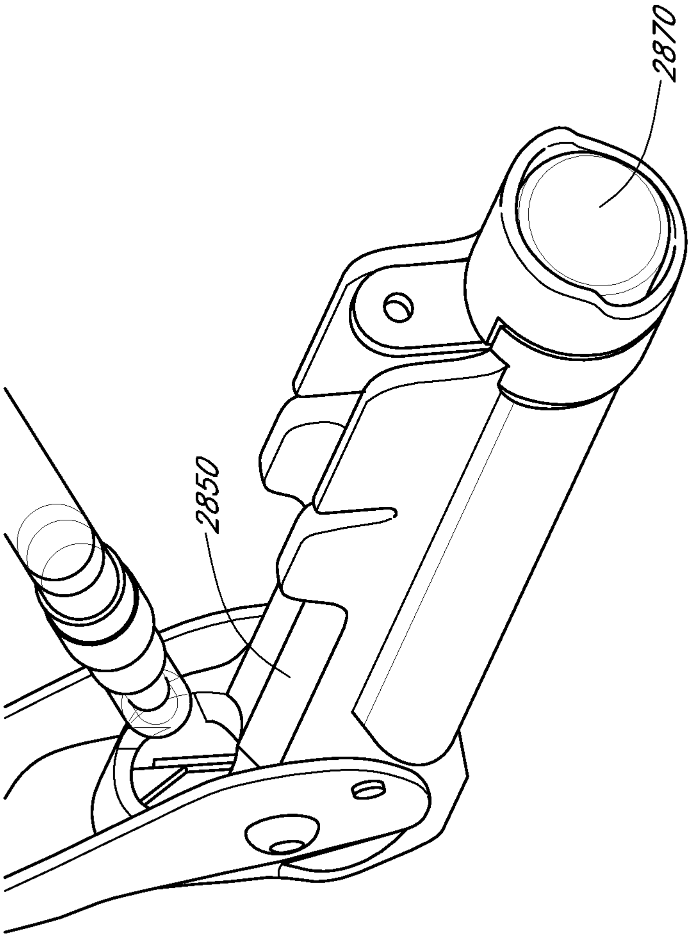

FIGS. 28A-B illustrate perspective views of an adjustable delivery unit being operated with an intracellular delivery device having a micro-hub attached to a syringe. Referring to FIGS. 28A and 28B, the adjustable delivery unit comprises a cavity 2850 configured to receive a syringe and micro-hub intracellular delivery device, a locking handle 2860, and a button 2870. The syringe and micro-hub injection device are positioned within cavity 2850 such that the needle barrels are protruding from a first end of the adjustable delivery device. Once positioned within the cavity, locking handle 2850 is lowered. Lowering handle 2860 primes a charging element within adjustable delivery device, which is coupled to button 2870, which is disposed near a second end of the adjustable delivery device. The charging element may be a spring, which is compressed by the action of lowering handle 2860. Once the handle is completely lowered, the syringe and micro-hub device are within cavity 2850, and the charging element is primed, the adjustable delivery device may be inserted in to a subject or tissue, as desired. User may press button 2870 which releases the charging element, causing the plunger of the syringe to be operated. Operating the plunger of the syringe expels fluid or therapeutic agent out of the syringe, through the luer connector, through the needle barrels, out the apertures, and ultimately into the tissue or subject, as described elsewhere herein.

The needle barrels and intracellular delivery device embodiments described herein may be used in conjunction with other known methods and systems for enhancing gene delivery. Accordingly, some embodiments of the present invention utilize control circuitry to generate an electric current or an electromagnetic field to alter cell permeabilities. In some embodiments, it may be desired to utilize one or more of the needle barrels themselves to conduct or transmit the generated current or field into the tissue. The needle barrels may be used in conjunction with any number of known alternative microporation methods using optionally one or more of sonic, electromagnetic, mechanical and thermal energy or a chemical enhancer, such as that disclosed in U.S. Pat. No. 6,527,716 to Eppstein, which is included by its entirety herein.

Aspects of the invention also concern use of the aforementioned devices as intracellular delivery devices or in conjunction with electroporation. Electroporation is a known therapeutic treatment, which uses electrodes to generate electric fields in a tissue or sample to increase permeability of a cell's outer membrane, thus allowing greater cell uptake of therapeutic agents. (See U.S. Pat. No. 6,241,701, U.S. Pat. No. 6,516,223, U.S. Pat. No. 6,678,556, U.S. Pat. No. 6,610,044, and U.S. Pat. No. 6,110,161, all of which are hereby expressly incorporated by reference in their entireties.)

The skilled artisan, guided by the teaching of the present application, can readily configure the intracellular delivery devices and adjustable delivery units of the present application to comprise electrodes for use in electroporation. In some embodiments, the needles of an intracellular delivery device described herein may comprise electrodes (also referred to as needle-electrodes or combined needle and electrode) configured to apply an electric field to a tissue or sample. The needles may be configured as electrodes for use in electroporation. In some embodiments, the needles of the aforementioned devices may be inserted into a sample or a tissue. The needles, configured as electrodes, may generate an electric field in the tissue or sample in order to permeabilize the cell membranes of cells in the vicinity of the needles. The therapeutic agent may then be delivered via the intracellular delivery devices described herein, and cell uptake may be improved. In some embodiments, the needles of the aforementioned devices may be inserted into a sample or a tissue and deliver a therapeutic agent, as described herein. The needles, configured as electrodes, may also be used to generate an electric field in the sample or tissue, which permeabilizes the cell membranes of the cells in the vicinity of the needles. Upon permeabilization of the cell membranes, cell uptake of the therapeutic agent can be improved.

In some embodiments, injection speed and pressure may be varied by using various delivery units. The delivery unit may have a pressure generation element actuated by spring, gas spring, electromechanical mechanism, compressed air, or other similar device. By varying the force with which the pressure generation element is actuated, the injection speed, and/or injection pressure may be varied. In some embodiments the intracellular delivery apparatus is configured to rapidly deliver an agent to an area defined by the needle array. The rapid injection of prophylactic and/or therapeutic along with increased intracellular pressure overloads a tissue locally, thereby increasing permeability of the cell membrane. By varying injection pressure and/or speed, the local tissue overload can be varied, resulting in varying uptake of the prophylactic and/or therapeutic agent.

Figure 29A:
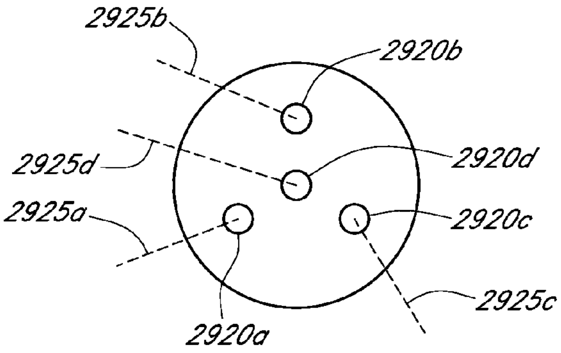
FIGS. 29A-C illustrate the electrical connections to one or more needles of an intracellular delivery apparatus for use in electroporation.
Figure 29B:
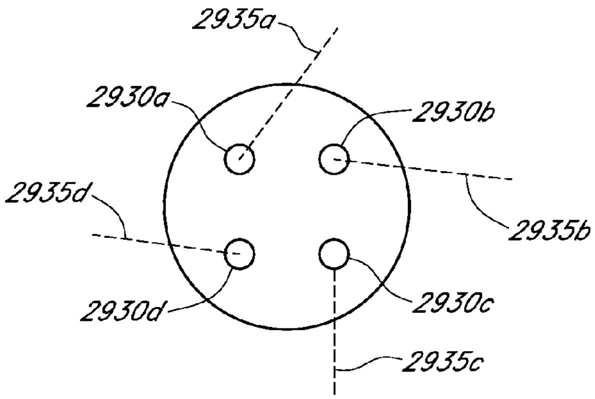
Figure 29C:
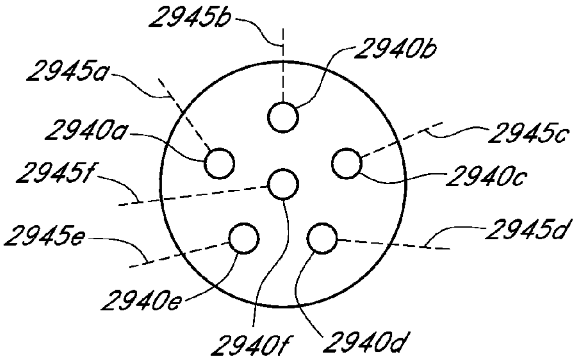

FIGS. 29A-C illustrate the electrical connections to one or more needles of an intracellular delivery device for use in electroporation. Referring to FIG. 29A, needles 2920*a-d*, are constructed of an electrically conductive material, and are individually electrically connected via electrical connectors 2925*a-d*, to a voltage source, current source, or other power source (not depicted). In some embodiments, the voltage source can be battery powered. The voltage source may be configured to apply signals of varying polarity to individual needles to achieve a desired electric field. In some embodiments, a positive voltage may be applied to needles 2920*a*, 2920*b*, and 2920*c*, and a negative voltage may be applied to needle 2920*d*. In some embodiments, a negative voltage may be applied to needles 2920*a*, 2920*b*, and 2920*c*, and a positive voltage may be applied to needle 2920*d*. In some embodiments, a constant voltage may be applied to needles 2920*a-d*. In some embodiments, the voltage may be pulsed or varying. In some embodiments, the same voltage may be applied to each needle 2920*a-d*. In some embodiments, different voltages or voltage patterns may be applied to needles 2920*a-d*. A person of skill in the art would understand that needles 2920*a-d* may have any combination of polarities or voltages.

Referring to FIG. 29B, needles 2930*a-d* are constructed of an electrically conductive material, and are individually electrically connected via electrical connectors 2935*a-d* to a voltage source (not depicted). In some embodiments, a positive voltage may be applied to needles 2930*a* and 2930*b*, and a negative voltage may be applied to needles 2930*c* and 2930*d*. In some embodiments, a positive voltage may be applied to needles 2930*a* and 2930*c*, and a negative voltage may be applied to needles 2930*b* and 2930*d*.

Referring to FIG. 29C, needles 2940*a-f* are constructed of an electrically conductive material, and are individually electrically connected via electrical connectors 2945*a-f* to a voltage source (not depicted). The voltage source may be configured to apply signals of varying polarity to individual needles. In some embodiments, a positive charge may be applied to needles 2940*a-e* and a negative voltage may be applied to needle 2940*f*. In some embodiments, a negative charge may be applied to needles 2940*a-e* and a positive voltage may be applied to needle 2940*f*. In some embodiments, a positive charge may be applied to needles 2940*a*, 2940*c*, and 2940*f*, and a negative voltage may be applied to needles 2940*b*, 2940*d*, and 2940*e*. Although specific embodiments of voltage polarity patterns are disclosed, the skilled artisan will appreciate that the polarity of the voltage applied to the needles in the present application can be varied, and, without limitation, any combination of polarities may be applied to the individual needles in any pattern.

FIGS. 30A-F illustrate embodiments of needle and electrode configurations of a microhub injection device. The microhub injection device 3001 can include needles 3010, electrodes 3020 and/or combined needle-electrodes 3030.

Figure 30A:
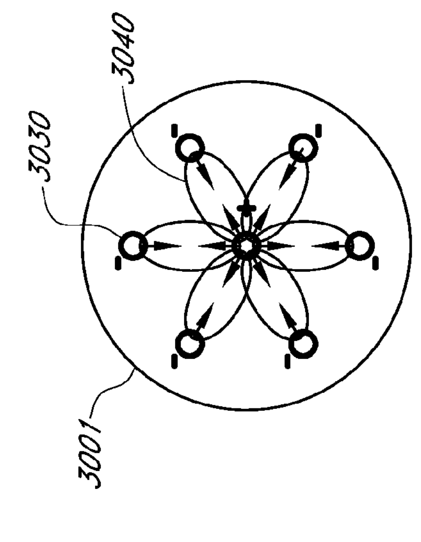
FIGS. 30A-F illustrate embodiments of needle and electrode configurations of a microhub injection device showing polarity of needles or electrodes, electric fields, and direction of spray flow.
Figure 30B:
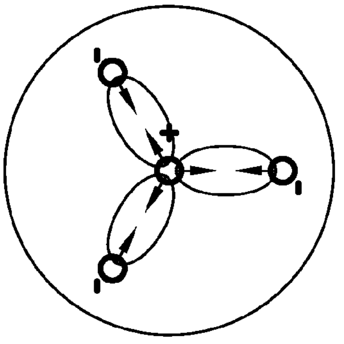
Figure 30C:
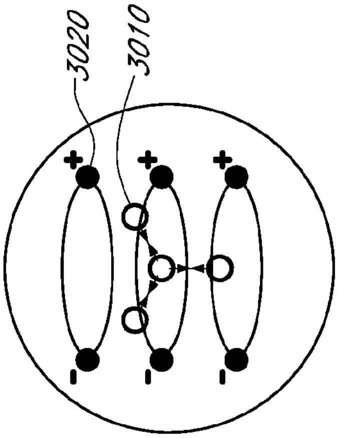
Figure 30D:
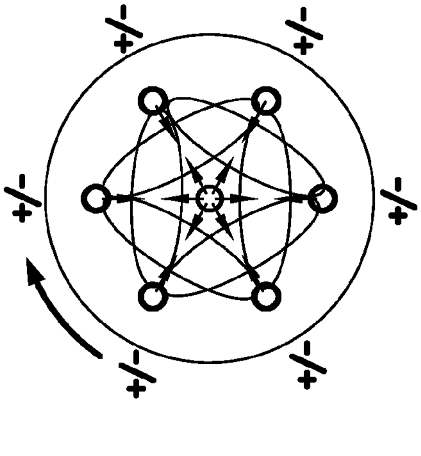
Figure 30E:
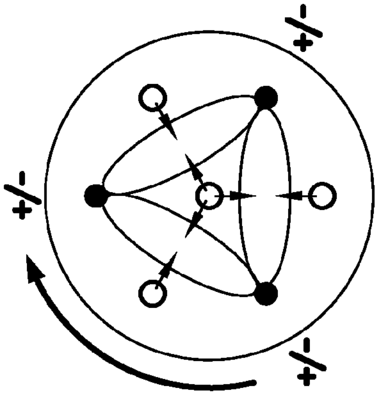
Figure 30F:
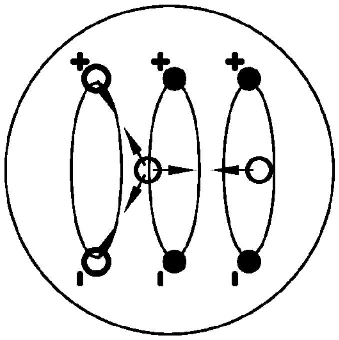

Combined needle-electrodes 3030 and/or separate needles 3010 can be utilized for delivery of a prophylactic or therapeutic agent as described elsewhere herein. The direction of flow of prophylactic or therapeutic agent out of the needles of the microhub injection device is depicted by arrows extending from needle-electrodes 3030. Combined needle-electrodes 3030 and/or separate electrodes 3020 can be utilized to produce one or more electrode fields 3040. A plurality of needles 3010, electrodes 3020, and/or combined needle-electrodes 3030 may be configured to produce a desired delivery type and a desired field pattern of the electrode fields. Delivery types can include, but are not limited to 'star' type, 'X' type and 'Y' type. Field patterns can include, but are not limited to parallel field pattern, 'O' field pattern and 'Δ' field pattern. Field patterns can be commutating. Referring to FIG. 30A, combined needle-electrodes 3030 are configured for 'star' type delivery and field pattern. Referring to FIG. 30B, combined needle-electrodes 3030 are configured for 'Y' type delivery and field pattern. Referring to FIG. 30C, separate needles 3010 are configured for 'Y' type delivery and separate electrodes 3020 are configured for parallel field pattern. Referring to FIG. 30D, combined needle-electrodes 3030 and a central needle 3010 are configured for 'star' type delivery and commutating 'O' field pattern. Referring to FIG. 30E, separate needles 3010 are configured for 'Y' type delivery and commutating electrodes 3020 are configured for 'Δ' field pattern. Referring to FIG. 30F, combined needle-electrodes 3030 and separate needles 3010 are configured for 'Y' type delivery and separate electrodes 3020 are configured for parallel field pattern. Polarities of needles 3010 shown in FIGS. 30A-F are for illustrative purposes only. The polarities may be reversed or commutated. Needle polarity pairings and field patterns may be different from that shown. For example, the needle polarity pairings and field patterns may be altered to enhance electroporation. FIGS. 30A-F also depict the direction of flow of a prophylactic and/or therapeutic material out of the needles and/or the apertures located thereon. The direction is indicated by arrows extending from each needle and/or needle electrode. For example, FIGS. 30A and B depict two types of arrays of needles having one needle at the center and outer needles disposed in a hexagonal or triangular shape, respectively, around the center needle. The arrays of needles enclose an active zone or area into which flow of prophylactic and/or therapeutic material is directed. As depicted, the center needle/needle-electrode has apertures positioned along the needle barrel to direct the flow of prophylactic and/or therapeutic material toward each outer needle. The outer needles have apertures positioned along the needle barrels which direct flow toward the center needle. In some embodiments (for example, FIG. 33D, described later), the outer needles may also have apertures positioned along the needle barrels which direct flow of a prophylactic and/or therapeutic agent toward an adjacent needle, or to one of the outer needles, as well as, apertures directing flow toward the center needles. In some embodiments, the outer needles do not have apertures which direct flow out of the active zone defined by the area within the needle array.

Figure 31A:
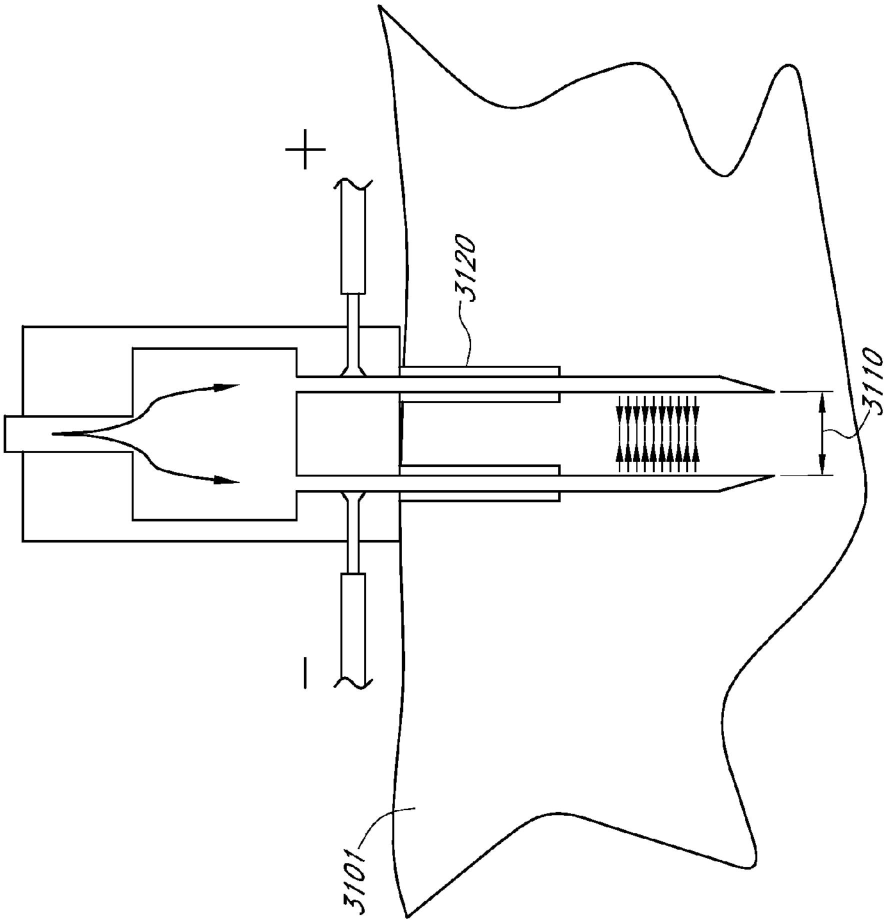
FIG. 31A illustrates an example of a distal end of an intracellular delivery apparatus having a non-pocket hub.
Figure 31B:
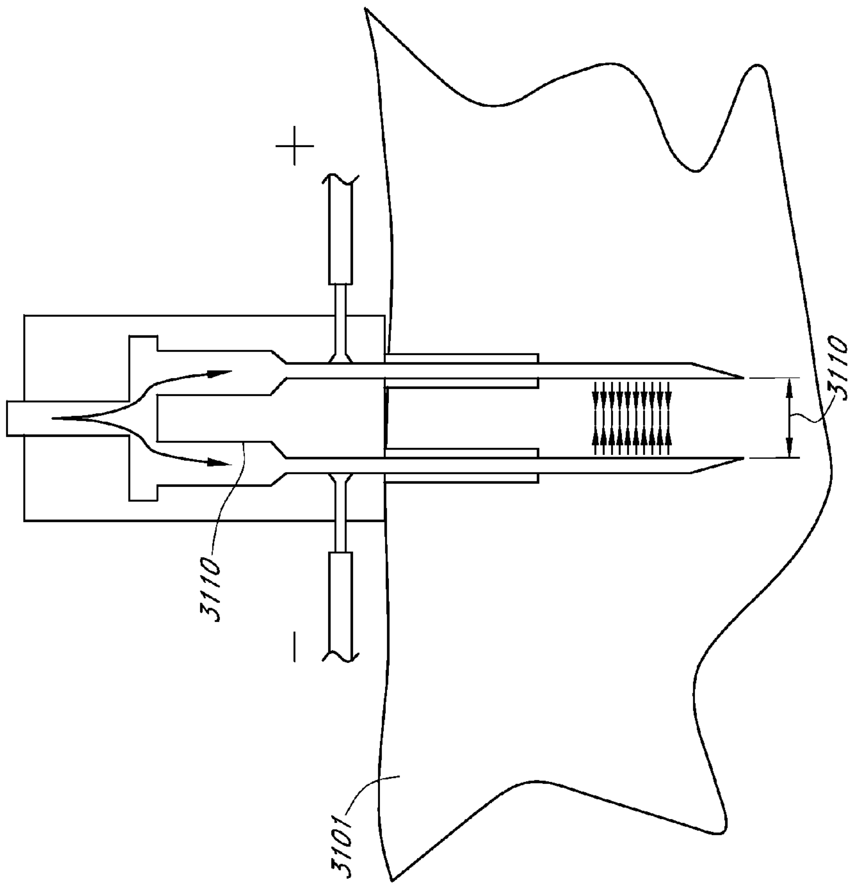
FIG. 31B illustrates another example of a distal end of an intracellular delivery apparatus having a pocket hub.

FIG. 31A-31B illustrate examples of a distal end of an intracellular delivery device having needle hub configurations. FIG. 31A, illustrates a non-pocket hub, while FIG. 31B, illustrates a pocket hub having a distance between electrodes 3110, a sleeve layer 3120 and an isolated area of the electrode 3130. The sleeve layer 3120 may be insulated to prevent electroporation of patients. Non-pocket hub assumes acceptable field losses at distal end of the needles 3010/electrodes 3020. The isolated area of the electrode 3130 can create a localized field. Pocket hub assumes the increased distance between distal ends of the needles 3010 and/or electrodes 3020 results in acceptable system losses at distal end of the needles 3010 and/electrode 3020. In some embodiments, the pocket hub reduces electrical losses at the distal end of the needles 3010.

Figure 32A:
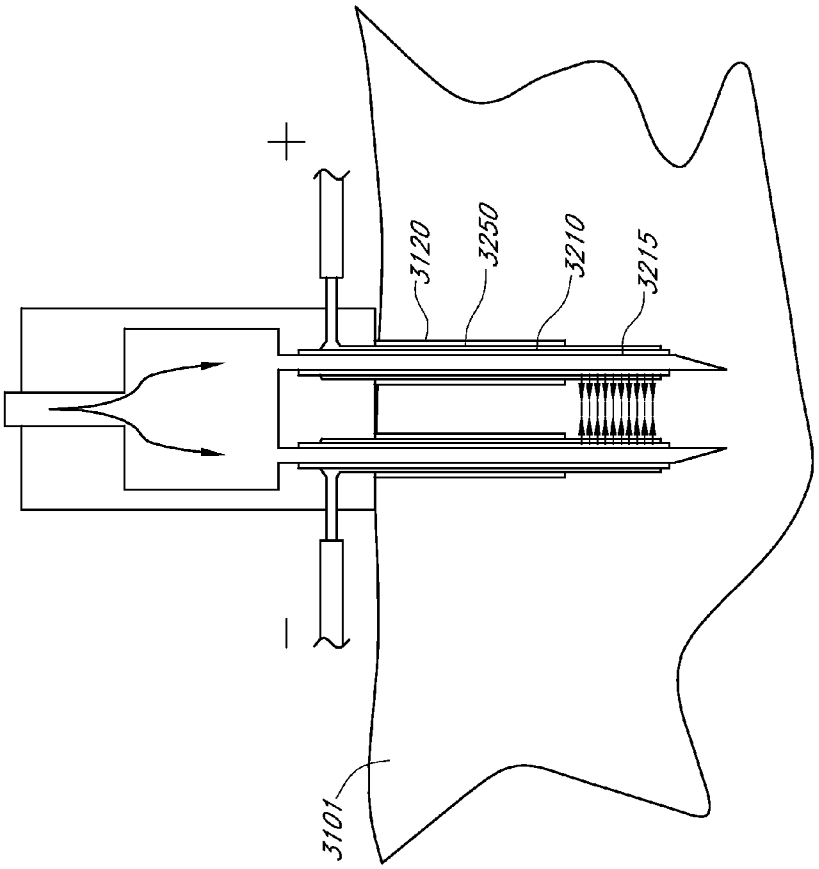
FIGS. 32A-B illustrate examples of an intracellular delivery apparatus having laminated needles, which are partially electrically insulated.
Figure 32B:
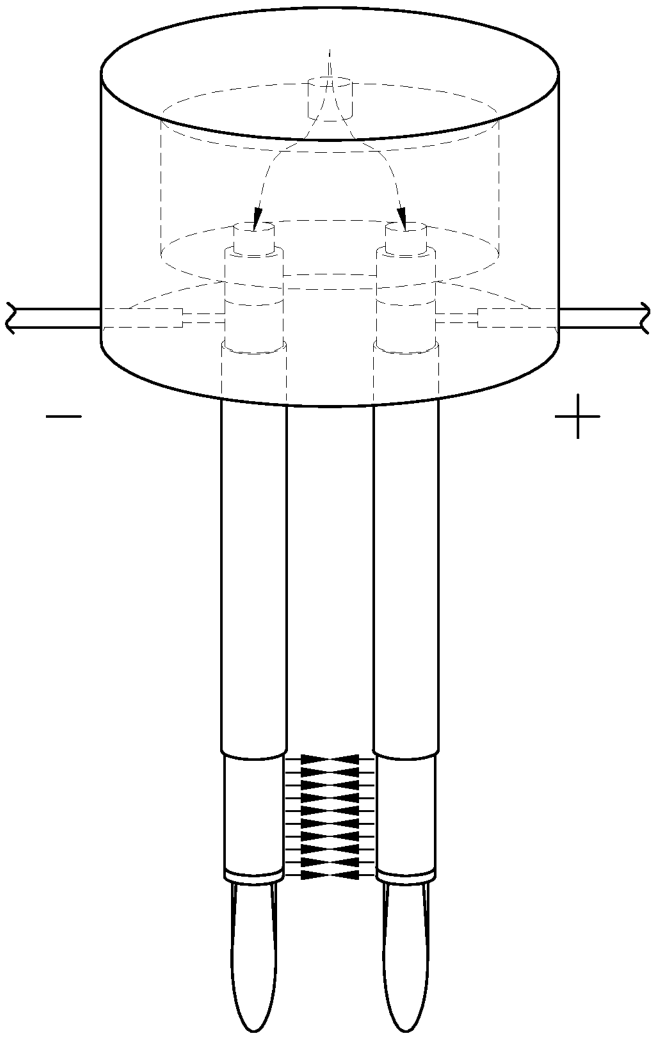

FIGS. 32A-B illustrate examples of intracellular delivery devices having laminated needles 3010. Laminated needles 3010 may be used to focus charge and minimize losses. For example, the flow of electrical current through the drug within the hub can be minimized to minimize the electrical power losses. Laminated needles 3010 can include a conductive coating 3250 positioned between two insulated layers 3210. In some embodiments, the conductive coating 3250 can act as the electrode, while the needle and drug do not have a direct coupling to the electrical signal. In other embodiments, the laminated needle 3010 can act as the electrode and the inside of the needle can be coated with a non-conductive coating 3215. Non-conductive coating 3215 prevents the prophylactic and/or therapeutic agent from being in direct electrical contact with the electrodes while in the needle barrel. This arrangement may prevent breakdown or degradation of the prophylactic or therapeutic material due to the electrical field inside the needle barrel. Laminated needles 3010 may be any needle described herein. For example, as depicted, needles 3010 have apertures along the length of each barrel oriented to direct flow of therapeutic material toward an aperture on the barrel of an adjacent or opposite needle.

Figure 33A:
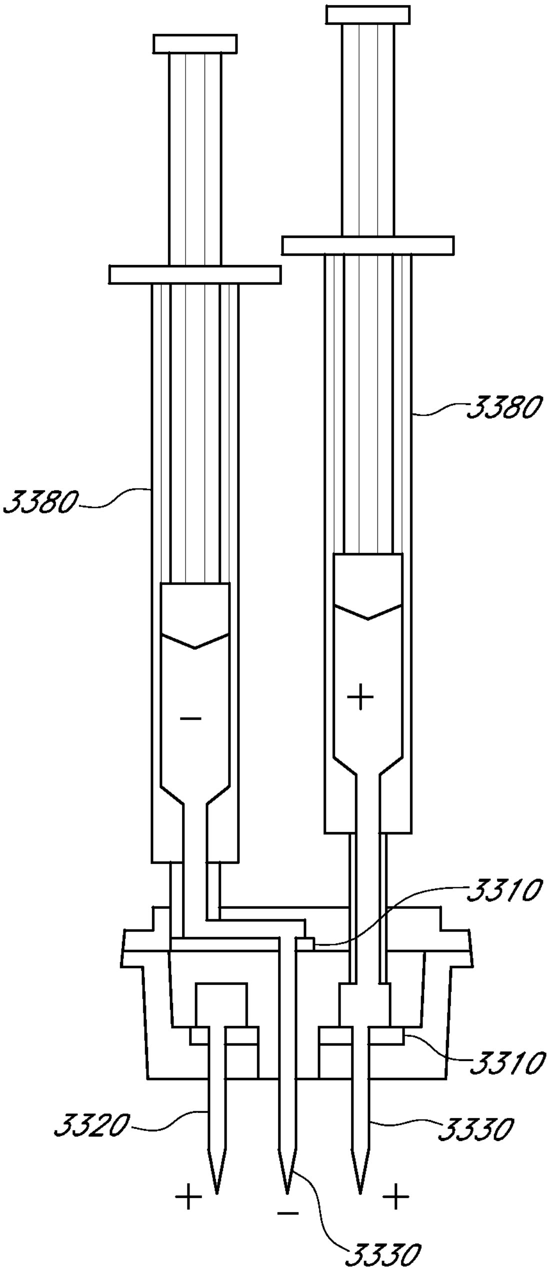
FIG. 33A-D illustrate examples of an intracellular delivery apparatus having dual syringes and delivery and electric field patterns of a hypodermic needle device having dual syringes.

FIG. 33A illustrates an example of an intracellular delivery device having dual syringes. Dual syringes 3380 can include two or more syringes. The dual syringes 3380 can be used to control needle-electrode polarity. Dual drug chambers of the dual syringes 3380 can prevent electrical current from flowing through the drug within the hub. The hub can include electrical connections 3310 to the needle-electrodes 3330. The hub may comprise one or more electrodes which is not coupled to a reservoir containing a prophylactic and/or therapeutic material, but acts only as an electrode.

Figure 33B:
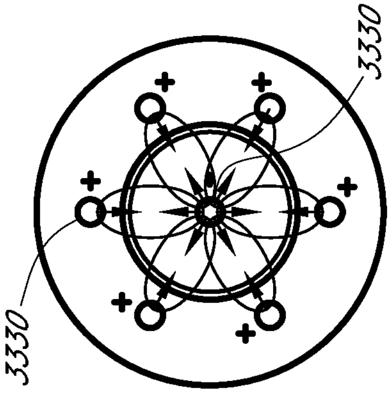
Figure 33C:
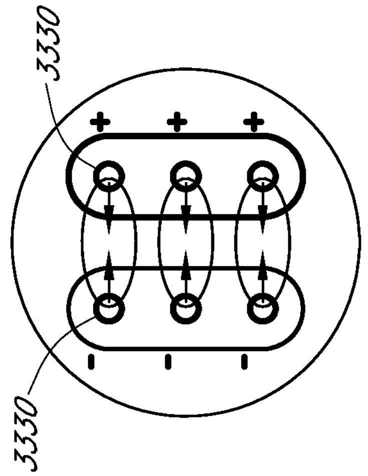
Figure 33D:
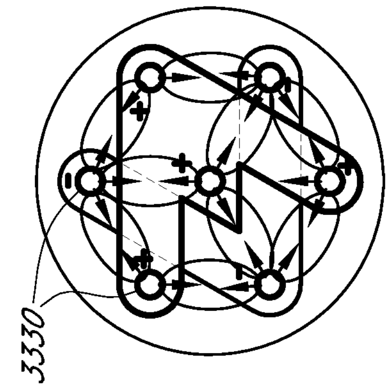

FIGS. 33B-D illustrate examples of delivery and field patterns of an intracellular delivery device having dual syringes. Each syringe 3380 of the dual syringes may be coupled to one or more needle electrodes 3330. The number of needle-electrodes 3330 is not particularly limited, and can be chosen as desired to accomplish a desired configuration or pattern of injection and electroporation. As discussed herein, combination needle-electrodes 3330 can be configured to produce any desired delivery type and/or field pattern. FIG. 33B illustrates a hexagonal shaped delivery and field pattern, the arrows indicating the direction of flow of prophylactic and/or therapeutic material from the apertures on the barrel of the needle-electrodes 3330. FIG. 33C illustrates 'Row' type delivery and field pattern. FIG. 33D illustrates 'O & Y' type delivery and 'O & Y' field pattern, where the arrows indicate the direction of flow of prophylactic and/or therapeutic material from the apertures on the barrel of the needle-electrodes 3330. In a 'row' type delivery and field pattern, six needles are needle electrodes, configured in pairs, wherein one of each pair has a positive polarity and the other in each pair has a negative polarity. The pairs may be aligned across from one another as depicted in FIG. 33C, or they may be arranged in another pattern of pairs, as depicted in FIG. 33D. In some embodiments, the there may be one, two, three, four, or five or more pairs of needle electrodes, arranged to provide electroporation. In some embodiments, the electric field can be commutated, or, the polarity of individual needle-electrodes or needle-electrode pairs may have alternating polarity as the electrical signal is applied.

Figure 34A:
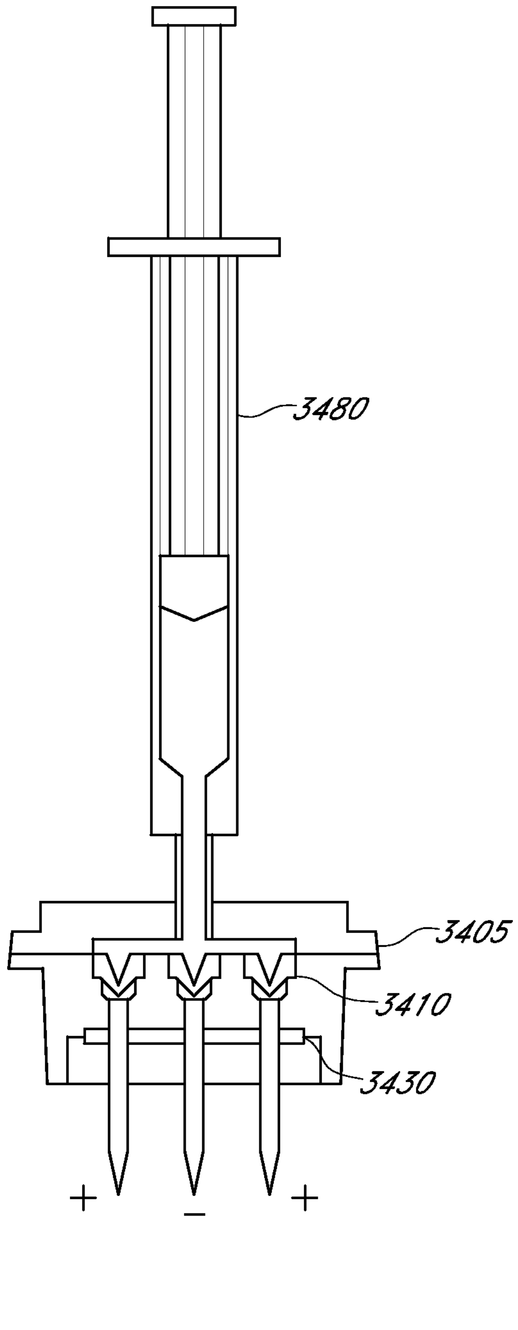
FIG. 34A-C illustrate examples of an intracellular delivery apparatus having isolating valves and needle and electrode configurations of a hypodermic needle device having isolating valves.
Figure 34C:
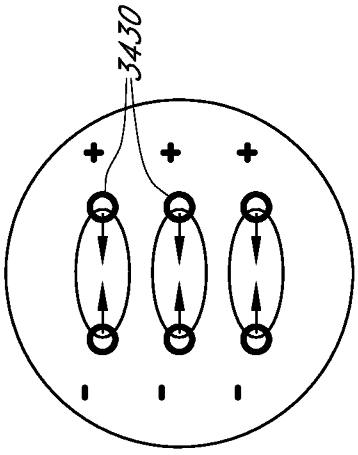
Figure 34B:
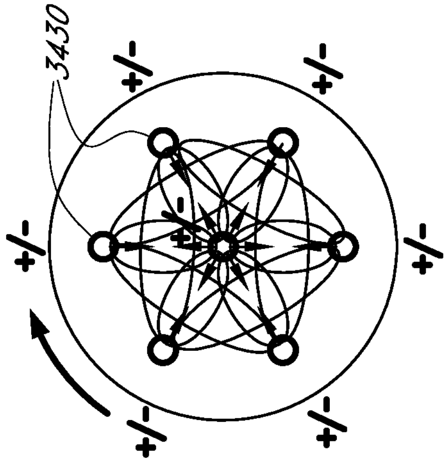

FIG. 34A illustrates an example of an intracellular delivery device having isolating valves. Hub 3405 can include isolation valves 3410. The isolation valves 3410 can help to eliminate losses at the distal end of the needle-electrode. For example, the isolation valves can help to prevent electrical current from flowing through the drug within the hub. One or more of the needle-electrodes 3010 can include an isolation valve 3410. Isolation valves can be in the form of non-conductive mechanical check-valves. Isolation valves can include, but are not limited to, membrane, ball valve, or other. The hypodermic needle device can include electrical connections to the needle-electrodes 3430. The electrical connections to needle-electrodes 3430 can be configured to provide a desired polarity or pattern FIGS. 34B-C illustrate examples of needle and electrode configurations of an intracellular delivery device having isolating valves. Isolation valves allow any configuration of combined needle-electrodes 3430, such as those described herein. FIG. 34B illustrates a commutating field in a ‘star’ type pattern, wherein individual needles are commutated in pairs in a clockwise or counter clockwise direction, leading to a commutating and varying electric field produced in an area bounded by the array of needles within a subject tissue.

Figure 35C:
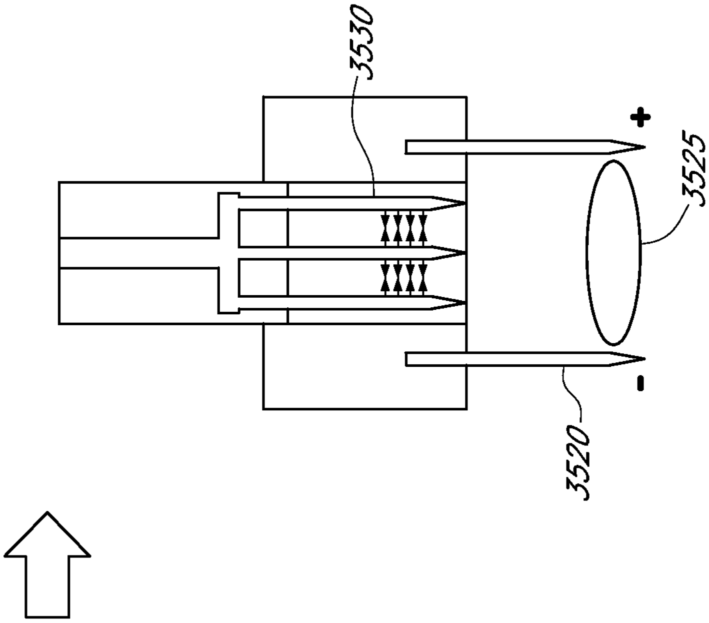
FIG. 35C illustrates an example of an intracellular delivery apparatus during a second stage of a two stage delivery.
Figure 35A:
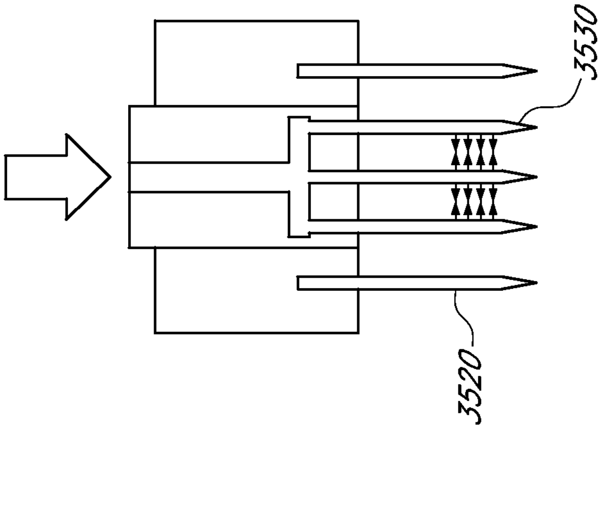
FIG. 35A illustrates an example of an intracellular delivery apparatus during a first stage of a two stage delivery process.

FIG. 35A illustrates an example of an intracellular delivery device during a first stage of a two stage delivery. In some embodiments, the methods described herein can include a two stage delivery including a first stage and a second stage. The needles can be separate from the electrodes and may be of any type described herein. During the first stage, retractable needles 3510 are inserted into a subject. The prophylactic and/or therapeutic material is delivered substantially within an active area 3525 of the electrodes 3520.

Figure 35D:
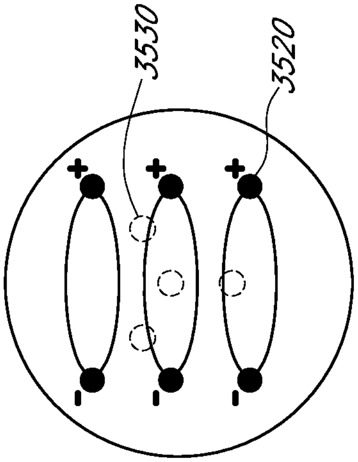
FIG. 35D illustrates the needle and electrode configuration of the device of FIG. 35B during the second stage of a two stage delivery.
Figure 35B:
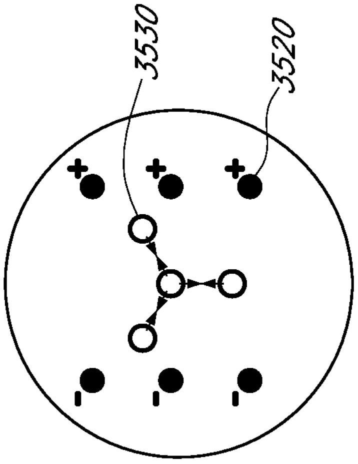
FIG. 35B illustrate an example of a needle and electrode configuration during a first stage of a two stage delivery.

FIG. 35B illustrates an example of a needle and electrode configuration during the first stage of a two stage delivery. As discussed herein, needles 3530 and electrodes 3520 can be configured to produce any desired delivery type and/or field pattern. For example, in the illustrated configuration, the needles 3530 are configured for ‘Y’ delivery and the electrodes 3520 are configured to provide parallel electrical field.

FIG. 35C illustrates an example of an intracellular delivery device in a second stage of a two stage delivery. During the second stage, the retractable needles 3530 are removed or retracted following delivery of the therapeutic and/or prophylactic material, and the electrodes 3520 are energized. Energized electrodes 3520 deliver an electrical field during electroporation. The retractable needles 3530 can include metal parts. It will be appreciated that retracting the needles 3530 removes metal parts of the needles 3530 from the electrical filed during the electroporation.

FIG. 35D illustrates the example needle and electrode configuration of FIG. 35B during the second stage of a two stage delivery.

Figure 36:
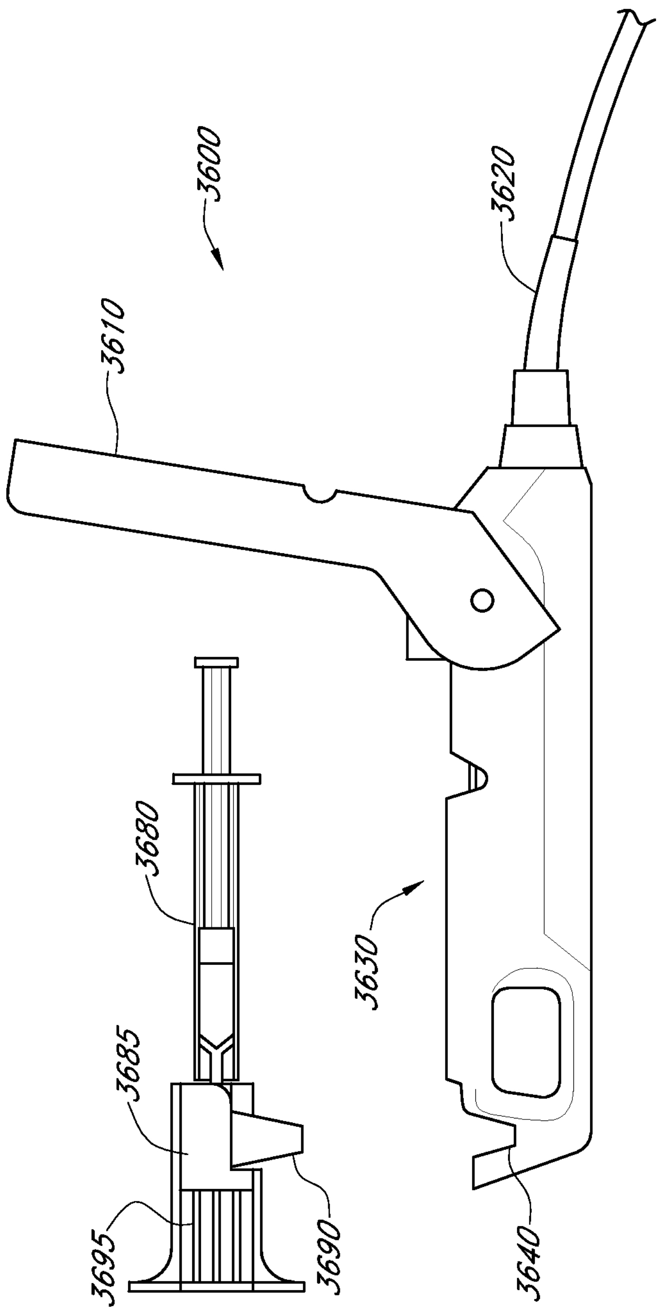
FIG. 36 illustrates perspective views of a reusable delivery device providing an electric power supply being operated with an intracellular delivery device having a micro-hub attached to a syringe.

FIG. 36 illustrates a perspective view of a reusable delivery device configured for use with an intracellular delivery device comprising a micro-hub attached to a syringe and electrical connections for electroporation. Reusable delivery device 3600 comprises priming lever 3610, an electrical supply cable 3620, a syringe receiving portion 3630, and electrical port 3640. Reusable delivery device 3600 is configured to receive a syringe 3680. Syringe 3680 comprises a hub 3685 and electrical connector 3690. Syringe 3680 is inserted into syringe receiving portion 3630 such that electrical connector 3690 mates with electrical port 3640, thereby creating a conductive path from an electrical power supply (not shown) through electrical supply cable 3620, and to the needle electrodes in hub 3685. Priming lever 3610 is configured to operate to retain syringe 3680 within syringe receiving portion 3630, and to actuate a compression spring within reusable delivery device, which upon actuation is primed to operate syringe 3680 when delivery is desired.

Figure 37:
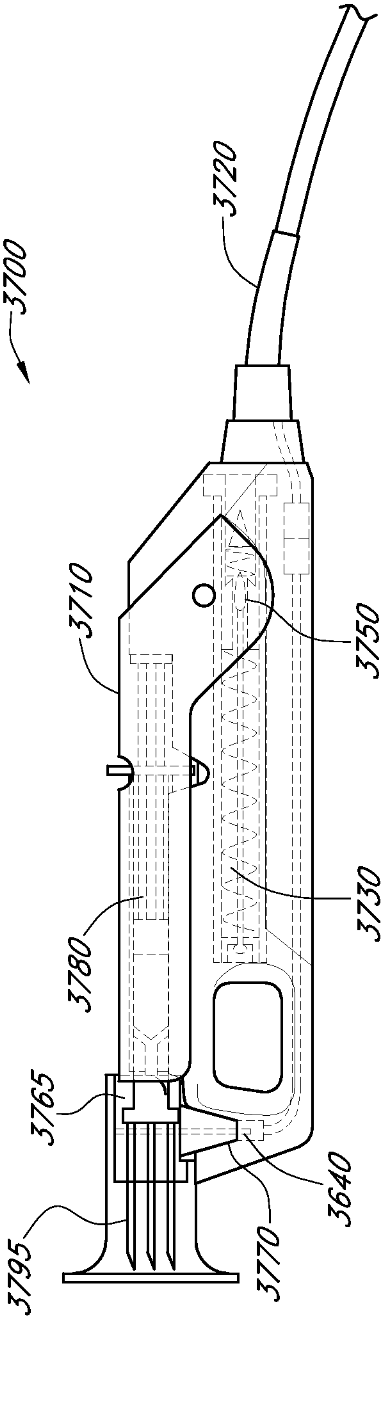
FIG. 37 illustrates an internal view of reusable delivery device providing an electric power supply with an intracellular delivery apparatus disposed within.

FIG. 37 depicts reusable delivery device 3600 with syringe 3680 disposed within following actuation of priming lever 3610. As depicted, priming lever 3610 actuates compression spring 3730 for release upon operation of trigger device 3750. Upon operation of trigger device 3750, compression spring 3730 expands and operates either directly, or indirectly through one or more components, syringe 3680, forcing therapeutic and/or prophylactic material out of syringe 3680, through needles 3695 disposed within hub 3685, and into a subject. Needles 3695 may be electrode-needles or needles as described elsewhere herein. Reusable delivery device 3600 is electrically connected to a power supply via electrical supply cable 3620. Reusable delivery device 3600 may also be connected to an electric signal generator (not shown) controllable by an operator, to deliver a desired electroporation pattern or signal to a subject via electrodes or needle-electrodes disposed within hub 3685. It will be appreciated by those skilled in the art that the trigger device could be operated and/or released by an electrical or electromechanical mechanism, e.g., solenoid, motor, shape memory alloy muscle wire, and other similar mechanisms.

Figure 38A:
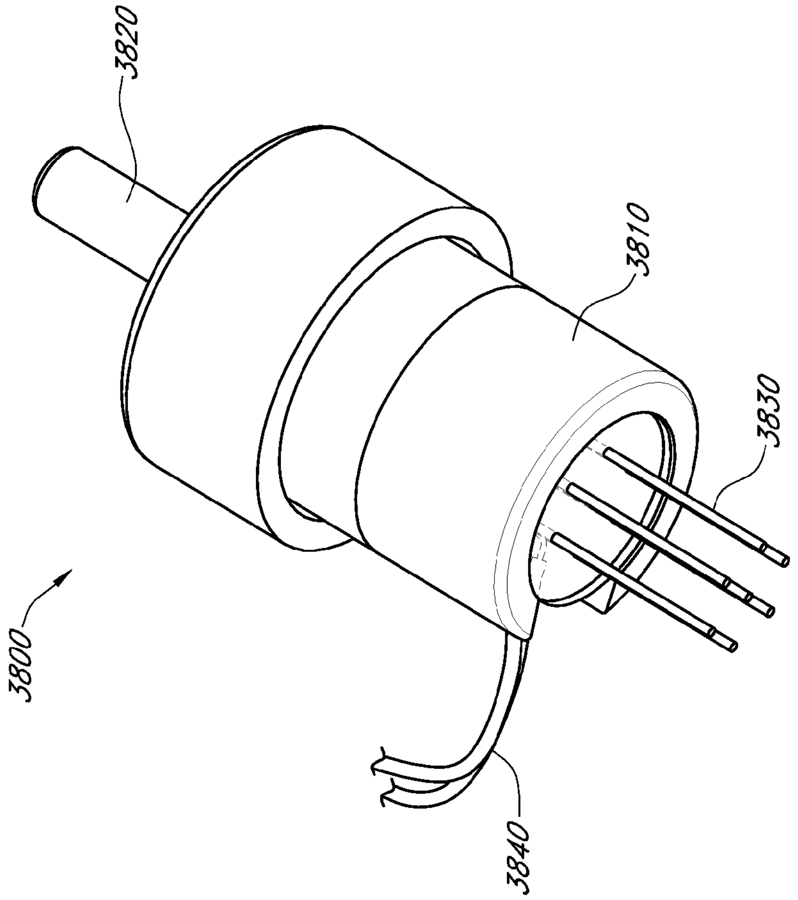
FIGS. 38A-C illustrate embodiments of an intracellular delivery apparatus having a micro-hub configured for electroporation.
Figure 38C:
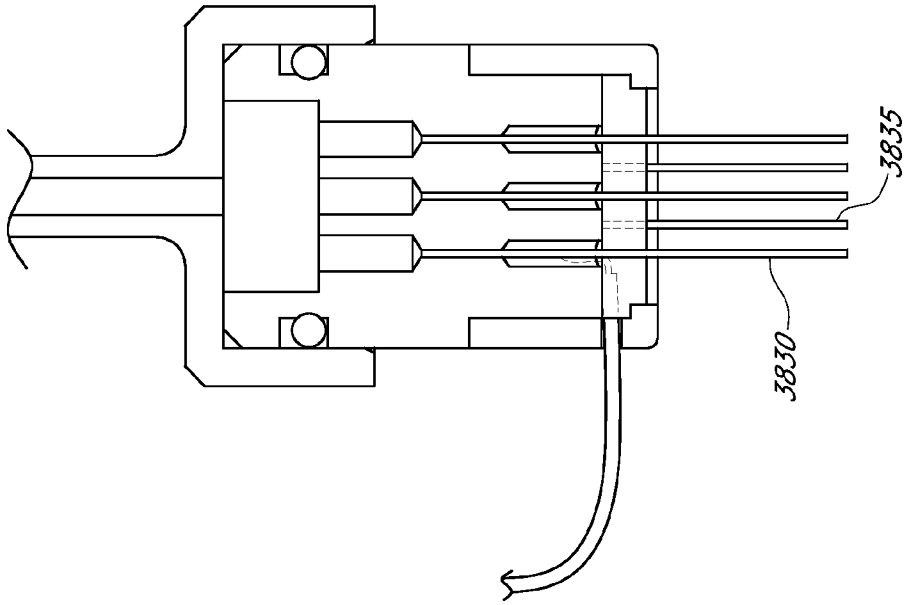
Figure 38B:
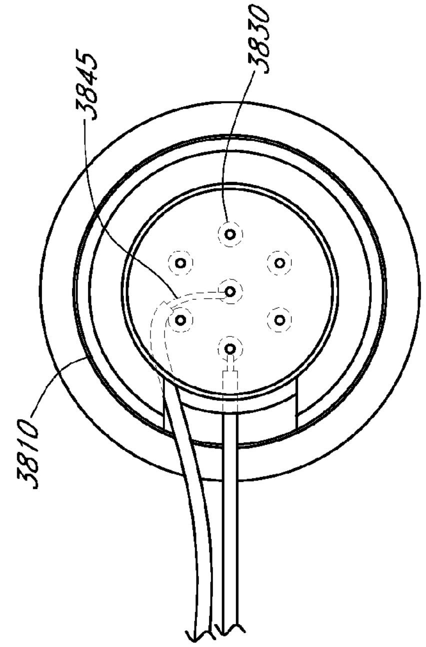

FIGS. 38A-C illustrate embodiments of an intracellular delivery device having a micro-hub configured for electroporation. Intracellular delivery device 3800 comprises a micro-hub 3810 and syringe attachment portion 3820. Micro-hub 3810 comprises needles 3830. In some embodiments, needles 3830 may comprise electrode-needles or non-electrode needles in any combination. Electrodes and needle electrodes are in electrical contact with electrical conduits 3840. As depicted in FIG. 38B, two needles 3830 are in electrical contact with connecters 3845 which are in electrical contact with electrical conduits 3840. In some embodiments, one or more needles 3830 may be in electrical contact with one or more electrical connectors 3845 and arranged in any pattern or shape to provide a desirable electrical field. Needles 3830 may be similar to any of the needles described elsewhere herein, for example, needles having apertures along the barrel where the apertures are zoned for a particular spray pattern, or any other suitable design. For example, one or more of needles 3830 may have a positive polarity when charged, or one or more of needles 3830 may have a negative polarity when charged, as described elsewhere herein.

FIG. 38C illustrates a micro-hub 3810 comprising needles 3830 and electrodes 3835. As described elsewhere herein, one of skill in the art would understand that needles 3830 and electrodes 3835 could be electrically connected in various patterns in order to provide various electrical fields in a subject or tissue.

Figure 39A:
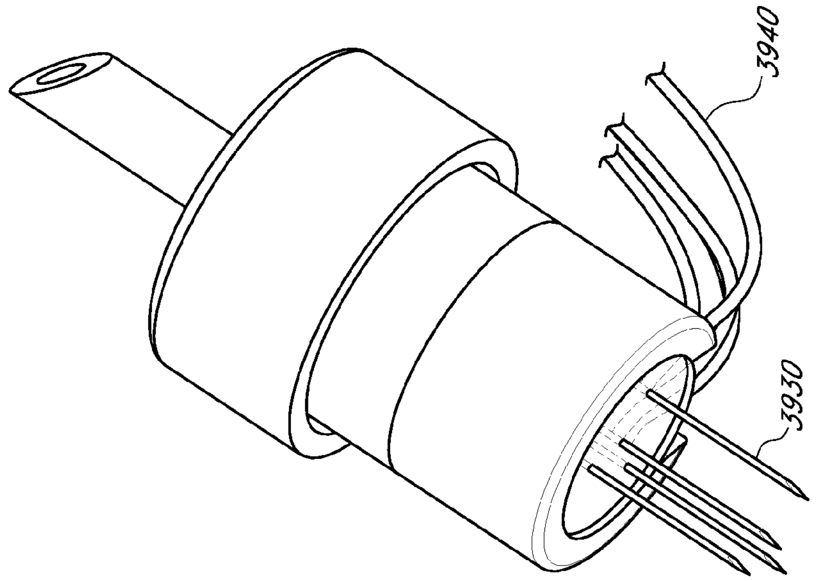
FIGS. 39A-C illustrate embodiments of an intracellular delivery apparatus with a Y-type configuration having a micro-hub configured for electroporation.
Figure 39C:
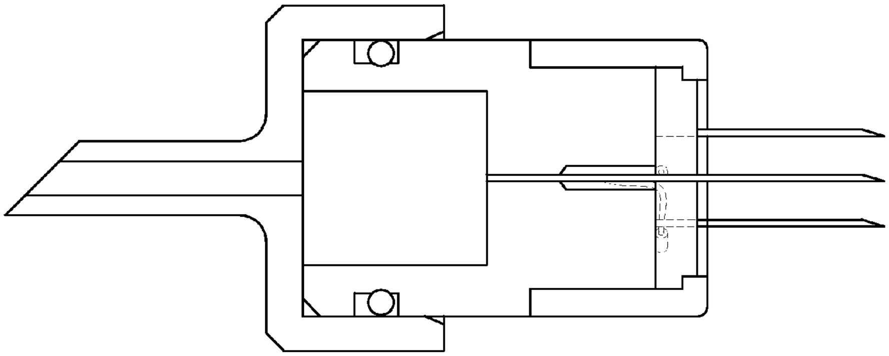
Figure 39B:
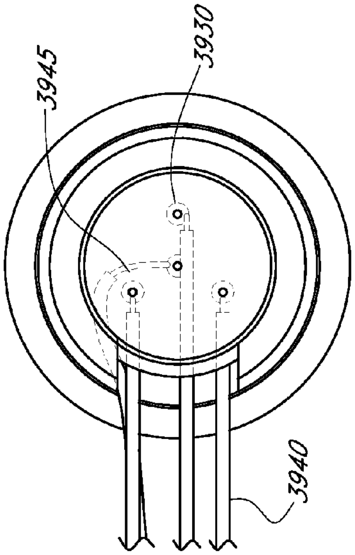

FIGS. 39A-C illustrate embodiments of an intracellular delivery device with a Y-type configuration having a micro-hub configured for electroporation. As depicted, needles 3930 are arranged in a Y-type pattern, and have apertures along the barrel to provide a Y-type spray pattern as described elsewhere herein. Needles 3930 are all in electrical contact with electrical connectors 3945 and thus in electrical contact with electrical conduits 3940. Micro-hub 3910 and syringe connecting portion 3920 may be configured to provide either a pocket design or non-pocket design. FIG. 38C depicts a pocket design, FIG. 39C depicts a non-pocket design.

In some embodiments, the electric field applied to a subject may vary based on the voltage applied to the needle electrodes. As cell types vary, so does the electrical field strength required to electroporate the cells. The voltage required across a cell is inversely proportional to the radius of the cell. For example, muscle cells require a lower voltage, and liver cells require a higher voltage. Therefore, the electric field created by the hypodermic needle devices as described herein may be variable according to the target cell type. The electric field strength delivered by the hypodermic needle devices described herein may range from a few Volts/cm, 100 Volts/cm, 200 Volts/cm, 300 Volts/cm, 400 Volts/cm, 500 Volts/com, 600 Volts/cm, 800 Volts/cm, 900 Volts/cm, 1000 Volts/cm, 1500 Volts/cm, 2000 Volts/cm or greater, or any value in between the listed values. If the electric field strength gets too high, for example, 3000 Volts/cm, cell death becomes a possibility.

The injection systems described herein may be termed in vivo intracellular injection (IVIN), to achieve a highly localized injection and uptake of the DNA. During the injection the therapeutic and/or prophylactic agent will overload the volume between the needles in a subject or tissue, thereby the increase local pressure forces the prophylactic and/or therapeutic agent into the cells. Thus, WIN, as described herein, achieves both a highly localized deposit of a therapeutic and/or prophylactic agent, such as DNA, and an improved local uptake into target cells when compared to injection with a standard hypodermic needle. Electroporation (EP) devices can be combined with the technology, as has been described. For example, WIN may be used to locally overload a volume of muscle cells with DNA that will be treated with in vivo EP. Without EP, standard intra-muscular IVIN greatly improves the efficiency of DNA uptake and expression.

The IVIN technology may overload muscle tissue with a DNA-containing solution such that the cells become permeable and the DNA is taken up. With the WIN technology this can be achieved at a highly localized site in a muscle with needles placed along a circle surround the tissue and injects the DNA tissue. Thus, the tissue is locally overloaded resulting in both a local inflammation and an improved uptake of DNA and antigen expression.

More importantly, in a larger muscle, here represented by the rabbit tibialis anterior, the IVIN shows a similar efficiency in transfecting muscle fibres in vivo as a regular needle injection combined with in vivo EP.

In some embodiments, when WIN is combined with in vivo EP the uptake is further improved without causing additional tissue damage. In some embodiments, the in vivo EP pulse pattern has one short high-voltage pulse to make cells permeable, and a second longer low-voltage pulse to promote cellular uptake of DNA. The pulse pattern has a minimal destructive effect on the tissue and is more tolerable than pulse patterns also intended to cause tissue destruction and inflammation. Thus, the combination of WIN and in vivo EP may result in a highly effective and tolerable mode of DNA delivery. Furthermore, the combination of WIN and in vivo EP results in a synergistic effect, as is shown below in Example 12.

When IVIN is combined with in vivo EP, both a significant inflammation and transfection is seen, as is demonstrated in the Examples below.

The in vivo EP pulse pattern may have one short high-voltage pulse to make cells permeable, and a second longer low-voltage pulse to promote cellular uptake of DNA. The pulse pattern may have a minimal destructive effect on the tissue and may be more tolerable than pulse patterns also intended to cause tissue destruction and inflammation. Thus, the combination of WIN and in vivo EP results in a highly effective and tolerable mode of DNA delivery.

In some embodiments sequences from the highly immunogenic hepatitis B core antigen (HBcAg) have been added. By doing this the immunogenicity is not much improved as determined in a wild-type animal. However, when the combined NS3/4A-HBAcg vaccine is used in a host with dysfunctional T cells to HCV, as in the chronically infected human, responses are greatly improved.

Accordingly, an embodiment may include HBcAg of a non-human origin since around 2 billion humans already have been in contact with HBV, for example, avian (stork) HBcAg (sHBcAg), which no human has been in contact with. In addition, there is no cross reactivity between human and non-human HBcAg. Ideally, four final genotype-1 and -2 plasmids will be tested in the wild-type and NS3/4A-Tg models to identify the most immunogenic version, i.e. selection of the best version of sHBcAg added to NS3/4A. The genotype 3 and 4 NS3/4A-sHBcAg vaccines are built as copies of these since they are expected to behave similarly. Optimized vaccine sequences for all four NS3/4A genotype have been generated. Thus, the complete vaccine-mix contains HCV NS3/4A(gt1)-sHBcAg, NS3/4A(gt2)-sHBcAg, NS3/4A(gt3)-sHBcAg, and NS3/4A(gt4)-sHBcAg. This is then combined with the correct dose of IL-12 plasmid and be formulated in to a final optimal mix, which constitutes the final vaccine.

The following examples are given to illustrate various embodiments of the present invention in the field of DNA immunization, which can be delivered to a subject in need of an immune response to the antigen contained therein. It is to be understood that the following examples are not comprehensive or exhaustive of the many types of embodiments which can be prepared in accordance with the present invention.

EXAMPLE 1

New Zealand white rabbits weighing 3.5 Kg were injected with a solution containing 0.3 ml 0.9% NaCl containing 0.9 mg of either ChronVac-C (coNS3/4A DNA) or coHBcAg in the tibialis anterior using either a large high injection pressure (HIP) injector, a small HIP injector, or a regular 27 gauge needle. Rabbits were injected either in the right tibialis (TA) anterior, left tibialis anterior (TA), or both.

Figure 40A:
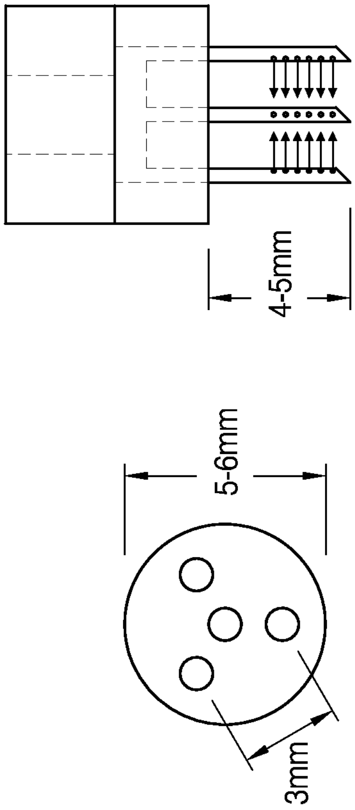
FIGS. 40A-B depict a small HIP (high injection pressure) injector and a large HIP injector.
Figure 40B:
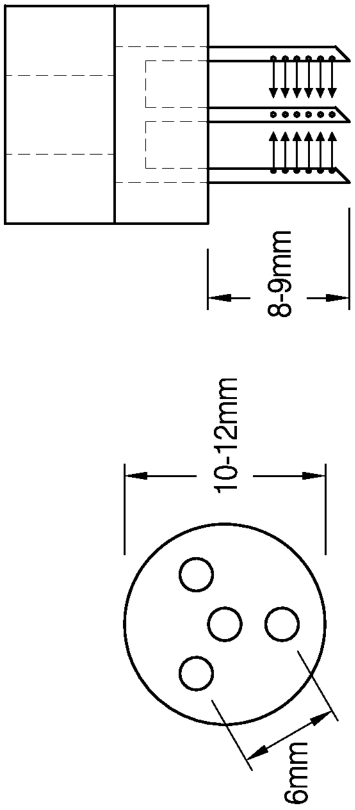

As depicted in FIG. 40A, the small HIP injector has needles 4-5 mm in length. The small HIP injector has 4 needles. As depicted in the figure, the three outer needles are oriented in a triangular formation, equally spaced with approximately 3 mm between each needle to form an equilateral triangle. The center needle is placed in the middle of the triangle formed by the three outer needles. Each needle has 6 apertures. The outer needles all have apertures opening to the center and the center needle has apertures opening at four directions at 90 degree angles. The large HIP injector, as depicted in FIG. 40B has needles 8-9 mm in length. The large HIP injector has 4 needles oriented in a triangular formation, equally spaced with 6 mm between each needle. The center needle is placed in the middle of the equilateral triangle formed by the three outer needles. Each needle of the large HIP injector has 10 apertures. The outer needles all have apertures opening to the center and the center needle has apertures opening at four directions at 90 degree angles. The injection scheme is shown in table 1 below:

TABLE 1

| Rabbit # | Needle Type | Injection Site | Plasmid | Dose | Sacrificed |
|---|---|---|---|---|---|
| 115 | HIP-large | Right TA | coNS3/4A | 0.9 mg/0.3 ml | Day 5 |
| | Regular Needle | Left TA | coNS3/4A | 0.9 mg/0.3 ml | |
| 116 | HIP-large | Right TA | coNS3/4A | 0.9 mg/0.3 ml | Day 5 |
| | Regular Needle | Left TA | coNS3/4A | 0.9 mg/0.3 ml | |
| 117 | HIP-small | Right TA | coNS3/4A | 0.9 mg/0.3 ml | Day 5 |
| | None | — | — | — | |
| 118 | HIP-small | Right TA | coNS3/4A | 0.9 mg/0.3 ml | Day 5 |
| | None | — | — | — | |
| 119 | HIP-large | Right TA | coNS3/4A | 0.9 mg/0.3 ml | Day 10 |
| | HIP-large | Left TA | coHBcAg | 0.9 mg/0.3 ml | |
| 120 | HIP-large | Right TA | coNS3/4A | 0.9 mg/0.3 ml | Day 10 |
| | HIP-large | Left TA | coHBcAg | 0.9 mg/0.3 ml | |
| 121 | Regular | Right TA | coNS3/4A | 0.9 mg/0.3 ml | Day 10 |
| | Regular | Left TA | coHBcAg | 0.9 mg/0.3 ml | |
| 122 | None | — | — | — | Day 10 |
| | none | — | — | — | |

Figure 41:
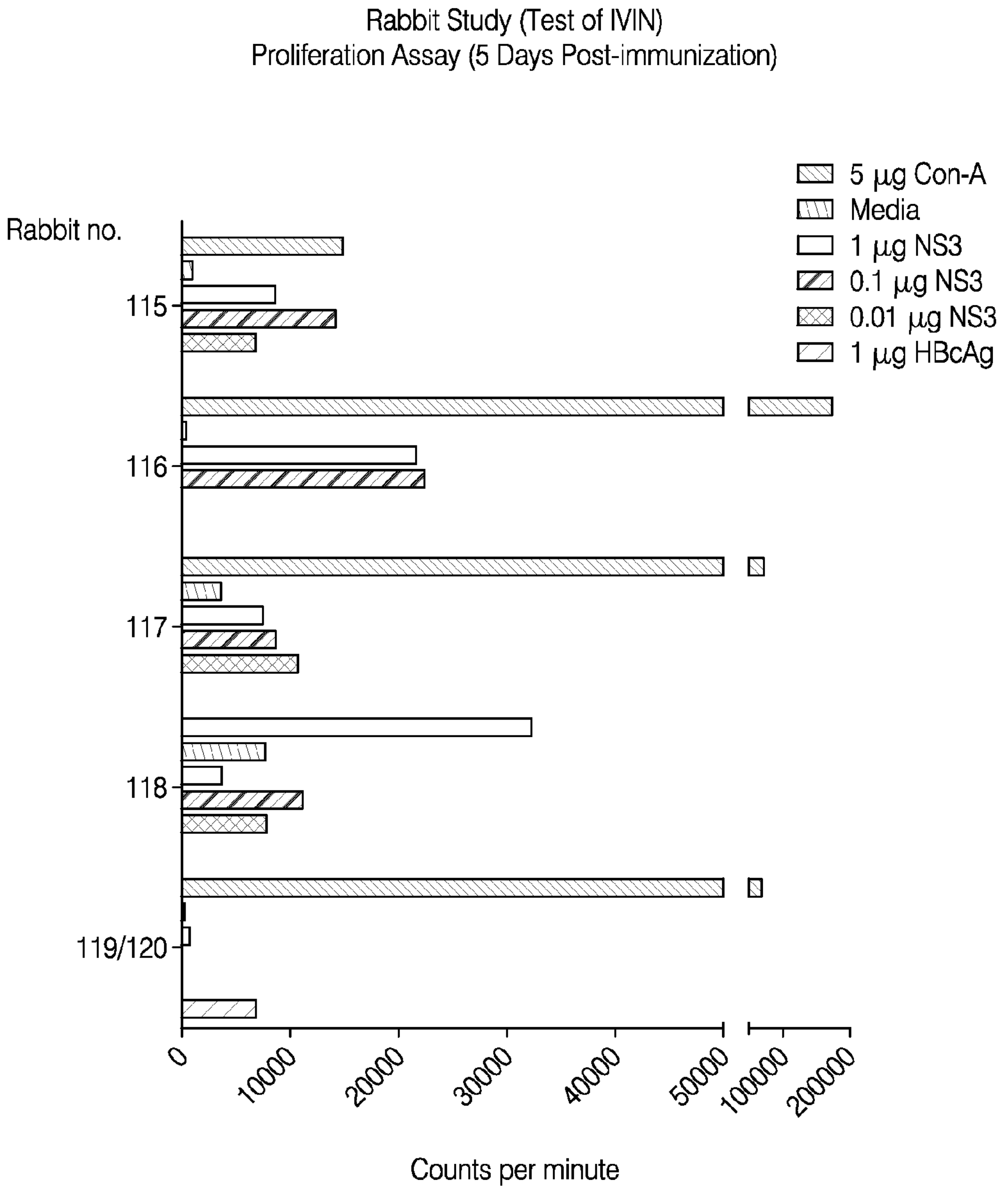
FIG. 41 is a graphical depiction of a rabbit study five days post immunization with a nucleic acid encoding NS3/4A, the radioactivity of cells, as counts per minute, when incubated with various antigens at various concentrations to show radioactive thymidine uptake in a T cell proliferation assay is provided.
Figure 42:
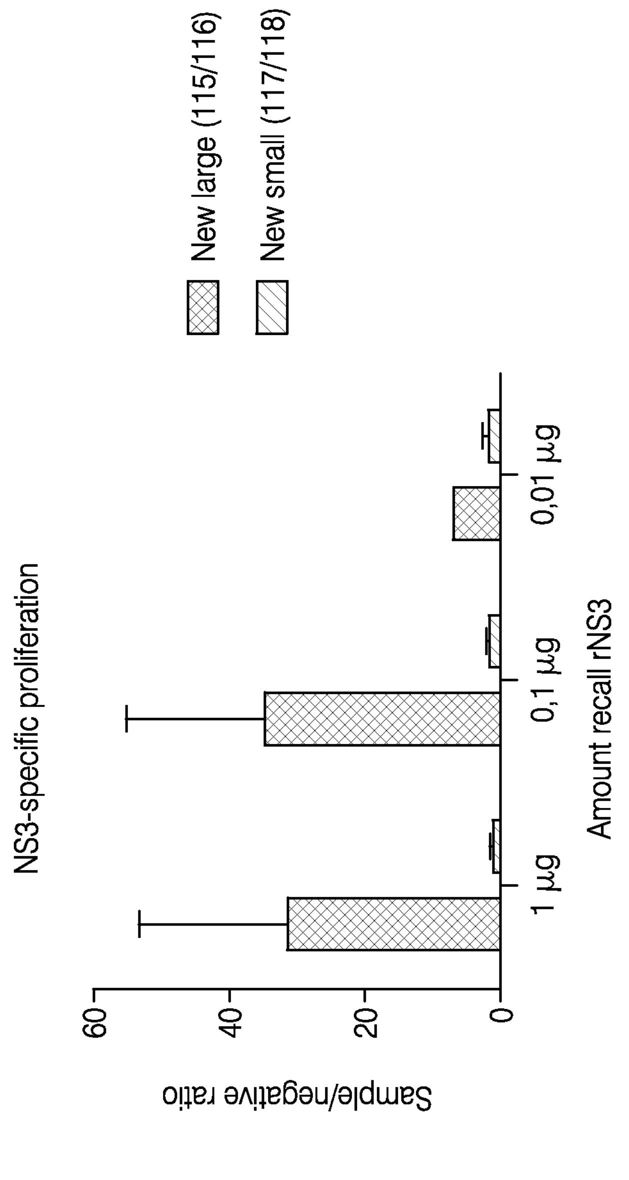
FIG. 42 is a chart illustrating HCV NS3-specific T cell proliferation as a result of immunization with the HIP injector. Proliferation is measured as radioactivity of cells incubated with antigen divided by the radioactivity of cells incubated with media alone.

At day 5, rabbits 115-118 were sacrificed and peripheral blood mononuclear cells (PBMCs) were analyzed for T cell proliferation. The PBMCs were assayed for in-vitro proliferative recall responses using a standard 96 h proliferation assay. (See Lazinda et al., J. Gen. Virol. 82:1299-1308 (2001), herein expressly incorporated by reference in its entirety.) In brief, microtiter plates were seeded with approximately 200,000 cells/well and the cells were incubated with media alone, recombinant NS3 or HBcAg. PBMCs were also incubated with Concanavalin A (ConA) as a positive control. After 72 hours, radioactive thymidine was added and 16-24 hours later the cells were harvested. The radioactivity of the cells as counts per minute are depicted in FIG. 41 and listed in TABLE 2. The proliferation was determined as radioactivity of the cells as the counts per minute (cpm) of cells incubated with the antigen divided by the CPM of the cells incubated with the media alone (sample to negative ration; S/N). The results are shown in FIG. 42.

TABLE 2

| Rabbit | 5 μg Con-A | media | 1 μg NS3 | 0.1 μg NS3 | 0.01 μg NS3 | 1 μg HBcAg |
|---|---|---|---|---|---|---|
| 115 | 14792 | 958 | 8570 | 14141 | 6816 | Not tested |
| 116 | 172935 | 406 | 21595 | 22360 | Not tested | Not tested |
| 117 | 71133 | 3632 | 7465 | 8625 | 10658 | Not tested |
| 118 | 32152 | 7632 | 3705 | 11152 | 7724 | Not tested |
| 119/120 | 67470 | 191 | 717 | Not tested | Not tested | 6838 |

The results show that rabbits immunized with the large HIP injector show a more robust immune response displayed through greater T cell proliferation than rabbits immunized with the small HIP injector. The data also provide strong evidence that the DNA that was introduced into the muscle tissue by the HIP injectors was effectively transferred into the cell, wherein it was transcribed, translated, and was used by the immune system of the animal to generate a potent immune response. Both the DNA encoding the HCV antigen NS3/4A and the DNA encoding the HBV antigen HBcAg effectively generated a potent immune response in mammals demonstrating that a variety of DNAs that encode immunogens can be effectively introduced into mammals using a delivery device described herein to induce an immune response in the inoculated animal.

The injection site for each rabbit was also collected for histological evaluation (as described in Ahlen et al., In Vivo Electroporation Enhances the Immunogenicity of Hepatitis C Virus Nonstructural 3/4A DNA by Increased Local DNA Uptake, Protein Expression, Inflammation and Infiltration of CD3+ T Cells. J. Immunol. 2007 179(7):4741-53, herein incorporated by reference in its entirety). Briefly, the tissue was fixed in a buffered 4% formaldehyde solution, dehydrated, and embedded in paraffin. The embedded tissues were sectioned in 4-6 μm sections. The sections were mounted onto glass slides and stained with hematoxylin and eosin stain (H&E), or polyclonal mouse sera from a coNS3/4A DNA-immunized mouse, which was detected by a biotinylated goat anti-mouse secondary antibody and peroxidase labeled streptavidin using an insoluble peroxidase substrate.

Figure 43A:
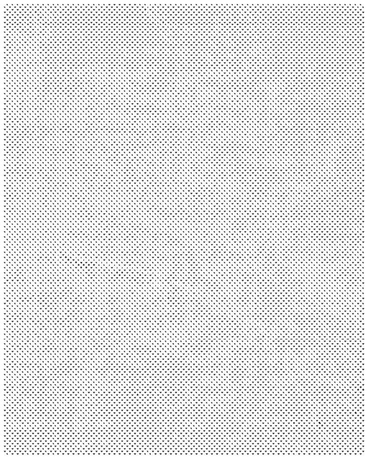
FIGS. 43A-C are histological evaluations of tissue at the site of injection with a regular 27 gauge needle (FIG. 43A), a small HIP injector (FIG. 43B), and a large HIP injector (FIG. 43C).
Figure 43B:
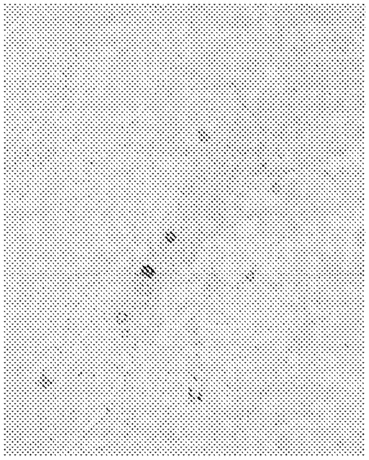
Figure 43C:
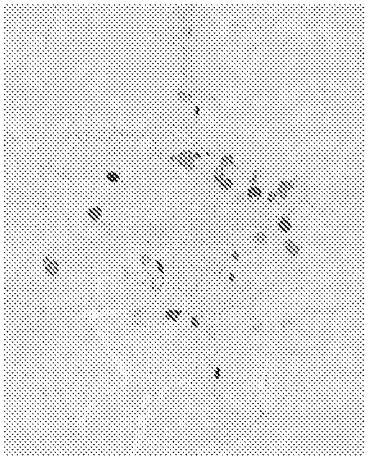
Figure 44A:
FIGS. 44A-I depict various constructs containing the NS3/4A platform and the HBcAg with and without NS3 protease cleavage sites.
Figure 44B:
Figure 44C:
Figure 44D:
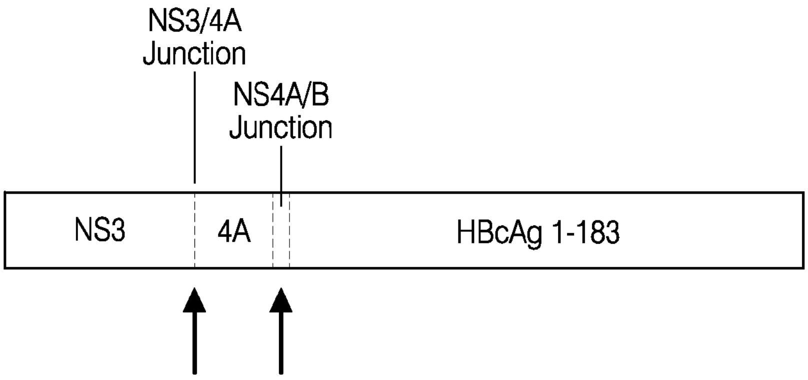
Figure 44E:
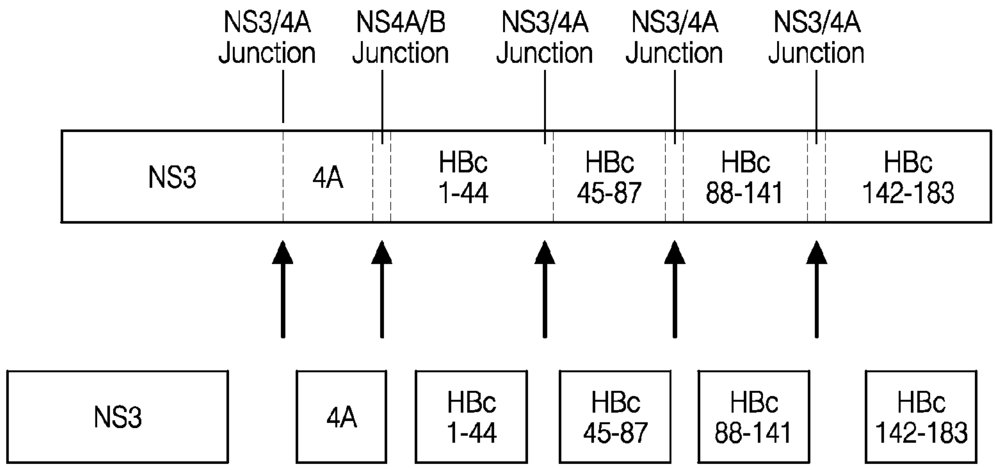
Figure 44F:
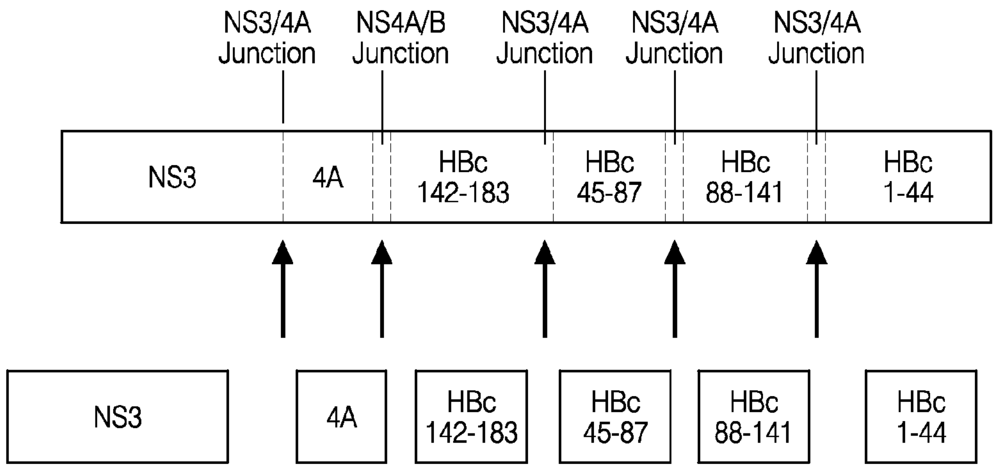
Figure 44G:
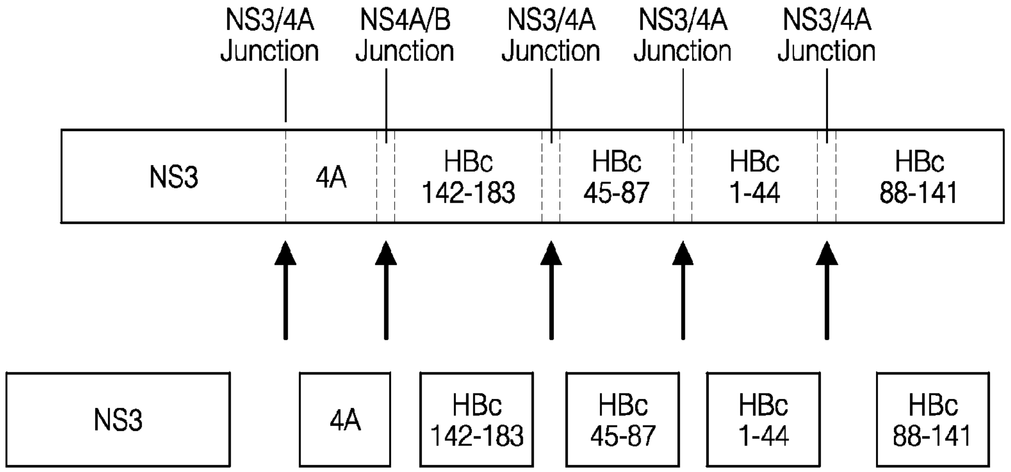
Figure 44H:
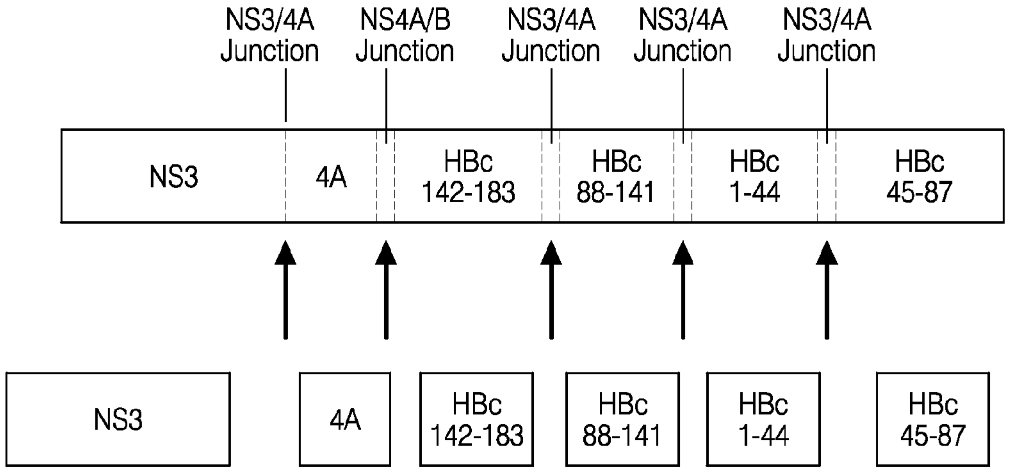
Figure 44I:
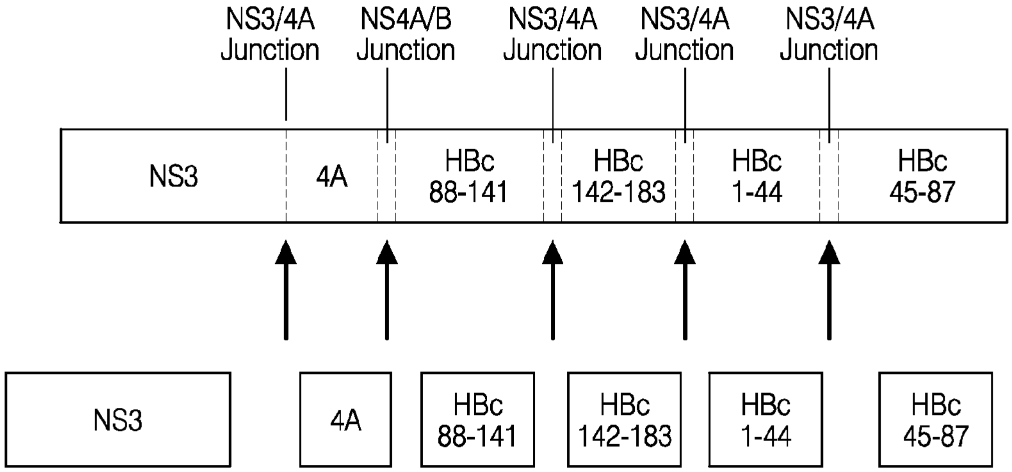

The results are shown in FIG. 43A-C. The injection of 0.9 mg of coNS3/4A with both HIP injectors produced significant amounts of local inflammation, regeneration, and fibrosis, as indicated by the high concentration of stained immune cells that localized to the injection site, in particular, between the needles. The data show that the large injector produced a better inflammatory response than the small injector in the rabbits. The injection of 0.9 mg of coNS3/4A with the conventional 27 gauge needle caused very little local inflammation, regeneration, and fibrosis, as indicated by the almost absent stained immune cells localized to the injection site. Additionally, both the HIP injectors induced the cells surrounding the injection site to produce significant amounts of NS3 protein, as indicated by the antibody labeling; whereas, the conventional injection with the 27 gauge needle under these conditions produced no detectable NS3 protein. Accordingly, the data show that the HIP injectors effectively delivered DNA into the cells, wherein it was transcribed and translated in significant amounts, which could be detected by an antibody specific for NS3 but the conventional injection with the 27 gauge needle did not.

The results provided in this example demonstrate that the HIP injectors described herein effectively deliver an expression plasmid that encodes an antigen into a cell of a subject in quantities sufficient to allow for a level of protein expression that is detectable by an antibody directed to the antigen and in an amount that is sufficient to generate appreciable amounts of antigen-specific T cells. That is, the data show that the HIP injectors described herein effectively deliver nucleic acids to cells of the body in an amount sufficient to produce a potent immune response in the subject. Thus, injecting a DNA vaccine using the HIP injector improves the immune response relative to standard methods of delivering vaccines.

EXAMPLE 2

The mechanisms by which a high injection pressure (HIP) needle improves the potency of intramuscular DNA vaccination are characterized by using the hepatitis C virus nonstructural (NS) 3/4A gene. Sustained control and clearance of HCV infection is related to an effective immune response, in particular a T cell response targeted to the nonstructural NS3 protein. By activating T cells outside the liver via vaccination, one may allow for the complementing or reshaping of the existing T cell repertoire. The present NS3/4A plasmid-based vaccine example is tested in mice. In vivo HIP needle administered vaccine is contemplated to increase the permeability of myocyte cell members, wherein the plasmid is effectively taken up in the nucleus and expressed, thereby inducing a functional in vivo immune response. The use of an in vivo HIP needle enhances the immunogenicity of coNS3/4A by both increasing protein expression levels and the duration of expression and by enhancing the infiltration of CD3+ T cells and a local inflammatory response at the site of injection.

Male and female C57BL/6 mice are bred and caged at five mice per cage. The mice are fed a commercial diet (RM3 (p) PL IRR diet; Special Diet Service) with free access to food and water. All animals are at least 6 weeks of age before start of the experiment. The SV40-luciferase plasmid (pGL4.13-[Luc2-SV40]; Promega) is produced in-house by standard technologies. The coNS3/4A plasmid is produced under Good Manufacturing Practice regulations.

The coNS3/4A DNA vaccine is administered by a single intramuscular injection (0.05 ml in mice) with a two-barrel 27-gauge HIP needle into the right tibialis anterior (TA) muscle. Doses range from 0.5 to 50 μg of DNA in mice. One two-barrel needle is used per injection and per animal. The procedure is repeated up to three times in mice at monthly intervals.

Detection of mouse antibody to NS3 by enzyme immunoassay is performed using standard immunoassay techniques. Antibodies titers are determined as the last serum dilution giving an OD at 405 nm of three times the OD at the same dilution of a non-immunized animal serum. With respect to NS3 antibody levels, a dose-response relationship is seen after vaccination with different doses of coNS3/4A-DNA administered with or without using the HIP needle. The boost effect is seen after immunization. The lower dose given with the HIP needle induces the same mean NS3-specific antibody levels as a greater dose delivered without the HIP needle. In conclusion, the HIP needle makes the coNS3/4A DNA-based immunization more effective with respect to antibody responses, supporting the benefits of the adjuvant effects mediated by using a HIP needle.

EXAMPLE 3

New Zealand White rabbits weighing 2.5-3.5 kg, are purchased from commercial vendors. The coNS3/4A DNA vaccine is administered by a single intramuscular injection with a four-barrel 27-gauge HIP needle into the right tibialis anterior (TA) muscle. Doses range from 70 to 700 μg of DNA. One four-barrel needle is used per injection and per animal. The procedure is repeated up to five times in rabbits at monthly intervals.

Detection of rabbit antibodies to NS3 by enzyme immunoassay is performed using standard immunoassay techniques. Antibodies titers are determined as the last serum dilution giving an OD at 405 nm of three times the OD at the same dilution of a non-immunized animal serum.

Proliferative responses to NS3 are determined in rabbit whole blood. A total of 4 ml of whole blood is obtained from the ear artery of each rabbit immediately before the first vaccination and 2 weeks after each vaccination and collected in heparin tubes. Plasma and peripheral mononuclear cells (PMBC) are isolated by gradient centrifugation. Plasma is stored at −80° C. until the analysis of NS3-specific antibody by enzyme immunoassay. PBMCs are immediately assayed for in vitro proliferative recall responses using a standard 96 hour proliferation assay. In brief, microplates are seeded with 200,000 cells per well and the cells are incubated with medium alone, ConA, PHA, or rNS3. After 72 hours, radioactive thymidine is added and 16-24 hours later, the cells are harvested. Proliferation is determined from the radioactivity of the cells as the counts per minute (cpm) of cells incubated with an antigen divided by the cpm of the cells incubated with medium alone, sample to negative (S/N) ratio. Groups are compared by the mean S/N ratios at each time point.

Rabbits are injected in the right TA with 0.3 ml of saline containing the indicated amount of coNS3/4A DNA. Antibody levels are recorded as the mean end point titers. Peak antibody end point titers are reached after several injections.

Data is recorded showing the dose-response relation with respect to induction of NS3-specific proliferative responses in PBMC in rabbits immunized using a HIP needle. Data is collected to indicate a proliferative result as the mean S/N of duplicate or triplicate determinations in the presence of rNS3 in vitro.

NS3-specific proliferation will be detectable. The mean NS3-recalled proliferation is consistently higher in the groups receiving higher doses of coNS3/4A DNA as compared with the control group. Thus, the vaccination primes in vitro detectable T cell responses in rabbits.

EXAMPLE 4

In a next series of experiments, the injection needle(s) described herein are modified for use with existing gene transfer technologies, including gene gun delivery systems, delivery systems using electroporation, and microneedle delivery systems. In these experiments, the NS3/4A-pVAX1 vector is administered to mice or rabbits via the modified gene gun delivery system, the modified electroporation device, or the modified microneedle delivery system. Purified NS3/4A-pVAX1 vector is used to immunize groups of mice or rabbits. The plasmid is injected directly into regenerating tibialis anterior (TA) muscle via either the modified gene gun delivery system, the modified electroporation device, or the modified microneedle delivery system. Immunization of is performed with approximately 0.25 mg/kg of DNA of plasmid DNA. Immunizations are performed on weeks 0, 4, and 8.

Enzyme immunosorbent assays (EIAs) are used to detect the presence of murine NS3-specific antibodies. These assays are performed essentially as described (Chen et al., *Hepatology* 28(1): 219 (1998)). Briefly, rNS3 is passively adsorbed overnight at 4° C. to 96-well microtiter plates (Nunc, Copenhagen, Denmark) at 1 μg/ml in 50 mM sodium carbonate buffer (pH 9.6). The plates are then blocked by incubation with dilution buffer containing PBS, 2% goat serum, and 1% bovine serum albumin for one hour at 37° C. Serial dilutions of mouse sera starting at 1:60 are then incubated on the plates for one hour. Bound murine and rabbit serum antibodies are detected by an alkaline phosphatase conjugated goat anti-mouse or goat anti-rabbit IgG (Sigma Cell Products, Saint Louis, Mo.) followed by addition of the substrate pNPP (1 tablet/5 ml of 1M Diethanol amine buffer with 0.5 mM $MgCl_2$). The reaction is stopped by addition of 1M NaOH and absorbency is read at 405 nm.

After four and six weeks, all mice and rabbits immunized with NS3/4A-pVAX1 will develop NS3 antibodies. Similarly, all mice and rabbits immunized with NS3/4A-pVAX1 will develop potent T cell responses. All mice and rabbits immunized with NS3/4A-pVAX1 via either the modified gene gun delivery system, the modified electroporation device, or the modified microneedle delivery system will develop a potent immune response to the desired antigen.

EXAMPLE 5

It is well known that the exogenous capsid protein (HBcAg) of the hepatitis B virus (HBV) is highly immunogenic on a CD4+ T cell level in all species tested. However, HBcAg has not been explored as an adjuvant for genetic vaccines, and in particular the non-human forms of HBcAg. A key feature of using non-human HBcAg is that HBV is a very common infection that affects almost a third of the worlds population. Thus, HBcAg sequences from highly distant species should be used in order to be able to use these vaccines also in areas highly endemic for HBV. The use of HBcAg as a DNA vaccine adjuvant is explored here. HBcAg-sequences effectively improved the immunogenicity of hepatitis C virus derived genes supporting that HBcAg can act as a intracellular adjuvant (iac). Importantly, the major role of the addition of HBcAgsequences was seen in models mimicking the human HCV infection. HBcAg-based vaccines could overcome the profound T cell tolerance in transgenic mice co-expressing the human leucocyte antigen (HLA)-A2 and the HCV non-structural (NS) 3/4A complex. Here the presence of "healthy" non-tolerized heterologous T cells aided in the activation of the dysfunctional HCV NS3/4A-specific T cells. Thus, HBcAg effectively acts as an intracellular adjuvant that can help restoring a dysfunctional T cell response in a host with persistent presence of a viral antigen, as generally seen in chronic viral infections.

Some embodiments include, for example, one or more of the HBcAg nucleic acid or protein sequences disclosed in International Patent Application Publication Number WO 2009/130588, which designated the United States and was published in English, the disclosure of which is hereby expressly incorporated by reference in its entirety. Some embodiments include the NS3/4A/HBcAg fusions or a nucleic acid encoding said fusion identified in FIGS. 44 A-I, or a nucleic acid or a nucleic acid or a nucleic acid encoding a protein described in SEQ. ID NOS 1-32. Additional nucleic acid sequences encoding antigenic peptides, such as those described in WO 2009/130588 (e.g., birch antigen) and WO 2010/086743, both of which designated the United States and published in English, the disclosure of which is hereby expressly incorporated by reference in their entirety can also be joined to an HBcAg encoding nucleic acid sequence and said fusions can be administered to a subject in need thereof using one or more of the injection devices described herein. Some embodiments also include additional adjuvants, including but not limited to ribavirin or a CPG nucleotide e.g., SEQ. ID NO. 33. Any of the aforementioned embodiments can be incorporated into one or more of the injection devices described herein and can be administered to a subject in need thereof.

EXAMPLE 6

The force requirements for injecting material using an intracellular delivery device described herein were studied. Placebo liquid was injected into open space or chicken breast and the applied forces were measured using a Lloyd force tensometer.

Figure 45:
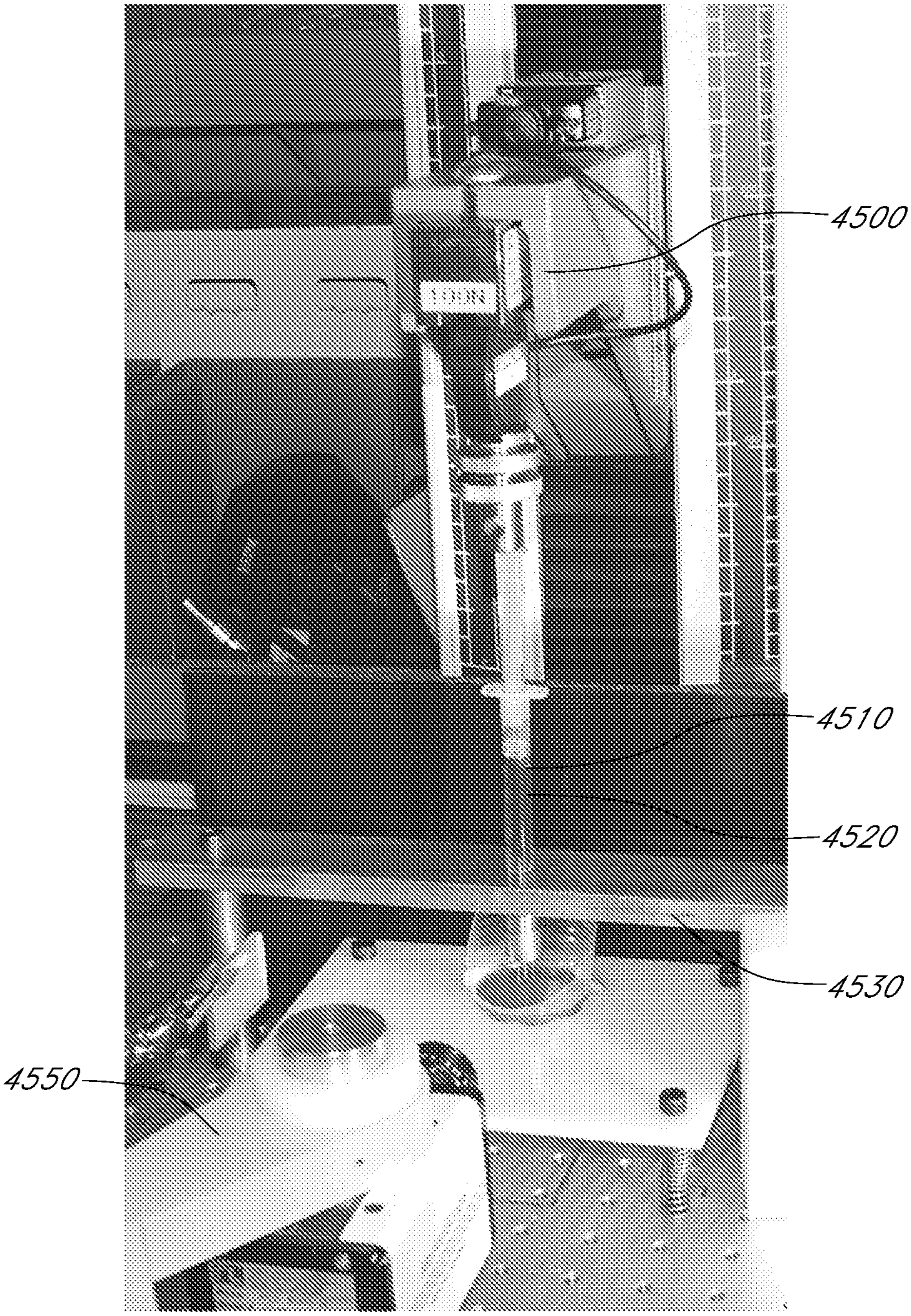
FIG. 45 depicts an embodiment of a setup for measuring the force requirements when injecting material using one of the injection needle devices disclosed herein.
Figure 46:
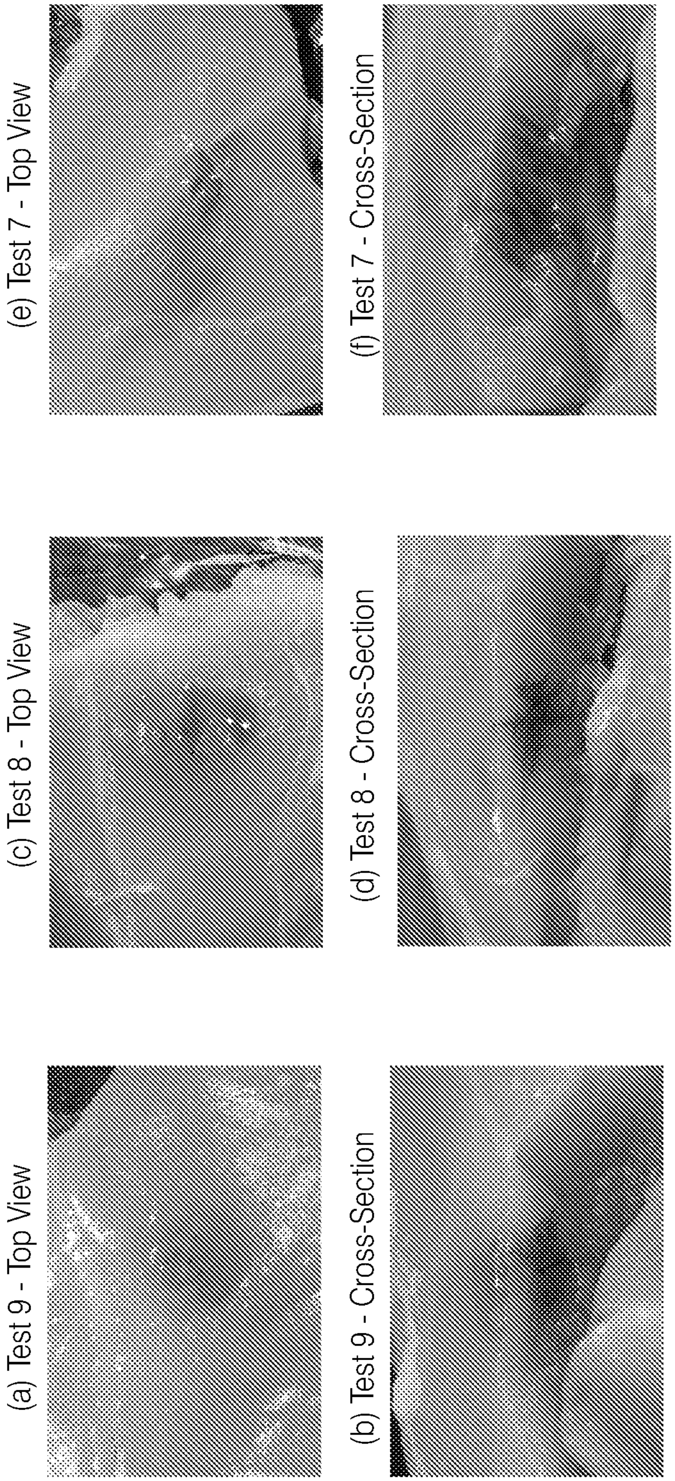
FIG. 46A-F are top and cross-sectional views of Tests 7-9 showing dyed water injected into chicken breast using an intracellular delivery apparatus described herein.
Figure 47:
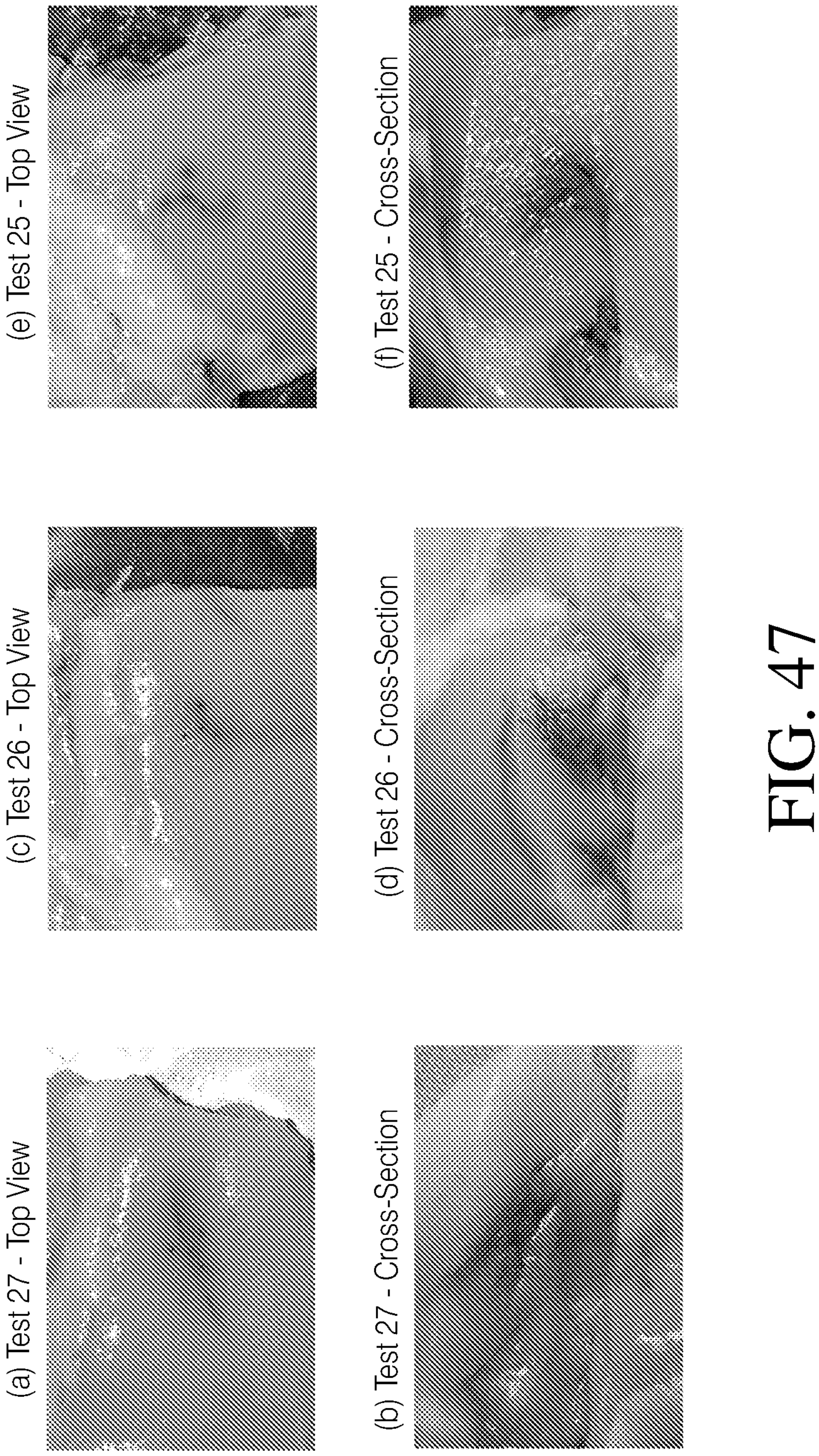
FIG. 47A-F are top and cross-sectional views of Tests 25-27 showing dyed water injected into chicken breast using an intracellular delivery apparatus described herein.
Figure 48:
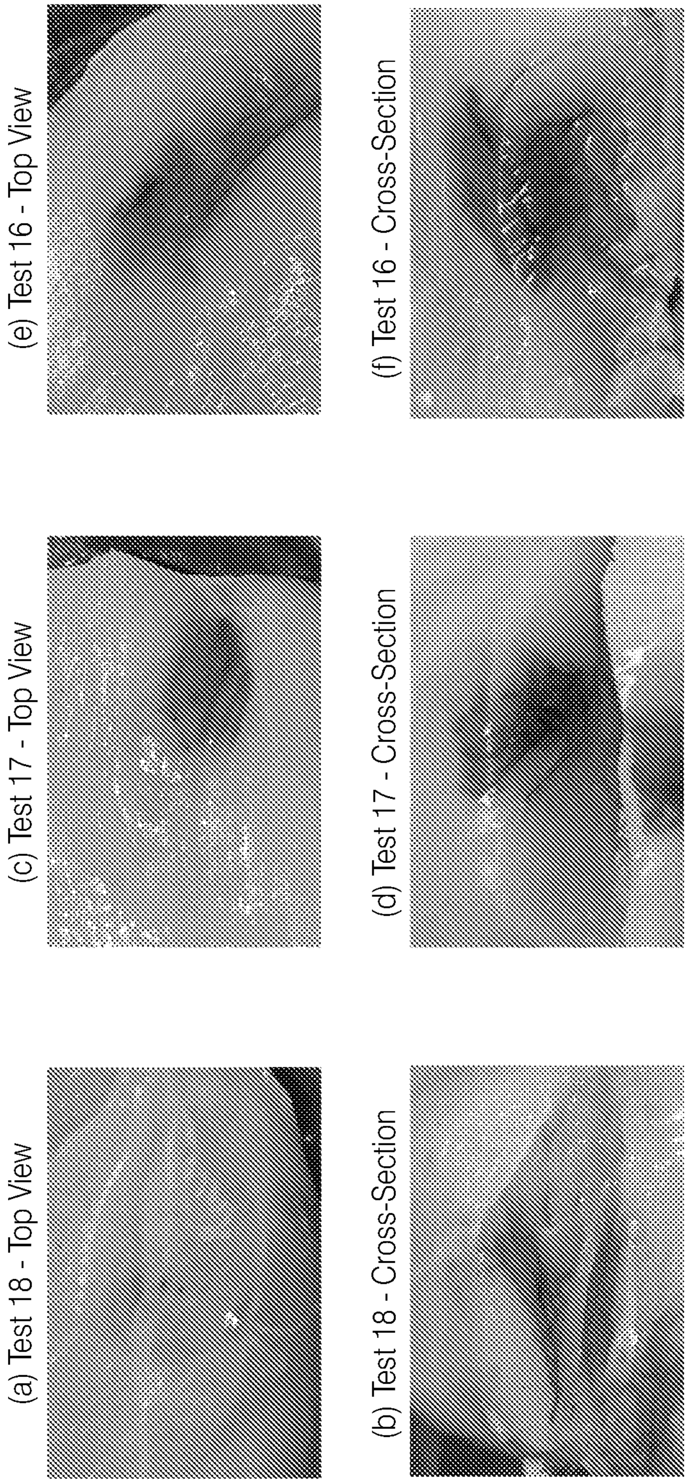
FIG. 48A-F are top and cross-sectional views of Tests 16-18 showing dyed water injected into chicken breast using an intracellular delivery apparatus described herein.
Figure 49:
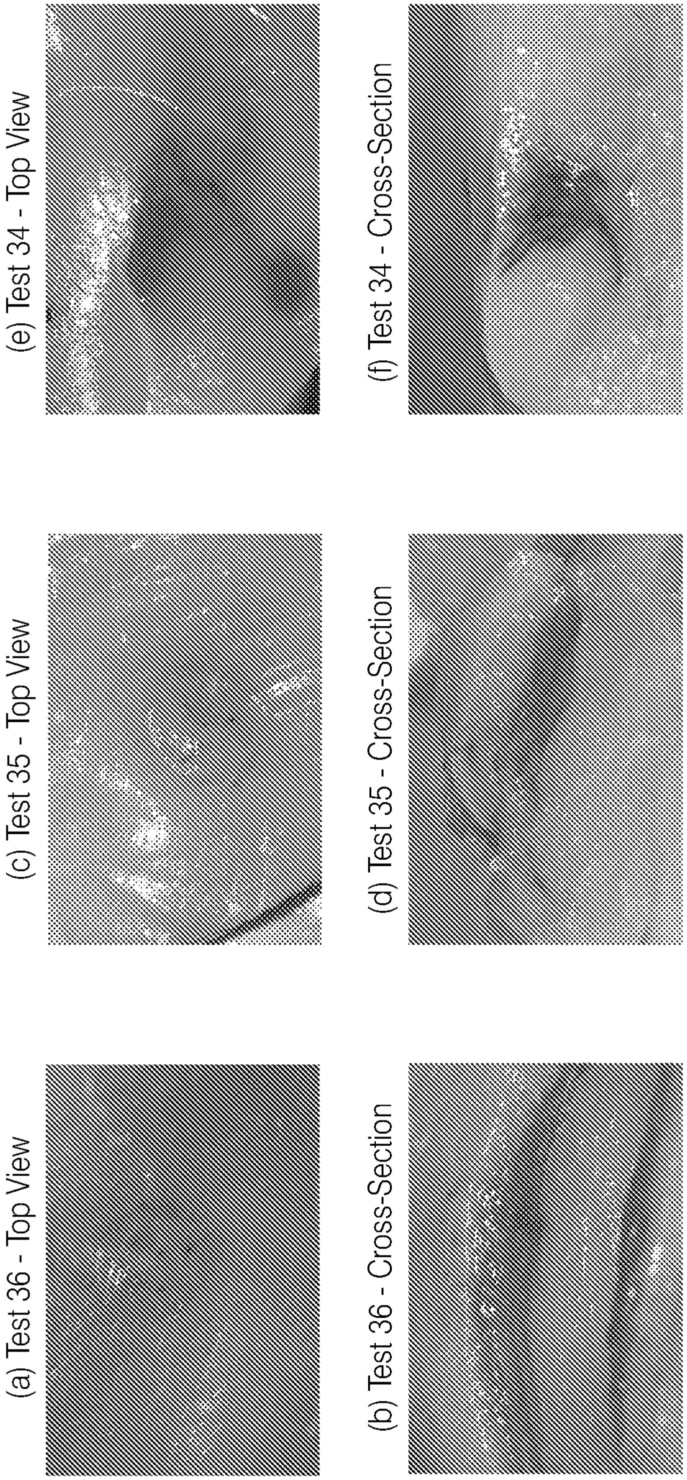
FIG. 49A-F are top and cross-sectional views of Tests 34-36 showing dyed water injected into chicken breast using an intracellular delivery apparatus described herein.

FIG. 45 is an example of the setup for measuring the force requirements when injecting material using one of the injection needle devices disclosed herein. Lloyd Force Tester 4500 was used to compress syringe 4510 containing fluid 4520 at a predetermined velocity to measure the applied force while injecting 0.3 mL of fluid (e.g., air or water). Support jig 4530 secured syringe 4510 during compression and high-speed camera 4540 recorded the spray pattern from the needles barrels 4550. Two different syringes were tested: (i) a 3 mL syringe requiring a plunger depth of 5.09 mm to inject 0.3 mL, and (ii) a 5 mL syringe requiring a plunger depth of 2.63 mm to inject 0.3 mL. An initial test studied the force required for injecting air into an open area (i.e., not positioned within muscle tissue). Tests were also completed for injecting died water into an open area or into chicken breast.

The tested injection device comprises four needles configured with generally the same structure depicted in FIG. 8B. The length $L_6$ is 6 mm. Specifically, needle 820*b* includes three zones, each having 15 apertures that all face one of the adjacent needles 820*a*, 820*c*, and 820*d*. That is, needle 820*b* include a first zone having 15 apertures that all face needle 820*a*, a second zone having 15 apertures that all face needle 820*b*, and a third zone having 15 apertures that all face needle 820*c*. Meanwhile, needles 820*a*, 820*c*, and 820*d* each include one zone of 15 apertures that all face needle 820*b*. All of the apertures in a given zone were spaced vertically apart along the axis of the needle barrel. Each aperture was separated by distance of about 0.2 mm between the centers of each apertures. Needles with 0.05 mm circular apertures or 0.1 mm circular apertures were tested.

The results are shown Table 3.

TABLE 3

| Test | Aperture Size (mm) | Syringe Volume (mL) | Compression Speed (mm/s) | Flow Rate (mL/s) | Fluid | Target Material | Maximum Force (N) |
|---|---|---|---|---|---|---|---|
| 1 | 0.1 | 3 mL | 17 | 1.0 | Air | None | 2.9 |
| 2 | 0.1 | 3 mL | 10.2 | 0.6 | Air | None | 2.6 |
| 3 | 0.1 | 3 mL | 5.1 | 0.3 | Air | None | 2.1 |
| 4 | 0.1 | 3 mL | 17 | 1.0 | $H_2O$ | None | 16.0 |
| 5 | 0.1 | 3 mL | 10.2 | 0.6 | $H_2O$ | None | 8.5 |
| 6 | 0.1 | 3 mL | 5.1 | 0.3 | $H_2O$ | None | 4.0 |
| 7 | 0.1 | 3 mL | 17 | 1.0 | Died $H_2O$ | Chicken | 18.0 |
| 8 | 0.1 | 3 mL | 10.2 | 0.6 | Died $H_2O$ | Chicken | 9.8 |
| 9 | 0.1 | 3 mL | 5.1 | 0.3 | Died $H_2O$ | Chicken | 5.25 |
| 10 | 0.1 | 5 mL | 17 | 1.9 | Air | None | 1.9 |
| 11 | 0.1 | 5 mL | 10.2 | 1.2 | Air | None | 1.2 |
| 12 | 0.1 | 5 mL | 5.1 | 0.6 | Air | None | 0.6 |
| 13 | 0.1 | 5 mL | 17 | 1.9 | $H_2O$ | None | 36.0 |
| 14 | 0.1 | 5 mL | 10.2 | 1.2 | $H_2O$ | None | 36.5 |
| 15 | 0.1 | 5 mL | 5.1 | 0.6 | $H_2O$ | None | 15.9 |
| 16 | 0.1 | 5 mL | 17 | 1.9 | Died $H_2O$ | Chicken | 46.0 |

TABLE 3-continued

| Test | Aperture Size (mm) | Syringe Volume (mL) | Compression Speed (mm/s) | Flow Rate (mL/s) | Fluid | Target Material | Maximum Force (N) |
|---|---|---|---|---|---|---|---|
| 17 | 0.1 | 5 mL | 10.2 | 1.2 | Died $H_2O$ | Chicken | 37.0 |
| 18 | 0.1 | 5 mL | 5.1 | 0.6 | Died $H_2O$ | Chicken | 16.9 |
| 19 | 0.05 | 3 mL | 17 | 1.0 | Air | None | 2.8 |
| 20 | 0.05 | 3 mL | 10.2 | 0.6 | Air | None | 2.7 |
| 21 | 0.05 | 3 mL | 5.1 | 0.3 | Air | None | 2.25 |
| 22 | 0.05 | 3 mL | 17 | 1.0 | $H_2O$ | None | 18.25 |
| 23 | 0.05 | 3 mL | 10.2 | 0.6 | $H_2O$ | None | 10.1 |
| 24 | 0.05 | 3 mL | 5.1 | 0.3 | $H_2O$ | None | 5.0 |
| 25 | 0.05 | 3 mL | 17 | 1.0 | Died $H_2O$ | Chicken | 24.4 |
| 26 | 0.05 | 3 mL | 10.2 | 0.6 | Died $H_2O$ | Chicken | 12.9 |
| 27 | 0.05 | 3 mL | 5.1 | 0.3 | Died $H_2O$ | Chicken | 7.6 |
| 28 | 0.05 | 5 mL | 17 | 1.9 | Air | None | 1.9 |
| 29 | 0.05 | 5 mL | 10.2 | 1.2 | Air | None | 1.2 |
| 30 | 0.05 | 5 mL | 5.1 | 0.6 | Air | None | 0.6 |
| 31 | 0.05 | 5 mL | 17 | 1.9 | $H_2O$ | None | 47.0 |
| 32 | 0.05 | 5 mL | 10.2 | 1.2 | $H_2O$ | None | 41.0 |
| 33 | 0.05 | 5 mL | 5.1 | 0.6 | $H_2O$ | None | 18.2 |
| 34 | 0.05 | 5 mL | 17 | 1.9 | Died $H_2O$ | Chicken | 42.0 |
| 35 | 0.05 | 5 mL | 10.2 | 1.2 | Died $H_2O$ | Chicken | 47.0 |
| 36 | 0.05 | 5 mL | 5.1 | 0.6 | Died $H_2O$ | Chicken | 23.0 |

The spray patterns for water into an open area were studied using a high-speed camera. Generally, tests that produced a 1 mL/s flow rate or higher produced a well-defined, symmetric spray pattern that is expected to increase pressure and may be suitable for delivering therapeutic material. FIGS. 46-49 show top and cross-sectional views of chicken breast after injection with dyed water.

EXAMPLE 7

This example describes using an intracellular delivery device disclosed herein to inject material into a tissue sample by hand to consider the practical pressure limits for manually delivering material. The needles were configured the same is Example 6 and included 0.05 mm apertures with a 3 mm spacing between needles. The 3 mL syringe was supported using a support jig and the plunger was manually depressed as quickly as possible. The plunger motion was recorded using a high-speed camera and used to calculate the time for injecting 0.3 mL of died water into the chicken breast.

Figure 50:
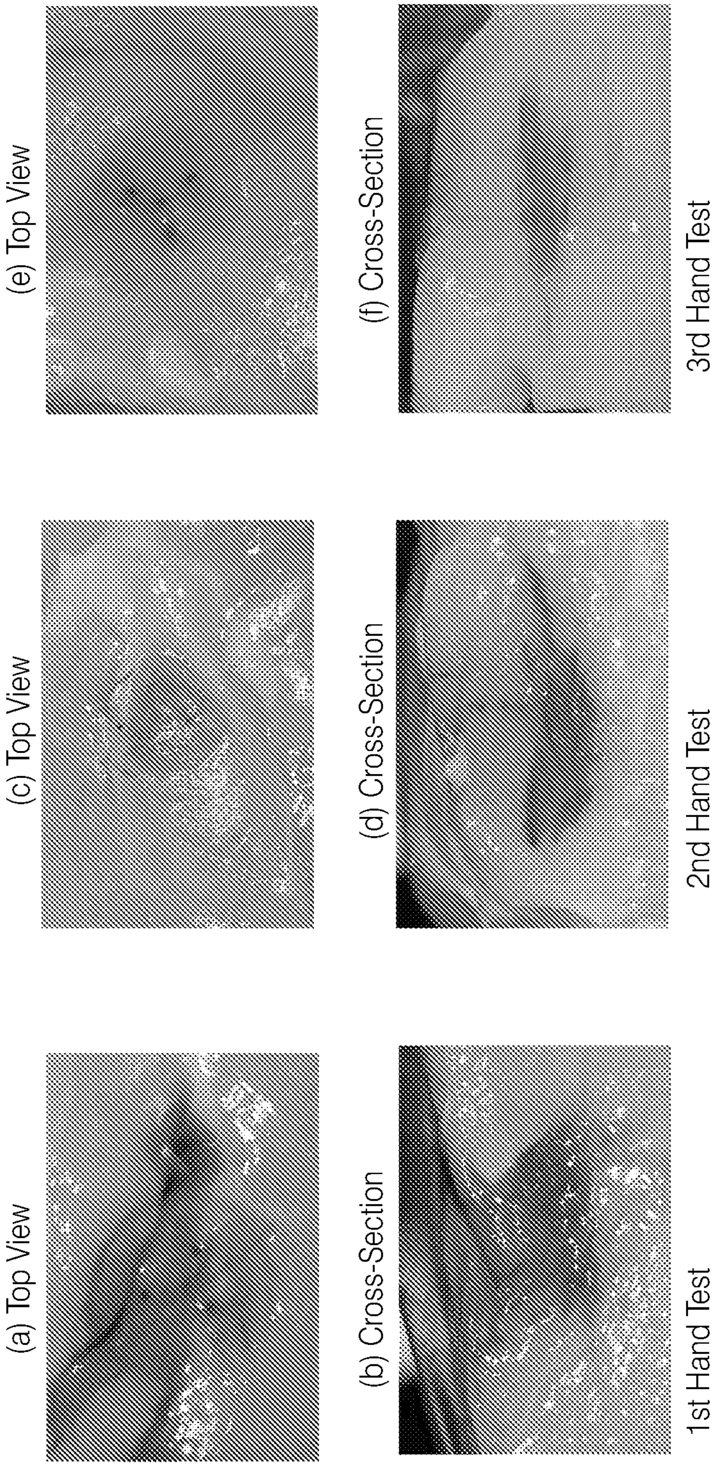
FIG. 50A-F are top and cross-sectional views of chicken breast having dyed water injected by hand using an intracellular delivery apparatus described herein.
Figure 51:
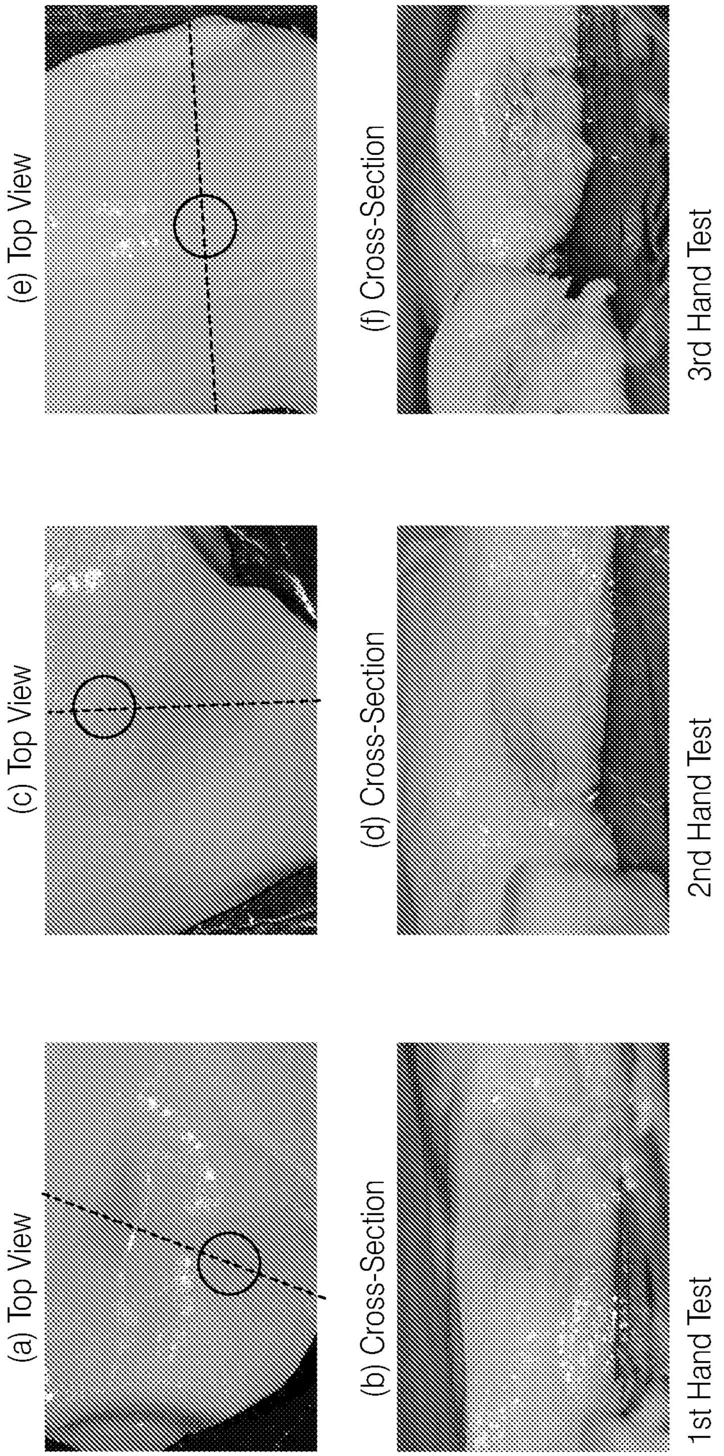
FIG. 51A-F are top and cross-sectional views of chicken breast having dyed water injected by hand using a single needle.

The test was repeated three times and the time required for delivering the material was 0.48 s, 0.40 s, and 0.48 s. Therefore, the average hand delivery speed was about 0.45 seconds. FIG. 50 shows top and cross-sectional views of chicken breast after manual injection with died water. FIG. 51 is a comparative example showing top and cross-sectional views of chicken breast after manual injection with died water using only a single needle.

EXAMPLE 8

The force requirements for injecting material using an intracellular delivery device described herein were studied using generally the same procedures described in Example 6.

Several different injection devices were tested. Injection device "3Y01(72)" included four needles as depicted in FIG. 8B, where $L_6$ was 3 mm. The total number of apertures in the four needles was 72. The center needle included 36 apertures distributed in three rows along the axis of the needle, each row facing an outer needle. The three outer needles each include a single row of 12 apertures facing the center needle to produce a cross-flow between needles. The apertures had a diameter of 0.1 mm and a spacing of about 0.2 mm.

Injection device "3O01(96)" included needles as depicted in FIG. 8C, where $L_7$ was 3 mm and each needle includes 24 apertures (4 times 24 is 96 apertures) distributed in two rows along the axis of the needle. Each row faces an adjacent needle to produce a cross-flow between needles. The apertures had a diameter of 0.1 mm and a spacing of about 0.2 mm.

Injection device "6X01(144)" included needles as depicted in FIG. 8C, where $L_7$ was 6 mm and each needle includes 36 apertures (4 times 36 is 144 apertures) distributed in three rows along the axis of the needle. Each row faced one of the three other needles to produce a cross-flow between needles and also converging at about the center equidistant from the four needles. The apertures had a diameter of 0.1 mm and a spacing of about 0.2 mm.

Injection device "3O05(72)" had generally the same configuration as "3O01(96)" except that each aperture was 0.05 mm, $L_7$ was 3 mm, and each needle included 18 apertures. Injection device "3X05(72)" had generally the same configuration as "6X01(144)" except that each aperture was 0.05 mm, $L_7$ was 3 mm, and each needle included 18 apertures. Injection device "3Y05(72)" had generally the same configuration as "3Y01(72)" except that each aperture was 0.05 mm and, $L_6$ was 3 mm.

Figure 52:
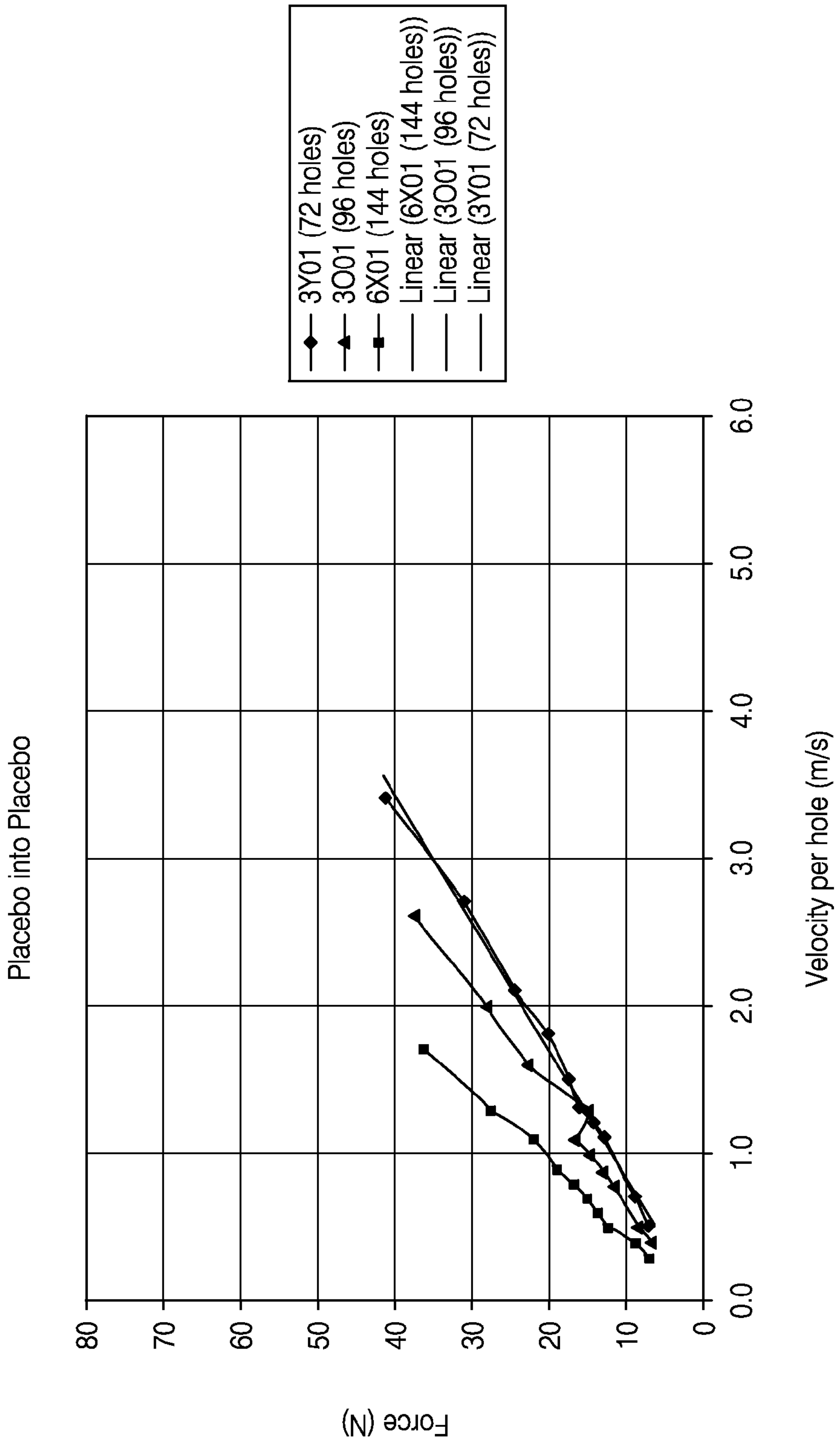
FIG. 52 shows a graph of the maximum force for injecting a placebo fluid with needle configurations "3Y01(72)", "3O01(96)", and "6X01(144)" using a 5 mL syringe.

FIG. 52 shows the maximum force at varying jet velocities (in mm/sec.) for the water exiting the aperture using a 5 mL syringe.

Figure 53:
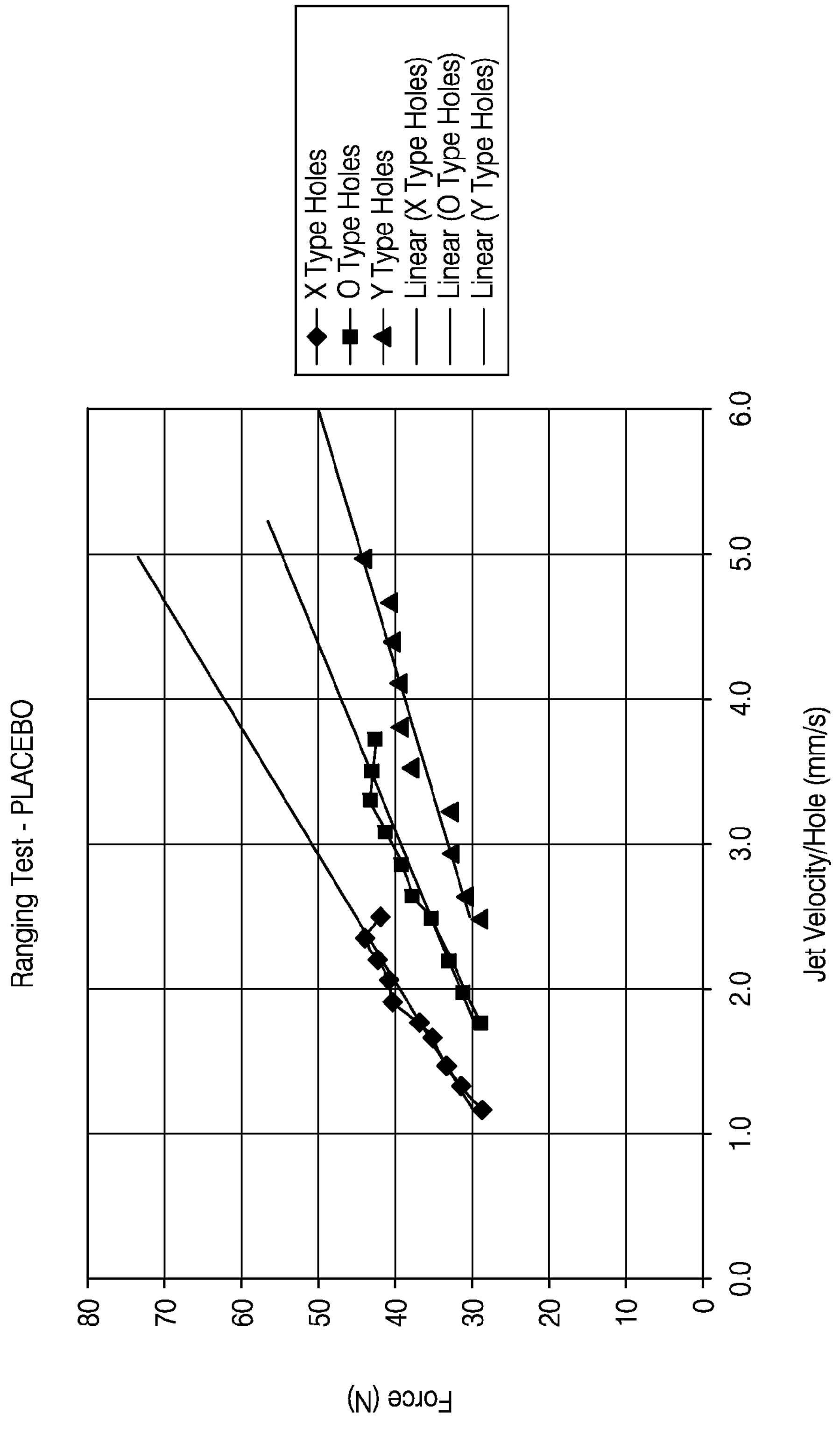
FIG. 53 shows a graph of the maximum force for injecting water into air with needle configurations "3Y01(72)", "3O01(96)", and "6X01(144)" using a 10 mL syringe.

FIG. 53 shows the maximum force at varying jet velocities (in mms/sec.) for the water exiting the aperture using a 10 mL syringe. The 'X', 'O', and 'Y' type holes are "6X01(144)", "3O01(96)", and "3Y01(72)", respectively.

Figure 54:
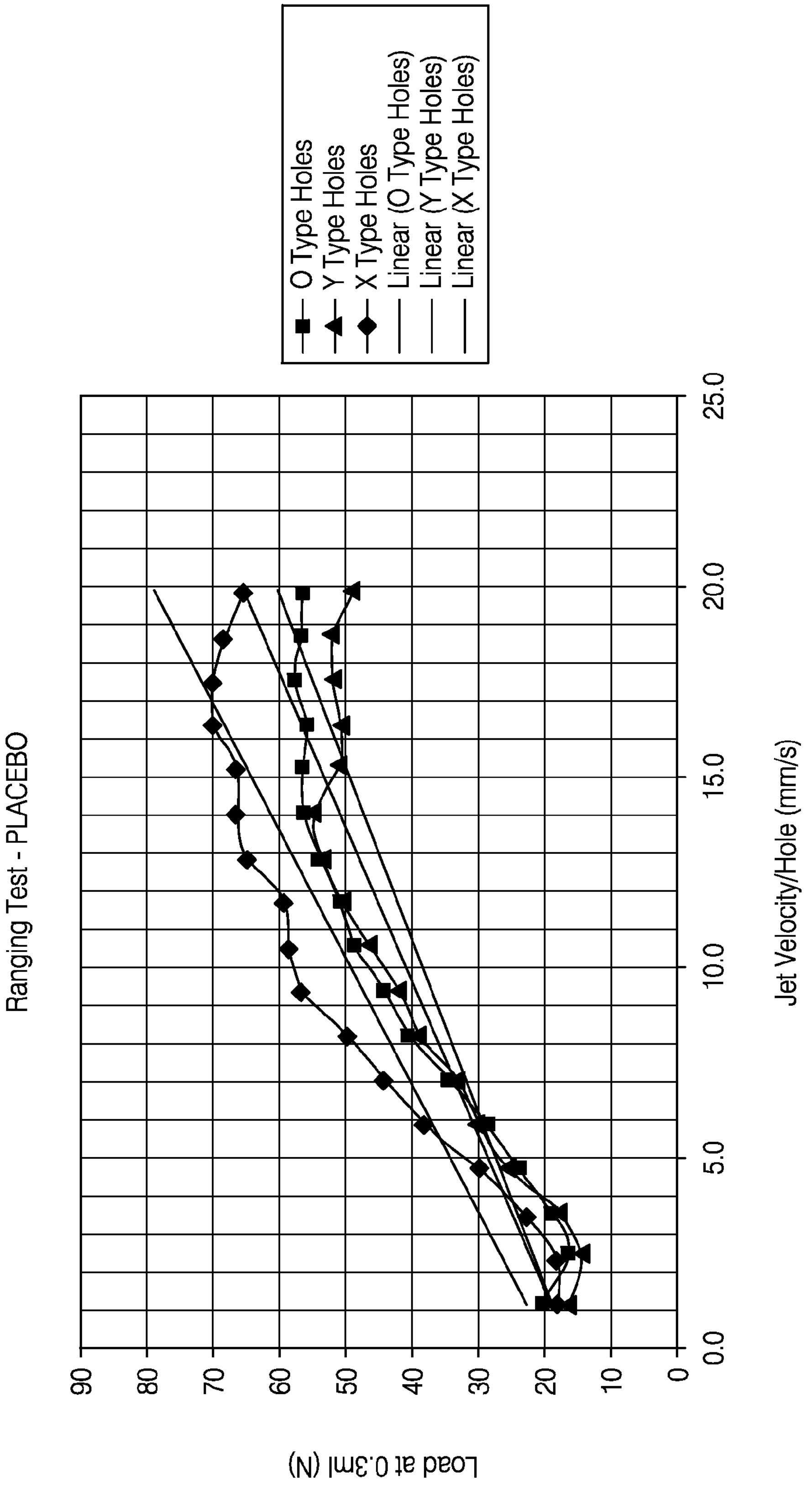
FIG. 54 shows a graph of the maximum force for injecting water into air with needle configurations "3Y05(72)", "3O05(72)", and "3X05(72)" using a 10 mL syringe.

FIG. 54 shows the maximum force at varying jet velocities (in mm/sec.) for the water exiting the aperture using a 10 mL syringe. The 'X', 'O', and 'Y' type holes are "3X05(72)", "3O05(72)", and "3Y05(72)", respectively. The maximum injection forces for the six needle devices described above were tested when (i) injecting air into open space; (ii) injecting water into open space; and (iii) injecting water into chicken. The maximum forces are shown in the Table 4 below.

Figure 55:
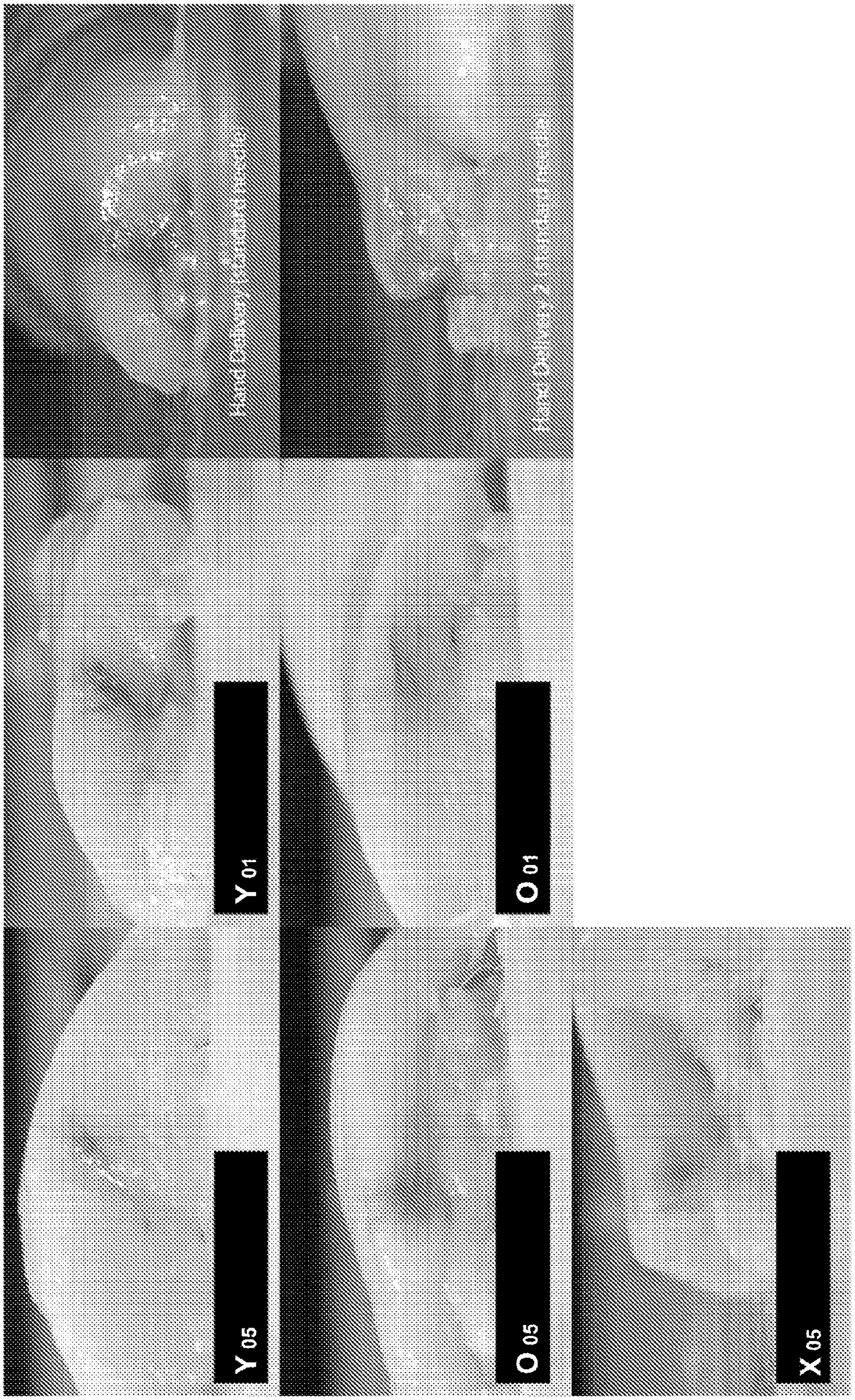
FIG. 55 shows images of dyed water injected into chicken by hand delivery with a standard needle, or using a Lloyd force tensometer with the 3Y05(72)", "3O05(72)", "3X05 (72)", 3Y01(72)", or "3O01(96)" needle configurations.

The delivery of dyed water into the chicken breast was tested. The dyed water was injected using the Lloyd force tensometer with needles "3Y05(72)", "3O05(72)", "3X05 (72)", "3Y01(72)", and "3O01(96)". As a comparative example, dyed water was delivered into chicken bread using a single needle with one aperture at the end of the barrel. 0.3 mL was injected for each test and FIG. 55 shows the results. The results show improved, localized tissue delivery for the needles "3Y05(72)", "3O05(72)", "3X05(72)", "3Y01(72)", and "3O01(96)".

TABLE 4

| Hub | Number of Holes/Hub | Velocity/ Hole (m/sec) | AIR: Load @ 0.3 ml (N) | PLACEBO: Load @ 0.3 ml (N) | CHICKEN: Load @ 0.3 ml (N) |
|---|---|---|---|---|---|
| 3Y01 | 72 | 5.0 | 38.0 | 44.3 | 53.6 |
| 3O01 | 96 | 3.7 | 33.4 | 42.5 | 59.5 |
| 6X01 | 144 | 2.5 | 36.9 | 42.1 | N/A |
| 3Y05 | 72 | 19.9 | 60.4 | 49.1 | 93.7 |
| 3O05 | 72 | 19.9 | 56.1 | 56.7 | 62.4 |
| 3X05 | 72 | 19.9 | 57.3 | 65.5 | 73.2 |

EXAMPLE 9

A combined acute and repeated toxicology study is performed using a total of 72 rabbits (36 females and 36 males). After two weeks of acclimatization all animals are injected intramuscularly with either buffer, the clinical dose (amount DNA)/kg or 10×the clinical dose (amount DNA)/kg intended for human use in combination with electroporation, using needles and methods described herein. The health status of the animals is monitored daily after injection of DNA. At 7 days after the first vaccination 4 animals from each group of animals is subjected to blood sampling for haematology and clinical chemistry analyses. The animals are thereafter euthanized and relevant organs are be dissected for histopathological analyses. Of particular interest for histopathology is the site of injection.

To study toxicity after repeated administration the remaining 48 animals (24 males, 24 females) are vaccinated, totally 4 times with one month between vaccinations, with buffer, the clinical dose or 10× the clinical dose (amount DNA)/kg intended for human use. At 7 days after the last injection the animals are subjected to blood sampling for haematology and clinical chemistry analyses. The animals are thereafter euthanized and relevant organs are dissected for histopathological analyses. Of particular interest for histopathology is the site of injection. During the period of repeated administration, blood samples are taken to determine the development of antibodies in response to the vaccination and to validate the effectiveness of the vaccine.

EXAMPLE 10

In a first study, HCV infected individuals are injected with a solution containing approximately 0.5 ml 0.9% NaCl containing approximately 0.25 mg/kg bodyweight of ChronVac-C (coNS3/4A DNA), an expression plasmid encoding codon-optimized HCV NS3/4A, in the thigh muscle using a large high injection pressure (HIP) injector. In a second study, HBV infected individuals are injected with a solution containing approximately 0.5 ml 0.9% NaCl containing approximately 0.25 mg/kg bodyweight of coHBcAg (an expression plasmid encoding codon-optimized HBV core antigen) in the thigh muscle using a large HIP injector. The large HIP injector has 4 needles oriented in a triangular formation, equally spaced with 6 mm between each needle. The center needle is placed in the middle of the equilateral triangle formed by the three outer needles. Each needle of the large HIP injector has 10 apertures. The outer needles all have apertures opening to the center and the center needle has apertures opening at four directions at 90 degree angles.

At day 5 and 10 blood is drawn from the inoculated individuals, peripheral blood mononuclear cells (PBMCs) are isolated, and the PBMCs are analyzed for T cell proliferation. The PBMCs are assayed for in-vitro proliferative recall responses using a standard 96 h proliferation assay. (See Lazinda et al., J. Gen. Virol. 82:1299-1308 (2001), herein expressly incorporated by reference in its entirety.) Microtiter plates are seeded with approximately 200,000 cells/well and the cells are incubated with media alone or recombinant NS3 or HBcAg. PBMCs are also incubated with Concanavalin A (ConA) as a positive control. After 72 hours, radioactive thymidine is added and 16-24 hours later the cells are harvested. The radioactivity of the cells as counts per minute are measured. Additionally, the presence of antibodies specific for NS3/4A and or HBcAg can be determined using standard assays (e.g., ELISA). Optionally, a boost injection is provided at two or three week intervals. The results will show that humans immunized with the large HIP injector show appreciable immune response to NS3/4A and/or HBcAg.

EXAMPLE 11

Electrification of needle electrodes in various combinations were studied to determine the effect of electric field generation on a prophylactic and/or therapeutic material contained within an electrified needle electrode and to determine the effect on the electrical properties of electrode needles, e.g. current draw, voltage, etc. as the injection medium and subject changed. The combinations and the results are described in Table 5.

In Table 5, two embodiments of intracellular delivery devices as described herein configured with needle electrodes were tested. Probe IV is a seven needle injection device having a pocket hub, as described herein. Probe VII is a 4 needle, Y-type injection device having a pocket hub, as described herein. The configuration column depicts which needles, identified by number had a positive polarity, and which had a negative polarity. Needles were numbered in a clockwise progression with the center needle having the highest number. Voltage was adjusted to maintain a desired 600 V/cm electrical field created in the subject or EP medium. The electrical field strength at the tips of the needles changes depending on needle pitch.

TABLE 5

| Test | Probe | Voltage | Configuration + | Configuration − | EP Medium | Needle Contents | Max. Current |
|---|---|---|---|---|---|---|---|
| 1 | IV | 240 | 1 | 7 | Saline | Empty | 4.32 |
| 2 | IV | 190 | 1 | 7 | Saline | Empty | 3.52 |
| 3 | IV | 190 | 2 | 7 | Saline | Empty | 3.68 |
| 4 | IV | 190 | 3 | 7 | Saline | Empty | 3.41 |
| 5 | IV | 190 | 4 | 7 | Saline | Empty | 3.41 |
| 6 | IV | 190 | 1 | 3 | Saline | Empty | 2.95 |
| 7 | IV | 220 | 1 | 3 | Saline | Empty | 3.45 |
| 8 | VII | 190 | 1 | 4 | Saline | Empty | 3.82 |
| 9 | VII | 180 | 1 | 4 | Saline | Empty | 3.59 |
| 10 | VII | 170 | 1 | 4 | Saline | Empty | 3.41 |
| 11 | VII | 170 | 2 | 4 | Saline | Empty | 3.41 |
| 12 | VII | 170 | 2 | 4 | Saline | Saline | 3.57 |
| 13 | VII | 170 | 1 | 4 | Saline | DNA | 3.59 |
| 14 | VII | 170 | 1 | 4 | Banana | DNA | 0.70 |
| 15 | VII | 240 | 1 | 4 | Banana | DNA | 1.27 |
| 16 | VII | 170 | 1 | 4 | Chicken | Empty | 1.27 |
| 17 | VII | 240 | 1 | 4 | Chicken | Empty | 1.43 |
| 18 | VII | 240 | 1 | 4 | Chicken | DNA | 1.73 |
| 19 | VII | 170 | 1 | 4 | Chicken | DNA | 1.07 |
| 20 | VII | 170 | 1 | 4 | Chicken | DNA | 1.16 |
| 21 | VII | 170 | 1 | 4 | Chicken | DNA | 1.18 |
| 22 | VII | 170 | 1 | 4 | Chicken | DNA | 0.59 |
| 23 | VII | 170 | 1 | 4 | Chicken | DNA | 1.27 |

The testing of the present example demonstrated that using needles as electrodes and as carriers of prophylactic and/or therapeutic material (delivered agents) can be accomplished without degrading the prophylactic and/or therapeutic agent, and without undesirably increasing the current draw. Needle electrodes may be manufactured from electrically conducing material. In some embodiments, the hub is constructed from electrically non-conductive material.

EXAMPLE 12

As will be appreciated from the example disclosed herein, it has been found that utilizing WIN delivery followed by electroporation in a two stage delivery, achieves a synergistic response over either method alone or the additive effect of both methods. Delivery, uptake and expression results, in larger muscles, represented by the rabbit tibialis anterior, are illustrated in FIGS. 56A1-B2 and FIGS. 57A1-C2.

In the current experiment, a first group of animals was injected with NS3/4A using a regular hypodermic needle (may also be referred to as a regular needle). A second group of animals was injected with NS3/4A using a regular needle followed by in vivo EP. A third group of animals was injected with NS3/4A, using an IVIN device as described herein. A fourth group of animals was injected with NS3/4A followed by in vivo EP, using the same IVIN device.

In the present example, the EC marked Cliniporator EP device provided by IGEA/Kiritec was used to deliver the in vivo EP. The pulse pattern of the in vivo EP had one short high-voltage pulse followed by a second longer low-voltage pulse. Without being limited by theory, it is believed the one short high-voltage pulse helped to make cells permeable, while the second longer low-voltage pulse helped to promote cellular uptake of DNA. As observed, the pulse pattern had a minimal destructive effect on the tissue and was more tolerable than pulse patterns also intended to cause tissue destruction and inflammation.

Following injection and in vivo EP (if any) tissue samples from each sample population were assayed for NS3/4A expression levels.

As shown in FIG. 56A1, moderate to no expression of NS3/4A was observed in the tissue sample injected with the regular needle and no in vivo EP. As shown in FIG. 56A2, appreciable expression levels of NS3/4A were detected in the tissue sample injected with the regular needle and receiving in vivo EP. Thus, as shown in FIG. 56A1 and FIG. 56A2, results from the use of a regular needle are greatly enhanced when coupled with in vivo EP (FIG. 96A1) than the use of a regular needle when not coupled with in vivo EP (FIG. 96A2).

Similarly, as shown in FIG. 56B1-B2, results from the use of an IVIN needle with a 125N injection force were enhanced when coupled with in vivo EP (FIG. 56B1) than the use of the IVIN needle with a 125N injection force when not coupled with in vivo EP (FIG. 56B2).

Comparing FIG. 56A2 with FIG. 56B1, the WIN injection with a 125N injection force showed a similar efficiency in transfecting muscle fibres in vivo (FIG. 56B1) as a regular needle injection combined with in vivo EP (FIG. 56A2).

Without being limited in theory, it is believed injection with the WIN technology achieved a highly localized site in the tissue since the configuration of the hub placed the needles along a circle fixing the tissue and injecting the NS3/4A centrally in the tissue. It is believed the tissue was locally overloaded resulting in both a local inflammation and an improved uptake of DNA and antigen expression.

Further, as can be seen by comparing FIG. 56A2 and FIG. 56B1 with FIG. 56B2, the combined WIN needle with a 125N injection force and in vivo EP (FIG. 56B2), showed both an enhanced inflammation and transfection over either the in vivo EP (FIG. 56A2) or the IVIN needle (FIG. 56B1) alone. Furthermore, as can be seen in FIG. 56B2 the combined WIN needle with a 125N injection force and in vivo EP, producing a truly synergistic effect over the additive effect of in vivo EP (FIG. 56A2) and the WIN needle (FIG. 56B1).

FIG. 57A1-C2 are example results of injection using the hypodermic needle device described above with two injection force values coupled with electroporation as compared to a regular needle with electroporation. As shown in FIG. 57A1-A2, results from the use of a regular needle are greatly enhanced when coupled with in vivo EP (FIG. 57A1) than the use of a regular needle when not coupled with in vivo EP (FIG. 57A2). Similarly, as shown in FIG. 57B1-B2, results from the use of an WIN needle with a 75N injection force were enhanced when coupled with in vivo EP (FIG. 57B1) than the use of the WIN needle with a 75N injection force when not coupled with in vivo EP (FIG. 57B2). Similarly, as shown in FIG. 57C1-C2, results from the use of an IVIN needle with a 125N injection force were enhanced when coupled with in vivo EP (FIG. 57C1) than the use of the IVIN needle with a 125N injection force when not coupled with in vivo EP (FIG. 57C2).

As seen in FIG. 57C2, the combination of IVIN with a 125N injection force and in vivo EP transfection was highly effective.

Figure 58A:
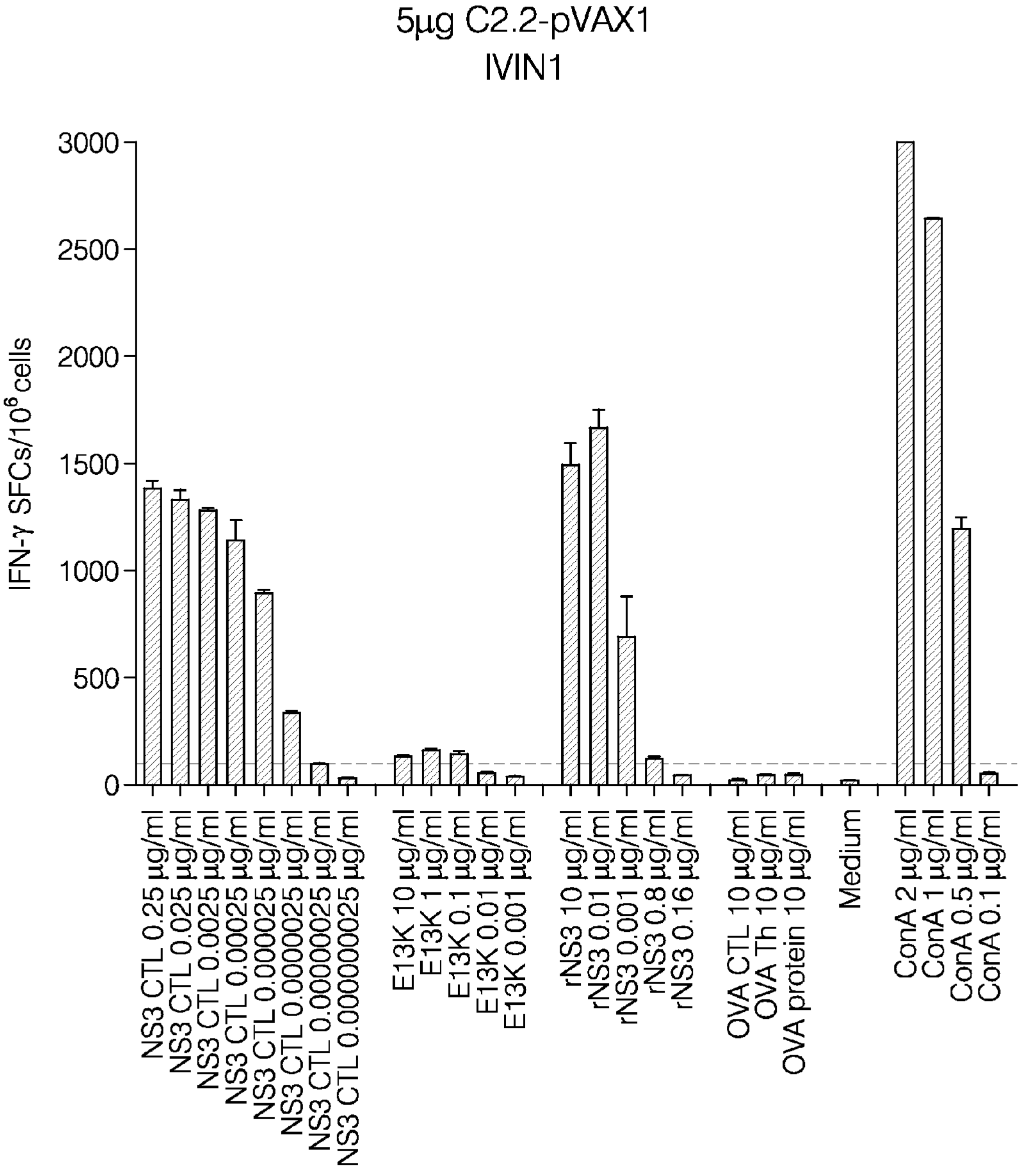
FIG. 58A illustrates immunization data in a mouse using an IVIN intracellular delivery apparatus, without electroporation.

FIG. 58A illustrates the number of interferon gamma producing cells/million splenocytes from a C57BL/6 mouse injected with 5 μg NS3/4A DNA in using an WIN intracellular delivery apparatus into the tibialis anterior muscle, with no electroporation.

Figure 58B:
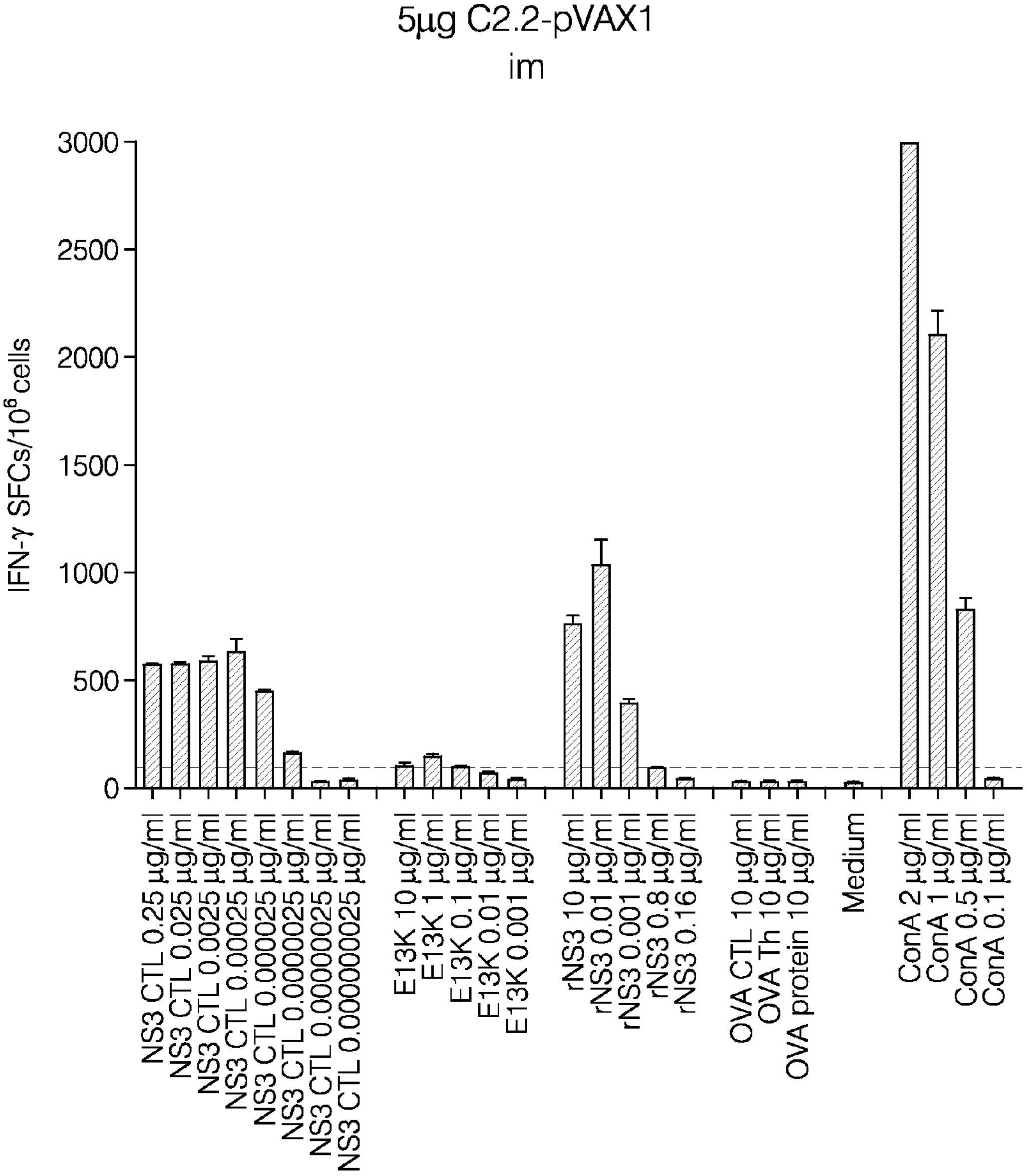
FIG. 58B illustrates immunization data in a mouse using an a conventional injection needle, without electroporation.

FIG. 58B illustrates the same quantity using standard injection methods to deliver 514 NS3/4A DNA in a C57BL/6 mouse.

Figure 58C:
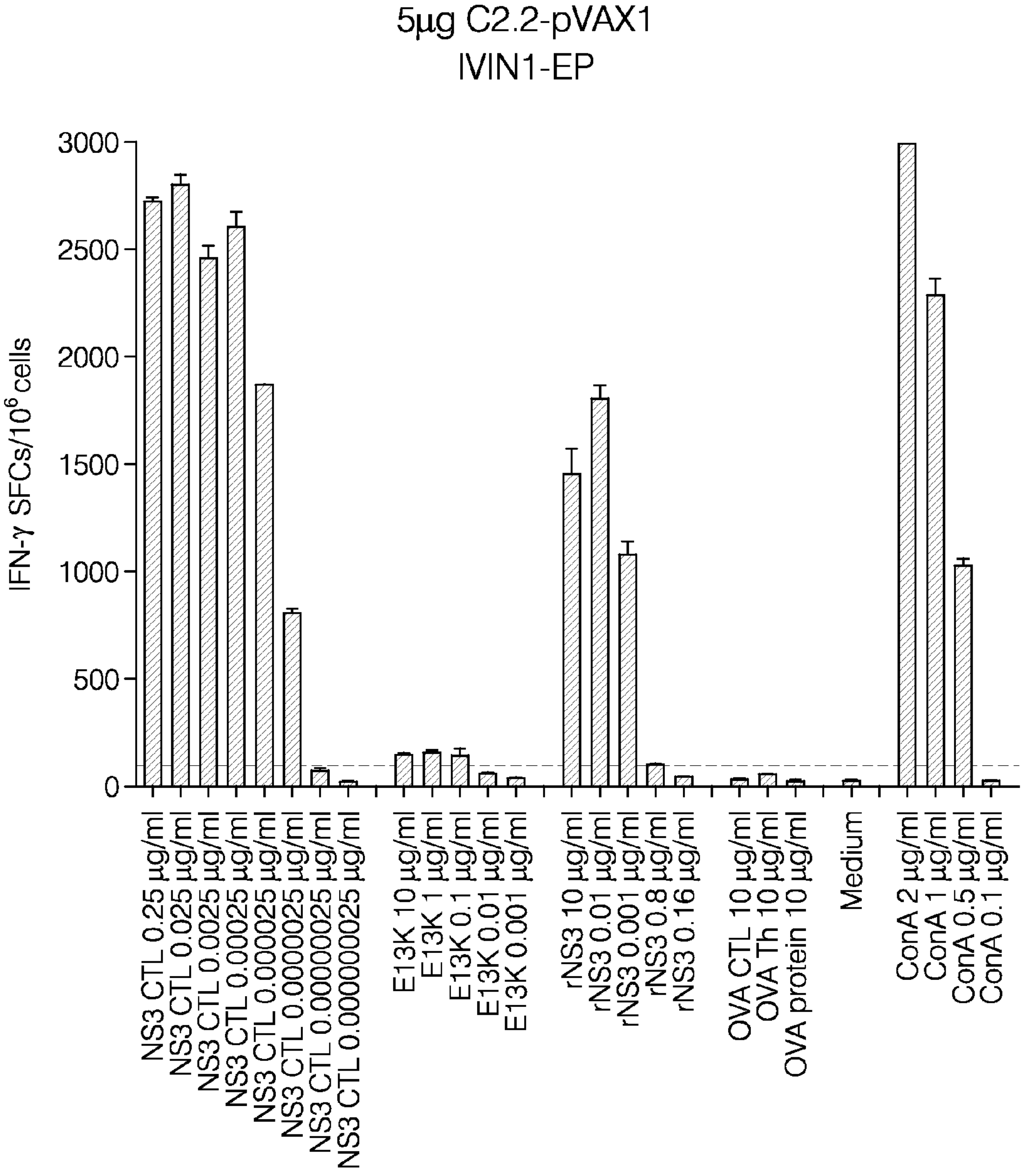
FIG. 58C illustrates immunization data in a mouse using an WIN intracellular delivery apparatus, with electroporation.

FIG. 58C illustrates number of interferon gamma producing cells/million splenocytes from a C57BL/6 mouse injected with 5 μg NS3/4A DNA in using an WIN intracellular delivery apparatus into the tibialis anterior muscle together with electroporation.

Figure 58D:
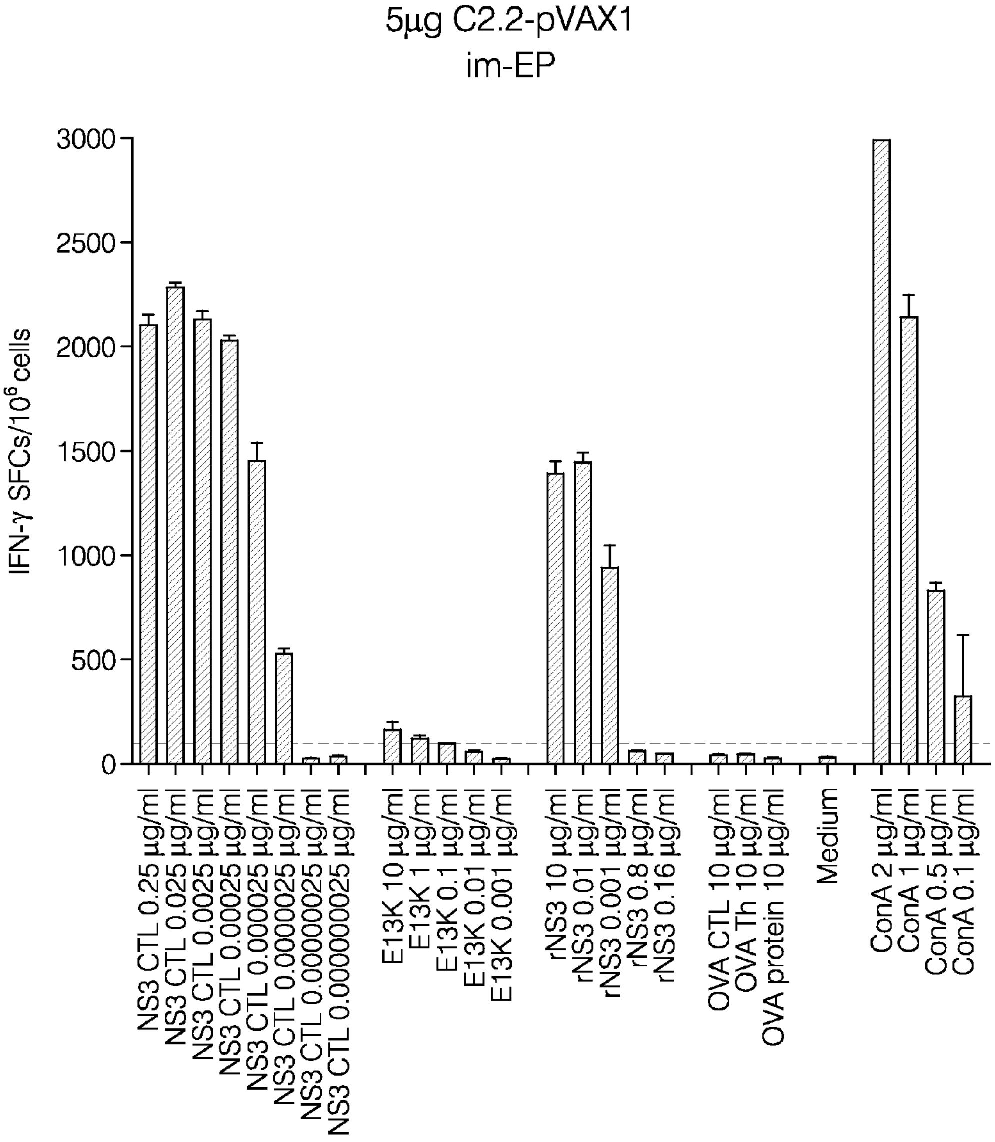
FIG. 58D illustrates immunization data in a mouse using a conventional injection needle with electroporation.

FIG. 58D illustrates the number of interferon gamma producing cells/million splenocytes from a C57BL/6 mouse injected with 5 μg NS3/4A DNA in using a conventional needle into the tibialis anterior muscle combined with electroporation.

Thus, DNA delivery using WIN results in a localized deposition and uptake and expression of the DNA, as well as a local inflammation. Also, when combined with in vivo EP the uptake and expression is further improved without causing additional tissue damage. Thus, the combination of IVIN and in vivo EP results in a highly effective and tolerable mode of DNA delivery, which can be particularly useful for delivering genetic vaccines (e.g., nucleic acid constructs encoding a desired antigen, such as NS3/4A with or without HBcAg).

EXAMPLE 13

Figure 59A:
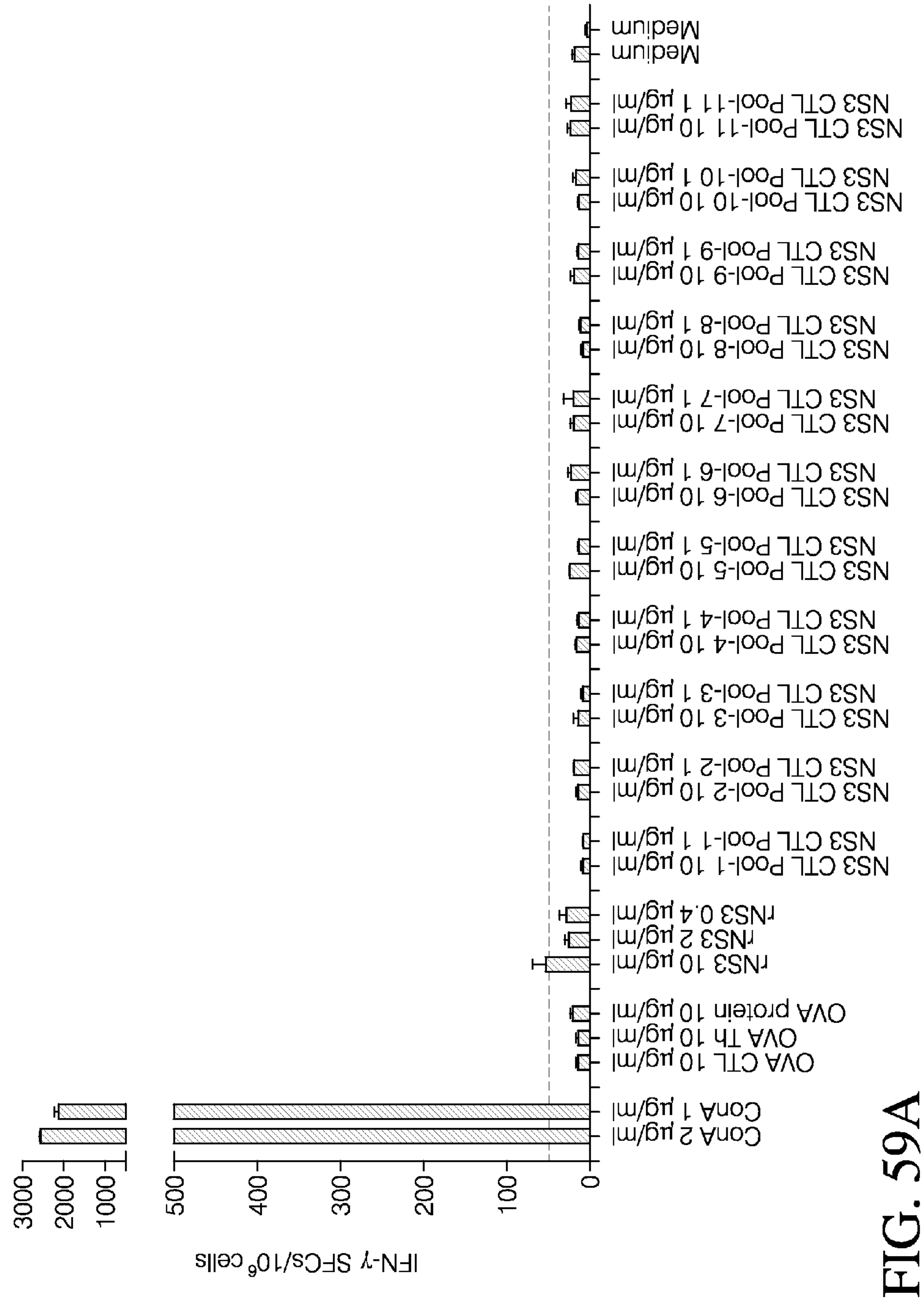
FIGS. 59A-B illustrate immunization data of non-immunized pigs.
Figure 59B:
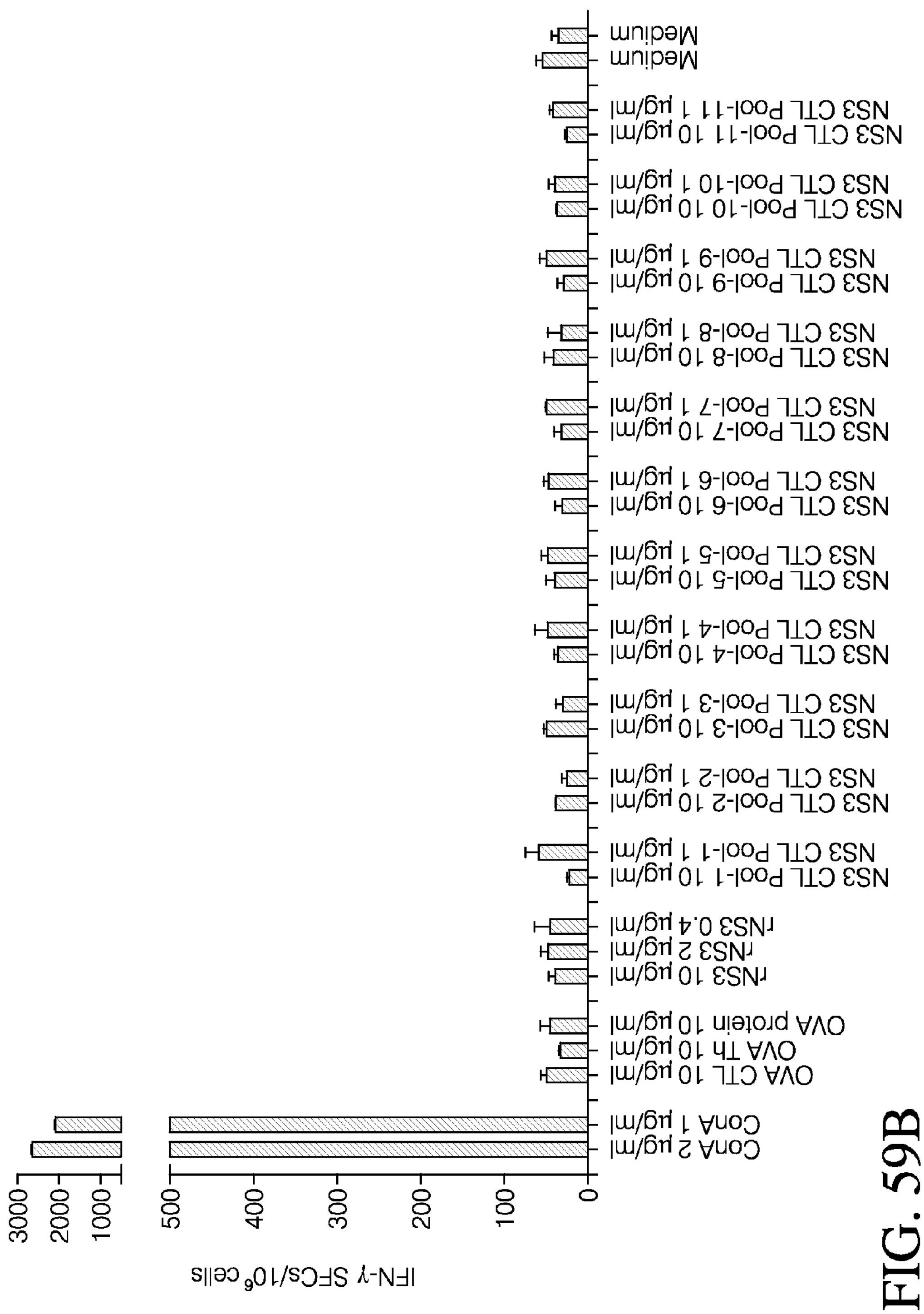
Figure 59C:
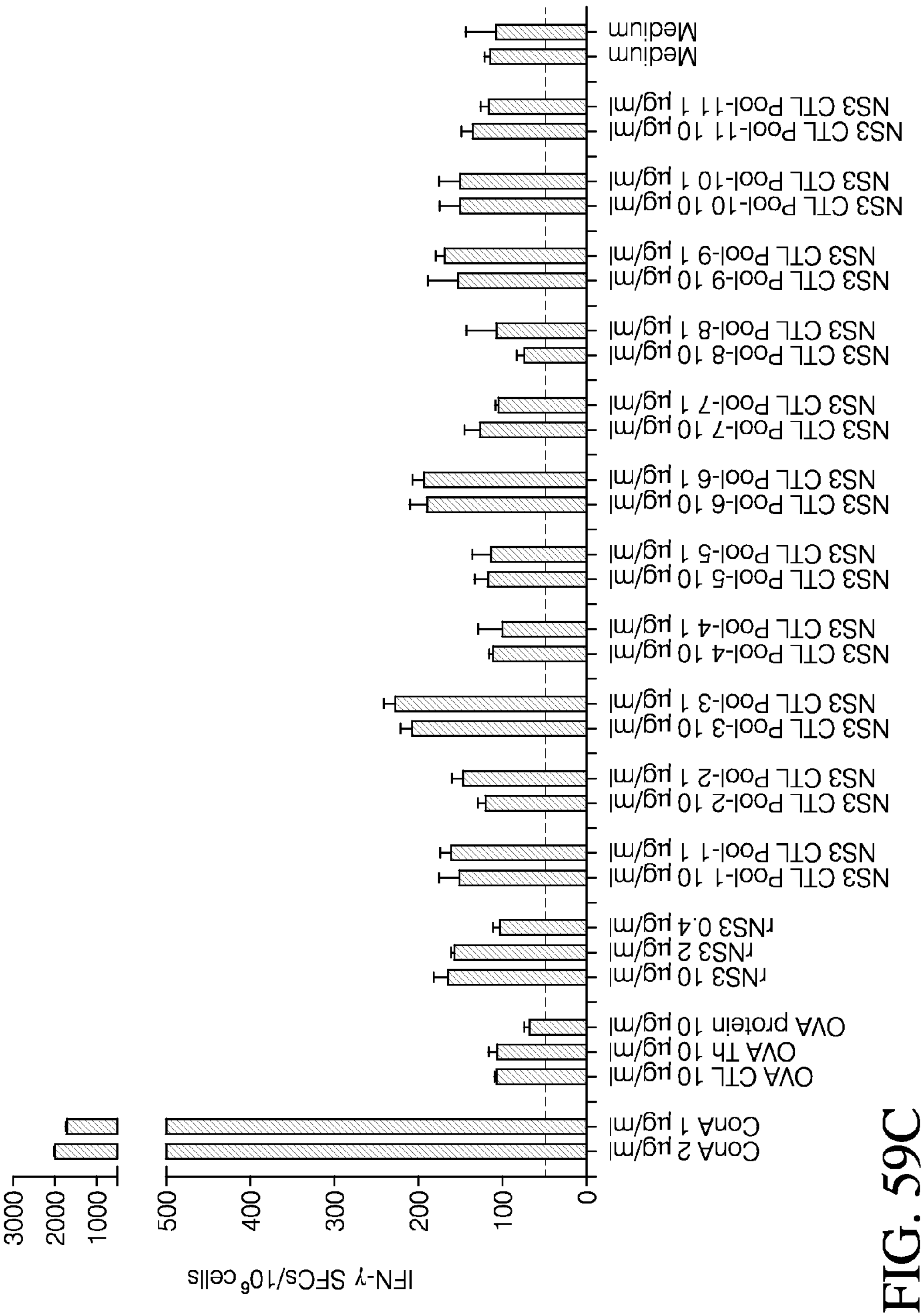
FIG. 59C illustrates immunization data of immunized pigs.

Outbred pigs were injected using an intracellular delivery apparatus having an WIN injection system to deliver NS3/4A DNA in the skin (6×50 ug) or in the right thigh muscle (1×500 ug). FIGS. 59A and B illustrate the number of pig-interferon gamma producing cells/million peripheral blood mononuclear cells of pigs receiving no NS3/4A DNA WIN injection (non-immunized pigs). FIGS. 59C and D illustrate the number of pig-interferon gamma producing cells/million peripheral blood mononuclear cells of pigs after injection with NS34A DNA (immunized pigs). As the data shows, an appreciable immune response was induced after using an intracellular delivery device delivering the NS3/4A construct.

What is claimed is:

1. An apparatus for intracellular delivery of a delivered agent comprising:

a hub comprising at least one electrical connector;

a plurality of needles connected to the hub, wherein each needle of the plurality of needles comprises:

a closed end;

a needle barrel; and a plurality of apertures that are disposed on the needle barrel;

an electrode; and an electrical power supply configured to generate an electric field at the electrode, wherein the electrical power supply is connected to the electrode through the at least one electrical connector, wherein the plurality of needles is arranged in an array of four needles arranged in a Y-type pattern comprising a center needle and three outer needles disposed around the center needle, wherein the center needle is a needle-electrode configured to apply a first polarity voltage, and the three outer needles are needle-electrodes, configured to apply a second polarity voltage; and wherein the center needle comprises apertures along the needle barrel, which are configured to direct delivery of the delivered agent toward apertures that are present on each of the three outer needles and each of the three outer needles comprises apertures along the needle barrel, which are configured to direct delivery of a delivered agent toward apertures that are present on the center needle so as to generate an opposing direction of delivery of the delivered agent.

2. The intracellular delivery apparatus of claim 1, wherein said needle-electrodes, are electrically connected to the electrical power supply and are configured to generate an electric field.

3. An intracellular delivery apparatus comprising:

a hub comprising at least one electrical connector:

a plurality of needles connected to the hub, wherein each needle of the plurality of needles comprises:

a closed end;

a needle barrel; and a plurality of apertures that are disposed on the needle barrel;

an electrode; and an electrical power supply configured to generate an electric field at the electrode, wherein the electrical power supply is connected to the electrode through the at least one electrical connector, wherein apertures on at least one needle barrel oppose the apertures on at least one other needle barrel wherein the plurality of needles is arranged in an array comprising a center needle and a plurality of outer needles disposed around the center needle, wherein the center needle comprises apertures along the needle barrel, which are configured to direct delivery of the delivered agent toward the outer needles and the outer needles comprise apertures along the needle barrel which are configured to direct delivery of a delivered agent toward the center needle so as to generate an opposing direction of delivery of the delivered agent;

a syringe in fluid communication with the hub; and a delivery unit comprising:

a channel configured to receive the hub and the syringe;

a collar operable to fasten the syringe within the channel;

a handle, which operates to enclose the syringe and hub within the channel such that the closed ends of the needle barrels protrude from the channel and are available to engage a subject;

a charging element configured to be charged by the operation of the handle, the charging element coupled to a trigger and the syringe such that operation of the trigger releases the charging element and the charging element acts on the syringe, thereby displacing prophylactic and/or therapeutic material out of the syringe; and an electrical port configured to mate with the electrical connector on the hub of the intracellular delivery apparatus thereby establishing electrical contact between the electrical power supply and the electrodes and/or needle-electrodes.

4. The intracellular delivery apparatus of claim 1, wherein the hub is a pocket hub, comprising an individual reservoir of a delivered agent for each needle or needle electrode.

5. The intracellular delivery apparatus of claim 1, wherein the hub comprises a single reservoir of a delivered agent for each needle or needle-electrode.

6. The intracellular delivery apparatus of claim 1, wherein at least one needle of the plurality of needles is at least partially laminated with an electrically non-conductive material.

7. The intracellular delivery apparatus of claim 1, further comprising an electrical power supply controller configured to control generation of the electric field.

8. The intracellular delivery apparatus of claim 7, wherein controlling generation of the electric field comprises controlling one or more of a pulse voltage, polarity of the needle-electrodes, a number of pulses, a pulse pattern, or a pulse duration.

9. The intracellular delivery apparatus of claim 3, wherein the charging element is a spring configured to be compressed by the operation of the handle and configured to decompress upon operation of the trigger or when activated by an electrically operated transducer.

10. The intracellular delivery apparatus of claim 1, wherein the electric field applied at the electrode and/or needle electrodes is commutating.

11. The intracellular delivery apparatus of claim 3, wherein the delivery unit is configured to control injection speed.

12. The intracellular delivery apparatus of claim 3, wherein the delivery unit is configured to control injection pressure.

13. A method of nucleic acid immunization comprising:

providing the intracellular delivery apparatus of claim 1;

providing a voltage source;

inserting a plurality of needles and a plurality of electrodes or a plurality of needle-electrodes of the intracellular delivery apparatus into a tissue of a subject;

displacing a nucleic acid through the plurality of apertures on the plurality of needles or the plurality of needle-electrodes and into the tissue of the subject; and applying an electric field to the tissue of the subject.

14. The method of claim 13, wherein the nucleic acid immunization comprises introduction of a polynucleotide encoding a hepatitis antigen.

15. The method of claim 14, wherein the hepatitis antigen is a hepatitis C virus (HCV) antigen.

16. The method of claim 15, wherein the HCV antigen comprises NS3.

17. A method of nucleic acid immunization comprising:

providing the intracellular delivery apparatus of claim 3;

providing a voltage source;

inserting a plurality of needles and a plurality of electrodes or a plurality of needle-electrodes of the intracellular delivery apparatus into a tissue of a subject;

displacing a nucleic acid through the plurality of apertures on the plurality of needles or the plurality of needle-electrodes and into the tissue of the subject; and applying an electric field to the tissue of the subject.

* * * * *